United States Patent
Ohkawa et al.

[11] Patent Number: 6,034,239
[45] Date of Patent: Mar. 7, 2000

[54] TRICYCLIC COMPOUNDS, THEIR PRODUCTION AND USE

[75] Inventors: Shigenori Ohkawa, Osaka; Osamu Uchikawa, Hyogo; Kohji Fukatsu, Hyogo; Masaomi Miyamoto, Hyogo, all of Japan

[73] Assignee: Takeda Chemical Industries, Ltd., Osaka, Japan

[21] Appl. No.: 08/812,168

[22] Filed: Mar. 6, 1997

Related U.S. Application Data

[60] Provisional application No. 60/013,733, Mar. 20, 1996, and provisional application No. 60/023,090, Jul. 25, 1996.

[30] Foreign Application Priority Data

| Mar. 8, 1996 | [JP] | Japan | 8-051491 |
| Jul. 12, 1996 | [JP] | Japan | 8-183667 |
| Feb. 13, 1997 | [JP] | Japan | 9-029185 |

[51] Int. Cl.$^7$ .............. C07D 413/00; C07D 493/00; C07D 307/92; C07C 233/00

[52] U.S. Cl. .......... 544/147; 544/153; 549/387; 549/458; 564/189

[58] Field of Search ............ 564/189; 544/387, 544/458, 153, 147

[56] References Cited

U.S. PATENT DOCUMENTS

| 5,296,482 | 3/1994 | Peglion et al. ............ 514/213 |
| 5,552,418 | 9/1996 | Depreux et al. ............ 514/348 |
| 5,661,186 | 8/1997 | Takaki et al. ............ 514/630 |

FOREIGN PATENT DOCUMENTS

| 0420064 | 4/1991 | European Pat. Off. ...... C07C 233/23 |
| 0527687 | 2/1993 | European Pat. Off. ...... C07D 209/16 |
| 0708099 | 4/1996 | European Pat. Off. . |
| WO 17405 | 6/1995 | WIPO . |
| WO 29173 | 11/1995 | WIPO . |
| WO 95-35320 | 12/1995 | WIPO . |

OTHER PUBLICATIONS

Macor et al., J. Med. Chem., vol. 35, No. 20 (1992) 3625–32.
Tetrahedron Letters, vol. 36, No. 39 (1995) 7019–7022.

*Primary Examiner*—John Kight
*Assistant Examiner*—Raymond Covington
*Attorney, Agent, or Firm*—Fitzpatrick, Cella, Harper & Scinto

[57] ABSTRACT

A compound of the formula:

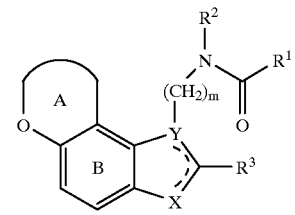

wherein $R^1$ is an optionally substituted hydrocarbon, amino or heterocyclic group; $R^2$ is H or an optionally substituted hydrocarbon group; $R^3$ is H or an optionally substituted hydrocarbon or heterocyclic group; X is $CHR^4$, $NR^4$, O or S in which $R^4$ is H or an optionally substituted hydrocarbon group; Y is C, CH or N; ring A is optionally substituted 5- to 7-membered ring; ring B is an optionally substituted benzene ring; and m is 1 to 4, or a salt thereof, a process for producing it, an intermediate for the production and a pharmaceutical composition comprising it are provided.

41 Claims, No Drawings

TRICYCLIC COMPOUNDS, THEIR PRODUCTION AND USE

This application claims priority of provisional application 60/013,733, filed Mar. 20, 1996 and provisional application 60/023,090, filed Jul. 25, 1996.

TECHNICAL FIELD

The present invention relates to a tricyclic compound with excellent binding affinity for melatonin receptor, a process for producing and use thereof.

BACKGROUND ART

Melatonin (N-acetyl-5-methoxytryptamine), which is a hormone synthesized and secreted principally in the pineal gland, increases in dark circumstances and decreases in light circumstances. Melatonin exerts suppressively on pigment cells and the female gonads, and acts as a synchronous factor of biological clock while taking part in transmittance of photoperiodic code. Therefore, melatonin is expected to be used for the therapy of diseases related with melatonin activity, such as reproduction and endocrinic disorders, sleep-awake rhythm disorders, jet-lag syndrome and various disorders related to aging, etc.

Recently, it has been reported that the production of melatonin melatonin could reset the body's aging clock (see Ann. N. Y. Acad. Sci., Vol. 719, pp. 456–460 (1994)). As previously reported, however, melatonin is easily metabolized by metabolic enzymes in vivo (see Clinical Examinations, Vol. 38, No. 11, pp. 282–284 (1994)). Therefore, it cannot be said that melatonin is suitable as a pharmaceutical substance.

Various melatonin agonists and antagonists such as those mentioned below are known.

(1) EP-A-578620 discloses compounds of:

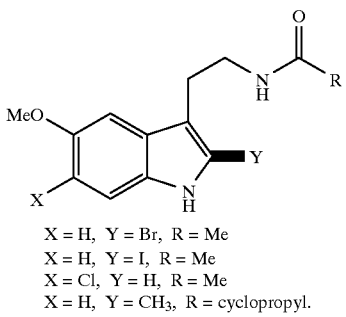

X = H, Y = Br, R = Me
X = H, Y = I, R = Me
X = Cl, Y = H, R = Me
X = H, Y = CH₃, R = cyclopropyl.

(2) EP-A-420064 U.S. Pat. No. 5,634,238 discloses a compound of:

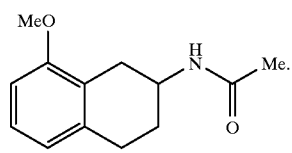

(3) EP-A-447285 discloses a compound of:

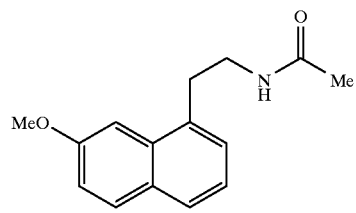

(4) U.S. Pat. No. 5,552,418 (FR-93 14630) discloses a compound of:

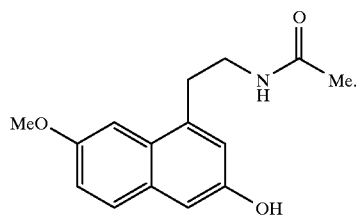

(5) EP-A-591057 discloses a compound of:

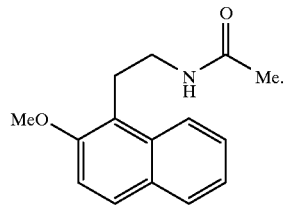

(6) EP-A-527687 discloses compounds of:

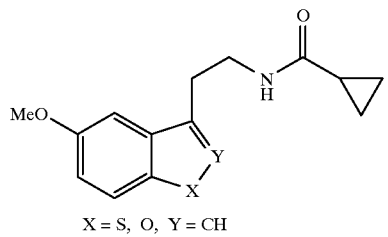

X = S, O, Y = CH
X = O, NH, Y = N

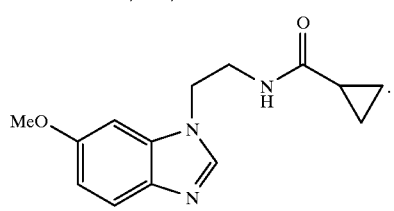

(7) EP-A-506539 discloses compounds of:
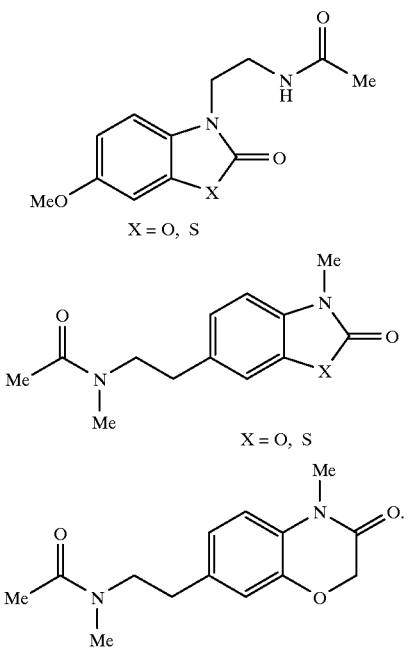
X = O, S
X = O, S
Tricyclic or more poly-cyclic compounds with a cyclic ether moiety, such as those mentioned below, are known.
(1) Compounds of:
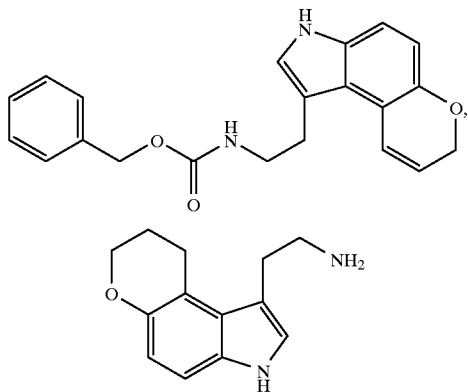
are disclosed in Tetrahedron Lett., Vol. 36, p. 7019 (1995).
(2) Compounds of:
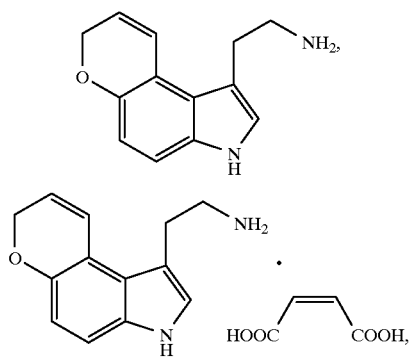
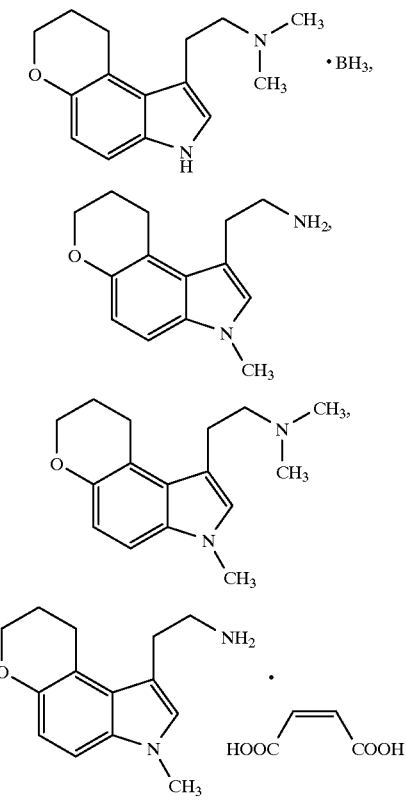
are disclosed in J. Med. Chem., Vol. 35, p. 3625 (1992).
(3) Compounds of:
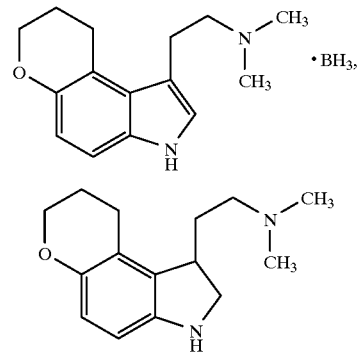
are disclosed in Tetrahedron, Vol. 48, p. 1039 (1992).
(4) Compounds of:
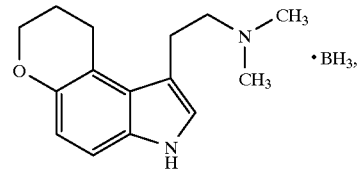

-continued

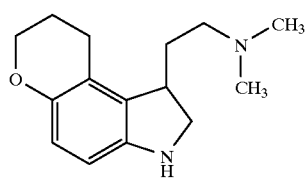

are disclosed in Tetrahedron Lett., Vol. 32, p. 3345 (1991).

(5) A compound of:

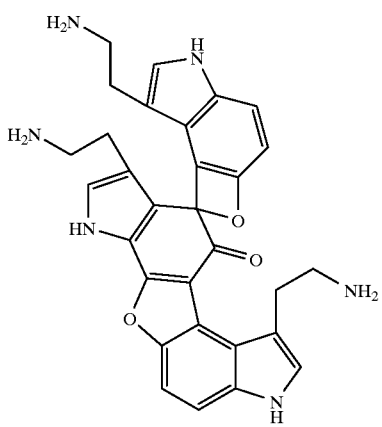

is disclosed in Bioorg. Chem., Vol. 18, p. 291 (1990).

(6) A compound of:

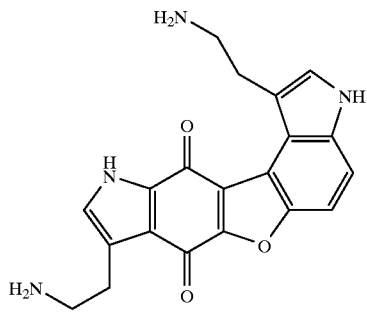

is disclosed in J. Electroanal. Chem. Interfacial Electrochem., Vol. 278, p. 249 (1990).

However, there is no report referring to the relationship between these compounds and melatonin receptors.

As tricyclic compounds with an affinity for melatonin receptor, known are compounds of:

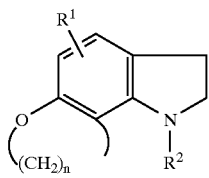

wherein $R^1$ represents a hydrogen atom, a halogen atom or a $C_{1-6}$ alkyl group; $R^2$ represents —$CR^3R^4(CH_2)_pNR^5COR^6$ (in which $R^3$, $R^4$ and $R^5$ are the same or different and each represents a hydrogen atom or a $C_{1-6}$ alkyl group, and $R^6$ represents a $C_{1-6}$ alkyl group or a $C_{3-7}$ cycloalkyl group); n represents an integer of 2 to 4; and p represents an integer of from 1 to 4 (WO-A-9517405), and compounds of:

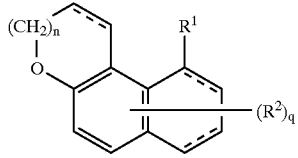

wherein $R^1$ represents —$CR^3R^4(CH_2)_pNR^5COR^6$ (in which $R^3$, $R^4$ and $R^5$ are the same or different and each represents a hydrogen atom or a $C_{1-6}$ alkyl group, and $R^6$ represents a $C_{1-6}$ alkyl group or a $C_{3-7}$ cycloalkyl group); $R^2$ represents a hydrogen atom, a halogen atom, a $C_{1-6}$ alkyl group, $OR^7$ or $CO_2R^7$ (in which $R^7$ represents a hydrogen atom or a $C_{1-6}$ alkyl group), provided that when q is 2, each of $R^2$ are the same or different and each represents a hydrogen atom, a halogen atom, a $C_{1-6}$ alkyl group, $OR^7$ or $CO_2R^7$; n represents an integer of 0 to 2; p represents an integer of 1 to 4; and q represents 1 or 2 (WO-A-9529173).

Melatonin agonists having different structures from that of melatonin and having an excellent binding affinity for melatonin receptor, excellent intracerebral mobility and excellent metabolical stability are expected to be more effective as a pharmaceutical remedy than melatonin.

At present, no compounds are known which are fully satisfactory with respect to their activity on melatonin receptor, and to their metabolical stability and the intracerebral mobility. Therefore, it is earnestly desired to develop compounds which are different from the above-mentioned known compounds in terms of their chemical structure, which have excellent agonistic or antagonistic activity towards melatonin receptor and which are therefore fully satisfactory for use in medicines such as pharmaceutical preparations.

SUMMARY OF THE INVENTION

The present invention relates to a novel compound which is characterized in having a $R^1$—CO-amino-$C_{1-4}$ alkylene group (in which $R^1$ is of the same meanings as defined hereinafter) at Y of the basic skeleton moiety of the formula:

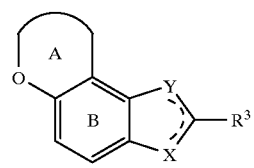

wherein all symbols are of the same meanings as defined hereinafter and is represented by the formula:

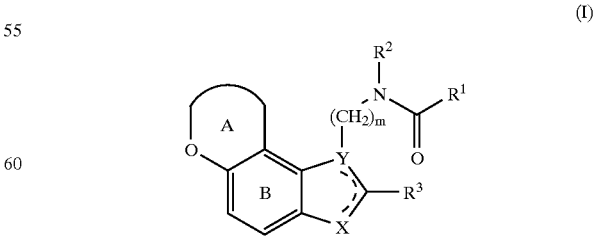

(I)

wherein $R^1$ represents an optionally substituted hydrocarbon group, an optionally substituted amino group or an optionally substituted heterocyclic group;

$R^2$ represents a hydrogen atom or an optionally substituted hydrocarbon group;

$R^3$ represents a hydrogen atom, an optionally substituted hydrocarbon group or an optionally substituted heterocyclic group;

X represents $CHR^4$, $NR^4$, O or S in which $R^4$ represents a hydrogen atom or an optionally substituted hydrocarbon group;

Y represents C, CH or N, provided that when X is $CH_2$, Y is C or CH;

......... represents a single bond or a double bond;

ring A represents an optionally substituted, 5- to 7-membered oxygen-containing heterocyclic ring;

ring B represents an optionally substituted benzene ring; and m represents an integer of 1 to 4, or a salt thereof, or a salt thereof [hereinafter referred to as compound (I)], which has an unexpected good binding affinity for melatonin receptor as a melatonin agonist and is therefore sufficiently satisfactory for use in medicines such as pharmaceutical preparations.

DETAILED EXPLANATION OF THE INVENTION

The present invention provides;

(1) the compound (I), (2) the compound of the above (1), wherein $R^1$ is
  (i) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxy, an optionally halogenated $C_{1-6}$ alkyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, $C_{6-10}$ aryl-carbamoyl, $C_{6-10}$ aryl, $C_{6-10}$ aryloxy and an optionally halogenated $C_{1-6}$ alkyl-carbonylamino,
  (ii) an amino group which may be substituted by 1 or 2 substituents selected from the group consisting of a $C_{1-6}$ alkyl, $C_{2-6}$ alkenyl, $C_{2-6}$ alkynyl, $C_{3-6}$ cycloalkyl and $C_{6-14}$ aryl group, each of which may be substituted by 1 to 5 substituents selected from the group consisting of a halogen, nitro, cyano, hydroxy, an optionally halogenated $C_{1-6}$ alkyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy and an optionally halogenated $C_{1-6}$ alkyl-carbonylamino, or
  (iii) a 5- to 14-membered heterocyclic group containing, besides carbon atoms, 1 to 3 hetero atoms selected from nitrogen atom, oxygen atom and sulfur atom, which group may be substituted by 1 to 5 substituents selected from the group consisting of a halogen, $C_{1-6}$ alkyl, $C_{3-6}$ cycloalkyl, $C_{2-6}$ alkynyl, $C_{2-6}$ alkenyl, $C_{7-11}$ aralkyl, $C_{6-10}$ aryl, $C_{1-6}$ alkoxy, $C_{6-10}$ aryloxy, formyl, $C_{1-6}$ alkyl-carbonyl, $C_{6-10}$ aryl-carbonyl, formyloxy, $C_{1-6}$ alkyl-carbonyloxy, $C_{6-10}$ aryl-carbonyloxy, carboxyl, $C_{1-6}$ alkoxy-carbonyl, $C_{7-11}$ aralkyloxy-carbonyl, carbamoyl, an optionally halogenated $C_{1-4}$ alkyl, oxo, amidino, imino, amino, mono-$C_{1-4}$ alkylamino, di-$C_{1-4}$ alkylamino, 3- to 6-membered cyclic amino, $C_{1-3}$ alkylenedioxy, hydroxy, nitro, cyano, mercapto, sulfo, sulfino, phosphono, sulfamoyl, mono-$C_{1-6}$ alkylsulfamoyl, di-$C_{1-6}$ alkylsulfamoyl, $C_{1-6}$ alkylthio, $C_{6-10}$ arylthio, $C_{1-6}$ alkylsulfinyl, $C_{6-10}$ arylsulfinyl, $C_{1-6}$ alkylsulfonyl and $C_{6-10}$ arylsulfonyl;

$R^2$ is (i) a hydrogen atom or (ii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxy, an optionally halogenated $C_{1-6}$ alkyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy and an optionally halogenated $C_{1-6}$ alkyl-carbonylamino;

$R^3$ is (i) a hydrogen atom, (ii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxy, an optionally halogenated $C_{1-6}$ alkyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy and an optionally halogenated $C_{1-6}$ alkyl-carbonylamino or (iii) a 5- to 14-membered heterocyclic group containing, besides carbon atoms, 1 to 3 hetero atoms selected from nitrogen atom, oxygen atom and sulfur atom, which group may be substituted by 1 to 5 substituents selected from the group consisting of a halogen, $C_{1-6}$ alkyl, $C_{3-6}$ cycloalkyl, $C_{2-6}$ alkynyl, $C_{2-6}$ alkenyl, $C_{7-11}$ aralkyl, $C_{6-10}$ aryl, $C_{1-6}$ alkoxy, $C_{6-10}$ aryloxy, formyl, $C_{1-6}$ alkyl-carbonyl, $C_{6-10}$ aryl-carbonyl, formyloxy, $C_{1-6}$ alkyl-carbonyloxy, $C_{6-10}$ aryl-carbonyloxy, carboxyl, $C_{1-6}$ alkoxy-carbonyl, $C_{7-11}$ aralkyloxy-carbonyl, carbamoyl, an optionally halogenated $C_{1-4}$ alkyl, oxo, amidino, imino, amino, mono-$C_{1-4}$ alkylamino, di-$C_{1-4}$ alkylamino, 3- to 6-membered cyclic amino, $C_{1-3}$ alkylenedioxy, hydroxy, nitro, cyano, mercapto, sulfo, sulfino, phosphono, sulfamoyl, mono-$C_{1-6}$ alkylsulfamoyl, di-$C_{1-6}$ alkylsulfamoyl, $C_{1-6}$ alkylthio, $C_{6-10}$ arylthio, $C_{1-6}$ alkylsulfinyl, $C_{6-10}$ arylsulfinyl, $C_{1-6}$ alkylsulfonyl and $C_{6-10}$ arylsulfonyl;

$R^4$ is (i) a hydrogen atom or (ii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxy, an optionally halogenated $C_{1-6}$ alkyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy and an optionally halogenated $C_{1-6}$ alkyl-carbonylamino;

ring A is a 5- to 7-membered heterocyclic group optionally containing, besides carbon atoms and an oxygen atom, 1 to 3 hetero atoms selected from nitrogen atom, oxygen atom and sulfur atom, which group may be substituted by 1 to 4 substituents selected from the group consisting of (i) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxy, an optionally halogenated $C_{1-6}$ alkyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy and an optionally halogenated $C_{1-6}$ alkyl-carbonylamino, (ii) a halogen, (iii) $C_{1-6}$ alkoxy, (iv) $C_{6-10}$ aryloxy, (v) formyl, (vi) $C_{1-6}$ alkyl-carbonyl, (vii) $C_{6-10}$ aryl-carbonyl, (viii) formyloxy, (ix) $C_{1-6}$ alkyl-carbonyloxy, (x) $C_{6-10}$ aryl-carbonyloxy, (xi) carboxyl, (xii) $C_{1-6}$ alkoxy-carbonyl, (xiii) $C_{7-11}$ aralkyloxy-carbonyl, (xiv) carbamoyl, (xv) an optionally halogenated $C_{1-4}$ alkyl, (xvi) oxo, (xvii) amidino, (xviii) imino, (xix) amino, (xx) mono-$C_{1-4}$ alkylamino, (xxi) di-$C_{1-4}$ alkylamino, (xxii) 3- to 6-membered cyclic amino, (xxiii) $C_{1-3}$ alkylenedioxy, (xxiv) hydroxy, (xxv) nitro, (xxvi) cyano, (xxvii) mercapto, (xxviii) sulfo, (xxix) sulfino, (xxx) phosphono, (xxxi) sulfamoyl, (xxxii) mono-$C_{1-6}$ alkylsulfamoyl, (xxxiii) di-$C_{1-6}$ alkylsulfamoyl, (xxxiv) $C_{1-6}$ alkylthio, (xxxv) $C_{6-10}$ arylthio, (xxxvi) $C_{1-6}$ alkylsulfinyl, (xxxvii) $C_{6-10}$ arylsulfinyl, (xxxviii) $C_{1-6}$ alkylsulfonyl and (xxxix) $C_{6-10}$ arylsulfonyl; and ring B is a benzene ring which may be substituted by 1 or 2 substituents selected from the group consisting of (i) a halogen, (ii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxy, an optionally halogenated $C_{1-6}$ alkyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy and an optionally halogenated $C_{1-6}$ alkyl-carbonylamino, (iii) an amino group which may be substituted by 1 or 2 substituents selected from the group consisting of a $C_{1-6}$ alkyl, $C_{2-6}$ alkenyl, $C_{2-6}$ alkynyl, $C_{3-6}$ cycloalkyl and $C_{6-14}$ aryl group, each of which may be substituted by 1 to 5 substituents selected from the group consisting of a halogen, nitro, cyano, hydroxy, an optionally halogenated $C_{1-6}$ alkyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy and an optionally halogenated $C_{1-6}$ alkyl-carbonylamino, (iv) a $C_{1-6}$ alkanoylamino group, (v) a $C_{1-6}$ alkoxy group which may be substituted by 1 to 3 substituents selected from the group consisting of a halogen, nitro, cyano, hydroxy, an optionally halogenated $C_{1-6}$ alkyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy and an optionally halogenated $C_{1-6}$ alkyl-carbonylamino or (vi) a $C_{1-3}$ alkylenedioxy group, (3) the compound of the above (1), wherein

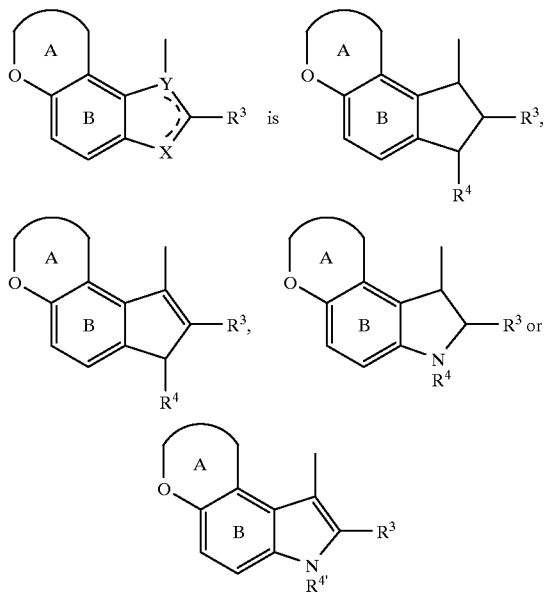

wherein $R^{4'}$ is an optionally substituted hydrocarbon group and the other symbols are as defined above, (4) the compound of the above (1), which is a compound of the formula:

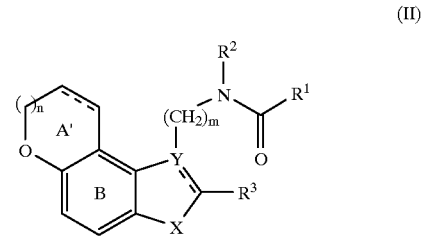

(II)

wherein ring A' is an optionally substituted, oxygen-containing heterocyclic ring;
n is an integer of 0 to 2;
----- and ......... are the same or different and each is a single bond or a double bond;
and the other symbols are as defined above, (5) the compound of the above (1), wherein $R^1$ is (i) an optionally substituted $C_{1-6}$ alkyl group, (ii) an optionally substituted $C_{3-6}$ cycloalkyl group, (iii) an optionally substituted $C_{2-6}$ alkenyl group, (iv) an optionally substituted $C_{6-14}$ aryl group, (v) an optionally substituted mono- or di-$C_{1-6}$ alkylamino group, (vi) an optionally substituted $C_{6-14}$ arylamino group, or (vii) an optionally substituted 5- or 6-membered nitrogen-containing heterocyclic group, (6) the compound of the above (1), wherein $R^1$ is an optionally halogenated $C_{1-6}$ alkyl group, (7) the compound of the above (1), wherein $R^2$ is a hydrogen atom or an optionally substituted $C_{1-6}$ alkyl group, (8) the compound of the above (1), wherein $R^2$ is a hydrogen atom, (9) the compound of the above (1), wherein $R^3$ is a hydrogen atom or an optionally substituted hydrocarbon group,

(10) the compound of the above (1), wherein $R^3$ is a hydrogen atom,

(11) the compound of the above (1), wherein $R^4$ is a hydrogen atom or an optionally substituted $C_{1-6}$ alkyl group,

(12) the compound of the above (1), wherein X is $CHR^4$,

(13) the compound of the above (1), wherein X is $CHR^4$ and ......... is a single bond,

(14) the compound of the above (13), wherein X is $CH_2$,

(15) the compound of the above (1), wherein X is $NR^4$,

(16) the compound of the above (1), wherein Y is C or CH,

(17) the compound of the above (1), wherein Y is CH,

(18) the compound of the above (1), wherein m is 2,

(19) the compound of the above (1), wherein ring A is a tetrahydrofuran ring,

(20) the compound of the above (1), wherein ring A is unsubstituted,

(21) the compound of the above (1), wherein ring B is unsubstituted,

(22) the compound of the above (4), wherein n is 0 or 1,

(23) the compound of the above (1) which is a compound of the formula:

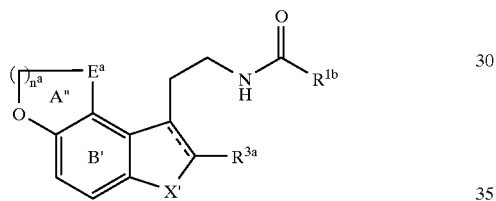

wherein $R^{1b}$ is $C_{1-6}$ alkyl,
X' is $CH_2$, NH or NCHO,
......... is a single bond or double bond,
$R^{3a}$ is a hydrogen atom or a phenyl,
$E^a$ is $CH_2CH_2$, CH=CH, $CH_2O$, CH=N, CONH or $CH_2NH$,
$n^a$ is 0 or 1,
ring A" is a 5- or 6-membered oxgen-containing heterocyclic ring which may be substituted by 1 or 2 $C_{1-6}$ alkyl optionally substituted by a hydroxy, and
ring B' is a benzene ring which may be substituted by a halogen,

(24) the compound of the above (23), wherein ......... is single bond and X' is NH,

(25) the compound of the above (1), which is (S)-N-[2-(1,6,7,8-tetrahydro-2H-indeno[5,4-b]furan-8-yl)ethyl]propionamide,

(26) the compound of the above (1), which is N-[2-(1,6,7,8-tetrahydro-2H-furo[3,2-e]indol-8-yl)ethyl]propionamide,

(27) the compound of the above (1), which is N-[2-(1,6,7,8-tetrahydro-2H-furo[3,2-e]indol-8-yl)ethyl]butyramide,

(28) the compound of the above (1), which is N-[2-(7-phenyl-1,6-dihydro-2H-indeno[5,4-b]furan-8-yl)ethyl]propionamide,

(29) the compound of the above (1), which is N-[2-(7-phenyl-1,6-dihydro-2H-indeno[5,4-b]furan-8-yl)ethyl]butyramide,

(30) a process for producing a compound of the above (1), which comprises reacting a compound of the formula (i):

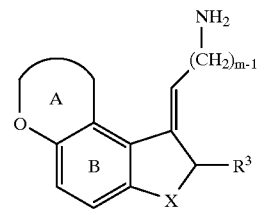

wherein all symbols are as defined in the above (1), or (ii):

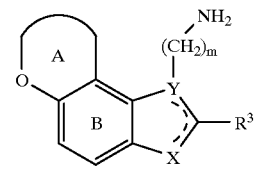

wherein all symbols are as defined above, or a salt thereof, with a compound of the formula:

$R^1COOH$ wherein $R^1$ is as defined above, or a salt thereof or a reactive derivative thereof, if necessary, subjecting the resultant compound to reduction and/or alkylation,

(31) a process for producing a compound of the above (4), which comprises subjecting a compound of the formula:

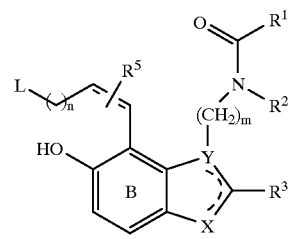

wherein $R^5$ represents a hydrogen atom, a halogen atom, an optionally substituted hydrocarbon group, an optionally substituted alkoxy group, a hydroxy group, a nitro group, a cyano group or an optionally substituted amino group; L represents a leaving group; and the other symbols are as defined above, or a salt thereof to cyclization, and if necessary, subjecting the resultant compound to reduction,

(32) a compound of the formula:

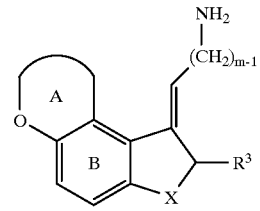

wherein the symbols are as defined above, or a salt thereof,

(33) a compound of the formula:

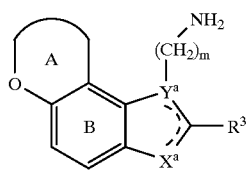

wherein X represents CHR$^{4a}$, NR$^{4a}$, O or S in which R$^{4a}$ represents a hydrogen atom or an optionally substituted hydrocarbon group; Y$^a$ represents C, CH or N, provided that when X$^a$ is NH, Y$^a$ is CH or N; and the other symbols are as defined above, or a salt thereof,

(34) a pharmaceutical composition which comprises the compound of the above (1),

(35) the composition of the above (34) which has a binding affinity for melatonin receptor,

(36) the composition of the above (35) which is a regulating agent of circadian rhythm,

(37) the composition of the above (35) which is a regulating agent of sleep-awake rhythm,

(38) the composition of the above (35) which is a regulating agent of time zone change syndrome, and

(39) the composition of the above (35) which is a therapeutic agent of sleep disorders.

The "hydrocarbon group" in "optionally substituted hydrocarbon group" as referred to herein includes, for example, an aliphatic hydrocarbon group, a mono-cyclic saturated hydrocarbon group, an aromatic hydrocarbon group, etc., and this preferably has from 1 to 16 carbon atoms. Concretely, this includes, for example, an alkyl group, an alkenyl group, an alkynyl group, a cycloalkyl group, an aryl group, etc.

The "alkyl group" is, for example, preferably a lower alkyl group and generally includes C$_{1-6}$ alkyl groups such as methyl, ethyl, propyl, isopropyl, butyl, isobutyl, sec-butyl, tert-butyl, pentyl, hexyl, etc.

The "alkenyl group" is, for example, preferably a lower alkenyl group and generally includes C$_{2-6}$ alkenyl groups such as vinyl, 1-propenyl, allyl, isopropenyl, butenyl, isobutenyl, etc.

The "alkynyl group" is, for example, preferably a lower alkynyl group and generally includes C$_{2-6}$ alkynyl groups such as ethynyl, propargyl, 1-propynyl, etc.

The "cycloalkyl group" is, for example, preferably a lower cycloalkyl group and generally includes C$_{3-6}$ cycloalkyl groups such as cyclopropyl, cyclobutyl, cyclopentyl, cyclohexyl, etc.

The "aryl group" is preferably a C$_{6-14}$ aryl group, including, for example, phenyl, 1-naphthyl, 2-naphthyl, biphenylyl, 2-anthryl, etc. Of these, phenyl is generally used.

The substituents for the "hydrocarbon group" of the "optionally substituted hydrocarbon group" include, for example, a halogen atom (e.g., fluorine, chlorine, bromine, iodine, etc.), a nitro group, a cyano group, a hydroxy group, an optionally halogenated lower alkyl group (e.g., an optionally halogenated C$_{1-6}$ alkyl group such as methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, 6,6,6-trifluorohexyl, etc.), a lower alkoxy group (e.g., a C$_{1-6}$ alkoxy group such as methoxy, ethoxy, propoxy, isopropoxy, butoxy, isobutoxy, pentyloxy, hexyloxy, etc.), an amino group, a mono-lower alkylamino group (e.g., a mono-C$_{1-6}$ alkylamino group such as methylamino, ethylamino, etc.), a di-lower alkylamino group (e.g., a di-C$_{1-6}$ lower alkylamino group such as dimethylamino, diethylamino, etc.), a carboxyl group, a lower alkylcarbonyl group (e.g., a C$_{1-6}$ alkyl-carbonyl group such as acetyl, propionyl, etc.), a lower alkoxycarbonyl group (e.g., a C$_{1-6}$ alkoxy-carbonyl group such as methoxycarbonyl, ethoxycarbonyl, propoxycarbonyl, butoxycarbonyl, etc.), a carbamoyl group, a mono-lower alkylcarbamoyl group (e.g., a mono-C$_{1-6}$ alkyl-carbamoyl group such as methylcarbamoyl, ethylcarbamoyl, etc.), a di-lower alkylcarbamoyl group (e.g., a di-C$_{1-6}$ alkyl-carbamoyl group such as dimethylcarbamoyl, diethylcarbamoyl, etc.), an arylcarbamoyl group (e.g., a C$_{6-10}$ aryl-carbamoyl group such as phenylcarbamoyl, naphthylcarbamoyl, etc.), an aryl group (e.g., a C$_{6-10}$ aryl group such as phenyl, naphthyl, etc.), an aryloxy group (e.g., a C$_{6-10}$ aryloxy group such as phenyloxy, naphthyloxy, etc.), an optionally halogenated lower alkylcarbonylamino group (e.g., an optionally halogenated C$_{1-6}$ alkylcarbonylamino group such as acetylamino, trifluoroacetylamino, etc.), an oxo group, etc. The "hydrocarbon group" of the "optionally substituted hydrocarbon group" may have 1 to 5, preferably 1 to 3 substituents selected from those mentioned above, at any substitutable positions in the group. When the number of the substituents is two or more, each of the substituents may be the same or different.

The "heterocyclic group" in "optionally substituted heterocyclic group" as referred to herein includes, for example, a 5- to 14-membered (preferably, 5- to 10-membered), mono- to tri-cyclic (preferably mono- or di-cyclic) heterocyclic group, each having 1 or 2 kinds, 1 to 4 (preferably 1 to 3) hetero atoms selected from nitrogen, oxygen and sulfur, in addition to carbon atoms. Concretely, it includes, for example, a 5-membered heterocyclic group having 1 to 4 hetero atoms selected from oxygen, sulfur and nitrogen, in addition to carbon atoms, such as 2- or 3-thienyl, 2-or 3-furyl, 1-, 2- or 3-pyrrolyl, 1-, 2- or 3-pyrrolidinyl, 2-, 4- or 5-oxazolyl, 3-, 4- or 5-isoxazolyl, 2-, 4- or 5-thiazolyl, 3-, 4- or 5-isothiazolyl, 3-, 4- or 5-pyrazolyl, 2-, 3- or 4-pyrazolidinyl, 2-, 4-, or 5-imidazolyl, 1,2,3-triazolyl, 1,2,4-triazolyl, 1H- or 2H-tetrazolyl; a 6-membered heterocyclic group having 1 to 4 hetero atoms selected from oxygen, sulfur and nitrogen atoms, in addition to carbon atoms, such as 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl, piperidino, 2-, 3- or 4-piperidyl, thiopyranyl, 1,4-oxazinyl, 1,4-thiazinyl, 1,3-thiazinyl, piperazinyl, triazinyl, 3- or 4-pyridazinyl, pyrazinyl, N-oxido-3- or 4-pyridazinyl; a di- or tricyclic condensed heterocyclic group having 1 to 4 hetero atoms selected from oxygen, sulfur and nitrogen atoms, in addition to carbon atoms (preferably, a group to be formed by condensing the above-mentioned 5- or 6-membered cyclic group with one or two 5- or 6-membered cyclic groups each optionally having 1 to 4 hetero atoms selected from oxygen, sulfur and nitrogen atoms, in addition to carbon atoms), such as indolyl, benzofuryl, benzothiazolyl, benzoxazolyl, benzimidazolyl, quinolyl, isoquinolyl, phthalazinyl, quinazolinyl, quinoxalinyl, indolidinyl, quinolidinyl, 1,8-naphthyridinyl, dibenzofuranyl, carbazolyl, acridinyl, phenanthridinyl, chromanyl, phenothiazinyl, phenoxazinyl, etc. Of these, preferred are 5- to 7-membered (preferably, 5- or 6-membered) heterocyclic groups each having 1 to 3 hetero atoms selected from oxygen, sulfur and nitrogen atoms, in addition to carbon atoms.

The substituents for the "heterocyclic group" of the "optionally substituted heterocyclic group" include, for example, a halogen atom (e.g., fluorine, chlorine, bromine, iodine, etc.), a lower alkyl group (e.g., a $C_{1-6}$ alkyl group such as methyl, ethyl, propyl, isopropyl, butyl, isobutyl, sec-butyl, tert-butyl, pentyl, hexyl, etc.), a cycloalkyl group (e.g., a $C_{3-6}$ cycloalkyl group such as cyclopropyl, cyclobutyl, cyclopentyl, cyclohexyl, etc.), a lower alkynyl group (e.g., a $C_{2-6}$ alkynyl group such as ethynyl, 1-propynyl, propargyl, etc.), a lower alkenyl group (e.g., a $C_{2-6}$ alkenyl group such as vinyl, allyl, isopropenyl, butenyl, isobutenyl, etc.), an aralkyl group (e.g., a $C_{7-11}$ aralkyl group such as benzyl, α-methylbenzyl, phenethyl, etc.), an aryl group (e.g., a $C_{6-10}$ aryl group such as phenyl, naphthyl, etc., preferably phenyl), a lower alkoxy group (e.g., a $C_{1-6}$ alkoxy group such as methoxy, ethoxy, propoxy, isopropoxy, butoxy, isobutoxy, sec-butoxy, tert-butoxy, etc.), an aryloxy group (e.g., a $C_{6-10}$ aryloxy group such as phenoxy, etc.), a lower alkanoyl group (e.g., formyl, a $C_{1-6}$ alkyl-carbonyl group such as acetyl, propionyl, butyryl, isobutyryl, etc.), an arylcarbonyl group (e.g., a $C_{6-10}$ aryl-carbonyl group such as benzoyl, naphthoyl, etc.), a lower alkanoyloxy group (e.g., formyloxy, a $C_{1-6}$ alkyl-carbonyloxy group such as acetyloxy, propionyloxy, butyryloxy, isobutyryloxy, etc.), an arylcarbonyloxy group (e.g., a $C_{6-10}$ arylcarbonyloxy group such as benzoyloxy, naphthoyloxy, etc.), a carboxyl group, a lower alkoxycarbonyl group (e.g., a $C_{1-6}$ alkoxy-carbonyl group such as methoxycarbonyl, ethoxycarbonyl, propoxycarbonyl, isopropoxycarbonyl, butoxycarbonyl, isobutoxycarbonyl, tert-butoxycarbonyl, etc.), an aralkyloxycarbonyl group (e.g., a $C_{7-11}$ aralkyloxycarbonyl group such as benzyloxycarbonyl, etc.), a carbamoyl group, a mono-, di- or tri-halogeno-lower alkyl group (e.g., a mono-, di- or tri-halogeno-$C_{1-4}$ alkyl group such as chloromethyl, dichloromethyl, trifluoromethyl, 2,2,2-trifluoroethyl, etc.), an oxo group, an amidino group, an imino group, an amino group, a mono-lower alkylamino group (e.g., a mono-$C_{1-4}$ alkylamino group, such as methylamino, ethylamino, propylamino, isopropylamino, butylamino, etc.), a di-lower alkylamino group (e.g., a di-$C_{1-4}$ alkylamino group such as dimethylamino, diethylamino, dipropylamino, diisopropylamino, dibutylamino, methylethylamino, etc.), a 3- to 6-membered cyclic amino group optionally having 1 to 3 hetero atoms selected from oxygen, sulfur and nitrogen atoms, in addition to carbon atoms and one nitrogen atom (e.g., a 3- to 6-membered cyclic amino group such as aziridinyl, azetidinyl, pyrrolidinyl, pyrrolinyl, pyrrolyl, imidazolyl, pyrazolyl, imidazolidinyl, piperidyl, morpholinyl, dihydropyridyl, pyridyl, N-methylpiperazinyl, N-ethylpiperazinyl, etc.), an alkylenedioxy group (e.g., a $C_{1-3}$ alkylenedioxy group such as methylenedioxy, ethylenedioxy, etc.), a hydroxy group, a nitro group, a cyano group, a mercapto group, a sulfo group, a sulfino group, a phosphono group, a sulfamoyl group, a monoalkylsulfamoyl group (e.g., a mono-$C_{1-6}$ alkylsulfamoyl group such as N-methylsulfamoyl, N-ethylsulfamoyl, N-propylsulfamoyl, N-isopropylsulfamoyl, N-butylsulfamoyl, etc.), a dialkylsulfamoyl group (e.g., a di-$C_{1-6}$ alkylsulfamoyl group such as N,N-dimethylsulfamoyl, N,N-diethylsulfamoyl, N,N-dipropylsulfamoyl, N,N-dibutylsulfamoyl, etc.), an alkylthio group (e.g., $C_{1-6}$ alkylthio group such as methylthio, ethylthio, propylthio, isopropylthio, butylthio, sec-butylthio, tert-butylthio, etc.), an arylthio group (e.g., a $C_{6-10}$ arylthio group such as phenylthio, naphthylthio, etc.), a lower alkylsulfinyl group (e.g., a $C_{1-6}$ alkylsulfinyl group such as methylsulfinyl, ethylsulfinyl, propylsulfinyl, butylsulfinyl, etc.), an arylsulfinyl group (e.g., a $C_{6-10}$ arylsulfinyl group such as phenylsulfinyl, naphthylsulfinyl, etc.), a lower alkylsulfonyl group (e.g., a $C_{1-6}$ alkylsulfonyl group such as methylsulfonyl, ethylsulfonyl, propylsulfonyl, butylsulfonyl, etc.), an arylsulfonyl group (e.g., a $C_{6-10}$ arylsulfonyl group such as phenylsulfonyl, naphthylsulfonyl, etc.), etc.

The "heterocyclic group" of the "optionally substituted heterocyclic group" may have 1 to 5, preferably 1 to 3 substituents selected from those mentioned above, at any substitutable positions in the group. In the case that the group has two or more substituents, these substituents may be the same or different.

The "optionally substituted amino group" as referred to herein includes amino groups each optionally having one or two substituents of, for example, the above-mentioned "optionally substituted hydrocarbon groups". Preferred substituents for the above "amino group" include, for example, an optionally substituted $C_{1-6}$ alkyl group and an optionally substituted $C_{6-10}$ aryl group. The substituents which the "$C_{1-6}$ alkyl group" or the "$C_{6-10}$ aryl group" may optionally have are, for example, the same ones as the above-mentioned "hydrocarbon group" may optionally have.

The "lower alkyl group" for "optionally substituted lower alkyl group" as referred to herein includes, for example, a $C_{1-6}$ alkyl group such as methyl, ethyl, propyl, isopropyl, butyl, isobutyl, sec-butyl and tert-butyl. The lower alkyl group may optionally have 1 to 3 substituents, such as the same ones as the above-mentioned "hydrocarbon group" may optionally have.

The "lower alkoxy group" in "optionally substituted lower alkoxy group" as referred to herein includes, for example, a $C_{1-6}$ alkoxy group such as methoxy, ethoxy, propoxy, isopropoxy, butoxy, isobutoxy, sec-butoxy and tert-butoxy. The lower alkoxy group may optionally have 1 to 3 substituents, such as the same ones as the above-mentioned "hydrocarbon group" may optionally have.

The "optionally substituted benzene ring" as referred to herein includes, for example, a benzene ring which may optionally have one or two substituents selected from, a halogen atom (e.g., fluorine, chlorine, bromine, iodine, etc.), an optionally substituted hydrocarbon group, an optionally substituted amino group, an amido group (e.g., a $C_{1-3}$ acylamino group such as formamido, acetamido, etc.), an optionally substituted lower alkoxy group and a lower alkylenedioxy group (e.g., a $C_{1-3}$ alkylenedioxy group such as methylenedioxy, ethylenedioxy, etc.), at any substitutable positions in the ring.

For these "optionally substituted hydrocarbon group", "optionally substituted amino group" and "optionally substituted lower alkoxy group", the same ones as those described in detail hereinabove are referred to. In the case that these "hydrocarbon group", "amino group" and "lower alkoxy group" each have two or more substituents, these substituents may be the same or different.

The "optionally substituted benzene ring" is preferably a benzene ring optionally substituted by 1 or 2 substituents selected from a halogen atom (e.g., fluorine, chlorine, etc.), a $C_{1-6}$ alkyl group (e.g., methyl, ethyl, etc.) and a mono-$C_{1-6}$ alkylamino group.

In the above-mentioned formulae, $R^1$ represents an optionally substituted hydrocarbon group, an optionally substituted amino group or an optionally substituted heterocyclic group.

The "hydrocarbon group" of the "optionally substituted hydrocarbon group" represented by $R^1$ is preferably, for example, an alkyl group (e.g., a $C_{1-6}$ alkyl group such as methyl, ethyl, propyl, isopropyl, etc.), an alkenyl group (e.g., $C_{2-6}$ alkenyl group such as vinyl, etc.), an alkynyl group (e.g., a $C_{2-6}$ alkynyl group such as ethynyl), a cycloalkyl group (e.g., a $C_{3-6}$ cycloalkyl group such as cyclopropyl, cyclobutyl, cyclopentyl, cyclohexyl, etc.), or an aryl group (e.g., a $C_{6-14}$ aryl group such as phenyl, etc.), especially preferably an alkyl group (e.g., a $C_{1-6}$ alkyl group such as methyl, etc.) or a cycloalkyl group (e.g., a $C_{3-6}$ cycloalkyl group such as cyclopropyl, etc.). These "alkyl group", "alkenyl group", "alkynyl group", "cycloalkyl group" and "aryl group" each may have 1 to 5, preferably 1 to 3 substituents, such as the same ones as the above-mentioned "hydrocarbon group" may optionally have, preferably halogen atoms such as fluorines.

Preferred substituents for the "optionally substituted amino group" represented by $R^1$, are one or two substituents selected from, for example, an optionally substituted lower alkyl group and an optionally substituted aryl group, more preferably one substituent of an optionally substituted lower alkyl group. The "lower alkyl group" includes, for example, a $C_{1-6}$ alkyl group such as methyl, ethyl, propyl, isopropyl, butyl, isobutyl, sec-butyl and tert-butyl. The "lower alkyl group" may optionally have 1 to 3 substituents, such as the same ones as the above-mentioned "hydrocarbon group" may optionally have. The "aryl group" includes, for example, a $C_{6-10}$ aryl group such as phenyl, etc. The "aryl group" may optionally have 1 to 5, preferably 1 to 3 substituents, such as the same ones as the above-mentioned "hydrocarbon group" may optionally have, preferably those selected from, for example, a halogen atom such as fluorine and chlorine and a $C_{1-6}$ alkoxy group such as methoxy and ethoxy. The "optionally substituted amino group" includes, for example, a phenylamino group substituted by, 1 to 3 lower alkoxy groups (e.g., $C_{1-4}$ alkoxy groups such as methoxy, etc.) or a monoalkylamino group substituted by one lower alkyl group (e.g., a $C_{1-4}$ alkyl group such as methyl, ethyl, propyl, butyl, tert-butyl, etc.)

The "heterocyclic group" of the "optionally substituted heterocyclic group" represented by $R^1$ is, for example, preferably a 5- or 6-membered heterocyclic group having 1 to 3 hetero atoms selected from nitrogen, oxygen and sulfur atoms in addition to carbon atoms. Concretely, it includes, for example, 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2- or 3-thienyl, 2-, 3- or 4-pyridyl, 2- or 3-furyl, pyrazinyl, 2-pyrimidinyl, 3-pyrrolyl, 3-pyridazinyl, 3-isothiazolyl and 3-isoxazolyl. Especially preferably, it is a 6-membered nitrogen-containing heterocyclic group (e.g., pyridyl, etc.).

Preferred substituents for the "optionally substituted heterocyclic group" represented by $R^1$ include, for example, a halogen atom (e.g., chlorine, fluorine, etc.), a $C_{1-6}$ alkyl group (e.g., methyl, ethyl, etc.), a $C_{1-6}$ alkoxy group (e.g., methoxy, ethoxy, etc.) and an aralkyloxycarbonyl group (e.g., a $C_{7-12}$ aralkyloxy-carbonyl group such as benzyloxycarbonyl, etc.).

$R^1$ is, for example, preferably (i) an optionally substituted lower alkyl group, (ii) an optionally substituted lower cycloalkyl group, (iii) an optionally substituted lower alkenyl group, (iv) an optionally substituted aryl group, (v) an optionally substituted mono- or di-lower alkylamino group, (vi) an optionally substituted arylamino group or (vii) an optionally substituted 5- or 6-membered nitrogen-containing heterocyclic group.

The "lower alkyl group" is preferably a $C_{1-6}$ alkyl group such as methyl, ethyl, propyl, isopropyl, butyl, pentyl and hexyl. The "lower cycloalkyl group" is preferably a $C_{3-6}$ cycloalkyl group such as cyclopropyl, cyclobutyl, cyclopentyl and cyclohexyl. The "lower alkenyl group" is preferably a $C_{2-6}$ alkenyl group such as vinyl, 1-propenyl and butenyl. The "aryl group" is preferably a $C_{6-10}$ aryl group such as phenyl, 1-naphthyl and 2-naphthyl. The "lower alkylamino group" is preferably a mono- or di-$C_{1-6}$ alkylamino group such as methylamino, ethylamino, propylamino, isopropylamino, butylamino, tert-butylamino, dimethylamino, diethylamino and methylethylamino. The "arylamino group" is preferably a $C_{6-10}$ arylamino group such as phenylamino. The "5- or 6-membered nitrogen-containing heterocyclic group" is, for example, preferably 2-, 3- or 4-pyridyl or the like. These groups may each optionally have 1 to 5 substituents such as those referred to the mentioned-above "hydrocarbon group" may optionally have.

More preferably, $R^1$ is (i) a $C_{1-6}$ alkyl group optionally substituted by 1 to 4 substituents selected from a halogen atom and a $C_{1-6}$ alkoxy group, (ii) a $C_{3-6}$ cycloalkyl group, (iii) a $C_{2-6}$ alkenyl group, (iv) a $C_{6-10}$ aryl group optionally substituted by 1 to 4 substituents selected from a $C_{1-6}$ alkoxy group, a nitro group, a halogeno-$C_{1-6}$ alkyl-carbonylamino group and a halogen atom, (v) a mono- or di-$C_{1-6}$ alkylamino group, (vi) a $C_{6-10}$ arylamino group optionally substituted by one to three $C_{1-6}$ alkoxy groups, or (vii) a 6-membered nitrogen-containing heterocyclic group optionally substituted by one or two $C_{7-11}$ aralkyloxycarbonyl groups. Even more preferably, $R^1$ is an optionally halogenated $C_{1-6}$ alkyl group (e.g., methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5, 5-trifluoropentyl, hexyl, 6,6,6-trifluorohexyl, etc.), a $C_{3-6}$ cycloalkyl group (e.g., cyclopropyl, cyclobutyl, cyclopentyl, cyclohexyl, etc.) or a mono-$C_{1-6}$ alkylamino group (e.g., methylamino, ethylamino, propylamino, isopropylamino, butylamino, tert-butylamino, etc.) Among ohters, $R^1$ is preferably an optionally halogenated $C_{1-6}$ alkyl group or a mono-$C_{1-6}$ alkylamino group, especially an optionally halogenated $C_{1-6}$ alkyl, in particular $C_{1-3}$ alkyl group (e.g., methyl, ethyl, propyl, etc.).

In the above-mentioned formulae, $R^2$ represents a hydrogen atom or an optionally substituted hydrocarbon group.

$R^2$ is preferably a hydrogen atom or an optionally substituted lower ($C_{1-6}$) alkyl group, more preferably a hydrogen atom or a lower ($C_{1-6}$) alkyl group, even more preferably a hydrogen atom.

In the above-mentioned formulae, $R^3$ represents a hydrogen atom, an optionally substituted hydrocarbon group or optionally substituted heterocyclic group.

The "hydrocarbon group" of the "optionally substituted hydrocarbon group" represented by $R^3$ is preferably, for example, an alkyl group (e.g., a $C_{1-6}$ alkyl group such as methyl, ethyl, propyl, isopropyl, etc.), an alkenyl group (e.g., a $C_{2-6}$ alkenyl group such as vinyl, etc.), an alkynyl group (e.g., a $C_{2-6}$ alkynyl group such as ethynyl, etc.), a cycloalkyl group (e.g., a $C_{3-6}$ cycloalkyl group such as cyclopropyl, cyclobutyl, cyclopentyl, cyclohexyl, etc.) or an aryl group (e.g., a $C_{6-14}$ aryl group such as phenyl, etc.). It is more preferably an alkyl group (e.g., a $C_{1-6}$ alkyl group such as methyl, etc.) or an aryl group (e.g., a $C_{6-14}$ aryl groups such as phenyl, etc.). These "alkyl group", "alkenyl group", "alkynyl group", "cycloalkyl group" and "aryl group" each may optionally have 1 to 5, preferably 1 to 3 substituents such as the same ones the mentioned-above "hydrocarbon group" may optionally have (e.g., halogen atoms such as fluorines, etc.).

The "heterocyclic group" of the "optionally substituted heterocyclic group" represented by $R^3$ is preferably a 5- or 6-membered heterocyclic group having 1 to 3 hetero atoms selected from nitrogen, oxygen and sulfur atoms, in addition to carbon atoms. Concretely, it includes, for example, 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2- or 3-thienyl, 2-, 3- or 4-pyridyl, 2- or 3-furyl, pyrazinyl, 2-pyrimidinyl, 3-pyrrolyl, 3-pyridazinyl, 3-isothiazolyl, 3-isoxazolyl, etc. More preferred is a 6-membered nitrogen-containing heterocyclic group (e.g., pyridyl, etc.).

Preferred substituents for the "optionally substituted heterocyclic group" represented by $R^3$ include, for example, a halogen atom (e.g., chlorine, fluorine, etc.), a $C_{1-6}$ alkyl group (e.g., methyl, ethyl, etc.), a $C_{1-6}$ alkoxy group (e.g., methoxy, ethoxy, etc.), an aralkyloxycarbonyl group (e.g., a $C_{7-12}$ aralkyloxy-carbonyl group such as benzyloxycarbonyl, etc.), an amino group, a mono-$C_{1-6}$ alkylamino group (e.g., methylamino, ethylamino, etc.) a di-$C_{1-6}$ alkylamino group (e.g., dimethylamino, diethylamino, etc.) etc.

$R^3$ is, for example, preferably (i) a hydrogen atom, (ii) an optionally substituted lower alkyl group, (iii) an optionally substituted aryl group, (iv) an optionally substituted 5- or 6-membered heterocyclic group, etc., more preferably, for example, (i) a hydrogen atom, (ii) a lower alkyl group, (iii) an optionally substituted $C_{6-10}$ aryl group, (iv) an optionally substituted 6-membered nitrogen-containing heterocyclic group.

The above substituents include, for example, a hydrogen atom, a $C_{1-6}$ alkyl group, a $C_{1-6}$ alkoxy group, an amino group, a mono-$C_{1-6}$ alkylamino group, a di-$C_{1-6}$ alkylamino group, etc.

More preferably, $R^3$ is, for example, a hydrogen atom, a phenyl group and a 2-, 3- or 4-pyridyl group, especially preferably is a hydrogen atom.

In the above-mentioned formulae, X represents $CHR^4$, $NR^4$, O or S in which $R^4$ represents a hydrogen atom or an optionally substituted hydrocarbon group.

$X^a$ represents $CHR^{4a}$, $NR^{4a}$, O or S in which $R^{4a}$ represents a hydrogen atom or an optionally substituted hydrocarbon group.

$R^4$ and $R^{4a}$ are preferably a hydrogen atom or an optionally substituted lower ($C_{1-6}$) alkyl group, respectively. More preferred is a hydrogen atom.

X is preferably $CHR^4$ in which $R^4$ is as defined above, O or S. Or, X is preferably $CHR^4$ or $NR^4$ in which $R^4$ is as defined above.

$X^a$ is preferably $CHR^{4a}$ or $NR^{4a}$ in which $R^{4a}$ is as defined above.

In the above formulae, Y represents C, CH or N. Y is preferably C or CH.

$Y^a$ represents C, CH or N. $Y^a$ is preferably C or CH.

In the above-mentioned formulae, ring A or ring A' represents an optionally substituted, 5- to 7-membered oxygen-containing heterocyclic ring.

The "5- to 7-membered oxygen-containing heterocyclic ring" includes 5- to 7-membered (preferably 5- or 6-membered) heterocyclic rings optionally having 1 or 2 kinds, 1 to 3 hetero atoms selected from nitrogen, oxygen and sulfur atoms, in addition to carbon atoms and an oxygen atom.

The above-mentioned heterocyclic ring is preferably a ring represented by the formula:

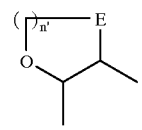

wherein E represents (i) $CH_2CH_2$, (ii) $CH=CH$, (iii) $CH_2O$, (iv) $OCH_2$, (v) $CH_2S(O)_{q'}$, wherein q' represents an integer of 0 to 2, (vi) $S(O)_{q'}CH_2$ wherein q' is as defined above, (vii) $CH_2NH$, (viii) $NHCH_2$, (ix) $N=N$, (x) $CH=N$, (xi) $N=CH$ or (xii) $CONH$; and n' represents an integer of 0 to 2.

E is preferably (i) $CH_2CH_2$, (ii) $CH=CH$, (iii) $CH_2O$, (iv) $OCH_2$, (v) $CH_2NH$, (vi) $NHCH_2$, (vii) $N=N$, (viii) $CH=N$ or (ix) $N=CH$, especially preferably (i) $CH_2CH_2$ or (ii) $CH=CH$.

Concretely, the above ring includes, for example, a 5-membered oxygen-containing heterocyclic ring such as 2,3-dihydrofuran, furan, 1,3-dioxole, oxazoline, isoxazole, 1,2,3-oxadiazole and oxazole and a 6-membered oxygen-containing heterocyclic ring such as 2H-3,4-dihydropyran, 2H-pyran, 2,3-dehydro-1,4-dioxane and 2,3-dehydromorpholine.

More preferably, the above ring is a ring represented by the formula:

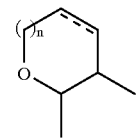

wherein n is as defined above.

Concretely, 2,3-dihydrofuran, furan, 2H-3,4-dihydropyran and 2H-pyran are preferred.

Substituents which ring A or ring A' may optionally have, include, for example, a halogen atom (e.g., fluorine, chlorine, bromine, iodine, etc.), an optionally. substituted lower alkyl (e.g., $C_{1-6}$ alkyl) group, an optionally substituted cycloalkyl (e.g., $C_{3-6}$ cycloalkyl) group, an optionally substituted lower alkynyl (e.g., $C_{2-6}$ alkynyl) group, an optionally substituted lower alkenyl (e.g., $C_{2-6}$ alkenyl) group, an optionally substituted aryl (e.g., $C_{6-10}$ aryl) group, a lower alkoxy group (e.g., a $C_{1-6}$ alkoxy group such as methoxy, ethoxy, propoxy, isopropoxy, butoxy, isobutoxy, sec-butoxy, tert-butoxy, etc.), an aryloxy group (e.g., a $C_{6-10}$ aryloxy group such as phenoxy, etc.), a lower alkanoyl group (e.g., formyl, a $C_{1-6}$ alkyl-carbonyl group such as acetyl, propionyl, butyryl, isobutyryl, etc.), an arylcarbonyl group (e.g., a $C_{6-10}$ aryl-carbonyl group such as benzoyl, naphthoyl, etc.), a lower alkanoyloxy group (e.g., formyloxy, a $C_{1-6}$ alkyl-carbonyloxy group such as acetyloxy, propionyloxy, butyryloxy, isobutyryloxy, etc.), an arylcarbonyloxy group (e.g., a $C_{6-10}$ arylcarbonyloxy group such as benzoyloxy, naphthoyloxy, etc.), a carboxyl group, a lower alkoxycarbonyl group (e.g., a $C_{1-6}$ alkoxy-carbonyl group such as methoxycarbonyl, ethoxycarbonyl, propoxycarbonyl, isopropoxycarbonyl, butoxycarbonyl, isobutoxycarbonyl, tert-butoxycarbonyl, etc.), an aralkyloxy group (e.g., a $C_{7-11}$ aralkyloxy-carbonyl group such as benzyloxycarbonyl, etc.), a carbamoyl group, a mono-, di- or tri-halogeno-lower alkyl group (e.g., a mono-, di- or tri-halogeno-$C_{1-4}$ alkyl group such as chloromethyl, dichloromethyl, trifluoromethyl, 2,2,2-trifluoroethyl, etc.), an oxo group, an amidino group, an imino group, an amino group, a mono-lower alkylamino group (e.g., a mono-$C_{1-4}$ alkylamino group such as methylamino, ethylamino, propylamino, isopropylamino, butylamino, etc.), a di-lower alkylamino group (e.g., a di-$C_{1-4}$ alkylamino group such as dimethylamino, diethylamino, dipropylamino, diisopropylamino, dibutylamino, methylethylamino, etc.), a 3- to 6-membered cyclic amino group optionally having 1 to 3 hetero atoms selected from, for example, oxygen, sulfur and nitrogen atoms, in addition to carbon atoms and one nitrogen atom (e.g., a 3- to 6-membered cyclic amino group such as aziridinyl, azetidinyl, pyrrolidinyl, pyrrolinyl, pyrrolyl, imidazolyl, pyrazolyl, imidazolidinyl, piperidyl, morpholinyl, dihydropyridyl, pyridyl, N-methylpiperazinyl, N-ethylpiperazinyl, etc.), an alkylenedioxy group (e.g., a $C_{1-3}$ alkylenedioxy group such as methylenedioxy, ethylenedioxy, etc.), a hydroxyl group, a nitro group, a cyano group, a mercapto group, a sulfo group, a sulfino group, a phosphono group, a sulfamoyl group, a monoalkylsulfamoyl group (e.g., a mono-$C_{1-6}$ alkylsulfamoyl group such as N-methylsulfamoyl, N-ethylsulfamoyl, N-propylsulfamoyl, N-isopropylsulfamoyl, N-butylsulfamoyl, etc.), a dialkylsulfamoyl group (e.g., a di-$C_{1-6}$ alkylsulfamoyl group such as N,N-dimethylsulfamoyl, N,N-diethylsulfamoyl, N,N-dipropylsulfamoyl, N,N-dibutylsulfamoyl, etc.), an alkylthio group (e.g., a $C_{1-6}$ alkylthio group such as methylthio, ethylthio, propylthio, isopropylthio, butylthio, sec-butylthio, tert-butylthio, etc.), an arylthio group (e.g., a $C_{6-10}$ arylthio group such as phenylthio, naphthylthio, etc.), a lower alkylsulfinyl group (e.g., a $C_{1-6}$ alkylsulfinyl group such as methylsulfinyl, ethylsulfinyl, propylsulfinyl, butylsulfinyl, etc.), an arylsulfinyl group (e.g., a $C_{6-10}$ arylsulfinyl group such as phenylsulfinyl, naphthylsulfinyl, etc.), a lower alkylsulfonyl group (e.g., a $C_{1-6}$ alkylsulfonyl group such as methylsulfonyl, ethylsulfonyl, propylsulfonyl, butylsulfonyl, etc.), an arylsulfonyl group (e.g., a $C_{6-10}$ arylsulfonyl group such as phenylsulfonyl, naphthylsulfonyl, etc.), etc.

The above "lower alkyl group", "lower alkenyl group", "lower alkynyl group", "lower cycloalkyl group" and "aryl group" each may optionally have the same ones as the above-mentioned 1 to 5, preferably 1 to 3 substituents such as those "hydrocarbon group" may optionally have.

Preferred substituents which ring A or ring A' may optionally have, include, for example, a halogen atom, an optionally substituted $C_{1-6}$ alkyl group, an optionally substituted $C_{1-6}$ alkoxy group, a hydroxyl group, a nitro group, a cyano group, an optionally substituted amino group and an oxo group. For the substituents in these "optionally substituted $C_{1-6}$ alkyl group", "optionally substituted $C_{1-6}$ alkoxy group" and "optionally substituted amino group", for example, referred to are the substituents which mentioned-above "hydrocarbon group" may optionally have.

Ring A and ring A' may have 1 to 4, preferably one or two substituents selected from those mentioned above at any substitutable positions, depending on the number of the carbon atoms constituting them. When the ring has two or more substituents, these substituents may be the same or different.

Ring A and ring A' are, for example;

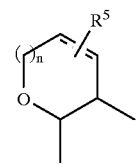

wherein n is as defined above; and $R^5$ represents a hydrogen atom or 1 or 2 substituents selected from the "preferred substituents for ring A or ring A'" mentioned hereinabove. $R^5$ is preferably a hydrogen atom and 1 or 2 optionally substituted lower ($C_{1-6}$) alkyl, more preferably, a hydrogen atom, which indicates unsubstituted ring A and unsubstituted ring A'.

In the above-mentioned formulae, ring B represents an optionally substituted benzene ring.

The substituents which ring B may optionally have, include, for example, the "substituents" mentioned hereinabove for the "optionally substituted benzene ring". Among others, the substituents on ring B are preferably a halogen atom and an optionally substituted lower ($C_{1-6}$) alkyl group, more preferably a halogen atom and a lower ($C_{1-6}$) alkyl group (especially, methyl). As for the substituents for the "optionally substituted lower ($C_{1-6}$) alkyl group", for example, referred to are the same ones as the mentioned-above "hydrocarbon group" may optionally have.

Ring B may have one or two, preferably one substituent selected from those mentioned hereinabove, at any substitutable position. When ring B has two substituents, they may be the same or different.

For example, ring B is preferably

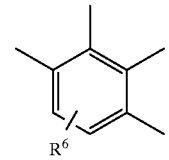

wherein $R^6$ represents a hydrogen atom, a halogen atom, an optionally substituted lower ($C_{1-6}$) alkyl group or an optionally substituted lower ($C_{1-6}$) alkoxy group. $R^6$ is preferably a hydrogen atom, a halogen atom or a lower ($C_{1-6}$) alkyl group (especially, methyl). More preferred, $R^6$ is a hydrogen atom.

In the above-mentioned formulae, m represents an integer of 1 to 4. Preferably, m is an integer of 1 to 3. More preferred is 2 or 3. Especially 2 is preferable.

In the above-mentioned formulae, n represents an integer of 0 to 2. Preferably, n is an integer of 0 or 1. Especially 0 is preferable.

Examples of

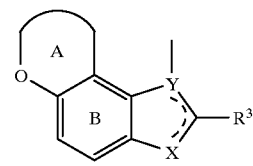

are

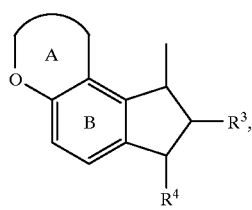 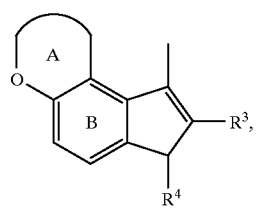

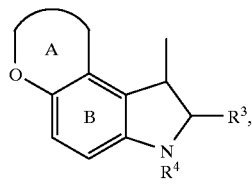 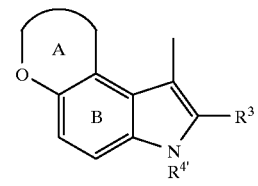

wherein R$^{4'}$ represents an optionally substituted hydrocarbon group and the other symbols are as defined above.

R$^{4'}$ is preferably an optionally substituted lower (C$_{1-3}$) alkyl group.

Preferred examples of

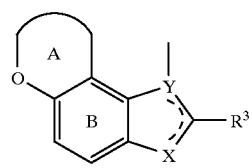

are

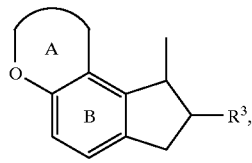 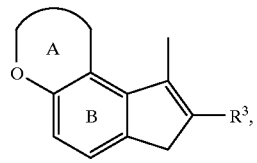

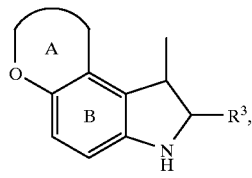 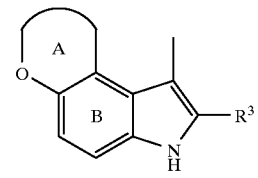

wherein are symbols are as defined above. Among them, preferred are

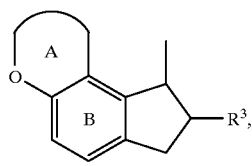

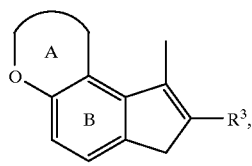

-continued

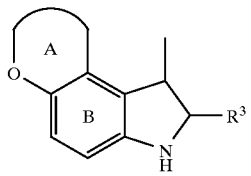

wherein the symbols are as defined above.

Further preferred are (i)

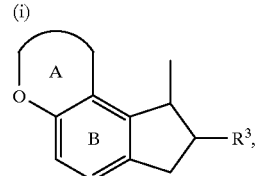 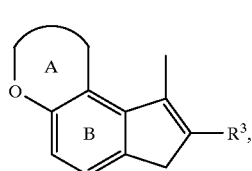

(ii)

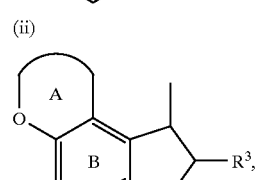 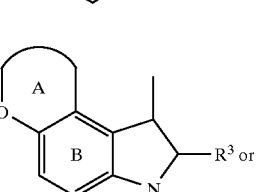

(iii)

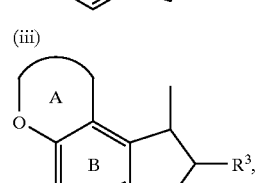 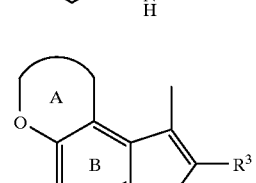

wherein the symbols are as defined above.

More preferred are

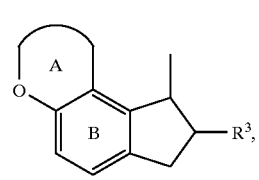 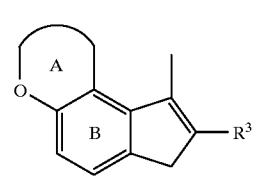

wherein the symbols are as defined above. Especially preferred is

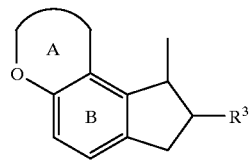

wherein the symbols are as defined above.

Preferred examples of

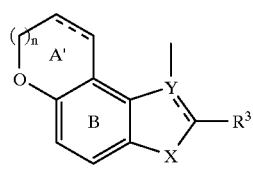

are

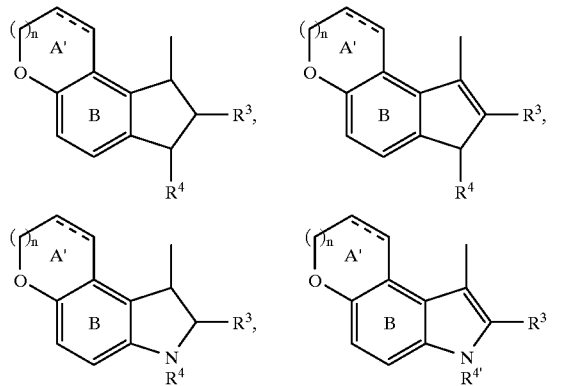

wherein the symbols are as defined above.

Especially preferred examples of

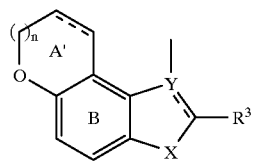

are

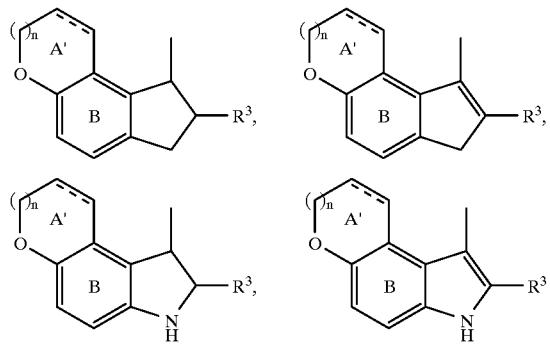

wherein the symbols are as defined above.

Preferred among them are

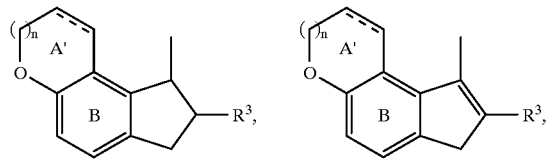

-continued

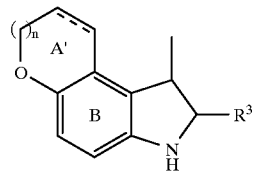

wherein the symbols are as defined above.

Further preferred are (i)

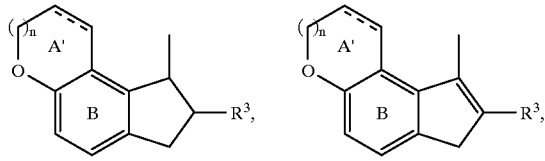

(ii)

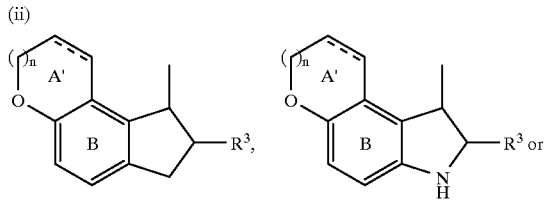

(iii)

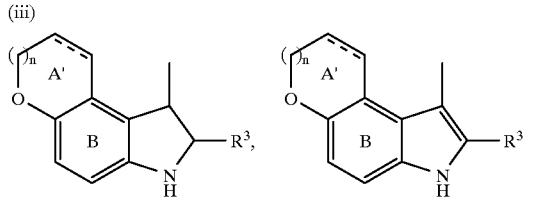

wherein the symbols are as defined above.

Among them, more preferred are

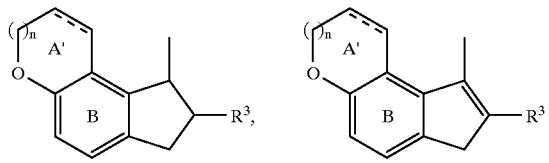

wherein the symbols are as defined above.

Among them, more preferred are also

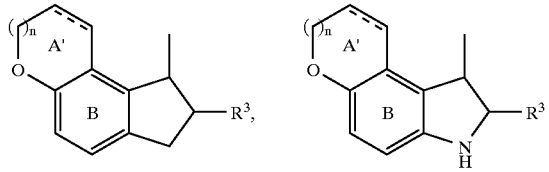

wherein the symbols are as defined above.

Especially preferred is

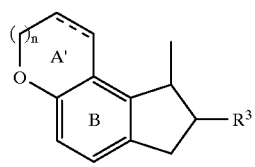

wherein the symbols are as defined above.

Example of the compound (I) of the present invention include compounds having the following structural formulae.

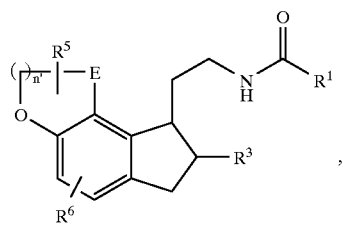

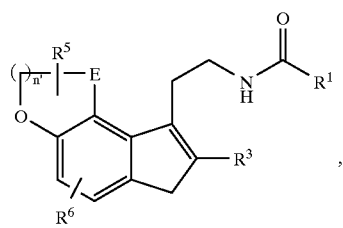

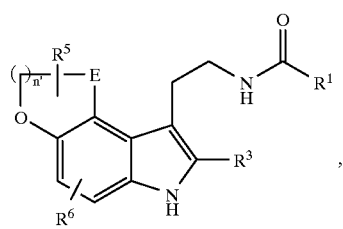

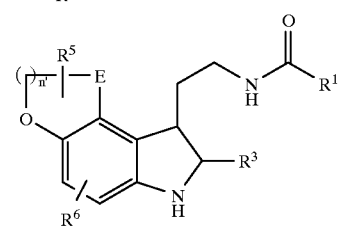

wherein the symbols are as defined above.

Preferred examples of the compound (I) include, for example, compounds of the following formulae:

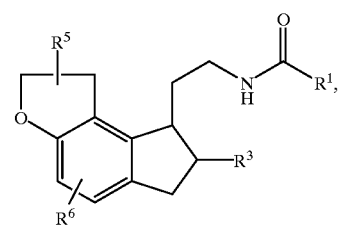

-continued

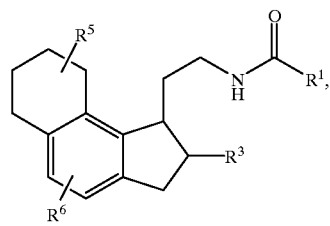

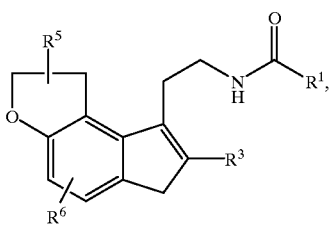

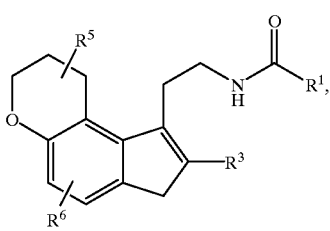

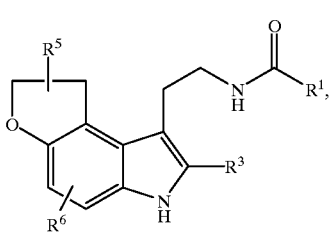

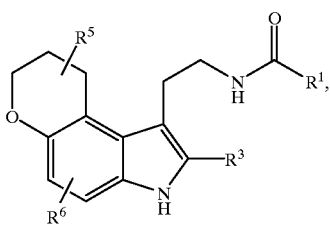

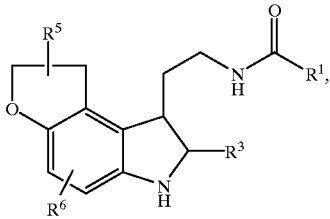

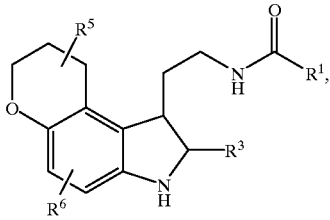

wherein the symbols are as defined above.

Also preferred examples of the compound (I) are the compound of the formula (I) wherein;

R¹ is (i) an optionally substituted lower alkyl group, (ii) an optionally substituted lower cycloalkyl group, (iii) an optionally substituted lower alkenyl group, (iv) an optionally substituted aryl group, (v) an optionally substituted mono- or di-lower alkylamino group, (vi) an optionally substituted arylamino group or (vii) an optionally substituted, 5- or 6-membered nitrogen-containing heterocyclic group;

R² is a hydrogen atom or an optionally substituted lower ($C_{1-6}$) alkyl group;

R³ is (i) a hydrogen atom, (ii) an optionally substituted lower alkyl group or (iii) an optionally substituted aryl group;

X is CHR⁴ or NR⁴ wherein R⁴ is a hydrogen atom or a lower ($C_{1-6}$) alkyl group optionally substituted by an oxo group;

Y is C, CH or N, provided that when X is CH₂, Y is C or CH;

......... is a single bond or a double bond;

ring A is an optionally substituted, 5- to 7-membered oxygen-containing heterocyclic ring;

ring B is an optionally substituted benzene ring; and m is 1 or 2.

More preferred is the compound wherein

R¹ is (i) a $C_{1-6}$ alkyl group optionally substituted by 1 to 4 substituents selected from the group consisting of a halogen and a $C_{1-6}$ alkoxy group, (ii) a $C_{3-6}$ cycloalkyl group, (iii) a $C_{2-6}$ alkenyl group, (iv) a $C_{6-10}$ aryl group optionally substituted by 1 to 4 substituents selected from the group consisting of a $C_{1-6}$ alkoxy group, a nitro group, a halogeno-$C_{1-6}$ alkyl-carbonylamino group and a halogen, (v) a mono- or di-$C_{1-6}$ alkylamino group, (vi) a $C_{6-10}$ arylamino group optionally substituted by 1 to 3 $C_{1-6}$ alkoxy groups or (vii) a 6-membered nitrogen-containing heterocyclic group optionally substituted by one or two $C_{7-11}$ aralkyloxycarbonyl groups;

R² is a hydrogen atom or a lower ($C_{1-6}$) alkyl group;

R³ is (i) a hydrogen atom, (ii) a lower ($C_{1-6}$) alkyl group or (iii) a $C_{6-14}$ aryl group;

X is CHR⁴ or NR⁴ wherein R⁴ is a hydrogen atom or a lower ($C_{1-6}$) alkyl group optionally substituted by an oxo group;

Y is C, CH or N, provided that when X is CH₂, Y is C or CH;

......... is a single bond or a double bond;

ring A is

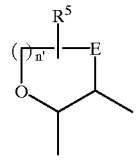

wherein the symbols are as defined above;

ring B is

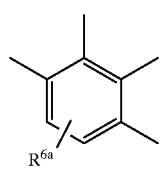

wherein $R^{6a}$ represents a hydrogen atom, a halogen atom or a lower ($C_{1-6}$) alkyl group; and m is 1 or 2.

Preferred among them is the compound represented by the formula:

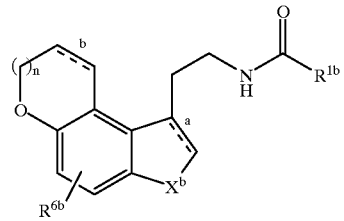

wherein $R^{1b}$ represents a $C_{1-6}$ alkyl group, $R^{6b}$ represents a hydrogen atom or a halogen atom, n represents 0 or 1, ==b== represents a single bond or a doulbe bond, ----a---- represents a single bond or a double bond when $X^b$ is CH₂, and ----a---- represents a single bond when $X^b$ is NH, and a salt thereof.

Preferred among them is also the compound by the formula:

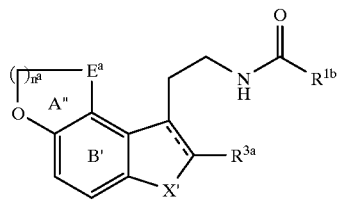

wherein $R^{1b}$ is $C_{1-6}$ alkyl, X' is CH₂, NH or NCHO, ......... is a single bond or double bond, $R^{3a}$ is a hydrogen atom or a phenyl, $E^a$ is CH₂CH₂, CH=CH, CH₂O, CH=N, CONH or CH₂NH, $n^a$ is 0 or 1, ring A" is a 5- or 6-membered oxgen-containing heterocyclic ring which may be substituted by 1 or 2 $C_{1-6}$ alkyl optionally substituted by a hydroxy, and ring B' is a benzene ring which may be substituted by a halogen, and a salt thereof. Among them, the compound wherein ......... is a single bond or double bond when X' is CH₂ or NCHO, and ......... is a single bond when X' is NH is also preferred.

Preferable examples of the compound (I) include,

N-[2-(1,6,7,8-tetrahydro-2H-indeno[5,4-b]furan-8-yl)ethyl]acetamide

N-[2-(1,6,7,8-tetrahydro-2H-indeno[5,4-b]furan-8-yl)ethyl]butyramide,

N-[2-(1,6,7,8-tetrahydro-2H-indeno[5,4-b]furan-8-yl)ethyl]propionamide,

N-[2-(3,7,8,9-tetrahydropyrano[3,2-e]indol-1-yl)ethyl]propionamide,

N-[2-(3,7,8,9-tetrahydropyrano[3,2-e]indol-1-yl)ethyl]butyramide,

N-[2-(1,2,3,7,8,9-hexahydropyrano[3,2-e]indol-1-yl)ethyl]propionamide,

N-[2-(1,2,3,7,8,9-hexahydropyrano[3,2-e]indol-1-yl)ethyl]butyramide,

N-[2-(4-fluoro-1,6,7,8-tetrahydro-2H-indeno[5,4-b]furan-8-yl)ethyl]butyramide,

N-[2-(4-fluoro-1,6,7,8-tetrahydro-2H-indeno[5,4-b]furan-8-yl)ethyl]propionamide, N-[2-(5-fluoro-3,7,8,9-tetrahydrocyclopenta[f][1]benzopyran-9-yl)ethyl]propionamide (S)-N-[2-(1,6,7,8-tetrahydro-2H-indeno[5,4-b]furan-8-yl)ethyl]propionamide, (R)-N-[2-(1,6,7,8-tetrahydro-2H-indeno[5,4-b]furan-8-yl)ethyl]propionamide, N-[2-(1,6,7,8-tetrahydro-2H-indeno[5,4-b]furan-8-yl) ethyl]butyramide,
N-[2-(1,6-dihydro-2H-indeno[5,4-b]furan-8-yl)ethyl] acetamide,
N-[2-(1,6-dihydro-2H-indeno[5,4-b]furan-8-yl)ethyl] propionamide,
N-[2-(1,6-dihydro-2H-indeno[5,4-b]furan-8-yl)ethyl] butyramide,
N-[2-(7,8-dihydro-6H-indeno[4,5-d]-1,3-dioxol-8-yl) ethyl]propionamide,
N-[2-(7,8-dihydro-6H-indeno[4,5-d]-1,3-dioxol-8-yl) ethyl]butyramide,
N-[2-(2,3,8,9-tetrahydro-7H-indeno[4,5-b]-1,4-dioxyn-9-yl)ethyl]propionamide,
N-[2-(2,3,8,9-tetrahydro-7H-indeno[4,5-b]-1,4-dioxyn-9-yl)ethyl]butyramide,
N-[2-(1,6,7,8-tetrahydro-2H-furo[3,2-e]indol-8-yl)ethyl] propionamide,
N-[2-(1,6,7,8-tetrahydro-2H-furo[3,2-e]indol-8-yl)ethyl] butyramide,
N-[2-(7-phenyl-1,6-dihydro-2H-indeno[5,4-b]furan-8-yl) ethyl]propionamide, and
N-[2-(7-phenyl-1,6-dihydro-2H-indeno[5,4-b]furan-8-yl) ethyl]butyramide.

More preferred are
N-[2-(1,6,7,8-tetrahydro-2H-indeno[5,4-b]furan-8-yl) ethyl]acetamide,
N-[2-(1,6,7,8-tetrahydro-2H-indeno[5,4-b]furan- 8-yl) ethyl]propionamide,
N-[2-(5-fluoro-3,7,8,9-tetrahydrocyclopenta[f][1]-benzopyran-9-yl)ethyl]propionamide,
N-[2-(5-fluoro-1,2,3,7,8,9-hexahydrocyclopenta[f][1] benzopyran-9-yl)ethyl]propionamide,
(S)-N-[2-(1,6,7,8-tetrahydro-2H-indeno[5,4-b]furan-8-yl)ethyl]propionamide,
(R)-N-[2-(1,6,7,8-tetrahydro-2H-indeno[5,4-b]furan-8-yl)ethyl]propionamide,
N-[2-(1,6,7,8-tetrahydro-2H-indeno[5,4-b]furan-8-yl) ethyl]butyramide,
N-[2-(1,6-dihydro-2H-indeno[5,4-b]furan-8-yl)ethyl] acetamide,
N-[2-(1,6-dihydro-2H-indeno[5,4-b]furan-8-yl)ethyl] propionamide,
N-[2-(1,6-dihydro-2H-indeno[5,4-b]furan-8-yl)ethyl] butyramide,
N-[2-(1,6,7,8-tetrahydro-2H-furo[3,2-e]indol-8-yl)ethyl] propionamide,
N-[2-(1,6,7,8-tetrahydro-2H-furo[3,2-e]indol-8-yl)ethyl] butyramide,
N-[2-(7-phenyl-1,6-dihydro-2H-indeno[5,4-b]furan-8-yl) ethyl]propionamide, and
N-[2-(7-phenyl-1,6-dihydro-2H-indeno[5,4-b]furan-8-yl) ethyl]butyramide.

Especially preferred are
(S)-N-[2-(1,6,7,8-tetrahydro-2H-indeno[5,4-b]furan-8-yl)ethyl]propionamide,
N-[2-(1,6,7,8-tetrahydro-2H-furo[3,2-e]indol-8-yl)ethyl] propionamide,
N-[2-(1,6,7,8-tetrahydro-2H-furo[3,2-e]indol-8-yl)ethyl] butyramide,
N-[2-(7-phenyl-1,6-dihydro-2H-indeno[5,4-b]furan-8-yl) ethyl]propionamide, and
N-[2-(7-phenyl-1,6-dihydro-2H-indeno[5,4-b]furan-8-yl) ethyl]butyramide.

Salts of the compound (I) of the present invention include, for example, pharmaceutically acceptable salts thereof. For example, mentioned are salts with inorganic bases, salts with organic bases, salts with inorganic acids, salts with organic acids, salts with basic or acidic amino acids. Preferred examples of salts with inorganic bases include, for example, alkali metal salts such as sodium salts and potassium salts, alkaline earth metal salts such as calcium salts and magnesium salts, aluminium salts and ammonium salts. Preferred examples of salts with organic bases include, for example, salts with trimethylamine, triethylamine, pyridine, picoline, 2,6-lutidine, ethanolamine, diethanolamine, triethanolamine, cyclohexylamine, dicyclohexylamine and N,N'-dibenzylethylenediamine. Preferred examples of salts with inorganic acids include, for example, salts with hydrochloric acid, hydrobromic acid, nitric acid, sulfuric acid and phosphoric acid. Preferred examples of salts with organic acids include, for example, salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid or p-toluenesulfonic acid. Preferred examples of salts with basic amino acids include, for example, salts with arginine, lysine and ornithine. Preferred examples of salts with acidic amino acids include, for example, salts with aspartic acid and glutamic acid.

Among others, preferred are pharmaceutically acceptable salts which include, for example, salts with inorganic acids such as hydrochloric acid, hydrobromic acid, nitric acid, sulfuric acid and phosphoric acid or salts with organic acids such as acetic acid, phthalic acid, fumaric acid, tartaric acid, maleic acid, citric acid, succinic acid, methanesulfonic acid and p-toluenesulfonic acid, when the compound (I) has basic functional group(s); and alkali metal salts such as sodium salts and potassium salts, or alkaline earth metal salts such as calcium salts and magnesium salts, and ammonium salts when the compound (I) has acidic functional group(s).

Compound (I) of the present invention may be hydrated or solvated.

A process for producing the compound (I) and a salt thereof (referred to Compound (I) as hereinunder) of the present invention is mentioned below.

Compound (I) of the present invention can be produced in accordance with, for example, the reaction processes illustrated in the following reaction schemes or the analogous thereto.

Compounds (III) to (LXXIV) in the following reaction schemes encompass their salts, for which the salts of Compound (I) mentioned hereinabove are referred to.

The symbols for the compounds in the following reaction schemes are as defined those mentioned above.

Reaction Process 1:

$R^7O$—[B]—CHO (III) →(Condensation)→ $R^7O$—[B]—CH=CH—COOH (IV)

↓ Reduction

-continued
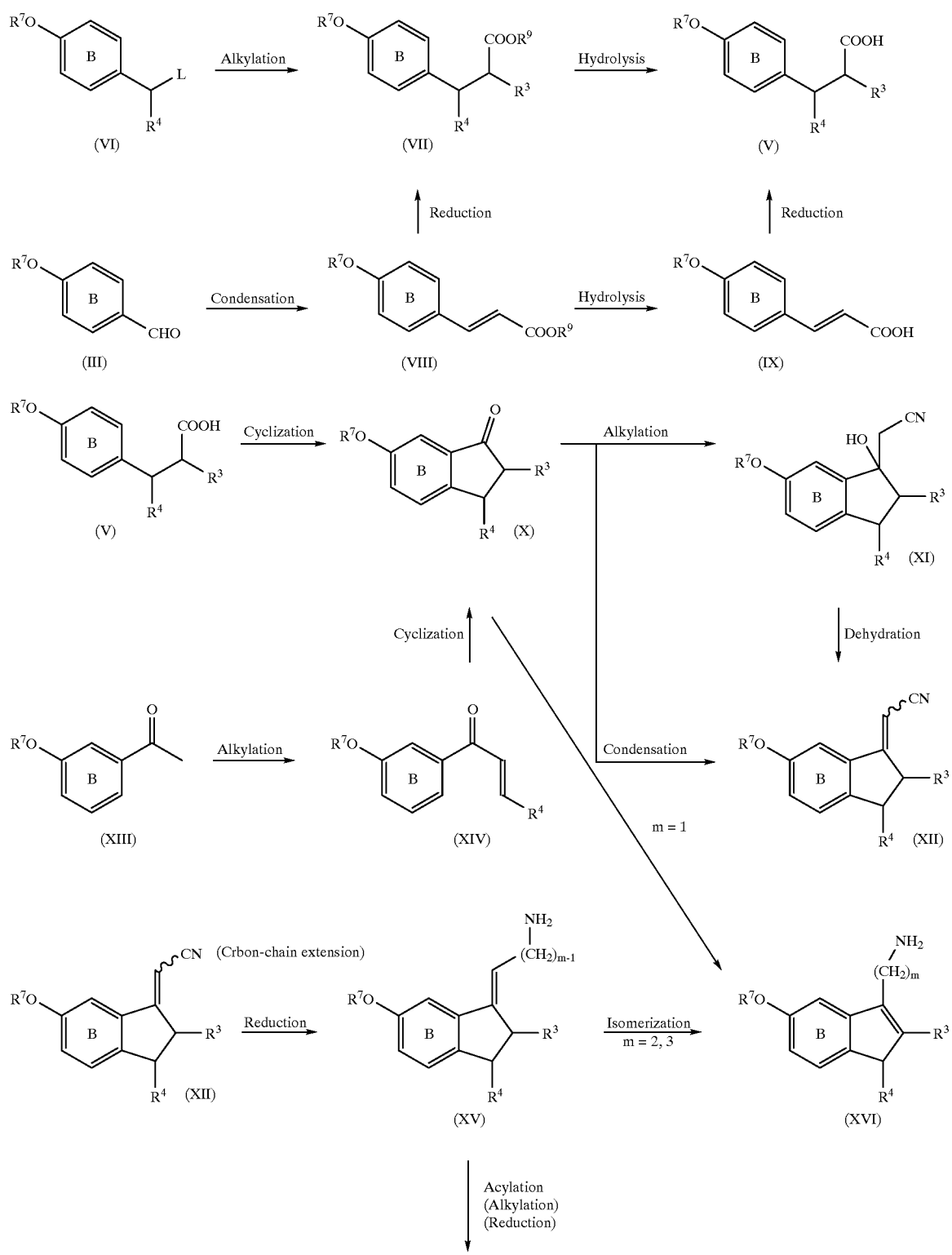

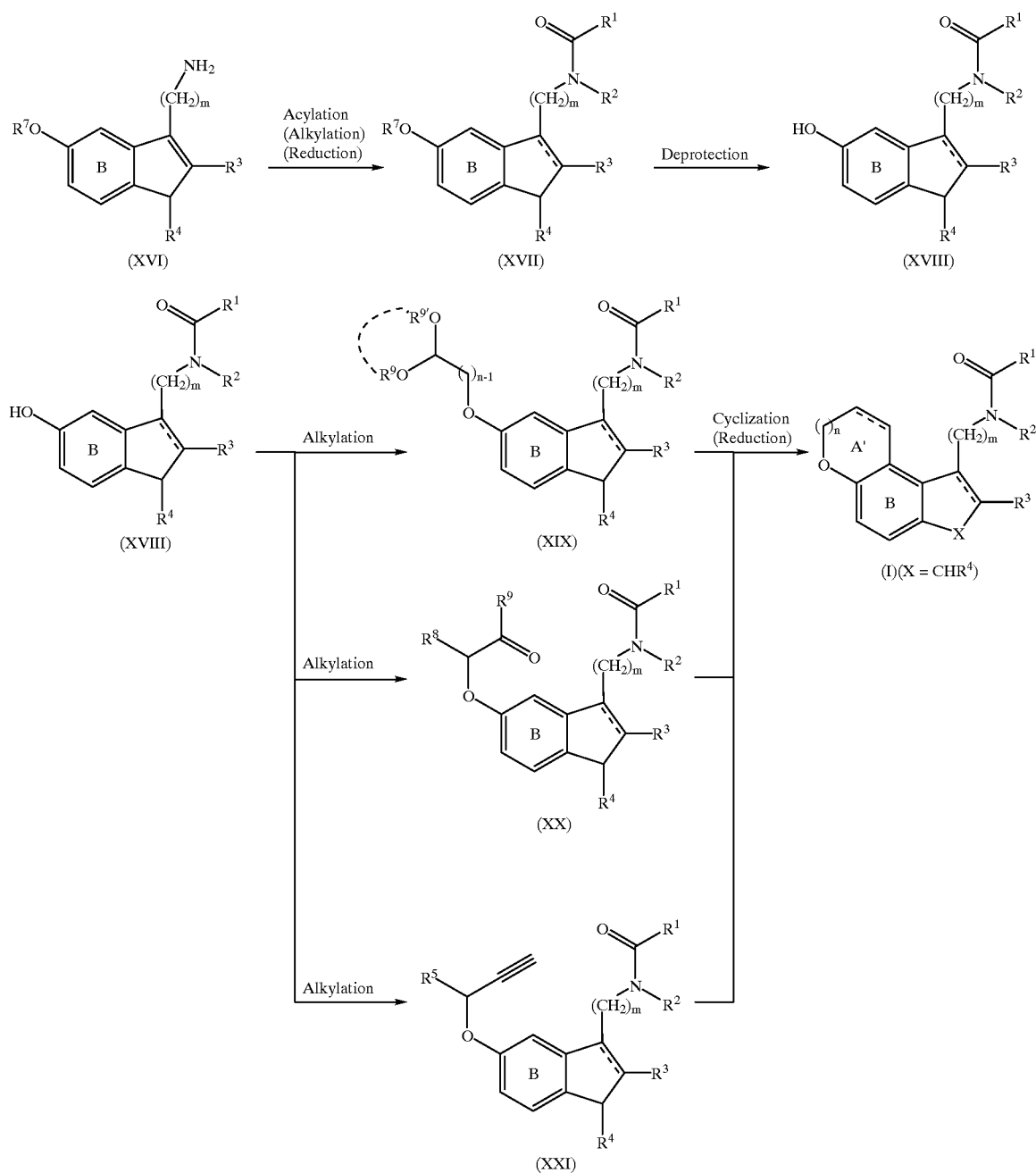

Compound (III) can be produced using per se known methods, for example, using the methods described in Jikken Kagaku Koza (Lectures on Experimental Chemistry), 4th Ed., Vol. 21, pp. 1–148 (edited by the Japan Chemical Society) or methods analogous thereto.

Compound (VI) wherein L represents a leaving group such as a halogen atom, an alkylsulfonyl group, an alkyl-sulfonyloxy group and an arylsulfonyloxy group, and $R^7$ represents an optionally substituted hydrocarbon group can be produced using per se known methods, for example, using the methods described in Bull. Chem. Soc. Japan, Vol. 64, p. 1410 (1991), J. Indian Chem. Soc., Vol. 66, p. 656 (1989), J. Med. Chem., Vol. 29, p. 1586 and p. 1904 (1986), or methods analogous thereto.

Compound (XIII) can be produced using per se known methods, for example, using the methods described in J. Chem. Soc., p. 4691 (1963), Chem. Lett., p. 165 (1986) or methods analogous thereto.

The halogen atom represented by L includes, for example, fluorine, chlorine, bromine and iodine. The alkylsulfonyl group represented by L includes, for example, a $C_{1-5}$ alkyl-sulfonyl group (e.g., methanesulfonyl, ethanesulfonyl, etc.). The alkylsulfonyloxy group represented by L includes, for example, an optionally halogenated $C_{1-5}$ alkylsulfonyloxy group (e.g., methanesulfonyloxy, ethanesulfonyloxy, trichloromethanesulfonyloxy, etc.). The arylsulfonyloxy group represented by L includes, for example, an optionally substituted benzenesulfonyloxy group (e.g., p-toluenesulfonyloxy, benzenesulfonyloxy, etc.).

For the compounds in the above-mentioned reaction schemes, commercial products, if available, can be directly used.

Compound (IV) can be produced from compound (III) and malonic acid through the Knoevenagel condensation thereof in the presence of a base. One mol of compound (III) is reacted with approximately 1.0 to 5.0 mols, preferably approximately 1.0 to 2.0 mols of malonic acid. The base includes, for example, inorganic bases such as sodium hydroxide, potassium hydroxide, etc.; basic salts such as sodium carbonate, potassium carbonate, cesium carbonate, sodium hydrogencarbonate, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc. The base is used in an amount of approximately 0.1 to 10.0 mols, preferably approximately 0.1 to 5.0 mol per mol of compound (III). The reaction is advantageously conducted in a solvent inert thereto. While, as the solvent, any one can be used so far as the reaction advances therein, for example, alcohols such as methanol, ethanol, propanol, etc.; hydrocarbons such as benzene, toluene, cyclohexane, hexane, etc.; amides such as N,N-dimethylformamide, N,N-dimethylacetamide, etc.; organic acids such as formic acid, acetic acid, etc.; halogenated hydrocarbons such as dichloromethane, chloroform, carbon tetrachloride, 1,2-dichloroethane, etc., or a suitable mixture of these solvents are preferable. The reaction time varies, depending on the reagents and solvents used, and is generally 30 minutes to 24 hours, preferably 30 minutes to 8 hours. The reaction temperature is generally 0 to 150° C., preferably 0 to 130° C. The product (IV) can be used in the next reaction step, while it is in the reaction mixture or in the form of a crude product. If desired, however, it may be isolated from the reaction mixture by ordinary methods, and it can be easily purified by means of, for example, recrystallization, distillation and chromatography.

Compound (VIII) (in which $R^9$ represents a hydrocarbon group) can be obtained by reacting a phosphonato-carbanion, which is produced by the treatment of a trialkyl phosphonoacetate with a base, with compound (III). This is obtained as a single E-form or Z-form configurational isomer or as a mixture of such E- and Z-isomers. The trialkyl phosphonoacetate includes, for example, triethyl phosphonoacetate, etc. One mol of compound (III) is reacted with approximately 1.0 to 3.0 mols, preferably approximately 1.0 to 1.5 mols of the trialkyl phosphonoacetate. The base includes, for example, alkali metal hydrides such as sodium hydride, potassium hydride, etc., metal amides such as sodium amide, lithium diisopropylamide, lithium hexamethyldisilazide, etc.; metal alkoxides such as sodium methoxide, sodium ethoxide, potassium tert-butoxide, etc. The base is used in an amount of approximately 1.0 to 5.0 mols, preferably approximately 1.0 to 1.5 mols, per mol of compound (III). The reaction is advantageously conducted in a solvent inert thereto. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; sulfoxides such as dimethylsulfoxide, etc., or a suitable mixture of these solvents are preferable. The reaction time is generally 1 hour to 50 hours, preferably 1 hour to 10 hours. The reaction temperature is generally −78 to 200° C., preferably 0 to 150° C. The mixture of isomers of compound (VIII) can be used in the next reaction step, while it is in the reaction mixture or in the form of a crude product. If desired, however, it may be isolated from the reaction mixture by ordinary methods, and it can be easily purified by means of, for example, recrystallization, distillation and chromatography.

Compound (IX) can be produced by hydrolyzing the ester moiety of compound (VIII) with an acid or base. For the acid hydrolysis, generally used are mineral acids such as hydrochloric acid, sulfuric acid, etc.; Lewis acids such as boron trichloride, boron trifluoride, etc.; a combination of a Lewis acid and a thiol or sulfide; organic acids such as trifluoroacetic acid, p-toluenesulfonic acid, etc. For the alkali hydrolysis, generally used are inorganic bases such as sodium hydroxide, potassium hydroxide, barium hydroxide, etc.; basic salts such as sodium carbonate, potassium carbonate, etc.; metal alkoxides such as sodium methoxide, sodium ethoxide, potassium tert-butoxide, etc.; organic bases such as triethylamine, imidazole, formamidine, etc. These acids and bases are used in an amount of approximately 0.5 to 10 mols, preferably approximately 0.5 to 3.0 mols per mol of compound (VIII). The reaction is advantageously conducted either in the absence of a solvent or the presence of a solvent inert to the reaction. While, as the solvent, any one can be used so far as the reaction advances therein, for example, alcohols such as methanol, ethanol, propanol, etc.; aromatic hydrocarbons such as benzene, toluene, etc.; saturated hydrocarbons such as cyclohexane, hexane, etc.; organic acids such as formic acid, acetic acid, etc.; ethers such as tetrahydrofuran, dioxane, 1,2-dimethoxyethane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; ketones such as acetone, methylethylketone, etc.; sulfoxides such as dimethylsulfoxide, etc.; water, or a suitable mixture of these solvents are preferable. The reaction time is generally 10 minutes to 60 hours, preferably 10 minutes to 12 hours. The reaction temperature is generally −10 to 200° C., preferably 0 to 120° C. The product (IX) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (VII) (in which $R^9$ represents a hydrocarbon group) can be produced by reacting compound (VI) with an ester derivative of the formula $R^3CH_2COOR^9$ (in which $R^3$ and $R^9$ are as defined above) in the presence of a base. For the "hydrocarbon group" represented by $R^9$, for example, referred to is the above-mentioned "hydrocarbon group". Among others, $R^9$ is preferably a lower alkyl group (e.g., a $C_{1-6}$ alkyl group such as methyl, ethyl, isopropyl, etc.) or an optionally substituted benzyl group. The "optionally substituted benzyl group" may have 1 to 3 substituents such as halogen atoms and $C_{1-3}$ alkyl at any substitutable positions in the benzyl group. Concretely, it includes, for example, benzyl, p-chlorobenzyl, p-methylbenzyl, etc.

The above ester derivative is used in an amount of approximately 1.0 to 5.0 mols, preferably approximately 1.0 to 2.0 mols per mol of compound (VI). The base includes, for example, inorganic bases such as sodium hydroxide, potassium hydroxide, etc.; basic salts such as sodium carbonate, potassium carbonate, cesium carbonate, sodium hydrogencarbonate, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.; alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc. The base is used in an amount of approximately 1.0 to 5.0 mols, preferably approximately 1.0 to 2.0 mols per mol of compound (VI). The reaction is advantageously conducted in the presence of a solvent inert to the reaction. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; ketones such as acetone, methyl ethyl ketone, etc.; sulfoxides such as dimethylsulfoxide, etc., or a suitable mixture of these solvents are preferable. The reaction time is generally 30 minutes to 48 hours, preferably 30 minutes to 5 hours. The reaction temperature is generally −20 to 200° C., preferably −10 to 150° C. The product (VII) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (VII) in which $R^3$ and $R^4$ are hydrogens can also be produced by catalytically reducing compound (VIII) in a hydrogen atmosphere in the presence of various catalysts. The catalysts usable for the reduction include, for example, platinum oxide, platinum on activated carbon, palladium on activated carbon, palladium on barium sulfate, nickel, copper-chromium oxide, rhodium, cobalt, ruthenium, etc. The amount of the catalyst to be used may be approximately 5 to 1000% by weight, preferably approximately 5 to 300% by weight relative to compound (VIII). The reaction is advantageously conducted in a solvent inert to the reaction. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; saturated hydrocarbons such as cyclohexane, hexane, etc.; amides such as N,N-dimethylformamide, N,N-dimethylacetamide, etc.; organic acids such as formic acid, acetic acid, etc.; water, or a suitable mixture of these solvents are preferable. The reaction time varies, depending on the activity of the catalyst used and the amount thereof, and is generally 30 minutes to 24 hours, preferably 30 minutes to 6 hours. The reaction temperature is generally 0 to 120° C., preferably 20 to 80° C. The pressure for the reaction is generally 1 to 100 atmospheres. Additives (promoters) that enhance the activity of the catalyst used can be added to the reaction system. Acidic additives advantageously usable for the purpose include, for example, inorganic acids such as hydrochloric acid, sulfuric acid, nitric acid, perchloric acid, hydrobromic acid, phosphoric acid, etc.; organic acids such as acetic acid, trifluoroacetic acid, oxalic acid, phthalic acid, fumaric acid, tartaric acid, citric acid, succinic acid, methanesulfonic acid, p-toluenesulfonic acid, 10-camphorsulfonic acid, etc. Basic additives are also advantageously usable and include, for example, sodium hydroxide, potassium hydroxide, etc. The product (VII) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (V) in which $R^3$ and $R^4$ are hydrogens can be produced by catalytically reducing compound (IV) or compound (IX) in a hydrogen atmosphere in the same manner as in the reduction to produce compound (VII).

Compound (V) can also be produced by hydrolyzing the ester moiety of compound (VII) with an acid or a base. For the acid hydrolysis, generally used are mineral acids such as hydrochloric acid, sulfuric acid, etc.; Lewis acids such as boron trichloride, boron trifluoride, etc.; a combination of a Lewis acid and a thiol or sulfide; organic acids such as trifluoroacetic acid, p-toluenesulfonic acid, etc. For the alkali hydrolysis, generally used are inorganic bases such as sodium hydroxide, potassium hydroxide, barium hydroxide, etc.; basic salts such as sodium carbonate, potassium carbonate, etc.; metal alkoxides such as sodium methoxide, sodium ethoxide, potassium tert-butoxide, etc.; organic bases such as triethylamine, imidazole, formamidine, etc. These acids and bases are used in an amount of approximately 0.5 to 10 mols, preferably approximately 0.5 to 6.0 mols per mol of compound (VII). The reaction is advantageously conducted in either the absence of a solvent or the presence of a solvent inert to the reaction. While, as the solvent, any one can be used so far as the reaction advances therein, for example, alcohols such as methanol, ethanol, propanol, etc.; aromatic hydrocarbons such as benzene, toluene, etc.; saturated hydrocarbons such as cyclohexane, hexane, etc.; organic acids such as formic acid, acetic acid, etc.; ethers such as tetrahydrofuran, dioxane, 1,2-dimethoxyethane, etc.; amides suchas N,N-dimethylformamide, N,N-dimethylacetamide, etc.; halogenated hydrocarbons such as dichloromethane, chloroform, carbon tetrachloride, 1,2-dichloroethane, etc.; nitrites such as acetonitrile, propionitrile, etc.; ketones such as acetone, methylethylketone, etc.; sulfoxides such as dimethylsulfoxide, etc.; water, or a suitable mixture of these solvents are preferable. The reaction time is generally 10 minutes to 60 hours, preferably 10 minutes to 12 hours. The reaction temperature is generally −10 to 200° C., preferably 0 to 120° C. The product (V) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (XIV) can be produced from compound (XIII) and an aldehyde derivative of the formula $R^4CHO$ (in which $R^4$ is as defined above), through aldol condensation in the presence of a base. This is obtained as a single E-form or Z-form configurational isomer or as a mixture of such E- and Z-isomers. The aldehyde derivative is used in an amount of approximately 1.0 to 5.0 mols, preferably approximately 1.0 to 2.0 mols per mol of compound (XIII). The base includes, for example, inorganic bases such as sodium hydroxide, potassium hydroxide, etc.; basic salts such as sodium carbonate, potassium carbonate, cesium carbonate, sodium hydrogencarbonate, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.; alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc. These bases are used in an amount of approximately 1.0 to 5.0 mols, preferably 1.0 to 2.5 mols per mol of compound (XIII). The reaction is advantageously conducted in a solvent inert thereto. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; sulfoxides such as dimethylsulfoxide, etc., or a suitable mixture of these solvents are preferable. The reaction time is generally 30 minutes to 48 hours, preferably 30 minutes to 5 hours. The reaction temperature is generally −78 to 200° C., preferably −10 to 150° C. Compound (XIV) can also be produced by subjecting an aldol intermediate obtained in the presence of a base such as lithium diisopropylamide to dehydration at room temperature or under heat in the presence of an acid catalyst such as p-toluenesulfonic acid. The product (XIV) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (X) can be produced by subjecting compound (V) or compound (XIV) to cyclization. The cyclization is conducted by a per se known method, for example, a method by heating, a method using an acidic substance, a method comprising the reaction with a halogenating agent and then conducting cyclization in the presence of a Lewis acid, or methods analogous thereto.

The cyclization under heating is advantageously conducted in either the absence of a solvent or the presence of a solvent inert to the reaction. While, as the solvent, any one can be used so far as the reaction advances therein, for example, high-boiling-point hydrocarbons such as 1,2,3,4-tetrahydronaphthalene, etc.; high-boiling-point ethers such as diphenyl ether, diethyleneglycol dimethyl ether, etc., or a suitable mixture of these solvents are preferable. The reaction time is generally 10 minutes to 24 hours, preferably 10 minutes to 10 hours. The reaction temperature is generally 100 to 300° C., preferably 100 to 200° C.

In the case where the cyclization is conducted by using an acid substance, the acidic substance includes, for example, phosphorus oxychloride, phosphorus pentoxide, phosphorus trioxide, thionyl chloride, hydrochloric acid, sulfuric acid, polyphosphoric acid, p-toluenesulfonic acid, etc. The acidic substance is used in an amount of approximately 0.5 to 100 mols, preferably approximately 5.0 to 20 mols per mol of compound (V) or compound (XIV). The reaction is advantageously conducted in either the absence of a solvent or the presence of a solvent inert to the reaction. While, as the solvent, any one can be used so far as the reaction advances therein, for example, aromatic hydrocarbons such as benzene, toluene, etc.; saturated hydrocarbons such as cyclohexane, hexane, etc.; ethers such as tetrahydrofuran, dioxane, 1,2-dimethoxyethane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; acid anhydrides such as acetic anhydride, etc.; sulfoxides such as dimethylsulfoxide, etc., or a suitable mixture of these solvents are preferable. The reaction time is generally 30 minutes to 12 hours, preferably 30 minutes to 6 hours. The reaction temperature is generally 0 to 200° C., preferably 0 to 150° C.

In the case where the cyclization is conducted in the presence of a Lewis acid after compound (V) is allowed to react with a halogenating agent, the halogenating agent is examplified thionyl halides such as thionyl chloride, thionyl bromide, etc.; phosphoryl halides such as phosphoryl chloride, phosphoryl bromide, etc.; phosphorus halides such as phosphorus pentachloride, phosphorus trichloride, phosphorus pentabromide, phosphorus tribromide, etc.; oxalyl halides such as oxalyl chloride, etc.; phosgene, etc. The halogenating agent is used in an amount of approximately 1.0 to 30 mols, preferably approximately 1.0 to 10 mols per mol of compound (V). The reaction is advantageously conducted in either the absence of a solvent or the presence of a solvent inert to the reaction. While, as the solvent, any one can be used so far as the reaction advances therein, for example, aromatic hydrocarbons such as benzene, toluene, etc.; saturated hydrocarbons such as cyclohexane, hexane, etc.; ethers such as tetrahydrofuran, dioxane, 1,2-dimethoxyethane, etc.; amides such as N,N-dimethylformamide, N,N-dimethylacetamide, etc.; halogenated hydrocarbons such as dichloromethane, chloroform, carbon tetrachloride, 1,2-dichloroethane, etc., or a suitable mixture of these solvents are preferable. The reaction time is generally 10 minutes to 12 hours, preferably 10 minutes to 5 hours. The reaction temperature is generally −10 to 200° C., preferably −10 to 120° C. The product can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography. The Lewis acid to be used in the next cyclization includes, for example, anhydrous aluminium chloride, anhydrous zinc chloride, anhydrous iron chloride, etc. The Lewis acid is used in an amount of approximately 0.1 to 20 mols, preferably approximately 0.2 to 5.0 mols per mol of compound (V). The reaction is advantageously conducted in either the absence of a solvent or the presence of a solvent inert to the reaction. While, as the solvent, any one can be used so far as the reaction advances therein, for example, aromatic hydrocarbons such as benzene, toluene, etc.; halogenated hydrocarbons such as monochlorobenzene, o-dichlorobenzene, 1,2,4-trichlorobenzene, dichloromethane, chloroform, carbon tetrachloride, 1,2-dichloroethane, etc., or a suitable mixture of these solvents are preferable. The reaction time is generally 30 minutes to 12 hours, preferably 30 minutes to 6 hours. The reaction temperature is generally −20 to 200° C., preferably −5 to 120° C. The product (X) produced by the above-mentioned cyclization can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (XII) can be produced by reacting a carbanion, which is formed by the treatment of acetonitrile with a base, with compound (X) to give compound (XI) followed by dehydrating the resultant compound (XI). Compound (XII) is obtained as a single E-form or Z-form configurational isomer or as a mixture of such E- and Z-isomers. Acetonitrile is used in an amount of approximately 1.0 to 3.0 mols, preferably approximately 1.0 to 1.3 mols per mol of compound (X). The base includes, for example, alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc. These bases are used in an amount of approximately 1.0 to 5.0 mols, preferably approximately 1.0 to 1.5 mols per mol of compound (X). The reaction is advantageously conducted in the presence of a solvent inert to the reaction. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc., or a suitable mixture of these solvents are preferable. The reaction time is generally 30 minutes to 48 hours, preferably 30 minutes to 5 hours. The reaction temperature is generally −78 to 100° C., preferably −78 to 50° C. The product obtained can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

The catalyst to be used for the dehydration includes, for example, acidic catalysts such as hydrochloric acid, sulfuric acid, phosphoric acid, potassium hydrogensulfate, oxalic acid, p-toluenesulfonic acid, 10-camphorsulfonic acid, boron trifluoride-ether complex, etc.; basic catalysts such as sodium hydroxide, potassium hydroxide, etc. If desired, a dehydrating agent such as N,N'-dicyclohexylcarbodiimide, alumina, sodium dioxide, phosphorus oxychloride, thionyl chloride or methanesulfonyl chloride can also be used. The reaction is advantageously conducted in either the absence of a solvent or the presence of a solvent inert to the reaction. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; sulfoxides such as dimethylsulfoxide, etc., or a suitable mixture of these solvents are preferable. The reaction time is generally 30 minutes to 24 hours, preferably 30 minutes to 5 hours. The reaction temperature is generally 0 to 200° C., preferably 0 to 150° C.

Compound (XII) can also be produced by reacting a phosphonate-carbanion, which is produced by the treatment of a dialkyl cyanomethylphosphonate with a base, with compound (X). This is obtained as a single E-form or Z-form configurational isomer or as a mixture of such E- and Z-isomers. The dialkyl cyanomethylphosphonate includes, for example, diethyl cyanomethylphosphonate, etc. The dialkyl cyanomethylphosphonate is used in an amount of approximately 1.0 to 3.0 mols, preferably approximately 1.0 to 1.5 mols per mol of compound (X). The base includes, for example, alkali metal hydrides such as sodium hydride, potassium hydride, etc., metal amides such as sodium amide, lithium diisopropylamide, lithium hexamethyldisilazide, etc.; metal alkoxides such as sodium methoxide, sodium ethoxide, potassium tert-butoxide, etc. The base is used in an amount of approximately 1.0 to 5.0 mols, preferably approximately 1.0 to 1.5 mols per mol of compound (X). The reaction is advantageously conducted in a solvent inert thereto. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; sulfoxides such as dimethylsulfoxide, etc., or a suitable mixture of these solvents are preferable. The reaction time is generally 1 hour to 50 hours, preferably 1 hour to 10 hours. The reaction temperature is generally −78 to 200° C., preferably 0 to 150° C. The mixture of isomers of compound (XII) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

The extension of the carbon chain at the side chain of compound (XII) can be conducted by means of per se known carbon chain extension reaction, for example, a reaction comprising hydrolysis of cyano group under alkaline or acidic conditions to convert into carboxyl group, or leading the carboxyl to ester form, which is then subjecting to reduction to give an alcohol, followed by halogenation and cyanation.

Compound (XV) can be produced by reducing compound (XII). The reducing agent to be used, includes, for example, metal hydrides such as aluminium hydride, diisobutyl aluminium hydride, etc.; metal hydride complexes such as lithium aluminium hydride, sodium borohydride, etc., or the hydrogenation catalyst to be used includes, for example, Raney nickel, Raney cobalt, etc. Regarding the amount of the reducing agent, the metal hydride is used in an amount of approximately 1.0 to 10 mols, preferably approximately 1.0 to 3.0 mols per mol of compound (XII) while the metal hydride complex is used in an amount of approximately 1.0 to 10 mols, preferably 1.0 to 3.0 mols per mol of compound (XII). For the hydrogenation, a catalyst such as Raney nickel or Raney cobalt is used in an amount of approximately 10 to 1000% by weight, preferably approximately 80 to 300% by weight relative to compound (XII). The reaction is advantageously conducted in a solvent inert thereto. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, etc.; amides such as N,N-dimethylformamide, N,N-dimethylacetamide, etc.; organic acids such as formic acid, acetic acid, etc., or a suitable mixture of these solvents are preferable. In the case where a catalyst such as Raney nickel or Raney cobalt is used, amines such as ammonia may be added to the reaction system in order to prevent any possible side reactions. The reaction time varies, depending on the activity of the catalyst and the amount thereof used, and is generally 1 hour to 100 hours, preferably 1 hour to 50 hours. The reaction temperature is generally 0 to 120° C., preferably 20 to 80° C. In the case where a catalyst such as Raney nickel or Raney cobalt is used, the hydrogen pressure is generally 1 to 100 atmospheres. The product (XV) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (XVI) with m=2 or 3 can be produced by isomerizing compound (XV) with an acid. The acid catalyst to be used include, for example, inorganic acids such as hydrochloric acid, sulfuric acid, nitric acid, hydrobromic acid, phosphoric acid, etc.; organic acids such as acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid, etc.; boron trifluoride-ether complex, etc. The acid catalyst is used in an amount of approximately 0.01 to 10 mols, preferably approximately 0.01 to 5.0 mols per mol of compound (XV). The reaction is advantageously conducted in either the absence of a solvent or the presence of a solvent inert to the reaction. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; sulfoxides such as dimethylsulfoxide, etc.; water, or a suitable mixture of these solvents are preferable. The reaction time is generally 10 minutes to 12 hours, preferably 10 minutes to 2 hours. The reaction temperature is generally −10 to 200° C., preferably −10 to 100° C. The product (XVI) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (XVI) with m=1 can be produced by treating compound (X) with trimethylsilylcyanide in the presence of a Lewis acid, then treating the resultant intermediate with an acid to remove its trimethylsilyloxy group and thereafter reducing it at its cyano group. The Lewis acid includes, for example, zinc iodide, anhydrous aluminium chloride, anhydrous zinc chloride, anhydrous iron chloride, etc. The Lewis acid catalyst is used in an amount of approximately 0.01 to 10 mols, preferably approximately 0.01 to 1.0 mol per mol of compound (X). The reaction is advantageously conducted in either the absence of a solvent or the presence of a solvent inert to the reaction. While, as the solvent, any one can be used so far as the reaction advances therein, for example, ethers such as diethyl ether, tetrahydrofuran, dioxane, 1,2-dimethoxyethane, etc.; hydrocarbons such as benzene, toluene, cyclohexane, hexane, etc., or a suitable mixture of these solvents are preferable. The reaction time is generally 10 minutes to 12 hours, preferably 30 minutes to 3 hours. The reaction temperature is generally −10 to 200° C., preferably −10 to 100° C. The product can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography. Next, the above product is treated with an acid. Preferably, the acid includes, for example, inorganic acids such as hydrochloric acid, sulfuric acid, nitric acid, hydrobromic acid, phosphoric acid, etc.; organic acids such as acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid, etc.; boron trifluoride-ether complex, etc. The acid is used in an amount of approximately 1 to 100 mols, preferably approximately 1 to 10 mols per mol of compound (X). The reaction is advantageously conducted in either the absence of a solvent or the presence of a solvent inert to the reaction. While, as the solvent, any one can be used so far as the reaction advances therein, for example, ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; sulfoxides such as dimethylsulfoxide, etc., or a suitable mixture of these solvents are preferable. The reaction time is generally 30 minutes to 12 hours, preferably 30 minutes to 5 hours. The reaction temperature is generally 0 to 200° C., preferably 20 to 150° C. The reduction of the cyano group in the resultant compound can be conducted under the same conditions as those for the production of compound (XV) from compound (XII). The product (XVI) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (XVII) can be produced by reacting compound (XVI) with a carboxylic acid or a salt thereof or a reactive derivative thereof. The carboxylic acid includes, for example, compounds of the formula $R^1$—COOH (in which $R^1$ is as defined above). The reactive derivatives of the carboxylic acid include, for example, acid halides (e.g., acid chlorides, acid bromides, etc.), acid amides (e.g., acid amides with pyrazole, imidazole, benzotriazole, etc.), acid anhydrides (e.g., $C_{1-6}$ aliphatic carboxylic acid anhydrides such as acetic acid anhydrides, propionic acid anhydrides, butyric acid anhydrides, etc.), acid azides, active esters (e.g., diethoxyphosphates, diphenoxyphosphates, p-nitrophenyl esters, 2,4-dinitrophenyl esters, cyanomethyl esters, pentachlorophenyl esters, esters with N-hydroxysuccinimide, esters with N-hydroxyphthalimide, esters with 1-hydroxybenzotriazole, esters with 6-chloro-1-hydroxybenzotriazole, esters with 1-hydroxy-1H-2-pyridone, etc.), active thioesters (e.g., 2-pyridyl thioesters, 2-benzothiazolyl thioesters, etc.), etc.

In place of using the above reactive derivative, the carboxylic acid or its salt may be directly reacted with compound (XVI) in the presence of a suitable condensing agent. The condensing agent includes, for example, N,N'-disubstituted carbodiimides such as N,N'-dicyclohexylcarbodiimide, 1-ethyl-3-(3-dimethylaminopropyl)carbodiimide (WSC) hydrochloride, etc.; azolides such as N,N'-carbonyldiimidazole, etc.; dehydrating agents such as N-ethoxycarbonyl-2-ethoxy-1,2-dihydroquinoline, phosphorus oxychloride, alkoxyacetylenes, etc.; 2-halogenopyridinium salts such as 2-chloromethylpyridinium iodide, 2-fluoro-1-methylpyridinium iodide, etc. It is believed that the reaction with the condensing agent may advance via the reactive derivative of the carboxylic acid used. The carboxylic acid of $R^1$—COOH (in which $R^1$ is as defined above) or a reactive derivative thereof is used generally in an amount of approximately 1.0 to 5.0 mols, preferably approximately 1.0 to 2.0 mols per mol of compound (XVI). The reaction is advantageously conducted in a solvent inert to the reaction. While, as the solvent, any one can be used so far as the reaction advances therein, for example, ethers such as diethyl ether, tetrahydrofuran, dioxane, 1,2-dimethoxyethane, etc.; hydrocarbons such as benzene, toluene, cyclohexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; sulfoxides such as dimethylsulfoxide, etc.; water or a suitable mixture of these solvents are preferable. In the case where acid halides are used as the reactive derivatives of carboxylic acids, the reaction may be conducted in the presence of a de-acidifying agent in order to remove the released hydrogen halide from the reaction system. The de-acidifying agent includes, for example, basic salts such as sodium carbonate, potassium carbonate, sodium hydrogencarbonate, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc. It is desirable that such a de-acidifying agent is previously added to the reaction system. The reaction time varies, depending on the reagents and the solvents used, and is generally 30 minutes to 24 hours, preferably 30 minutes to 4 hours. The reaction temperature is generally 0 to 100° C., preferably 0 to 70° C.

Compound (XVII) can also be produced, while, accompanied by isomerization in the reaction system, by the following procedure, a carboxylic acid of the formula $R^1$—COOH (in which $R^1$ is as defined above) or its reactive derivative is added to compound (XV), and the mixture is stirred, under acidic conditions for 5 minutes to 3 hours, preferably 10 minutes to 1 hour, at 0 to 100° C., preferably 0 to 70° C., then the reaction mixture is subjected to acylation by adding the above-mentioned de-acidifying agent. The carboxylic acid or its reactive derivative is used generally in an amount of approximately 1.0 to 5.0 mols, preferably approximately 1.0 to 2.0 mols per mol of compound (XV). The reaction is advantageously conducted in a solvent inert to the reaction. While, as the solvent, any one can be used so far as the reaction advances therein, for example, ethers such as diethyl ether, tetrahydrofuran, dioxane, 1,2-dimethoxyethane, etc.; hydrocarbons such as benzene, toluene, cyclohexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; sulfoxides such as dimethylsulfoxide, etc., or a suitable mixture of these solvents are preferable. The product (XVII) thus obtained can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

For the production of optically active compound (XVII), a method, which comprises subjecting compound (XV) to reduction by using a catalyst for asymmetric reduction, e.g. a transition metal—optically active phosphine complex and, then, by subjecting the resultant to acylation, is employed. As the said transition metal—optically active phosphine complex, mention is made of, for example, ruthenium—optically active phosphine complex. Preferably, ruthenium-2,2'-bis(diphenylphosphino)-1,1'-binaphthyl derivatives including dirutheniumtetrachloro bis[2,2'-bis(diphenylphosphino)-1,1'-binaphthyl] triethylamine and [2,2'-bis(diphenylphosphino)-1,1'-binaphthyl]ruthenium diacetate are employed. The reaction conditions are substantially the same as those for the production of an optically active aminoalkyl derivative from compound (XXXV) to be described later. The conditions of acylation of the optically active aminoalkyl derivative thus obtained are substantially the same as those for the production of compound (I) from compound (XXXVI) to be described later.

And, for the production of the optically active compound (XVII), a method, which comprises subjecting acylated compound (XV) to reduction by using a catalyst for asymmetric reduction, e.g. a transition metal—optically active phosphine complex, is employed as well. As the transition metal—optically active phosphine complex, mention is made of, for example, ruthenium—optically active phosphine complex. Preferably, ruthenium-2,2'-bis(diphenylphosphino)-1,1'-binaphthyl derivatives including dirutheniumtetrachloro bis[2,2'-bis(diphenylphosphino)-1,1'-binaphthyl]triethylamine and [2,2'-bis(diphenylphosphino)-1,1'-binaphthyl]ruthenium diacetate are employed. The reaction conditions are substantially the same as those for the production of an optically active aminoalkyl derivative from compound (XXXV) to be described later. Conditions for acylation of compound (XV) are substantially the same as those for the production of compound (I) from compound (XXXVI) to be described later.

To obtain compound (XVII) in which $R^2$ is an alkyl group, the acylated compound obtained in the above process is alkylated with a corresponding alkylating agent (e.g., alkyl halides and sulfonates with alcohols) in the presence of a base. The alkylating agent is used in an amount of approximately 1.0 to 5.0 mols, preferably approximately 1.0 to 2.0 mols per mol of compound (XVII) to be alkylated therewith. The base includes, for example, inorganic bases such as sodium hydroxide, potassium hydroxide, etc.; basic salts such as sodium carbonate, potassium carbonate, cesium carbonate, sodium hydrogencarbonate, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.; alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc. The base is used in an amount of approximately 1.0 to 5.0 mols, preferably approximately 1.0 to 2.0 mols per mol of compound (XVII). The reaction is advantageously conducted in a solvent inert to the reaction. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; sulfoxides such as dimethylsulfoxide, etc., or a suitable mixture of these solvents are preferable. The reaction time is generally 30 minutes to 48 hours, preferably 30 minutes to 6 hours. The reaction temperature is generally −20 to 200° C., preferably −10 to 150° C. The product (XVII) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

To obtain compound (XVII) in which the double-bond moiety has been reduced, the double-bond moiety in compound (XVII) is catalytically reduced under the same conditions as those for the production of compound (VII) from compound (VIII).

Compound (XVIII) can be produced by removing the protective group for the hydroxyl group in compound (XVII). The de-protecting step is conducted by the per se known means. For example, referred to is the disclosure in the chapter "Protection for Phenols and Catechols" in "Protective Groups in Organic Synthesis" by T. W. Green (2nd Ed., 1991).

Compound (XIX) can be produced by reacting compound (XVIII) with a corresponding alkylating agent (e.g., alkyl halides, sulfonates with alcohols, etc.) in the presence of a base. The alkylating agent is used in an amount of approximately 1.0 to 5.0 mols, preferably approximately 1.0 to 2.0 mols per mol of compound (XVIII). The base includes, for example, inorganic bases such as sodium hydroxide, potassium hydroxide, etc.; basic salts such as sodium carbonate, potassium carbonate, cesium carbonate, sodium hydrogencarbonate, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.; alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc. The base is used in an amount of approximately 1.0 to 5.0 mols, preferably approximately 1.0 to 2.0 mols per mol of compound (XVIII). The reaction is advantageously conducted in a solvent inert to the reaction. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; sulfoxides such as dimethylsulfoxide, etc., or a suitable mixture of these solvents are preferable. The reaction time is generally 30 minutes to 48 hours, preferably 1 to 24 hours. The reaction temperature is generally −20 to 200° C., preferably 0 to 150° C. The product (XIX) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (XX) [wherein $R^8$ represents a hydrogen atom, a halogen atom, an optionally substituted hydrocarbon group, an optionally substituted alkoxy group, a hydroxyl group, a nitro group, a cyano group or an optionally substituted amino group, $R^9$ represents a hydrocarbon group and the other symbols are as defined above] can be produced by reacting compound (XVIII) with a corresponding α-haloketone (e.g., α-chloroketone, α-bromoketone, α-iodoketone, etc.) in the presence of a base. The α-haloketone is used in an amount of approximately 1.0 to 5.0 mols, preferably approximately 1.0 to 2.0 mols per mol of compound (XVIII). The base includes, for example, inorganic bases such as sodium hydroxide, potassium hydroxide, etc.; basic salts such as sodium carbonate, potassium carbonate, cesium carbonate, sodium hydrogencarbonate, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.; alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc. The base is used in an amount of approximately 1.0 to 5.0 mols, preferably approximately 1.0 to 2.0 mols per mol of compound (XVIII). The reaction is advantageously conducted in a solvent inert to the reaction. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; ketones such as acetone, methyl ethyl ketone, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; sulfoxides such as dimethylsulfoxide, etc., or a suitable mixture of these solvents are preferable. The reaction time is generally 30 minutes to 48 hours, preferably 1 to 24 hours. The reaction temperature is generally −20 to 200° C., preferably 0 to 150° C. The product (XX) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (XXI) can be produced by reacting compound (XVIII) with a corresponding alkylating agent (e.g., substituted acetylenealkyl halides, sulfonates with substituted acetyleue alcohols, etc.) in the presence of a base. The alkylating agent is used in an amount of approximately 1.0 to 20 mols, preferably approximately 1.0 to 10 mols per mol of compound (XVIII). The base includes, for example, inorganic bases such as sodium hydroxide, potassium hydroxide, etc.; basic salts such as sodium carbonate, potassium carbonate, cesium carbonate, sodium hydrogencarbonate, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.; alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc. The base is used in an amount of approximately 1.0 to 5.0 mols, preferably approximately 1.0 to 2.0 mols per mol of compound (XVIII). The reaction is advantageously conducted in a solvent inert to the reaction. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; sulfoxides such as dimethylsulfoxide, etc., or a suitable mixture of these solvents are preferable. The reaction time is generally 30 minutes to 48 hours, preferably 1 to 24 hours. The reaction temperature is generally −20 to 200° C., preferably 0 to 150° C. The product (XXI) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (I) can be produced by per se known cyclization of compound (XIX), (XX) or (XXI). The cyclization can be conducted by, for example, a method by heating the compound, a method using an acidic substance, a method using a basic substance, or methods analogous thereto.

The cyclization under heating is advantageously conducted in either the absence of a solvent or the presence of a solvent inert to the reaction. While, as the solvent, any one can be used so far as the reaction advances therein, for example, high-boiling-point hydrocarbons such as 1,2,3,4-tetrahydronaphthalene, bromobenzene etc.; high-boiling-point ethers such as diphenyl ether, diethyleneglycol dimethyl ether, etc.; N,N-dimethylaniline, N,N-diethylaniline, etc., or a suitable mixture of these solvents are preferable. The reaction time is generally 10 minutes to 24 hours, preferably 10 minutes to 10 hours. The reaction temperature is generally 100 to 300° C., preferably 150 to 250° C.

In the case where the cyclization is conducted by using an acid substance, the acidic substance includes, for example, phosphorus oxychloride, phosphorus pentoxide, phosphorus trioxide, thionyl chloride, hydrobromic acid, hydrochloric acid, sulfuric acid, phosphoric acid, polyphosphoric acid, p-toluenesulfonic acid, etc. The acidic substance is used in an amount of approximately 0.5 to 100 mols, preferably approximately 5.0 to 20 mols per mol of compound (XIX), (XX) or (XXI). The reaction is advantageously conducted in either the absence of a solvent or the presence of a solvent inert to the reaction. While, as the solvent, any one can be used so far as the reaction advances therein, for example, aromatic hydrocarbons such as benzene, toluene, etc.; saturated hydrocarbons such as cyclohexane, hexane, etc.; ethers such as tetrahydrofuran, dioxane, 1,2-dimethoxyethane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; acid anhydrides such as acetic anhydride, etc.; sulfoxides, such as dimethylsulfoxide, etc.; water, or a suitable mixture of these solvents are preferable. The reaction time is generally 30 minutes to 12 hours, preferably 30 minutes to 6 hours. The reaction temperature is generally 0 to 200° C., preferably 0 to 150° C.

In the case where the cyclization is conducted by using an basic substance, the basic substance includes, for example, sodium hydroxide, potassium hydroxide, sodium carbonate, potassium carbonate, sodium hydrogencarbonate, etc. The basic substance is used in an amount of approximately 0.5 to 100 mols, preferably approximately 5.0 to 20 mols per mol of compound (XIX), (XX) or (XXI). The reaction is advantageously conducted in either the absence of a solvent or the presence of a solvent inert to the reaction. While, as the solvent, any one can be used so far as the reaction advances therein, for example, alcohols such as methanol, ethanol, propanol, etc.; ketones such as acetone, methyl ethyl ketone, etc.; water, or a suitable mixture of these solvents are preferable. The reaction time is generally 30 minutes to 12 hours, preferably 30 minutes to 6 hours. The reaction temperature is generally 0 to 200° C., preferably 0 to 150° C.

The product (I) obtained by the above-mentioned cyclization can be isolated from the reaction mixture by per se known methods, and it can be easily purified by means of separation, for example, recrystallization, distillation and chromatography.

To obtain compound (I) in which the double-bond moiety has been reduced, the double-bond moiety in compound (I) is catalytically reduced under the same conditions as those for the production of compound (VII) from compound (VIII).

Reaction Process 2:

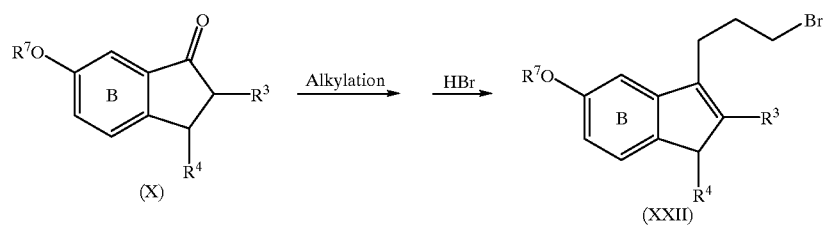

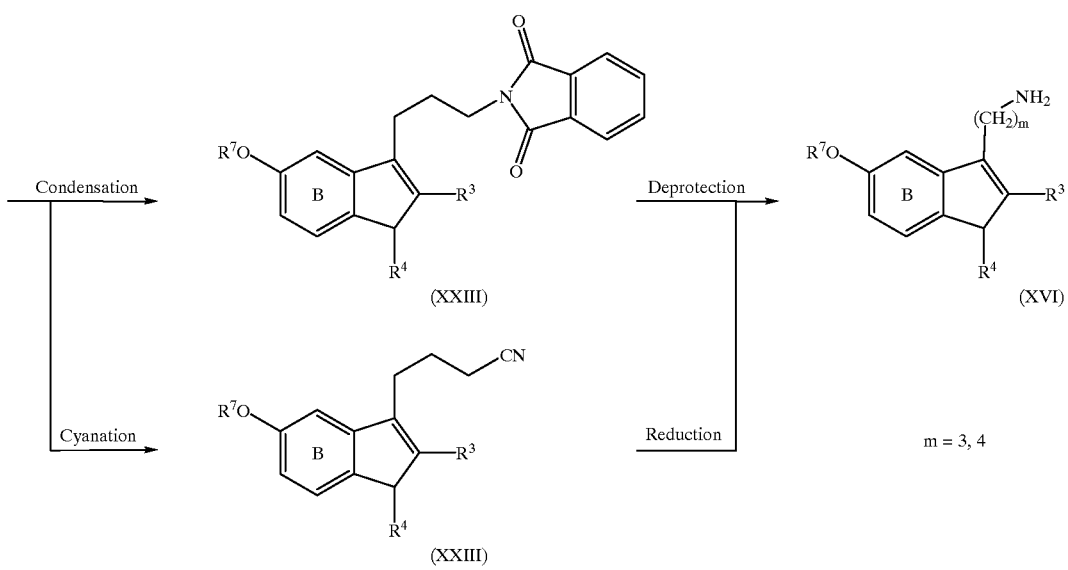

Compound (XXII) can be produced by alkylating compound (X) followed by treating it with hydrobromic acid. For the alkylation, a Grignard reagent to be prepared from cyclopropyl bromide and magnesium is diluted with an inert solvent and then applied to compound (X). The production of the Grignard reagent from cyclopropyl bromide may be conducted by known methods. Magnesium is used in an amount of approximately 1.0 to 5.0 mols, preferably approximately 1.0 to 1.5 mols, per mol of cyclopropyl bromide. The reaction is advantageously conducted in a solvent inert to the reaction.
so far as the reaction advances therein, for example, aromatic hydrocarbons such as benzene, toluene, etc.; saturated hydrocarbons such as cyclohexane, hexane, etc.; ethers such as tetrahydrofuran, dioxane, 1,2-dimethoxyethane, etc., or a suitable mixture of these solvents are preferable. The reaction time is generally 10 minutes to 10 hours, preferably 15 minutes to 3 hours. The reaction temperature is generally 0 to 150° C., preferably 40 to 80° C. A small amount of iodine may be present in the reaction system. The Grignard reagent thus produced is left at room temperature to complete the reaction. Then, after removing the solvent through distillation or without removing it, the Grignard reagent is diluted with a solvent added thereto, and compound (X) is dropwise added to and reacted with the reagent. Compound (X) is used in an amount of approximately 0.4 to 3.0 mols, preferably approximately 0.4 to 1.0 mol per mol of the Grignard reagent. The solvent to be used for diluting the Grignard reagent is not specifically defined so far as the intended reaction advances therein, and includes, for example, aromatic hydrocarbons such as benzene, toluene, etc.; saturated hydrocarbons such as cyclohexane, hexane, etc.; halogenated hydrocarbons such as chlorotoluene, etc.; ethers such as tetrahydrofuran, dioxane, 1,2-dimethoxyethane, etc., or a suitable mixture of these solvents are preferable. The amount of the solvent to be used for the dilution may be approximately 1.0 to 30 times by volume, preferably approximately 1.0 to 15 times by volume, relative to the Grignard reagent. The reaction time is generally 10 minutes to 10 hours, preferably 15 minutes to 3 hours. The reaction temperature is generally 0 to 150° C., preferably 40 to 100° C. The product can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography. The amount of the hydrobromic acid to be used is approximately 1.0 to 30 mols, preferably approximately 1.0 to 5.0 mols per mol of compound (X). The reaction is advantageously conducted in a solvent inert to the reaction. While, as the solvent, any one can be used so far as the reaction advances therein, for example, alcohols such as methanol, ethanol, propanol, etc.; organic acids such as formic acid, acetic acid, etc.; hydrocarbons such as benzene, toluene, cyclohexane, hexane, etc.; sulfoxides such as dimethylsulfoxide, etc.; water, or a suitable mixture of these solvents are preferable. The reaction time is generally 1 to 60 hours, preferably 1 to 15 hours. The reaction temperature is generally 0 to 200° C., preferably 0 to 80° C. The product (XXII) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (XXIII) can be produced by reacting compound (XXII) with a potassium phthalimide. The potassium phthalimide is used in an amount of approximately 1.0 to 5.0 mols, preferably approximately 1.0 to 1.5 mols per mol of compound (XXII). The condensation of compound (XXII) with potassium phthalimide is advantageously conducted in either the absence of a solvent or the presence of a solvent inert to the reaction and optionally in the presence of a base. The base includes, for example, inorganic bases such as sodium hydroxide, potassium hydroxide, etc.; basic salts such as sodium carbonate, potassium carbonate, cesium carbonate, sodium hydrogencarbonate, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.; alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc. The amount of the base to be used is approximately 1.0 to 5.0 mols, preferably approximately 1.0 to 2.0 mols per mol of compound (XXII). Preferably, the solvent includes, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; sulfoxides such as dimethylsulfoxide, etc., or a suitable mixture of these solvents. The reaction time is generally 30 minutes to 20 hours, preferably 30 minutes to 8 hours. The reaction temperature is generally 0 to 150° C., preferably 20 to 80° C. The product (XXIII) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (XXIV) can be produced by reacting compound (XXII) with a cyano compound. The cyano compound includes, for example, sodium cyanide, potassium cyanide and a mixture thereof. It may be produced in the reaction system by reacting hydrogen cyanide with a basic material such as sodium hydroxide, potassium hydroxide, sodium carbonate or potassium carbonate. The cyano compound is used in an amount of approximately 0.8 to 10 mols, preferably approximately 1.0 to 2.0 mols per mol of compound (XXII). The reaction is advantageously conducted in a solvent inert thereto. While, as the solvent, any one can be used so far as the reaction advances therein, for example, ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, chlorobenzene, ortho-dichlorobenzene, etc.; sulfoxides such as dimethylsulfoxide, etc., or a suitable mixture of these solvents are preferable. A combination of water and a water-insoluble or hardly water-soluble organic solvent such as that selected from the above solvents can also be employed in the presence of a phase-transfer catalyst. The phase-transfer catalyst includes, for example, quaternary ammonium salts such as tetrabutylammonium bromide, benzyltriethylammonium chloride, etc.; and quaternary phosphonium salts. The phase-transfer catalyst is used in amount of approximately 0.001 to 10 mols, preferably approximately 0.005 to 0.5 mols per mol of compound (XXII). The reaction time is generally 30 minutes to 20 hours, preferably 30 minutes to 8 hours. The reaction temperature is generally 0 to 200° C., preferably 20 to 150° C. The product (XXIV) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (XVI) can be produced by decomposing the imido group in compound (XXIII). For this, in general, 1 mol of compound (XXIII) is treated with approximately from 1.0 to 20 mols, preferably approximately from 1.0 to 5.0 mols of amines such as methylamine, ethylamine, etc., hydrazines such as hydrazine, phenylhydrazine, etc., alkali metal sulfides such as sodium sulfide, potassium sulfide, etc., mineral acids such as hydrochloric acid, sulfuric acid, etc. The reaction is advantageously conducted in a solvent inert thereto. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; sulfoxides such as dimethylsulfoxide, etc., or a suitable mixture of these solvents are preferable. The reaction time is generally 30 minutes to 12 hours, preferably 30 minutes to 5 hours. The reaction temperature is generally 0 to 200° C., preferably 20 to 100° C. The product (XVI) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography. Compound (XVI) can also be produced by reducing the cyano group in compound (XXIV) in the same manner as in the production of compound (XV) from compound (XII).

Reaction Process 3:

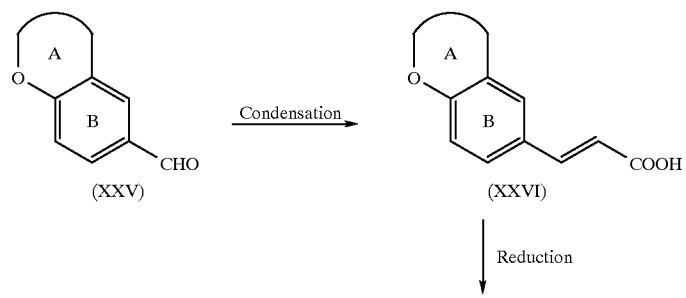

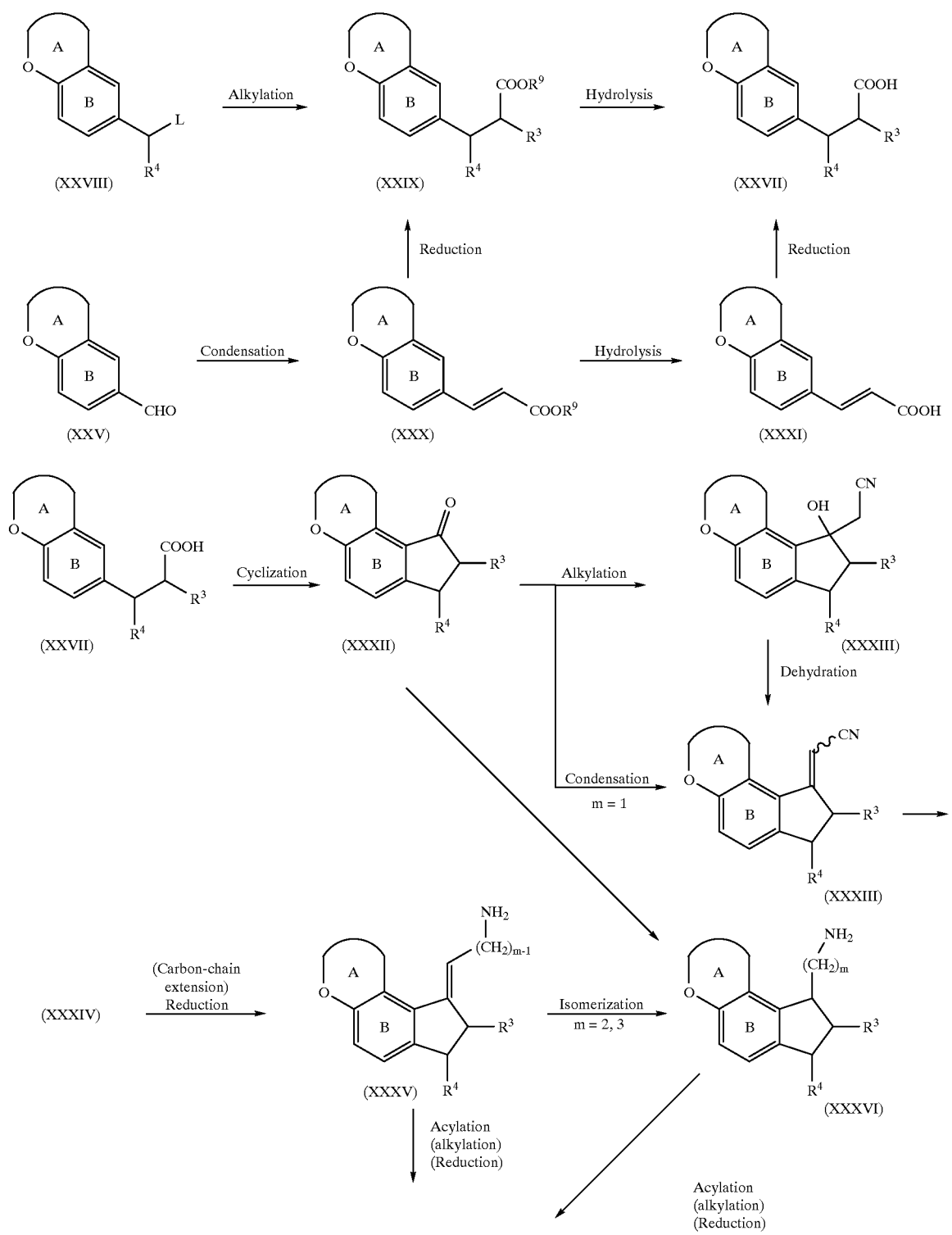

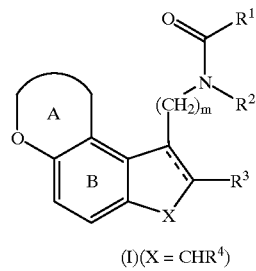

(I)(X = CHR⁴)

Compound (XXV) can be produced by per se known methods, for example, the methods described in J. Org. Chem., Vol. 49, p. 409 (1984) and J. Indian Chem. Soc., Vol. 36, p. 76 (1959), or methods analogous thereto.

Compound (XXVIII) (wherein L represents a leaving group such as a halogen atom, an alkylsulfonyl group, an alkylsulfonyloxy group or an arylsulfonyloxy group.) can be produced by per se known methods, for example, the methods described in J. Chem. Soc., p. 2455 (1956) and ibid., p. 4665 (1958), or methods analogous thereto.

The halogen atom to be represented by L includes, for example, fluorine, chlorine, bromine, iodine, etc. The alkylsulfonyl group to be represented by L includes, for example, a $C_{1-5}$ alkylsulfonyl group (e.g., methanesulfonyl, ethanesulfonyl, etc.), etc. The alkylsulfonyloxy group to be represented by L includes, for example, an optionally halogenated $C_{1-5}$ alkylsulfonyloxy group (e.g., methanesulfonyloxy, ethanesulfonyloxy, trichloromethanesulfonyloxy, etc.), etc. The arylsulfonyloxy group to be represented by L includes, for example, an optionally substituted benzenesulfonyloxy group (e.g., p-toluenesulfonyloxy, benzenesulfonyloxy, etc.), etc.

As the compounds in the above-mentioned reaction schemes are commercial products, if available, they can be directly used.

Compound (XXVI) can be produced from compound (XXV) and malonic acid through the Knoevenagel condensation thereof in the presence of a base, in the same manner as in the production of compound (IV) from compound (III) mentioned hereinabove. One mol of compound (XXV) is reacted with approximately 1.0 to 5.0 mols, preferably approximately 1.0 to 2.0 mols of malonic acid. The base includes, for example, inorganic bases such as sodium hydroxide, potassium hydroxide, etc.; basic salts such as sodium carbonate, potassium carbonate, cesium carbonate, sodium hydrogencarbonate, etc.; aromatic amines such as pyridine, lutidine, etc.; tertiary amines such as triethylamine, tripropylamine, tributylamine, cyclohexyldimethylamine, pyridine, 4-dimethylaminopyridine, N,N-dimethylaniline, piperidine, N-methylpiperidine, N-methylpyrrolidine, N-methylmorpholine, etc. The base is used in an amount of approximately 0.1 to 10.0 mols, preferably approximately 0.1 to 5.0 mol per mol of compound (XXV). The reaction is advantageously conducted in a solvent inert thereto. While, as the solvent, any one can be used so far as the reaction advances therein, for example, alcohols such as methanol, ethanol, propanol, etc.; hydrocarbons such as benzene, toluene, cyclohexane, hexane, etc.; amides such as N,N-dimethylformamide, N,N-dimethylacetamide, etc.; organic acids such as formic acid, acetic acid, etc.; halogenated hydrocarbons such as dichloromethane, chloroform, carbon tetrachloride, 1,2-dichloroethane, etc., or a suitable mixture of these solvents are preferable. The reaction time varies, depending on the reagents and solvents used, and is generally 30 minutes to 24 hours, preferably 30 minutes to 8 hours. The reaction temperature is generally 0 to 150° C., preferably 0 to 130° C. The product (XXVI) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (XXX) can be produced by reacting a phosphonate-carbanion, which is produced by the treatment of a trialkyl phosphonoacetate with a base, with compound (XXV), in the same manner as in the production of compound (VIII) from compound (III) mentioned hereinabove. This compound (XXX) is obtained as a single E-form or Z-form configurational isomer or as a mixture of such E- and Z-isomers. As mentioned hereinabove, the trialkyl phosphonoacetate includes, for example, ethyl diethylphosphonoacetate, etc. One mol of compound (XXV) is reacted with approximately 1.0 to 3.0 mols, preferably approximately 1.0 to 1.5 mols of a dialkyl alkylphosphonate. The base includes, for example, alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc. The base is used in an amount of approximately 1.0 to 5.0 mols, preferably approximately 1.0 to 1.5 mols, per mol of compound (XXV). The reaction is advantageously conducted in a solvent inert thereto. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; sulfoxides such as dimethylsulfoxide, etc., or a suitable mixture of these solvents are preferable. The reaction time is generally 1 hour to 50 hours, preferably 1 hour to 10 hours. The reaction temperature is generally –78 to 200° C., preferably 0 to 150° C. The mixture of isomers of compound (XXX) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (XXXI) can be produced by hydrolyzing the ester moiety of compound (XXX) with an acid or base, in the same manner as in the production of compound (IX) from compound (VIII) mentioned hereinabove. For the acid hydrolysis, generally used are mineral acids such as hydrochloric acid, sulfuric acid, etc.; Lewis acids such as boron trichloride, boron trifluoride, etc.; a combination of a Lewis acid and a thiol or sulfide; organic acids such as trifluoroacetic acid, p-toluenesulfonic acid, etc. For the alkali hydrolysis, generally used are metal hydroxides such as sodium hydroxide, potassium hydroxide, barium hydroxide, etc.; metal carbonates such as sodium carbonate, potassium carbonate, etc.; metal alkoxides such as sodium methoxide, sodium ethoxide, potassium tert-butoxide, etc.; organic bases such as triethylamine, imidazole, formamidine, etc. These acids and bases are used in an amount of approximately 0.5 to 10 mols, preferably approximately 0.5 to 3.0 mols per mol of compound (XXX). The reaction is advantageously conducted in either the absence of a solvent or the presence of a solvent inert to the reaction. While, as the solvent, any one can be used so far as the reaction advances therein, for example, alcohols such as methanol, ethanol, propanol, etc.; aromatic hydrocarbons such as benzene, toluene, etc.; saturated hydrocarbons such as cyclohexane, hexane, etc.; organic acids such as formic acid, acetic acid, etc.; ethers such as tetrahydrofuran, dioxane, 1,2-dimethoxyethane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; ketones such as acetone, methyl ethyl ketone, etc.; sulfoxides such as dimethylsulfoxide, etc.; water, etc., or a suitable mixture of these solvents are preferable. The reaction time is generally 10 minutes to 60 hours, preferably 10 minutes to 12 hours. The reaction temperature is generally −10 to 200° C., preferably from 0 to 120° C. The product (XXXI) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (XXIX) can be produced by reacting compound (XXVIII) and an ester derivative of the formula $R^3CH_2COOR^9$ (in which $R^3$ and $R^9$ are as defined above) in the presence of a base, in the same manner as in the production of compound (VII) from compound (VI) mentioned hereinabove. The "hydrocarbon group" to be represented by $R^9$ includes, for example, the above-mentioned "hydrocarbon group". Of the examples of the hydrocarbon group as mentioned above, $R^9$ is preferably a lower alkyl group (e.g., a $C_{1-6}$ alkyl group such as methyl, ethyl, isopropyl, etc.) or an optionally substituted benzyl group. The "optionally substituted benzyl group" may have one to three substituents such as halogen atoms or $C_{1-3}$ alkyl groups, at any substitutable position in the benzyl group. Concretely, it includes, for example, benzyl, p-chlorobenzyl, p-methylbenzyl, etc.

The ester derivative is used in an amount of approximately 1.0 to 5.0 mols, preferably approximately 1.0 to 2.0 mols per mol of compound (XXVIII). The base includes, for example, inorganic bases such as sodium hydroxide, potassium hydroxide, etc.; basic salts such as sodium carbonate, potassium carbonate, cesium carbonate, sodium hydrogencarbonate, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.; alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc.

The base is used in an amount of approximately 1.0 to 5.0 mols, preferably approximately 1.0 to 2.0 mols per mol of compound (XXVIII). The reaction is advantageously conducted in the presence of a solvent inert to the reaction. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; ketones such as acetone, methyl ethyl ketone, etc.; sulfoxides such as dimethylsulfoxide, etc., or a suitable mixture of these solvents are preferable. The reaction time is generally 30 minutes to 48 hours, preferably 30 minutes to 5 hours. The reaction temperature is generally −20 to 200° C., preferably −10 to 150° C. The product (XXIX) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (XXIX) can also be produced by catalytically reducing compound (XXX) in a hydrogen atmosphere in the presence of various catalysts, in the same manner as in the catalytic reduction of compound (VIII) into compound (VII) mentioned hereinabove. The catalysts to be used for the reduction include, for example, platinum oxide, platinum on activated carbon, palladium on activated carbon, palladium on barium sulfate, nickel, copper-chromium oxide, rhodium, cobalt, ruthenium, etc. The amount of the catalyst to be used may be approximately 5 to 1000% by weight, preferably approximately 5 to 300% by weight relative to compound (XXX). The reaction is advantageously conducted in a solvent inert to the reaction. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; saturated hydrocarbons such as cyclohexane, hexane, etc.; amides such as N,N-dimethylformamide, N,N-dimethylacetamide, etc.; organic acids such as formic acid, acetic acid, etc.; water, etc., or a suitable mixture of these solvents are preferable. The reaction time varies, depending on the activity of the catalyst and the amount thereof used. In general, it is 30 minutes to 24 hours, preferably 30 minutes to 6 hours. The reaction temperature is generally 0 to 120° C., preferably 20 to 80° C. The pressure for the reaction is generally 1 to 100 atmospheres. Additives (promoters) that enhance the activity of the catalyst used can be added to the reaction system. Acidic additives advantageously usable for this purpose include, for example, inorganic acids such as hydrochloric acid, sulfuric acid, nitric acid, perchloric acid, hydrobromic acid, phosphoric acid, etc.; organic acids such as acetic acid, trifluoroacetic acid, oxalic acid, phthalic acid, fumaric acid, tartaric acid, citric acid, succinic acid, methanesulfonic acid, p-toluenesulfonic acid, 10-camphorsulfonic acid, etc. Basic additives are also advantageously usable and include, for example, sodium hydroxide, potassium hydroxide, etc. The product (XXIX) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (XXVII) can be produced by catalytically reducing compound (XXVI) or compound (XXXI) in a hydrogen atmosphere in the same manner as in the catalytic reduction of compound (XXX) into compound (XXIX) or in the catalytic reduction of compound (IV) or compound (IX) into compound (V) mentioned hereinabove.

Compound (XXVII) can also be produced by hydrolyzing the ester moiety of compound (XXIX) with an acid or base, in the same manner as in the production of compound (V) from compound (VII) mentioned hereinabove. For the acid hydrolysis, generally used are mineral acids such as hydrochloric acid, sulfuric acid, etc.; Lewis acids such as boron trichloride, boron trifluoride, etc.; a combination of a Lewis acid and a thiol or sulfide; organic acids such as trifluoroacetic acid, p-toluenesulfonic acid, etc. For the alkali hydrolysis, generally used are metal hydroxides such as sodium hydroxide, potassium hydroxide, barium hydroxide, etc.; metal carbonates such as sodium carbonate, potassium carbonate, etc.; metal alkoxides such as sodium methoxide, sodium ethoxide, potassium tert-butoxide, etc.; organic bases such as triethylamine, imidazole, formamidine, etc. These acids and bases are used in an amount of approximately 0.5 to 10 mols, preferably approximately 0.5 to 6.0 mols per mol of compound (XXIX). The reaction is advantageously conducted in either the absence of a solvent or the presence of a solvent inert to the reaction. While, as the solvent, any one can be used so far as the reaction advances therein, for example, alcohols such as methanol, ethanol, propanol, etc.; aromatic hydrocarbons such as benzene, toluene, etc.; saturated hydrocarbons such as cyclohexane, hexane, etc.; organic acids such as formic acid, acetic acid, etc.; ethers such as tetrahydrofuran, dioxane, 1,2-dimethoxyethane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; ketones such as acetone, methyl ethyl ketone, etc.; sulfoxides such as dimethylsulfoxide, etc.; water, etc., or a suitable mixture of these solvents are preferable. The reaction time is generally 10 minutes to 60 hours, preferably 10 minutes to 12 hours. The reaction temperature is generally −10 to 200° C., preferably 0 to 120° C. The product (XXVII) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (XXXII) can be produced by per se known cyclization of compound (XXVII), in the same manner as in the cyclization of compound (V) into compound (X) mentioned hereinabove. The cyclization can be conducted by, for example, a method by heating the compound, a method of using an acidic substance, a method comprising the reaction with a halogenating agent and then conducting cyclization in the presence of a Lewis acid, or methods analogous thereto.

The cyclization under heating is advantageously conducted in either the absence of a solvent or the presence of a solvent inert to the reaction. While, as the solvent, any one can be used so far as the reaction advances therein, for example, high-boiling-point hydrocarbons such as 1,2,3,4-tetrahydronaphthalene, etc.; high-boiling-point ethers such as diphenyl ether, diethyleneglycol dimethyl ether, etc., or a suitable mixture of these solvents are preferable. The reaction time is generally 10 minutes to 24 hours, preferably 10 minutes to 10 hours. The reaction temperature is generally 100 to 300° C., preferably 100 to 200° C.

In the case where the cyclization is conducted by using an acid substance, the acidic substance is exemplified phosphorus oxychloride, phosphorus pentoxide, phosphorus trioxide, thionyl chloride, hydrochloric acid, sulfuric acid, polyphosphoric acid, p-toluenesulfonic acid, etc. The acidic substance is used in an amount of approximately 0.5 to 100 mols, preferably approximately 5.0 to 20 mols per mol of compound (XXVII). The reaction is advantageously conducted in either the absence of a solvent or the presence of a solvent inert to the reaction. While, as the solvent, any one can be used so far as the reaction advances therein, for example, aromatic hydrocarbons such as benzene, toluene, etc.; saturated hydrocarbons such as cyclohexane, hexane, etc.; ethers such as tetrahydrofuran, dioxane, 1,2-dimethoxyethane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; acid anhydrides such as acetic anhydride, etc.; sulfoxides, such as dimethylsulfoxide, etc., or a suitable mixture of these solvents are preferable. The reaction time is generally 30 minutes to 12 hours, preferably 30 minutes to 6 hours. The reaction temperature is generally 0 to 200° C., preferably 0 to 150° C.

In the case where the cyclization is conducted in the presence of a Lewis acid after compound (XXVII) is allowed to react with a halogenating agent, the halogenating agent to be used is exemplified thionyl halides such as thionyl chloride, thionyl bromide, etc.; phosphoryl halides such as phosphoryl chloride, phosphoryl bromide, etc.; phosphorus halides such as phosphorus pentachloride, phosphorus trichloride, phosphorus pentabromide, phosphorus tribromide, etc.; oxalyl halides such as oxalyl chloride, etc.; phosgene, etc. The halogenating agent is used in an amount of approximately 1.0 to 30 mols, preferably approximately 1.0 to 10 mols per mol of compound (XXVII). The reaction is advantageously conducted in either the absence of a solvent or the presence of a solvent inert to the reaction. While, as the solvent, any one can be used so far as the reaction advances therein, for example, aromatic hydrocarbons such as benzene, toluene, etc.; saturated hydrocarbons such as cyclohexane, hexane, etc.; ethers such as tetrahydrofuran, dioxane, 1,2-dimethoxyethane, etc.; amides such as N,N-dimethylformamide, N,N-dimethylacetamide, etc.; halogenated hydrocarbons such as dichloromethane, chloroform, carbon tetrachloride, 1,2-dichloroethane, etc., or a suitable mixture of these solvents are preferable. The reaction time is generally 10 minutes to 12 hours, preferably 10 minutes to 5 hours. The reaction temperature is generally −10 to 200° C., preferably from −10 to 120° C. The product can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography. The Lewis acid to be used in the next cyclization includes, for example, anhydrous aluminium chloride, anhydrous zinc chloride, anhydrous iron chloride, etc. The Lewis acid is used in an amount of approximately 0.1 to 20 mols, preferably approximately 0.2 to 5.0 mols per mol of compound (XXVII). The reaction is advantageously conducted in either the absence of a solvent or the presence of a solvent inert to the reaction. While, as the solvent, any one can be used so far as the reaction advances therein, for example, aromatic hydrocarbons such as benzene, toluene, etc.; halogenated hydrocarbons such as monochlorobenzene, o-dichlorobenzene, 1,2,4-trichlorobenzene, dichloromethane, chloroform, carbon tetrachloride, 1,2-dichloroethane, etc., or a suitable mixture of these solvents are preferable. The reaction time is generally 30 minutes to 12 hours, preferably 30 minutes to 6 hours. The reaction temperature is generally −20 to 200° C., preferably −5 to 120° C. The product (XXXII) obtained by the above cyclization can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

For causing these cyclization reactions to proceed predominantly in the desired direction, the cyclization may be carried out after substitution, with a halogen atom or atoms, of a position or positions on the benzene ring which are undesirable for the desired cyclization. In this case, the halogenation includes, for example, ordinary halogenation using a halogenating agent (e.g. halogen such as bromine or chlorine), halogeneation using a halogenating agent together with a metal catalyst such as iron, chlorination using titanium tetrachloride-trifluoroacetic acid, halogenation using a copper halide, chlorination using sulfuryl chloride-aluminum chloride, and so forth. Among these, the ordinary halogenation is preferred for the first-step halogenation and, when a next step halogenation is necessary, the method using iron as a catalyst is preferred. In this reaction, the halogenating agent is used in an amount of 0.8 to 3 moles, preferably 1 to 2 moles, per mole of compound (XXVII). The iron catalyst is used in an amount of 0.01 to 0.5 equivalent, preferably 0.05 to 0.2 equivalent, per mole of compound (XXVII). The reaction is carried out in the absence or presence of a solvent inert to the reaction. While, as the solvent, any one can be used so far as the reaction advances therein, for example, hydrocarbons such as cyclohexane, hexane, etc.; ethers such as tetrahydrofuran, dioxane, 1,2-dimethoxyethane, diethyl ether, etc.; amides such as N,N-dimethylformamide, N,N-dimethylacetamide, etc.; halogenated hydrocarbons such as dichloromethane, chloroform, carbon tetrachloride, 1,2-dichloroethane, etc., organic acids such as acetic acid, propionic acid, etc., or a suitable mixture of these solvents are preferable. The reaction time is generally 10 minutes to 10 hours, preferably 20 minutes to 5 hours. The reaction temperature is generally −20 to 120° C., preferably −10 to 80° C. It is also possible to effect two or three stages of halogenation in one step; in this case, the halogenating agent is used in an amount twice the amount mentioned above.

Compound (XXXIV) can be produced by reacting a carbanion, which is formed by the treatment of acetonitrile with a base, with compound (XXXII) to obtain compound (XXXIII) followed by dehydrating the resultant compound (XXXIII), in the same manner as in the production of compound (XII) from compound (X) mentioned hereinabove. Compound (XXXIV) is obtained as a single E-form or Z-form configurational isomer or as a mixture of such E- and Z-isomers. Acetonitrile is used in an amount of approximately 1.0 to 3.0 mols, preferably approximately 1.0 to 1.3 mols per mol of compound (XXXII). The base includes, for example, alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc. The base is used in an amount of approximately 1.0 to 5.0 mols, preferably approximately 1.0 to 1.5 mols per mol of compound (XXXII). The reaction is advantageously conducted in the presence of a solvent inert to the reaction. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc., or a suitable mixture of these solvents are preferable. The reaction time is generally 30 minutes to 48 hours, preferably 30 minutes to 5 hours. The reaction temperature is generally −78 to 100° C., preferably −78 to 50° C. The product obtained can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

The catalyst to be used for the dehydration includes, for example, acidic catalysts such as hydrochloric acid, sulfuric acid, phosphoric acid, potassium hydrogensulfate, oxalic acid, p-toluenesulfonic acid, 10-camphorsulfonic acid, boron trifluoride-ether complex, etc., and basic catalysts such as sodium hydroxide, potassium hydroxide, etc. If desired, a dehydrating agent such as N,N-cyclohexylcarbodiimide as well as alumina, sodium dioxide, phosphorus oxychloride, thionyl chloride, methanesulfonyl chloride, etc. can also be used. The reaction is advantageously conducted in either the absence of a solvent or the presence of a solvent inert to the reaction. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; sulfoxides such as dimethylsulfoxide, etc., or a suitable mixture of these solvents are preferable. The reaction time is generally 30 minutes to 24 hours, preferably 30 minutes to 5 hours. The reaction temperature is generally 0 to 200° C., preferably 0 to 150° C.

Compound (XXXIV) can also be produced by reacting a phosphonate-carbanion, which is produced by the treatment of a trialkyl phosphonoacetate with a base, with compound (XXXII), in the same manner as in the production of compound (XII) from compound (X) mentioned hereinabove. This compound (XXXIV) is obtained as a single E-form or Z-form configurational isomer or as a mixture of such E- and Z-isomers. The trialkyl phosphonoacetate includes, for example, diethyl cyanomethylphosphonate, etc. One mol of compound (XXXII) is reacted with approximately 1.0 to 3.0 mols, preferably approximately 1.0 to 1.5 mols of a trialkyl phosphonoacetate. The base includes, for example, alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc. The base is used in an amount of approximately 1.0 to 5.0 mols, preferably approximately 1.0 to 1.5 mols per mol of compound (XXXII). The reaction is advantageously conducted in a solvent inert thereto. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; sulfoxides such as dimethylsulfoxide, etc., or a suitable mixture of these solvents are preferable. The reaction time is generally 1 hour to 50 hours, preferably 1 hour to 10 hours. The reaction temperature is generally −78 to 200° C., preferably 0 to 150° C. The mixture of isomers of compound (XXXIV) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

In the case where the carbon chain at the side chain of compound (XXXIV) is extended, it can be conducted by per se known carbon-chain extension, for example, a reaction comprising hydrolysis of cyano group under alkaline or acidic conditions to convert into carboxyl group, or leading the carboxyl to ester form which is then subjecting to reduction to give an alcohol, followed by halogenation and cyanation.

Compound (XXXV) can be produced by reducing compound (XXXIV), in the same manner as in the production of compound (XV) from compound (XII) mentioned hereinabove. The reducing agent usable for this includes, for example, metal hydrides such as aluminium hydride, diisobutyl aluminium hydride, etc.; metal hydride complexes such as lithium aluminium hydride, sodium borohydride, etc. The hydrogenation catalyst usable includes, for example, a catalyst such as Raney nickel, Raney cobalt, etc. Regarding the amount of the reducing agent, the metal hydride is used in an amount of approximately 1.0 to 10 mols, preferably approximately 1.0 to 3.0 mols per mol of compound (XXXIV), the metal hydride complex is used in an amount of approximately 1.0 to 10 mols, preferably 1.0 to 3.0 mols per mol of compound (XXXIV). For the hydrogenation, a catalyst such as Raney nickel or Raney cobalt is used in an amount of approximately 10 to 1000% by weight, preferably approximately 80 to 300% by weight relative to compound (XXXIV). The reaction is advantageously conducted in a solvent inert thereto. While, as the solvent, anyone can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, etc.; amides such as N,N-dimethylformamide, N,N-dimethylacetamide, etc.; organic acids such as formic acid, acetic acid, etc., or a suitable mixture of these solvents are preferable. In the case where a Raney nickel or Raney cobalt catalyst is used, amines such as ammonia may be added to the reaction system in order to prevent any possible side reactions. The reaction time varies, depending on the activity of the catalyst and the amount thereof used, and is generally 1 hour to 100 hours, preferably 1 hour to 50 hours. The reaction temperature is generally 0 to 120° C., preferably 20 to 80° C. In the case where Raney nickel or Raney cobalt catalyst is used, the hydrogen pressure is generally 1 to 100 atmospheres. The product (XXXV) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

And, by employing stronger reaction conditions for producing compound (XXXV) (e.g. conducting the reaction at higher temperatures and for a longer time), reduction of the double bond portion and reduction of silano group can be performed simultaneously.

For producing an optically active compound (I), a method, which comprises subjecting compound (XXXV) to reduction using, for example, a catalyst for asymmetric reduction, followed by subjecting the resultant to acylation, is employed.

As the catalyst for asymmetric reduction, mention is made of, for example, transition metal—optically active phosphine complexes. Examples of the transition metal—optically active phosphine complexes include ruthenium—optically active phosphine complexes. Among them, for example, a ruthenium-2,2'-bis(diphenylphosphino)- 1,1'-binaphthyl derivative such as dirutheniumtetrachloro bis[2,2'-bis(diphenylphosphino)-1,1'-binaphthyl] triethylamine, is generally employed.

In the optically active tertiary phosphine in ruthenium—optically phosphine complexes, there exist two kinds of optical isomers, i.e. (R)- and (S)-isomers. By optionally selecting either one of (R)- or (S)-isomers of the optically active phosphine in the ruthenium—optically active phosphine complexes, the desired optically active compound can be obtained selectively (in substantially pure state).

The reduction reaction can be conducted under elevated pressure in, for example, an autoclave, under the hydrogen pressure described below, by heating and stirring.

The amount of ruthenium—optically active phosphine catalyst is, relative to compound (XXXV), ½ to ¹⁄₁₀₀₀ times as much mol., preferably ¹⁄₁₀ to ¹⁄₅₀₀ times as much mol.

This reaction can be conducted in an organic solvent. Examples of the organic solvent include aromatic hydrocarbons such as toluene, benzene, chlorobenzene, etc.; aliphatic esters such as ethyl acetate, n-propyl acetate, n-butyl acetate, etc.; ethers such as isopropyl ether, diethyl ether, tetrahydrofuran, etc.; halogenated hydrocarbons such as dichloromethane, dichloroethane, etc.; alcohols such as methanol, ethanol, isopropanol, etc.; amides such as N,N-dimethylformamide, etc.; or a mixture solvent of them. Among them, alcohols are preferable, and methanol is more preferable.

In the reaction, the volume of organic solvent is, relative to 1 weight part of compound (XXXV), usually 1 to 1000 times as much volume, preferably 2 to 20 times as much volume. The reaction temperature is usually 0 to 150° C., preferably 5 to 100° C., more preferably 10 to 80° C. The hydrogen pressure in the reaction ranges usually 5 to 150 kg/cm², preferably 30 to 110 kg/cm². The reaction time is usually 0.5 to 100 hours, preferably 1 to 50 hours, more preferably from 5 to 25 hours.

In the reaction, a Lewis acid, proton acid or the like may optionally added to the reaction mixture.

The reaction may be conducted, after adding to the reaction mixture beforehand the desired optically active compound among the compounds to be reduced, in an amount usually ranging, relative to 1 weight part of the starting compound (XXXV), from ¹⁄₂₀₀ to ⅕ times as much weight, preferably from ¹⁄₁₀₀ to ¹⁄₁₀ times as much weight.

The conversion rate of compound (XXXV) to the desired optically active compound can be determined by the following method.

Namely, an appropriate volume of the reaction mixture taken by sampling after completion of the reaction is subjected to high performance liquid chromatography (HPLC) using a per se known suitable chiral column [e.g. Chiralpak (manufactured by Daicel Chemical Industries Ltd.), ULTRON ES-OVM (SHINWA CHEMICAL INDUSTRIES LTD.)] so that the respective amounts of the desired optically active compounds can be determined.

From the reaction mixture obtained by the the above-mentioned reaction, optically active amine derivatives can be obtained by per se known methods (e.g. solvent extraction, phasic transfer, crystallization, recrystallization and chromatography).

The optically active compound (I) can be produced by subjecting the thus obtained optically active amine derivative to acylation. The reaction conditions are substantially the same as those for the production of compound (I) from compound (XXXVI) to be described later.

Compound (XXXVI) with m=2 or 3 can be produced by isomerizing compound (XXXV) with an acid, in the same manner as in the production of compound (XVI) from compound (XV) mentioned hereinabove. Preferred examples of the acid catalyst to be used include, for example, inorganic acids such as hydrochloric acid, sulfuric acid, nitric acid, hydrobromic acid, phosphoric acid, etc.; organic acids such as acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid, etc.; boron trifluoride-ether complex, etc. The acid catalyst is used in an amount of approximately 0.01 to 10 mols, preferably approximately 0.01 to 5.0 mols per mol of compound (XXXV). The reaction is advantageously conducted in either the absence of a solvent or the presence of a solvent inert to the reaction. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; sulfoxides such as dimethylsulfoxide, etc.; water, etc., or a suitable mixture of these solvents are preferable. The reaction time is generally 10 minutes to 12 hours, preferably 10 minutes to 2 hours. The reaction temperature is generally −10 to 200° C., preferably −10 to 100° C. The product (XXXVI) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (XXXVI) with m=1 can be produced by treating compound (XXXII) with trimethylsilylcyanide in the presence of a Lewis acid, then treating the resultant intermediate with an acid to remove its trimethylsilyloxy group and thereafter reducing it at its cyano group, in the same manner as in the production of compound (XVI) from compound (X) mentioned hereinabove. The Lewis acid includes, for example, zinc iodide, anhydrous aluminium chloride, anhydrous zinc chloride, anhydrous iron chloride, etc. The Lewis acid catalyst is used in an amount of approximately 0.01 to 10 mols, preferably approximately 0.01 to 1.0 mol per mol of compound (XXXII). The reaction is advantageously conducted in either the absence of a solvent or the presence of a solvent inert to the reaction. While, as the solvent, any one can be used so far as the reaction advances therein, for example, ethers such as diethyl ether, tetrahydrofuran, dioxane, 1,2-dimethoxyethane, etc.; hydrocarbons such as benzene, toluene, cyclohexane, hexane, etc., or a suitable mixture of these solvents are preferable. The reaction time is generally 10 minutes to 12 hours, preferably 30 minutes to 3 hours. The reaction temperature is generally −10 to 200° C., preferably −10 to 100° C. The obtained intermediate can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography. Next, the intermediate is treated with an acid. Preferably, the acid includes, for example, inorganic acids such as hydrochloric acid, sulfuric acid, nitric acid, hydrobromic acid, phosphoric acid, etc.; organic acids such as acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid, etc.; boron trifluoride-ether complex, etc. The acid is used in an amount of approximately 1 to 100 mols, preferably approximately 1 to 10 mols per mol of compound (XXXII). The reaction is advantageously conducted in either the absence of a solvent or the presence of a solvent inert to the reaction. While, as the solvent, any one can be used so far as the reaction advances therein, for example, ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; sulfoxides such as dimethylsulfoxide, etc., or a suitable mixture of these solvents are preferable. The reaction time is generally 30 minutes to 12 hours, preferably 30 minutes to 5 hours. The reaction temperature is generally 0 to 200° C., preferably 20 to 150° C. The reduction of the cyano group in the resultant intermediate can be conducted under the same conditions as those for the production of compound (XV) from compound (XII). The product (XXXVI) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (I) can also be produced by reacting compound (XXXVI) with a carboxylic acid or a salt or a reactive derivative thereof. The carboxylic acid includes, for example, compounds of the formula $R^1$—COOH (in which $R^1$ is as defined above). The reactive derivatives of the carboxylic acid include, for example, acid halides (e.g., acid chlorides, acid bromides, etc.), acid amides (e.g., acid amides with pyrazole, imidazole, benzotriazole, etc.), acid anhydrides (e.g., $C_{1-6}$ aliphatic carboxylic acid anhydrides such as acetic acid anhydrides, propionic acid anhydrides, butyric acid anhydrides, etc.), acid azides, active esters (e.g., diethoxyphosphates, diphenoxyphosphates, p-nitrophenyl esters, 2,4-dinitrophenyl esters, cyanomethyl esters, pentachlorophenyl esters, esters with N-hydroxysuccinimide, esters with N-hydroxyphthalimide, esters with 1-hydroxybenzotriazole, esters with 6-chloro-1-hydroxybenzotriazole, esters with 1-hydroxy-1H-2-pyridone, etc.), active thioesters (e.g., 2-pyridyl thioesters, 2-benzothiazolyl thioesters, etc.), etc.

In place of using the reactive derivative, the carboxylic acid or a salt thereof may be directly reacted with compound (XXXVI) in the presence of a suitable condensing agent. The condensing agent includes, for example, N,N'-disubstituted carbodiimides such as N,N'-dicyclohexylcarbodiimide, 1-ethyl-3-(3-dimethylaminopropyl)carbodiimide (WSC) hydrochloride, etc.; azolides such as N,N'-carbonyldiimidazole, etc.; dehydrating agents such as N-ethoxycarbonyl-2-ethoxy-1,2-dihydroquinoline, phosphorus oxychloride, alkoxyacetylenes, etc.; 2-halogenopyridinium salts such as 2-chloromethylpyridinium iodide, 2-fluoro-1-methylpyridinium iodide, etc. It is believed that the reaction with the condensing agent may advance via the reactive derivative of the carboxylic acid used. The carboxylic acid of the formula $R^1$—COOH (in which $R^1$ is as defined above) or its reactive derivative is used generally at approximately 1.0 to 5.0 mols, preferably approximately 1.0 to 2.0 mols per mol of compound (XXXVI). The reaction is advantageously conducted in a solvent inert to the reaction. While, as the solvent, any one can be used so far as the reaction advances therein, for example, ethers such as diethyl ether, tetrahydrofuran, dioxane, 1,2-dimethoxyethane, etc.; hydrocarbons such as benzene, toluene, cyclohexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; sulfoxides such as dimethylsulfoxide, etc.; water or a suitable mixture of these solvents are preferable. In the case where an acid halide is used as a reactive derivative of a carboxylic acid, the reaction may be conducted in the presence of a de-acidifying agent in order to remove the released hydrogen halide from the reaction system. The de-acidifying agent includes, for example, basic bases such as sodium carbonate, potassium carbonate, sodium hydrogencarbonate, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc. It is desirable that such a de-acidifying agent is previously added to the reaction system. The reaction time varies, depending on the reagents and the solvents used, and is generally 30 minutes to 24 hours, preferably 30 minutes to 4 hours. The reaction temperature is generally 0 to 100° C., preferably 0 to 70° C.

Compound (I) can also be produced by treating compound (XXXV) with a carboxylic acid of the formula $R^1$—COOH (in which $R^1$ is as defined above), a salt or a reactive derivative thereof, stirring them under acidic conditions for 5 minutes to 3 hours, preferably 10 minutes to 1 hour, at 0 to 100° C., preferably 0 to 70° C., and thereafter adding a de-acidifying agent such as that mentioned above to the reaction system to thereby make the resultant intermediate acylated. The process can be accompanied by isomerization of the reaction system to give compound (I). The carboxylic acid or its reactive derivative is used generally in amount of approximately 1.0 to 5.0 mols, preferably approximately 1.0 to 2.0 mols per mol of compound (XXXV). The reaction is advantageously conducted in a solvent inert to the reaction. While, as the solvent, any one can be used so far as the reaction advances therein, for example, ethers such as diethyl ether, tetrahydrofuran, dioxane, 1,2-dimethoxyethane, etc.; hydrocarbons such as benzene, toluene, cyclohexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; sulfoxides such as dimethylsulfoxide, etc., or a suitable mixture of these solvents are preferable. The product (I) thus obtained can be isolated from the reaction mixture by ordinary methods, and it can be easily purified by means of separation, for example, recrystallization, distillation and chromatography.

To obtain compound (I) wherein $R^2$ is an alkyl group, the acylated compound as obtained in the above is alkylated with a corresponding alkylating agent (e.g., alkyl halides, sulfonates with alcohols) in the presence of a base. The alkylating agent is used in an amount of approximately 1.0 to 5.0 mols, preferably approximately 1.0 to 2.0 mols per mol of compound (I) to be alkylated therewith. The base includes, for example, inorganic bases such as sodium hydroxide, potassium hydroxide, etc.; basic salts such as sodium carbonate, potassium carbonate, cesium carbonate, sodium hydrogencarbonate, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.; alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc. The base is used in an amount of approximately 1.0 to 5.0 mols, preferably approximately 1.0 to 2.0 mols per mol of compound (I). The reaction is advantageously conducted in a solvent inert to the reaction. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; sulfoxides such as dimethylsulfoxide, etc., or a suitable mixture of these solvents are preferable. The reaction time is generally 30 minutes to 48 hours, preferably 30 minutes to 6 hours. The reaction temperature is generally −20 to 200° C., preferably −10 to 150° C. The product (I) can be isolated from the reaction mixture by ordinary methods, and it can be easily purified by means of separation, for example, recrystallization, distillation and chromatography.

To obtain compound (I) wherein the double-bond moiety has been reduced, the double-bond moiety in compound (I) is catalytically reduced under the same conditions as those for the production of compound (VII) from compound (VIII).

Reaction Process 4:

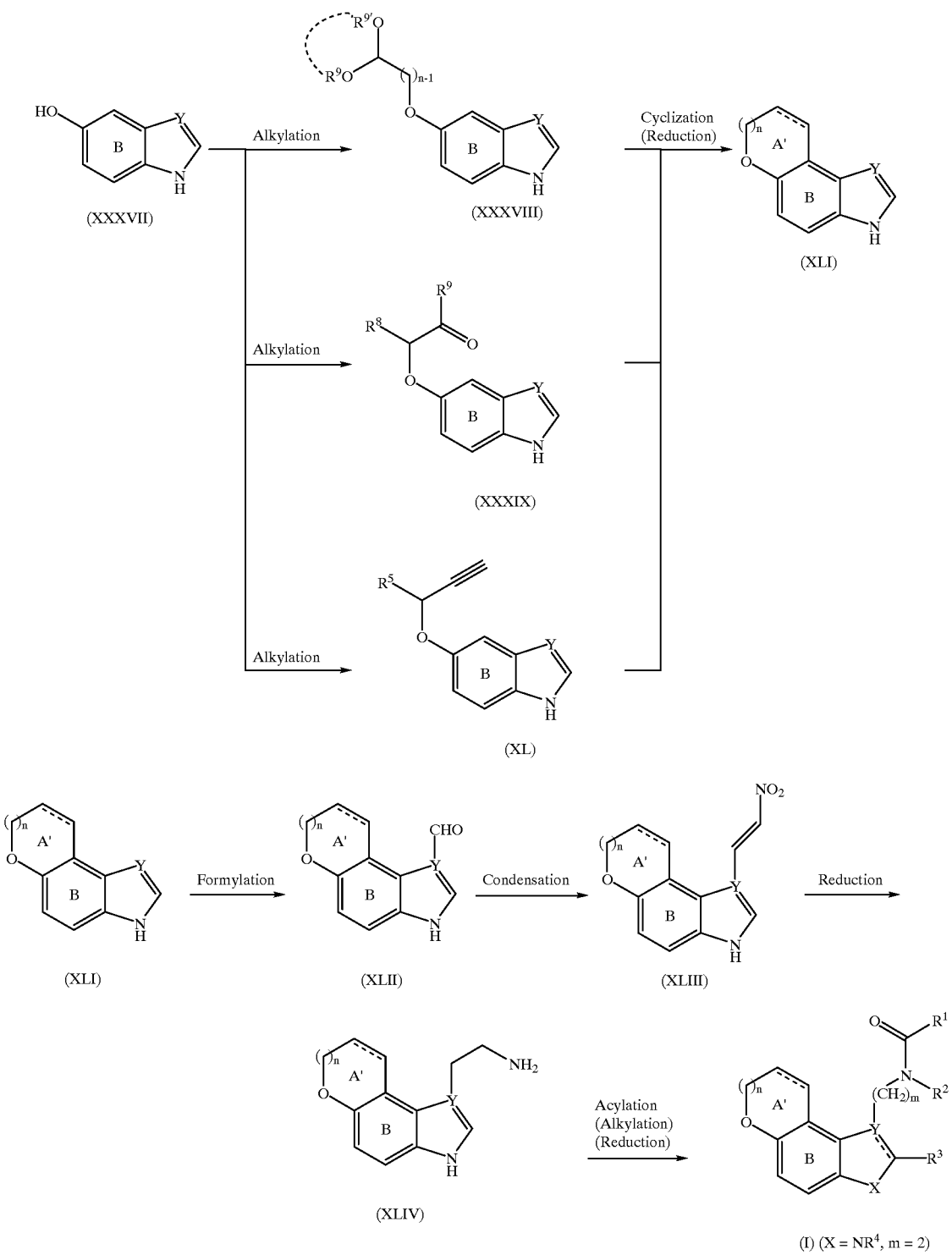

Compound (XXXVII) can be produced by per se known methods, for example, the methods described in J. Chem. Soc., p. 2525 (1952); ibid., p. 1165 (1954); J. Org. Chem. Vol. 49, p. 4833 (1984); J. Heterocyclic Chem., Vol. 24, p. 941 (1987); J. Med. Chem., Vol. 17, p. 747 (1974); Helv. Chim. Acta, Vol. 48, p. 252 (1965), or methods analogous thereto.

Compound (XXXVIII) can be produced by reacting compound (XXXVII) with a corresponding alkylating agent (e.g., alkyl halides, sulfonates with alcohols) in the presence of a base. The alkylating agent is used in an amount of approximately 0.5 to 5.0 mols, preferably approximately 0.8 to 2.0 mols per mol of compound (XXXVII) to be alkylated therewith. The base includes, for example, inorganic bases such as sodium hydroxide, potassium hydroxide, etc.; basic salts such as sodium carbonate, potassium carbonate, cesium carbonate, sodium hydrogencarbonate, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.; alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc. The base is used in an amount of approximately 1.0 to 5.0 mols, preferably approximately 1.0 to 2.0 mols per mol of compound (XXXVII). The reaction is advantageously conducted in a solvent inert to the reaction. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; sulfoxides such as dimethylsulfoxide, etc., or a suitable mixture of these solvents are preferable. The reaction time is generally 30 minutes to 48 hours, preferably 1 to 24 hours. The reaction temperature is generally −20 to 200° C., preferably 0 to 150° C. The product (XXXVIII) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (XXXIX) can be produced by reacting compound (XXXVII) with a corresponding α-haloketone in the presence of a base. The α-haloketone is used in an amount of approximately 1.0 to 10.0 mols, preferably approximately 1.0 to 5.0 mols per mol of compound (XXXVII). The base includes, for example, inorganic bases such as sodium hydroxide, potassium hydroxide, etc.; basic salts such as sodium carbonate, potassium carbonate, cesium carbonate, sodium hydrogencarbonate, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.; alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc. The base is used in an amount of approximately 1.0 to 5.0 mols, preferably approximately 1.0 to 2.0 mols per mol of compound (XXXVII). The reaction is advantageously conducted in a solvent inert to the reaction. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; ketones such as acetone, methyl ethyl ketone, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; sulfoxides such as dimethylsulfoxide, etc., or a suitable mixture of these solvents are preferable. The reaction time is generally from 30 minutes to 48 hours, preferably from 1 to 24 hours. The reaction temperature is generally −20 to 200° C., preferably 0 to 150° C. The product (XXXIX) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (XL) can be produced by reacting compound (XXXVII) with a corresponding alkylating agent (e.g., substituted acetylene-alkyl halides, sulfonates with substituted acetylene alcohols, etc.) in the presence of a base. The alkylating agent is used in an amount of approximately 1.0 to 20.0 mols, preferably approximately 1.0 to 10.0 mols per mol of compound (XXXVII). The base includes, for example, inorganic bases such as sodium hydroxide, potassium hydroxide, etc.; basic salts such as sodium carbonate, potassium carbonate, cesium carbonate, sodium hydrogencarbonate, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.; alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc. The base is used in an amount of approximately 1.0 to 5.0 mols, preferably approximately 1.0 to 2.0 mols per mol of compound (XXXVII). The reaction is advantageously conducted in a solvent inert to the reaction. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; sulfoxides such as dimethylsulfoxide, etc., or a suitable mixture of these solvents are preferable. The reaction time is generally 30 minutes to 48 hours, preferably 1 to 24 hours. The reaction temperature is generally −20 to 200° C., preferably 0 to 150° C. The product (XL) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

In the above-mentioned alkylation, if the alkylation is not selectively directed towards the hydroxyl group of the compound, the amino group of the compound shall be protected and de-protected, if necessary. The protection and the de-protection of the amino group may be conducted in accordance with conventional known methods. For example, referred to is the disclosure in the chapter "Protection for the Amino Group" in "Protecting Groups in Organic Synthesis" by T. W. Green (2nd Ed., 1991).

Compound (XLI) can be produced by per se known cyclization of compound (XXXVIII), (XXXIX) or (XL). The cyclization can be conducted by, for example, a method by heating, a method using an acidic substance, a method using a basic substance, or methods analogous thereto.

The cyclization under heating is advantageously conducted in either the absence of a solvent or the presence of a solvent inert to the reaction. While, as the solvent, any one can be used so far as the reaction advances therein, for example, high-boiling-point hydrocarbons such as 1,2,3,4-tetrahydronaphthalene, bromobenzene, etc.; high-boiling-point ethers such as diphenyl ether, diethyleneglycol dimethyl ether, etc.; N,N-dimethylaniline, N,N-diethylaniline, etc., or a suitable mixture of these solvents are preferable. The reaction time is generally 10 minutes to 24 hours, preferably 10 minutes to 10 hours. The reaction temperature is generally 100 to 300° C., preferably 100 to 250° C.

In the case where the cyclization is conducted by using an acidic substance, the acidic substance includes, for example, phosphorus oxychloride, phosphorus pentachloride, phosphorus pentoxide, phosphorus trioxide, thionyl chloride, hydrochloric acid, hydrochloric acid, sulfuric acid, phosphoric acid, polyphosphoric acid, p-toluenesulfonic acid, etc. The acidic substance is used in an amount of approximately 0.5 to 100 mols, preferably approximately 5.0 to 20 mols per mol of compound (XXXVIII), (XXXIX) or (XL). The reaction is advantageously conducted in either the absence of a solvent or the presence of a solvent inert to the reaction. While, as the solvent, any one can be used so far as the reaction advances therein, for example, aromatic hydrocarbons such as benzene, toluene, etc.; saturated hydrocarbons such as cyclohexane, hexane, etc.; ethers such as tetrahydrofuran, dioxane, 1,2-dimethoxyethane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; acid anhydrides such as acetic anhydride, etc.; sulfoxides, such as dimethylsulfoxide, etc.; water, or a suitable mixture of these solvents are preferable. The reaction time is generally 30 minutes to 12 hours, preferably 30 minutes to 6 hours. The reaction temperature is generally 0 to 200° C., preferably 0 to 150° C.

In the case where the cyclization is conducted by using a basic substance, the basic substance includes, for example, sodium hydroxide, potassium hydroxide, sodium carbonate, potassium carbonate, sodium hydrogencarbonate, etc. The basic substance is used in an amount of approximately 0.5 to 100 mols, preferably approximately 5.0 to 20 mols per mol of compound (XXXVIII), (XXXIX) or (XL). The reaction is advantageously conducted in either the absence of a solvent or the presence of a solvent inert to the reaction. While, as the solvent, any one can be used so far as the reaction advances therein, for example, alcohols such as methanol, ethanol, propanol, etc.; ketones such as acetone, methyl ethyl ketone, etc.; water, or a suitable mixture of these solvents are preferable. The reaction time is generally 30 minutes to 12 hours, preferably 30 minutes to 6 hours. The reaction temperature is generally 0 to 200° C., preferably 0 to 150° C.

The double-bond moiety in the ring as newly formed by the above cyclization may optionally be reduced in the same manner as in the production of compound (VII) from compound (VIII).

The product (XLI) obtained through the cyclization can be isolated from the reaction mixture by ordinary methods, and it can be easily purified by means of separation, for example, recrystallization, distillation and chromatography.

Compound (XLII) can be produced from compound (XLI) in accordance with per se known methods, for example, the methods described in The Chemistry of Heterocyclic Compounds, Vol. 25, Part 3 (W. J. Houlihan, ed., John Wiley and Sons, Inc., New York), p. 361 (1979); J. Chem. Soc., p. 3842 (1954); Tetrahedron, Vol. 36, p. 2505 (1980); Monatsh. Chem., Vol. 117, p. 375 (1986), or methods analogous thereto.

Compound (XLIII) can be produced from compound (XLII) and nitromethane through aldol condensation in the presence of a base. This is obtained as a single E-form or Z-form configurational isomer or as a mixture of such E- and Z-isomers. Nitromethane is used in an amount of approximately 1.0 to 100 mols, preferably approximately 1.0 to 50 mols per mol of compound (XLII). The base includes, for example, inorganic bases such as sodium hydroxide, potassium hydroxide, sodium carbonate, potassium carbonate, sodium hydrogencarbonate, etc.; primary amines such as methylamine, propylamine, butylamine, benzylamine, aniline, etc.; ammonium acetate, alumina, etc. The base is used in an amount of approximately 0.01 to 5.0 mols, preferably 0.1 to 1.0 mol per mol of compound (XLII). The reaction is advantageously conducted in a solvent inert thereto. While, as the solvent, any one can be used so far as the reaction advances therein, for example, alcohols such as methanol, ethanol, propanol, etc.; hydrocarbons such as benzene, toluene, cyclohexane, hexane, etc.; amides such as N,N-dimethylformamide, N,N-dimethylacetamide, etc.; water, or a suitable mixture of these solvents are preferable. The reaction time is generally 30 minutes to 72 hours, preferably 30 minutes to 24 hours. The reaction temperature is generally −20 to 200° C., preferably from −10 to 150° C. The product (XLIII) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (XLIV) can be produced by reducing compound (XLIII). The reducing agent usable for this includes, for example, metal hydrides such as aluminium hydride, diisobutyl aluminium hydride, etc.; metal hydride complexes such as lithium aluminium hydride, sodium borohydride, lithium borohydride, sodium borohydride cyanide, etc. As the hydrogenation catalyst, for example, usable are Raney nickel, platinum oxide, platinum on activated carbon, palladium on activated carbon, palladium on barium sulfate, nickel, copper-chromium oxide, rhodium, cobalt, ruthenium, etc. Additives (promoters) that enhance the activity of a catalyst used can be added to the reaction system. Acidic additives advantageously usable for this purpose include, for example, inorganic acids such as hydrochloric acid, sulfuric acid, nitric acid, perchloric acid, hydrobromic acid, phosphoric acid, etc.; organic acids such as acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid, etc. Basic additives are also advantageously usable and include, for example, sodium hydroxide, potassium hydroxide, etc. Regarding the amount of the reducing agent to be used, the metal hydride is used in an amount of approximately 1.0 to 10 mols, preferably approximately 1.0 to 3.0 mols per mol of compound (XLIII), and the metal hydride complex is used in an amount of approximately 1.0 to 10 mols, preferably 1.0 to 3.0 mols per mol of compound (XLIII). For the hydrogenation, a catalyst such as Raney nickel or Raney cobalt is used in an amount of approximately 10 to 1000% by weight, preferably approximately 100 to 300% by weight relative to compound (XLIII). The reaction is advantageously conducted in a solvent inert thereto. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, etc.; amides such as N,N-dimethylformamide, N,N-dimethylacetamide, etc.; organic acids such as formic acid, acetic acid, etc., or a suitable mixture of these solvents are preferable. The reaction time varies, depending on the activity of the catalyst or the reducing agent and the amount thereof used, and is generally 1 hour to 100 hours, preferably 1 hour to 50 hours. The reaction temperature is generally 0 to 120° C., preferably 20 to 80° C. In the case where Raney nickel or the like catalyst is used, the hydrogen pressure shall be generally 1 to 100 atmospheres. The product (XLIV) can be used in the next reaction step, while it is in the reaction mixture or in the form of a crude product. If desired, however, it may be isolated from the reaction mixture by ordinary methods, and it can be easily purified by means of separation, for example, recrystallization, distillation and chromatography.

Compound (XLIV) can also be produced in accordance with per se known methods, for example, the methods described in J. Med. Chem., Vol. 35, p. 3625 (1992); Tetrahedron, Vol. 48, p. 1039 (1992), or methods analogous thereto.

Compound (I) can be produced by reacting compound (XLIV) with a carboxylic acid or a salt thereof or a reactive derivative thereof. The carboxylic acid includes, for example, compounds of the formula $R^1$-COOH (in which $R^1$ is as defined above). The reactive derivatives of the carboxylic acid include, for example, acid halides (e.g., acid chlorides, acid bromides, etc.), acid amides (e.g., acid amides with pyrazole, imidazole, benzotriazole, etc.), acid anhydrides (e.g., $C_{1-6}$ aliphatic carboxylic acid anhydrides such as acetic acid anhydrides, propionic acid anhydrides, butyric acid anhydrides, etc.), acid azides, active esters (e.g., diethoxyphosphates, diphenoxyphosphates, p-nitrophenyl esters, 2,4-dinitrophenyl esters, cyanomethyl esters, pentachlorophenyl esters, esters with N-hydroxysuccinimide, esters with N-hydroxyphthalimide, esters with 1-hydroxybenzotriazole, esters with 6-chloro-1-hydroxybenzotriazole, esters with 1-hydroxy-1H-2-pyridone, etc.), active thioesters (e.g., 2-pyridyl thioesters, 2-benzothiazolyl thioesters, etc.), etc.

In place of using the reactive derivative, the carboxylic acid or its salt may be directly reacted with compound (XLIV) in the presence of a suitable condensing agent. The condensing agent includes, for example, N,N'-di-substituted carbodiimides such as N,N'-dicyclohexylcarbodiimide, 1-ethyl-3-(3-dimethylaminopropyl)carbodiimide (WSC) hydrochloride, etc.; azolides such as N,N'-carbonyldiimidazole, etc.; dehydrating agents such as N-ethoxycarbonyl-2-ethoxy-1,2-dihydroquinoline, phosphorus oxychloride, alkoxyacetylenes, etc.; 2-halogenopyridinium salts such as 2-chloromethylpyridinium iodide, 2-fluoro-1-methylpyridinium iodide, etc. It is believed that the reaction with the condensing agent may advance via the reactive derivative of the carboxylic acid used. The carboxylic acid of the formula $R^1$-COOH (in which $R^1$ is as defined above) or its reactive derivative is used generally in an amount of approximately 1.0 to 5.0 mols, preferably approximately 1.0 to 2.0 mols per mol of compound (XLIV). The reaction is advantageously conducted in a solvent inert to the reaction. While, as the solvent, any one can be used so far as the reaction advances therein, for example, ethers such as diethyl ether, tetrahydrofuran, dioxane, 1,2-dimethoxyethane, etc.; hydrocarbons such as benzene, toluene, cyclohexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; sulfoxides such as dimethylsulfoxide, etc.; water or a suitable mixture of these solvents are preferable. In the case that acid halides are used as the reactive derivatives of carboxylic acids, the reaction may be conducted in the presence of a deacidifying agent in order to remove the released hydrogen halide from the reaction system. The deacidifying agent includes, for example, basic bases such as sodium carbonate, potassium carbonate, sodium hydrogencarbonate, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc. It is desirable that such a de-acidifying agent is previously added to the reaction system. The reaction time varies, depending on the reagents and the solvents used, and is generally 30 minutes to 24 hours, preferably 30 minutes to 4 hours. The reaction temperature is generally 0 to 100° C., preferably 0 to 70° C.

To obtain compound (I) wherein $R^2$ is an alkyl group, the acylated compound as obtained in the above is alkylated with a corresponding alkylating agent (e.g., alkyl halides, sulfonates with alcohols) in the presence of a base. The alkylating agent is used in an amount of approximately 1.0 to 5.0 mols, preferably approximately 1.0 to 2.0 mols per mol of compound (I) to be alkylated therewith. The base includes, for example, inorganic bases such as sodium hydroxide, potassium hydroxide, etc.; basic salts such as sodium carbonate, potassium carbonate, cesium carbonate, sodium hydrogencarbonate, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc.; alkali metal hydrides such as sodium hydride, potassium hydride, etc.; metal amides such as sodium amide, lithium diisopropylamide, lithium hexamethyldisilazide, etc.; metal alkoxides such as sodium methoxide, sodium ethoxide, potassium tert-butoxide, etc. The base is used in an amount of approximately 1.0 to 5.0 mols, preferably approximately 1.0 to 2.0 mols per mol of compound (I). The reaction is advantageously conducted in a solvent inert to the reaction. While, as the solvent, any one can be used so far as the reaction advances therein, for example, alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; sulfoxides such as dimethylsulfoxide, etc., or a suitable mixture of these solvents are preferable. The reaction time is generally 30 minutes to 48 hours, preferably 30 minutes to 6 hours. The reaction temperature is generally −20 to 200° C., preferably −10 to 150° C. The product (I) can be isolated from the reaction mixture by ordinary methods, and it can be easily purified by means of separation, for example, recrystallization, distillation and chromatography.

Compound (I) in which the double-bond moiety has been reduced can be produced in the same manner as in the production of compound (VII) from compound (VIII).

Reaction Process 5:

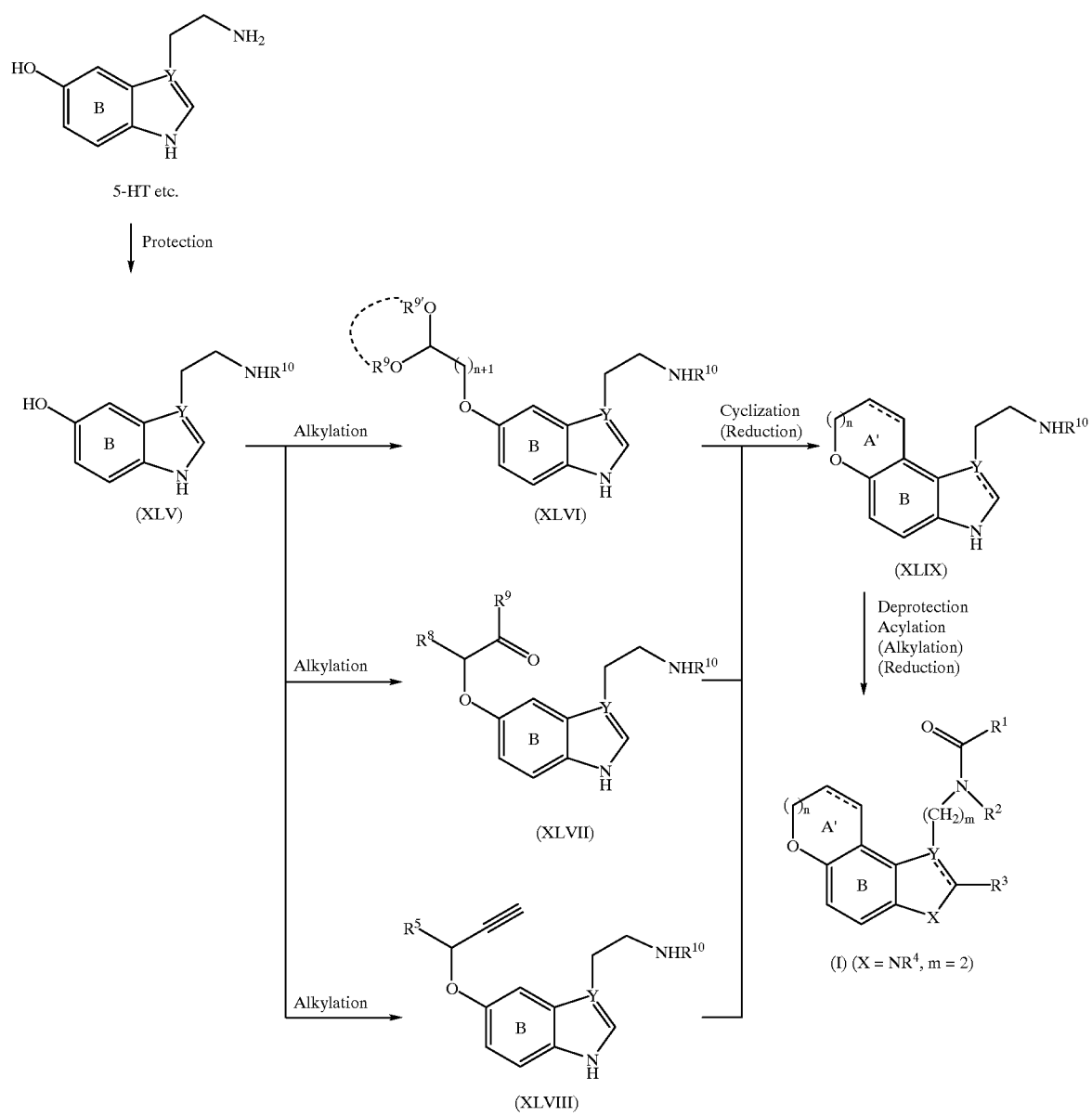

Compound (XLV) can be produced by, for example, protecting the primary amino group of 5-hydroxytryptamine (5-HT). $R^{10}$ represents a protective group and the "protective group" includes those "amino-protecting group" mentioned later herein. The protection of the amino group may be conducted in accordance with per se known methods. For example, referred to is the disclosure in the chapter "Protection for the Amino group" in "Protecting Groups in Organic Synthesis" by T. W. green (2nd Ed., 1991).

Compound (XLVI) can be produced from compound (XLV) in the same manner as in the production of compound (XXXVIII) from compound (XXXVII).

Compound (XLVII) can be produced from compound (XLV) in the same manner as in the production of compound (XXXIX) from compound (XXXVII).

Compound (XLVIII) can be produced from compound (XLV) in the same manner as in the production of compound (XL) from compound (XXXVII).

Compound (XLIX) can be produced from compound (XLVI), (XLVII) or (XLVIII) in the same manner as in the production of compound (XLI) from compound (XXXVIII), (XXXIX) or (XL). It can also be produced by per se known methods, for example, the methods described in Tetrahedron Lett., Vol. 36, p. 7019 (1995) or methods analogous thereto. Compound (XLIX) in which the double-bond moiety has been reduced can be produced in the same manner as in the production of compound (VII) from compound (VIII).

Compound (I) can be produced by de-protecting the protected amino group at the side chain in compound (XLIX) followed by processing the resultant compound in the same manner as in the production of compound (I) from compound (XLIV). The de-protection of the amino group may be conducted by per se known methods. For example, referred to is the disclosure in chapter "Protection for the Amino Group" in "Protecting Groups in Organic Synthesis" by T. W. Green (2nd Ed., 1991).

Reaction Process 6:

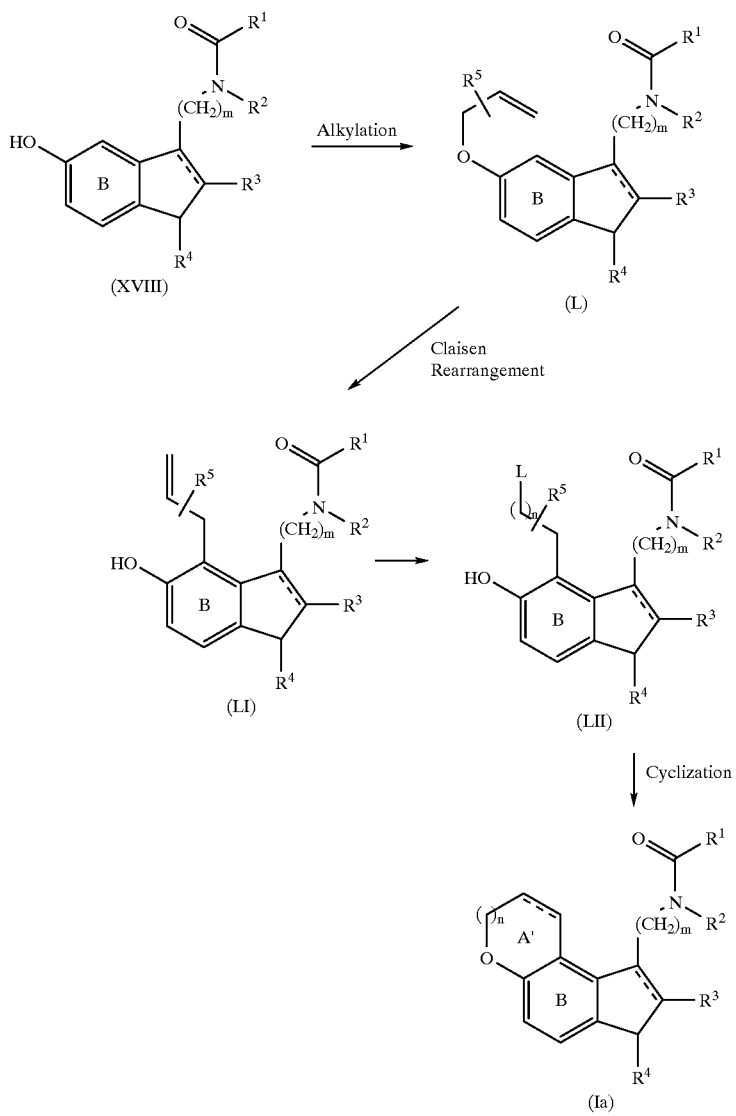

Compound (L) can be produced by allowing compound (XVIII) to react with a corresponding alkylating agent (e.g. substituted allyl halide or sulfonic acid ester of substituted allyl alcohol) in the presence of a base. Relative to 1 mol. of compound (XVIII), about 1.0 to 20.0 mol., preferably about 1.0 to 10.0 mol., of the alkylating agent is used. Examples of the base include basic salts such as sodium carbonate, potassium carbonate, cesium carbonate, sodium hydrogencarbonate, etc.; inorganic bases such as sodium hydroxide, potassium hydroxide, etc.; aromatic amines such as pyridine, lutidine, etc.; tertiary amines such as triethylamine, tripropylamine, tributylamine, cyclohexyldimethylamine, 4-dimethylaminopyridine, N,N-dimethylaniline, N-methylpiperidine, N-methyl pyrrolidine, N-methylmorpholine, etc.; alkali metal hydrides such as sodium hydride, potassium hydride, etc.; metal amides such as sodium amide, lithium diisopropylamide, lithium hexamethyl disilazide, etc.; and metal alkoxides such as sodium methoxide, sodium ethoxide and potassium tertiary butoxide, etc. Relative to 1 mol. of compound (XVIII), about 1.0 to 5.0 mol., preferably about 1.0 to 2.0 mol., of the base is used. It is advantageous to conduct this reaction using an inert solvent. As the solvent, any one can be used so long as it does not hamper the proceeding of the reaction. Preferable examples of the solvent include alcohols such as methanol, ethanol, propanol, etc.; ethers such as diethyl ether, tetrahydrofuran, dioxane, 1,2-dimethoxyethane, etc.: hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; sulfoxides such as dimethyl sulfoxide, etc.; and a mixture of these solvents. The reaction time is usually 30 minutes to 48 hours, preferably one hour to 24 hours. The reaction temperature is usually −20 to 200° C., preferably 0 to 150° C. While the product (L) can be used for the subsequent reaction as in the state of reaction mixture or as a crude product, it can optionally be isolated from the reaction mixture by a conventional method and can be readily purified by means of, for example, recrystallization, distillation and chromatography.

Compound (LI) can be produced by subjecting compound (L) to Claisen rearrangement reaction. The Claisen rearrangement reaction can be conducted by a per se known method described in, for example, "Shin Jikken Kagaku Koza Vol.14—Syntheses and Reactions of Organic Compounds (I), 3.2 Phenol, p.559 (compiled by The Chemical Society of Japan), Organic Reactions, Vol.2, pp.1–48, Vol.22, pp.1–252, or methods analogous to them. Concretely to state, the rearrangement reaction proceeds by heating compound (LI) in the absence or presence of a solvent. As the solvent, use is made of solvents having high boiling points, such as N,N-diethylaniline, diphenyl ether, 1,2,3,4-tetramethyl benzene, etc. The reaction time is usually 30 minutes to 48 hours, preferably one hour to 24 hours. The reaction temperature is usually 150 to 250° C., preferably 180 to 220° C. While the product (LI) can be used for the subsequent reaction as in the state of the reaction mixture or as a crude product, it can be isolated from the reaction mixture by a conventional method and can be easily purified by means of, for example, recrystallization, distillation and chromatography.

Compound (LII) can be produced by oxidatively cleaving the double bond of compound (LI), followed by subjecting the compound to reduction. The leaving group represented by L in compound (LII) is preferably a hydroxy, halogen atoms, alkylsulfonate, arylsulfonate. The oxidative cleavage can be conducted by a per se known method using, for example, permanganate, permanganate-periodate, chromic acid, lead tetraacetate-$N_3$ complex, ozone, osmium tetroxide-hydrogen peroxide, osmium tetroxide-periodic acid, ruthenium tetroxide, iodosyl compound, oxygen, hydrogen peroxide or organic peroxide, organic peracid, nitrobenzene and anodic oxidation, a method described in, for example, Shin Jikken Kagaku Koza, Vol.15—Oxidation and Reduction—(compiled by The Chemical Society of Japan), or methods analogous to them. In the case of ozone oxidation, for example, while any solvent can be used so long as it does not hamper the proceeding of the reaction, for example, alcohols such as methanol, ethanol and propanol, etc.; ethers such as diethyl ether, tetrahydrofuran, dioxane, 1,2-diethoxyethane, etc.; hydrocarbons such as benzene, toluene, cyclohexane, hexane, etc.; esters such as ethyl acetate, etc.; amides such as N,N-dimethylformamide, N,N-dimethylacetamide, etc; halogenated hydrocarbons such as dichloromethane, chloroform, carbon tetrachloride, 1,2-dichloroethane, etc.; nitriles such as acetonitrile, propionitrile, etc.; ketones such as acetone, etc.; sulfoxides such as dimethyl sulfoxide; or a mixture of them. The reaction time, depending on the capacity of the ozone generator, is usually 5 minutes to 48 hours, preferably 5 minutes to 12 hours. The reaction temperature is usually −100 to 0° C., preferably −75 to −20° C. As the reducing agent to be employed in the subsequent reduction, use is made of, for example, metal hydrides such as aluminum hydride and diisobutyl aluminum hydride, and metal hydride complex compounds such as lithium aluminum hydride and sodium borohydride. The amount of the reducing agent to be used, in the case of a metal hydride for example, is about 1.0 to 20 mol., preferably about 1.0 to 10 mol., relative to 1 mol. of compound (LI), and, in the case of a metal hydride complex compound, it is about 1.0 to 20 mol., preferably about 1.0 to 10 mol., relative to 1 mol. of compound (LI). Use of a solvent inert to the reaction is advantageous for conducting this reaction. As such solvent, while any one can be used so long as the reaction proceeds, alcohols such as methanol, ethanol, propanol, etc,; ethers such as diethyl ether, tetrahydrofuran, dioxane, 1,2-dimethoxyethane, etc.; hydrocarbons such as benzene, toluene, cyclohexane, etc.; amides such as N,N-dimethylformamide, N,N-dimethylacetamide, etc.; organic acids such as formic acid, acetic acid, etc.; or a mixture solvent of them are preferable. While the reaction time varies with the activity and amount of the reagent then employed, it usually is 5 minutes to 100 hours, preferably 5 minutes to 50 hours. The reaction temperature is usually −78° C. to 120° C., preferably from -78° C. to 50° C. While compound (LII) can be used for the subsequent reaction as it is or as a crude product, it can be isolated from the reaction mixture by a conventional method, which can readily be purified by means of recrystallization, distillation and chromatography.

Compound (Ia) can be produced by subjecting compound (LII) (wherein L is hydroxy), after converting to a sulfonate compound or a halogenate, to ring closure reaction.

The sulfonate compound can be produced by allowing compound (LII) to react with as a corresponding sulfonyl chloride compound (e.g. benzenesulfonyl chloride, toluenesulfonyl chloride, and $C_{1-4}$ alkylsulfonyl chloride such as methanesulfonyl chloride), in the presence of a base. Relative to 1 mol. of compound (LII), about 1.0 to 50.0 mol., preferably about 1.0 to 20.0 mol., of a sulfonyl chloride compound is employed. Examples of the base includes basic salts such as sodium carbonate, potassium carbonate, sodium hydrogencarbonate, etc.; aromatic amine such as pyridine, lutidine, etc.; tertiary amines such as triethylamine, tripropylamine, tributylamine, cyclohexyldimethylamine, 4-dimethylaminopyridine, N-methylmorpholine, etc.; alkali metal hydrides such as sodium hydride, potassium hydride, etc.; metal amides such as sodium amide, lithium diisopropylamide, lithium hexamethyl disilazide, etc.; and metal alkoxides such as sodium methoxide, sodium ethoxide and potassium tertiary butoxide, etc. Relative to 1 mol. of compound (LII), the base is used in an amount of about 1.0 to 10.0 mol., preferably about 1.0 to 3.0 mol. Use of a solvent inert to the reaction is advantageous for conducting this reaction. As the solvent, while any one can be used so long as the reaction proceeds, ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; sulfoxides such as dimethyl sulfoxide, etc.; or a mixture of them are preferable. The reaction time is usually 10 minutes to 6 hours, preferably 10 minutes to 2 hours. The reaction temperature is usually −78 to 150° C., preferably −30 to 30° C. While the sulfonate compound thus obtained can be used for the subsequent reaction as in the state of the reaction mixture or as a crude product, it can be isolated from the reaction mixture by a conventional method and readily purified by means of recrystallization, distillation and chromatography.

The halogenate can be produced by allowing compound (LII) to react with a halogenating agent. Examples of the halogenating agent include phosphohalogenide such as phosphorus trichloride, phosphorus oxychloride and phosphorus tribromide, halogen, and thionyl chloride. Relative to 1 mol. of compound (LII), about 1.0 to 100 mol., preferably about 1.0 to 10 mol. of the halogenating agent is used. It is advantageous to conduct this reaction in the absence of solvent or in the presence of an inert solvent. As the solvent, any one can be used so long as the reaction proceeds, ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; sulfoxides such as dimethyl sulfoxide, etc.; or a mixture of them are preferable. The reaction time ranges usually from 10 minutes to 24 hours, preferably from 30 minutes to 12 hours. The reaction temperature ranges usually from 0 to 200° C., preferably from 10 to 100° C. While the halogenide thus obtained can be used for the subsequent reaction in the state of the reaction mixture or as a crude product, it can be isolated from the reaction mixture by a conventional method, which can readily be purified by means of, for example, recrystallization, distillation and chromatography.

Compound (Ia) is produced by subjecting the sulfonate compound or halogenide thus obtained to ringclosure reaction in the presence of a base. Examples of the base include inorganic bases such as sodium hydroxide, potassium hydroxide, etc.; basic salts such as sodium carbonate, potassium carbonate, sodium hydrogencarbonate, etc.; aromatic amines such as pyridine, lutidine, etc.; tertiary amines such as triethylamine, tripropylamine, tributylamine, cyclohexyl dimethylamine, 4-dimethylaminopyridine, N,N-dimethylaniline, N-methyl piperidine, N-methyl pyrrolidine, N-methyl morpholine, etc.; alkali metal hydrides such as sodium hydride, potassium hydride, etc.; metal amides such as sodium amide, lithium diisopropylamide, lithium hexamethyl disilazide, etc.; and metal alkoxides such as sodium methoxide, sodium ethoxide, potassium tertiary butoxide, etc. Relative to 1 mol. of the sulfonate compound or the halogenide, about 1.0 to 50 mol., preferably about 1.0 to 10 mol. of the base is used. This reaction is conducted advantageously using a solvent inert to the reaction. As the solvent, while any one can be used so long as it does not hamper the proceeding of the reaction, preferable examples include alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; esters such as ethylacetate, etc.; sulfoxides such as dimethyl sulfoxide, etc.; water or a mixture of them. The reaction time is usually 10 minutes to 6 hours, preferably 10 minutes to 2 hours. The reaction temperature is usually 0 to 250° C., preferably 10 to 120° C. The product (Ia) can be isolated from the reaction mixture by a conventional method and can be readily purified by means of, for example, recrystallization, distillation and chromatography.

Reaction Process 7:

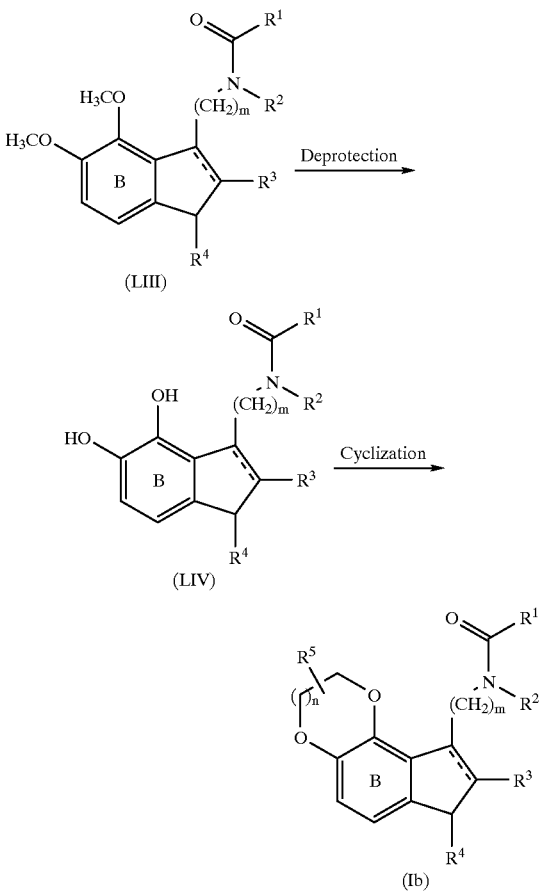

Compound (LIII) can be produced by a per se known method, for example, methods described in J. Chem. Soc. p.548 (1927), Tetrahedron, Vol.25, p.5475 (1969), Vol.34, p.1435 (1978), Vol.39, p.2803 (1983), and Can. J. Chem. Vol.57, p.1598 (1979), or in accordance with methods analogous to them.

Compound (LIV) can be produced by de-protecting the protected hydroxy group in the same manner as in the production of compound (XVIII) from compound (XVII). This de-protection is conducted by generally known processes. For example, referred to is the disclosure in Chapter "Protection for Phenols and Catechols" in "Protective Groups in Organic Synthesis" by T. W. Green (2nd Ed., 1991).

Compound (Ib) is produced by conducting ring formation reaction at the diol part of compound (LIV). This process is conducted in accordance with generally known steps, for example, methods disclosed in Chapter "Protection for 1,2- and 1,3-diols" in "Protective Groups in Organic Synthesis" by T. W. Green (2nd Ed. 1991), Synthesis p.839 (1986), Tetrahedron Letters, Vol.32, p.2461 (1991), Vol.33, p.4165 (1992), J. Heterocyclic Chem. Vol.26, p.193 (1989) or methods analogous to them.

Reaction Process 8:

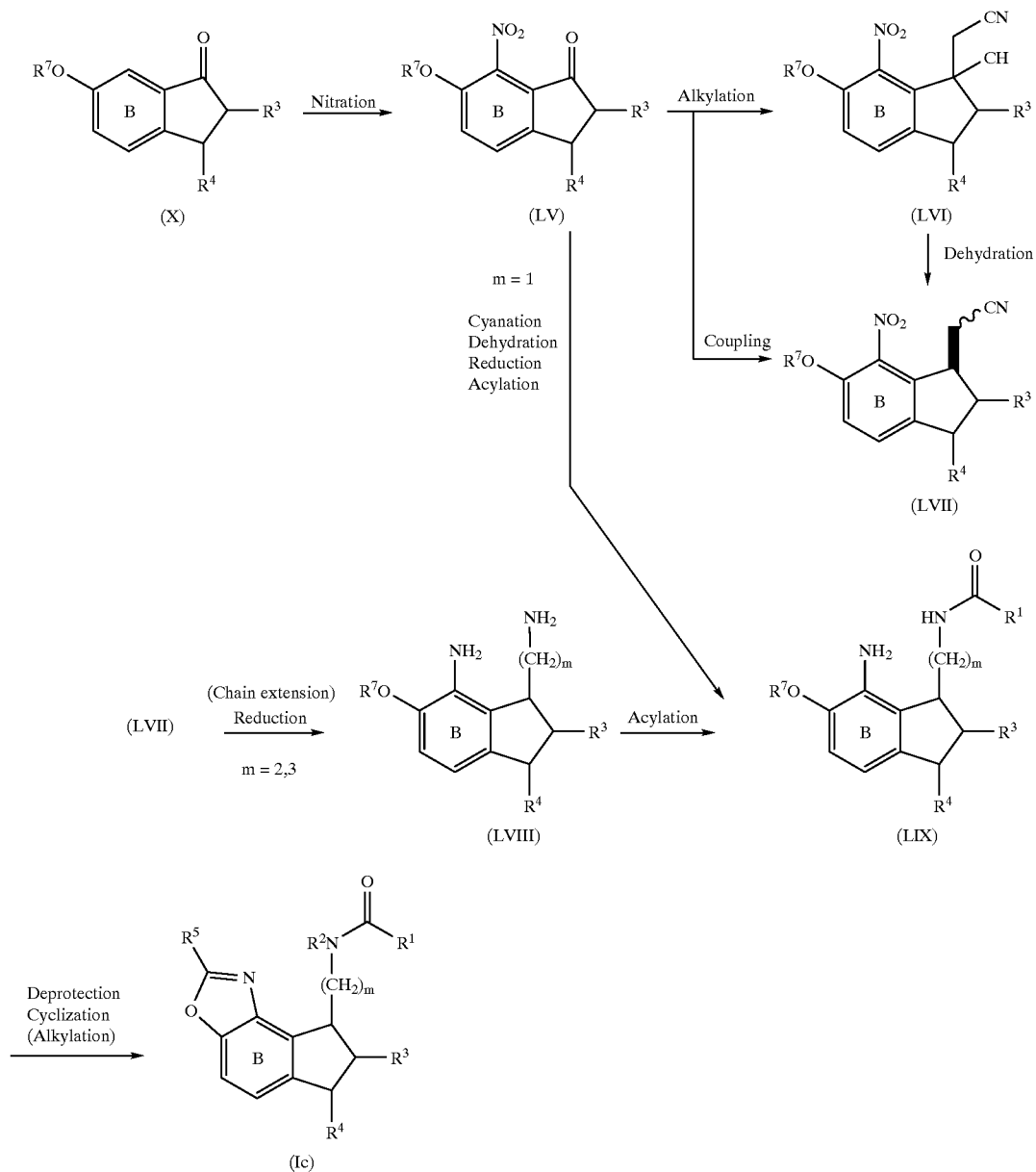

Compound (LV) is produced by subjecting compound (X) to nitration. For example, the nitration can be conducted in accordance with "Shin Jikken Kagaku Koza Vol.14, —Synthesis and Reaction of Organic Compounds (III), Chapter of "7 N-containing compounds" (Compiled by The Chemical Society of Japan). To state concretely, (1) synthesis using mixed acids of nitric acid and sulfuric acid, (2) synthesis using acetyl nitrate, (3) synthesis using nitric acid, (4) synthesis using nitronium trifluoromethanesulfonate and (5) synthesis using nitrate such as sodium nitrate or potassium nitrate with a mineral acid are employed, and, among them, nitration using nitrate and mineral acid is generally employed. In this case, relative to 1 mol. of compound (X), about 0.8 to 3.0 mol., preferably about 1.0 to 2.0 mol., of the nitrate is used. As the mineral acid, sulfuric acid is used in general in an amount of 10 to 2000 weight % of compound (X). This reaction is conducted advantageously using a solvent inert to the reaction. As the solvent, while any one can be used so long as it does not hamper proceeding of the reaction, usually a mineral acid employed as the catalyst is used also as solvent. The reaction time ranges usually from 5 minutes to 10 hours, preferably from 10 minutes to 3 hours. The reaction temperature ranges usually from –20 to 120° C., preferably from –10 to 20° C. The product (LV) can be isolated from the reaction mixture by a conventional method, and can be purified by means of, for example, recrystallization, distillation and chromatography.

Compound (LVII) can be produced, in the same manner as in the above-mentioned method of producing compound (XII) from compound (X), by allowing carbanion produced by processing acetonitrile with a base to react with compound (LV) to afford compound (LVI), followed by subjecting compound (LVI) to dehydration. Compound (LVII) is obtained as coordination isomer of E- or Z-singly or as a mixture of E- and Z-compounds. Relative to 1 mol. of compound (LV), about 1.0 to 3.0 mol., preferably about 1.0 to 1.3 mol. of acetonitrile is employed. Examples of bases include alkali metal hydrides such as sodium hydride, potassium hydride, etc.; metal amides such as sodium amide, lithium diisopropylamide, lithium hexamethyldisilazide, etc.; and metal alkoxides such as sodium methoxide, sodium ethoxide, potassium tertiary butoxide, etc. The amount of these bases to be employed ranges from about 1.0 to 5.0 mol., preferably from about 1.0 to 1.5 mol., relative to 1 mol. of compound (LV). It is advantageous that this reaction is conducted using a solvent inert to the reaction. As the solvent, while any one can be used so long as it does not hamper proceeding of the reaction, use is preferably made of alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; or a mixture of them. The reaction time ranges usually from 30 minutes to 48 hours, preferably from 30 minutes to 5 hours. The reaction temperature ranges usually from −78 to 100° C., preferably from −78 to 50° C. While the product can be used for the subsequent reaction in the state of reaction mixture or as a crude product, it can be isolated from the reaction mixture by a conventional method, which can readily be purified by means of, for example, recrystallization, distillation and chromatography.

Examples of the catalyst to be used for dehydration include an acid catalyst such as hydrochloric acid, sulfuric acid phosphoric acid, potassium hydrogensulfate, oxalic acid, p-toluenesulfonic acid, 10-camphorsulfonic acid and a boron trifluoride ether complex; and a basic catalyst such as sodium hydroxide and potassium hydroxide, and, further, use may optionally be made of a dehydrating agent such as N,N-cyclohexylcarbodiimide; alumina, sodium dioxide, phosphorus oxychloride, thionyl chloride and methanesulfonyl chloride. This reaction is conducted advantageously in the absence of solvent or using a solvent inert to the reaction. As the solvent, while any one can be used so long as it does not hamper proceeding of the reaction, preferable examples of the solvents include alcohols such as methanol, ethanol and propanol; ethers such as diethyl ether, tetrahydrofuran, dioxane and 1,2-dimethoxyethane; hydrocarbons such as benzene, toluene, cyclohexane and hexane; amides such as N,N-dimethylformamide and N,N-dimethylacetamide; sulfoxides such as dimethyl sulfoxide; or a mixture of them. The reaction time ranges usually from 30 minutes to 24 hours, preferably from 30 minutes to 5 hours. The reaction temperature ranges usually from 0 to 200° C., preferably from 0 to 150° C.

Compound (LVII) can be produced, in the same manner as in the above-mentioned method of producing compound (XII) from compound (X), by allowing phosphonate carbanion produced by processing alkylsulfonic acid diester with a base to react with compound (LV) to afford stereo isomer of E- or Z-singly or as a mixture of E- and Z-compounds. As alkylsulfonic acid diester, use is made of, for example, diethyl cyanomethyl phosphonate. Relative to 1 mol. of compound (LV), about 1.0 to 3.0 mol., preferably about 1.0 to 1.5 mol. of alkyl phosphonic acid diester is employed. Examples of bases include alkali metal hydrides such as sodium hydride, potassium hydride, etc.; metal amides such as sodium amide, lithium diisopropylamide, lithium hexamethyldisilazide, etc.; and metal alkoxides such as sodium methoxide, sodium ethoxide, potassium tertiary butoxide, etc. The amount of these bases to be employed ranges from about 1.0 to 5.0 mol., preferably from about 1.0 to 1.5 mol., relative to 1 mol. of compound (LV). It is advantageous that this reaction is conducted using a solvent inert to the reaction. As the solvent, while any one can be used so long as it does not hamper proceeding of the reaction, use is preferably made of alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; sulfoxides such as dimethylsulfoxide, etc.; or a mixture of them. The reaction time ranges usually from 1 hour to 50 hours, preferably from 1 hour to 10 hours. The reaction temperature ranges usually from −78 to 200° C., preferably from 0 to 150° C. While the product can be used for the subsequent reaction in the state of reaction mixture or as a crude product, it can be isolated from the reaction mixture by a conventional method, which can readily be purified by means of, for example, recrystallization, distillation and chromatography.

Elongation of the carbon-chain at the side-chain of the compound (LVII) is conducted in accordance with a known reaction for carbon-chain elongation. For example, the cyano group is subjected to hydrolysis under alkaline or acid conditions to convert to carboxyl group, or after leading the carboxyl group to ester, the resultant is subjected to reduction to give an alcohol, followed by halogenation and cyanation.

Compound (LVIII) is produced from compound (LVII), in combination of the same manner as in the below-mentioned reduction of nitro group of compound (LXII) and catalytic hydrogenation using Raney nickel. As the reducing agent, use is made of, for example, metal hydrides such as aluminum hydride and diisobutylaluminum hydride; metal hydride complex compounds such as lithium aluminum hydride and sodium borohydride; or, as catalyst for hydrogenation, use is made of catalysts such as Raney nickel and Raney cobalt; or a suitable combination of them may be resorted to. The amount of a reducing agent, in the case of using a metal hydride for example, ranges from about 1.0 to 10 mol., preferably from about 1.0 to 3.0 mol., relative to 1 mol. of compound (LVII), and, in the case of using a metal hydride complex compounds, its amount ranges, relative to 1 mol. of compound (LVII), from about 1.0 to 10 mol., preferably from about 1.0 to 3.0 mol., and, in the case of hydrogenation, the amount of a catalyst, e.g. Raney nickel or Raney cobalt, ranges from about 10 to 1000 weight %, preferably from about 80 to 300 weight %, relative to compound (LVII). It is advantageous to conduct this reaction by using a solvent inert to the reaction. As the solvent, while any one can be used so long as it does not hamper proceeding of the reaction, preferable examples include alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, etc.; amides such as N,N-dimethylformamide, N,N-dimethylacetamide, etc.; organic acids such as formic acid, acetic acid, etc.; and a mixture of these solvents. In the case of using a Raney nickel or Raney cobalt catalyst, amines such as ammonia may further be added optionally to suppress undesirable side reactions. While the reaction times varies with the activity and amount of the reagent then employed, it ranges usually from one hour to 100 hours, preferably from one hour to 50 hours. The reaction temperature ranges usually from 0 to 120° C., preferably from 20 to 80° C. In the case using a catalyst such as Raney nickel or Raney cobalt, the hydrogen pressure ranges usually from 1 to 100 atm. While the product (LVIII) can be used for the subsequent reaction as in the state of the reaction mixture or as a crude product, it can be isolated from the reaction mixture by a conventional method and can be readily purified by means of, for example, recrystallization, distillation and chromatography.

Compound (LIX) with m=1 can be produced in substantially the same manner as in the above-mentioned production of compound (XVI) from compound (X), namely, compound (LV) is processed with trimethyl silyl cyanide in the presence of a Lewis acid, resulting trimethyl silyloxy group is removed with an acid, then reducing the cyano group and the double bond, followed by acylating the resultant amine compound. As the Lewis acid to be used in the first step, mention is made of, for example, zinc iodide, anhydrous aluminum chloride, anhydrous zinc chloride and anhydrous iron chloride. The amount of these Lewis acids to be employed ranges from about 0.01 to 10 mol., preferably from about 0.01 to 1.0 mol., relative to 1 mol. of compound (LV). This reaction is conducted advantageously in the absence of solvent or in the presence of a solvent inert to the reaction. As the solvent any one can be used so long as it does not hamper proceeding of the reaction, and its preferable examples include ethers such as diethyl ether, tetrahydrofuran, dioxane, 1,2-dimethoxyethane, etc.; hydrocarbons such as benzene, toluene, cyclohexane, hexane, etc.; or a mixture of these solvents. The reaction time ranges usually from 10 minutes to 12 hours, preferably from 30 minutes to 3 hours. The reaction temperature ranges usually from −10 to 200° C., preferably from −10 to 100° C. While the product can be used for the subsequent reaction in the state of reaction mixture or as a crude product, it can be isolated from the reaction mixture by a conventional method, which can be readily purified by means of, for example, recrystallization, distillation and chromatography. The product is then treated with an acid to remove trimethylsilyloxy group. Preferable examples of the acid include inorganic acids such as hydrochloric acid, sulfuric acid, nitric acid, hydrobromic acid, phosphoric acid, etc.; organic acids such as acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphor sulfonic acid, etc.; and boron trifluoride ether complex. The amount of these acids to be used ranges from about 1 to 100 mol., preferably from about 1 to 10 mol., relative to 1 mol. of compound (LV). This reaction is advantageously conducted in the absence of solvent or in the presence of a solvent inert to the reaction. As the solvent, while any one can be used so long as it does not hamper proceeding of the reaction, preferable examples include ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; sulfoxides such as dimethyl sulfoxide, etc.; or a mixture of these solvents. The reaction time ranges usually from 30 minutes to 12 hours, preferably from 30 minutes to 5 hours. The reaction temperature ranges usually from 0 to 200° C., preferably from 20 to 150° C. The reduction of cyano group and the double bond can be conducted under the conditions employed for production of compound (XV) from compound (XII). Subsequent acylation can be conducted under the conditions employed for production of compound (XVII) from compound (XVI). While the product (LIX) can be used for the subsequent reaction in the state of reaction mixture or a crude product, it can be optionally isolated from the reaction mixture in accordance with a conventional method, and can be readily purified by means of, for example, recrystallization, distillation and chromatography.

Acylation of compound (LIX) with m=2 or 3 can be conducted under the conditions employed for production of compound (XVII) from compound (XVI). While the product (LIX) can be used for the subsequent reaction in the state of reaction mixture or a crude product, it can be optionally isolated from the reaction mixture in accordance with a conventional method, and can be readily purified by means of, for example, recrystallization, distillation and chromatography.

Compound (Ic) is produced by subjecting the protective group $R^7$ of the phenolic hydroxyl group of compound (LIX) to deprotection followed by allowing cyclization to form an oxazole ring . The deprotection is conducted usually in the presence of an acid catalyst. As the acid, use is made of, for example, a Lewis acid such as boron tribromide or anhydrous aluminum chloride, and a mineral acid such as hydrochloric acid and hydrobromic acid. The amount of these acids to be used ranges from about 0.1 to 100 mol., preferably from about 1 to 10 mol., relative to 1 mol. of compound (LIX). This reaction is advantageously conducted in the absence of solvent or in the presence of a solvent inert to the reaction. As the solvent, while any one can be used so long as it does not hamper proceeding of the reaction, its preferable examples include halogenocarbons such as dichloroethane, chloroform, carbon tetrachloride, 1,2-dichloroethane, etc.; hydrocarbons such as benzene, toluene, cyclohexane, hexane, etc.; amides such as N,N-dimethylformamide, N,N-dimethylacetamide, etc.; sulfoxides such as dimethyl sulfoxide, etc.; water or a mixture solvent of them. The reaction time ranges usually from 30 minutes to 12 hours, preferably from 30 minutes to 5 hours. The reaction temperature ranges usually from −10 to 120° C., preferably from 0 to 80° C. While the product can be used for the subsequent reaction in the state of reaction mixture or a crude product, it can optionally be isolated from the reaction mixture in accordance with a conventional method, which can be readily purified by means of, for example, recrystallization, distillation and chromatography. The subsequent cyclization reaction can be conducted by a per se known method, for example, methods disclosed in Synth. Commun. Vol.16, p.365 (1986) and Org. Prep. Proc. Int. Vol.22, p.613 (1990) or methods analogous to them.

To state further, compound (Ic) with $R^2$=alkyl group is produced by, after the above-mentioned cyclization reaction, alkylation in the presence of a base using a corresponding alkylating agent (e.g. alkyl halide or sulfonic acid ester of alcohol). Relative to 1 mol. of compound (1c), about 1.0 to 5.0 mol., preferably about 1.0 to 2.0 mol., of the alkylating agent is employed. Examples of the base include inorganic bases such as sodium hydroxide, potassium hydroxide, etc.; basic salts such as sodium carbonate, potassium carbonate, sodium hydrogencarbonate, etc.; aromatic amine such as pyridine and lutidine; tertiary amines such as triethylamine, tripropylamine, tributylamine, cyclohexyl dimethylamine, 4-dimethyl aminopyridine, N,N-dimethylaniline, N-methylpiperidine, N-methylpyrrolidine, N-methyl morpholine, etc.; alkali metal hydrides such as sodium hydride, potassium hydride, etc.; metal amides such as sodium amide, lithium diisopropyl amide, lithium hexamethyl disilazide, etc.; and metal alkoxides such as sodium methoxide, sodium ethoxide, potassium tertiary butoxide, etc. Relative to 1 mol. of compound (Ic), about 1.0 to 5.0 mol., preferably about 1.0 to 2.0 mol., of the base is used. This reaction is advantageously conducted by using a solvent inert to the reaction. As the solvent, while any one can be used so long as it does not hamper proceeding of the reaction, its preferable examples include alcohols such as methanol, ethanol, propanol, etc.; ethers such as diethyl conventional method, which can readily purified by means of, for example, recrystallization, distillation and chromatography.

Reaction Process 9:

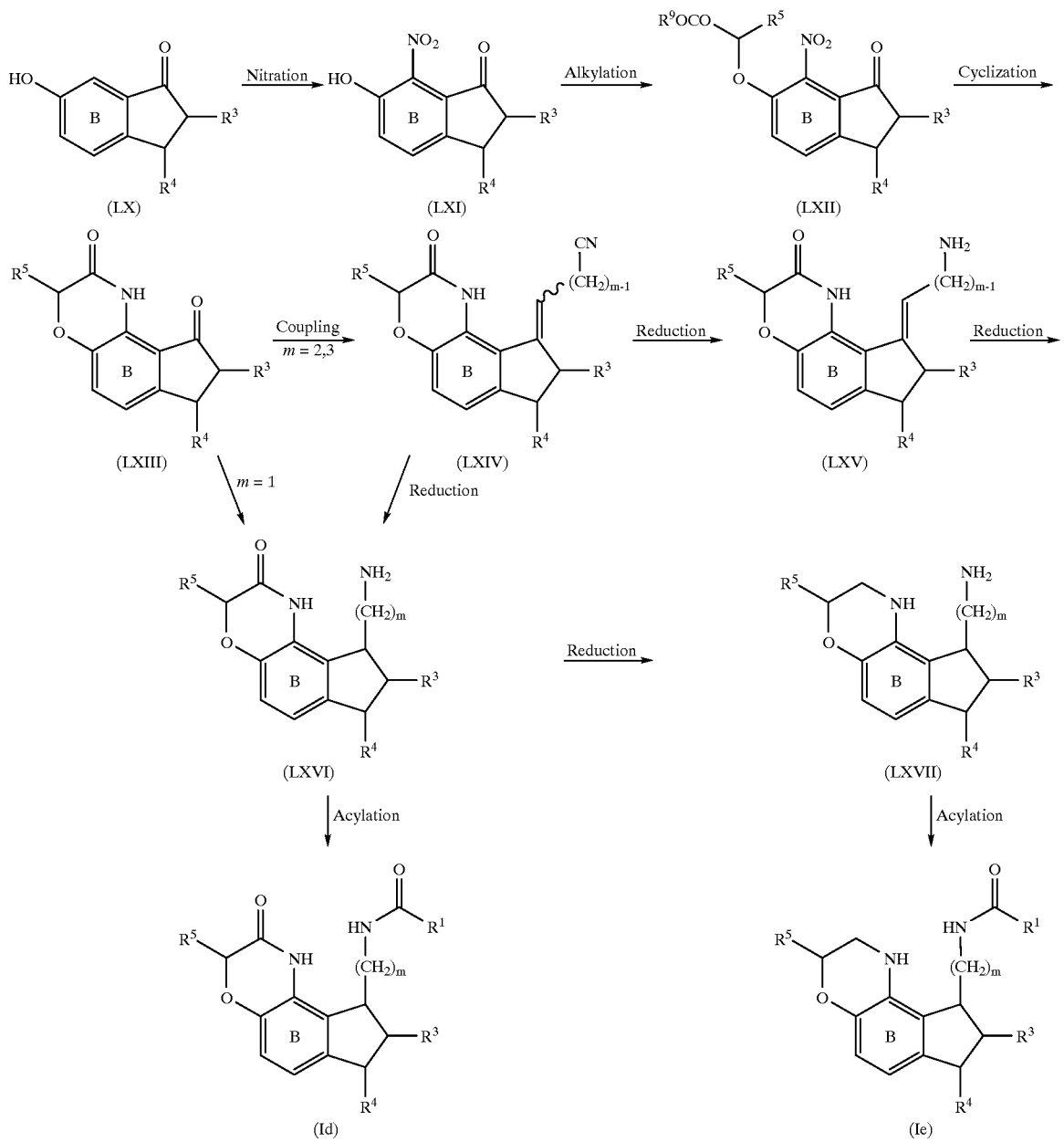

ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; sulfoxides such as dimethyl sulfoxide, etc.; or a mixture solvent of them. The reaction time ranges usually from 30 minutes to 48 hours, preferably form 30 minutes to 6 hours. The reaction temperature ranges usually from −20 to 200° C., preferably from −10 to 150° C. The product (Ic) can be isolated from the reaction mixture by a The compound (LXI) is produced from compound (LX) and corresponding alkylating agent in substantially the same manner as in the production of compound (LV) from compound (X).

Compound (LXII) is produced from compound (LXI), in substantially the same manner as in production of compound (XX) from compound (XVIII).

Production of compound (LXIII) from compound (LXII) is conducted by subjecting the nitro group of compound (LXII) to reduction of catalytic reduction with a reducing agent, followed by cyclization. The reduction of nitro group can be conducted by a per se known method described in, for example, "Shin Jikken Kagaku Koza Vol. 15—Oxidation and Reduction (compiled by The Chemical Society of Japan), or methods analogous to them. Concretely to state, as the reducing agent to be employed in the reduction of nitro group, use is made of, for example, metal such as zinc, iron, tin, etc.; metal halide such as stannous chloride, etc.; sulfur compound such as sodium sulfide, sodium hydrosulfide, sodium hydrosulfite, ammonium sulfide, etc.; metal hydride complex such as lithium aluminum hydride, etc.; or use is made of catalysts such as platinum, Raney nickel, Raney cobalt, platinum black, palladium carbon, rhodium alumina. The amount of the reducing agent, in the case of using metal hydride complex for example, ranges from about 1.0 to 10.0 mol., preferably from about 1.0 to 3.0 mol., relative to 1 mol. of compound (LXII), and, in the case of hydrogenation, the amount of catalyst ranges from about 10 to 1000 weight %, preferably 80 to 300 weight %, relative to compound (LXII). It is advantageous to condust this reaction by using a solvent inert to the reaction. As the solvent, while any one can be used so long as it does not hamper proceeding of the reaction, preferable examples include alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, etc.; amides such as N,N-dimethylformamide, N,N-dimethylacetamide, etc.; organic acids such as formic acid, acetic acid, etc.; and a mixture of these solvents. While the reaction times varies with the activity and amount of the reagent then employed, it ranges usually from one hour to 100 hours, preferably from one hour to 50 hours. The reaction temperature ranges usually from 0 to 120° C., preferably from 20 to 80° C. In the case using a catalyst such as Raney nicket or palladium carbon the hydrogen pressure ranges usually from 1 to 100 atm. While the product can be used for the subsequent reaction as in the state of the reaction mixture or as a crude product, it can be isolated from the reaction mixture by a conventional method and can be readily purified by means of, for example, recrystallization, distillation and chromatography. The cyclization is conducted under heating or in the presence of a basic catalyst. Examples of the base as the catalyst include metal alkoxides such as sodium methoxide, sodium ethoxide, potassium tertiary butoxide, etc.; metal hydrides such as sodium hydride, potassium hydride, etc.; lithium reagents such as butyl lithium, phenyl lithium, etc.; and Grignard reagents such as methyl magnesium bromide, phenyl magnesium bromide, etc.; and the amount ranges usually from 0.01 to 5 equivalents, preferably from 0.05 to 0.5 equivalents. This reaction is conducted advantageously in the presence of an solvent inert to the reaction. As the solvent, any one can be used so long as it does not hamper proceeding of the reaction, and its preferable examples include alcohols such as methanol, ethanol, propanol, etc.; ethers such as diethyl ether, tetrahydrofuran, dioxane, 1,2-dimethoxyethane, etc.; hydrocarbons such as benzene, toluene, cyclohexane, hexane, etc.; amides such as N,N-dimethylformamide, N,N-dimethylacetamide, etc.; halogenated hydrocarbons such as dichloromethane, chloroform, carbon tetrachloride, 1,2-dichloroethane, etc.; nitriles such as acetonitrile, propionitrile, etc.; and sulfoxides such as dimethyl sulfoxide, etc.; or a mixture solvent of them. The reaction time ranges usually from 30 minutes to 48 hours, preferably from 30 minutes to 12 hours. The reaction temperature ranges usually from −20 to 200° C., preferably from −10 to 150° C. The product (LXIII) can optionally be isolated from the reaction mixture and can be readily purified by means of, for example, recrystallization, distillation and chromatography.

Compound (LXIV) is produced from compound (LXIII) in substantially the same manner as in the production of compound (XII) from compound (X).

Elongation of carbon chain at the side chain of compound (LXIV) can be conducted in a manner analogous to known carbon-chain elongation reactions, for example, cyano group is hydrolized under alkaline or acid conditions to lead to carboxyl group, or leading the carboxyl group to an ester compound, which is then subjected to reduction to lead to an alcohol compound, followed by halogenation and cyanation.

Compound (LXV) is produced from compound (LXIV), in substantially the same manner as in the production of compound (XV) from compound (XII). Compound (LXVI) is produced from compound (LXV) by catalytic hydrogenation. And, compound (LXVI) can be produced directly from compound (LXIV), by employing stronger reaction conditions for producing compound (LXV).

Compound (LXVII) is produced by subjecting the amido moiety of compound (LXVI) to reduction. As the reducing agent, use is made of a metal hydride complex compound (e.g. lithium aluminum hydride). Usually, as the solvent, use is made of ethers such as diethyl ether, tetrahydrofuran, etc.; or a mixture of such ether with an inert solvent (e.g. hexane, cyclohexane, etc.). The amount of the reducing agent to be employed for the reaction ranges usually from 1 to 30 equivalents, preferably from 3 to 10 equivalents. The reaction temperature ranges from −20 to 150° C., preferably from 10 to 100° C. The product (LXVII) can optionally be isolated from the reaction mixture, which can readily be purified by means of, for example, recrystallization, distillation and chromatography.

Compounds (Id) and (Ie) can be produced respectively from compounds (LXVI) and (LXVII) in substantially the same manner as in the production of compound (XVII) from compound (XVI).

Compound (LXIX) can be produced from compound (LXVIII) in substantially the same manner as in the production of compound (XVII) from compound (XVI).

Reaction Process 10:

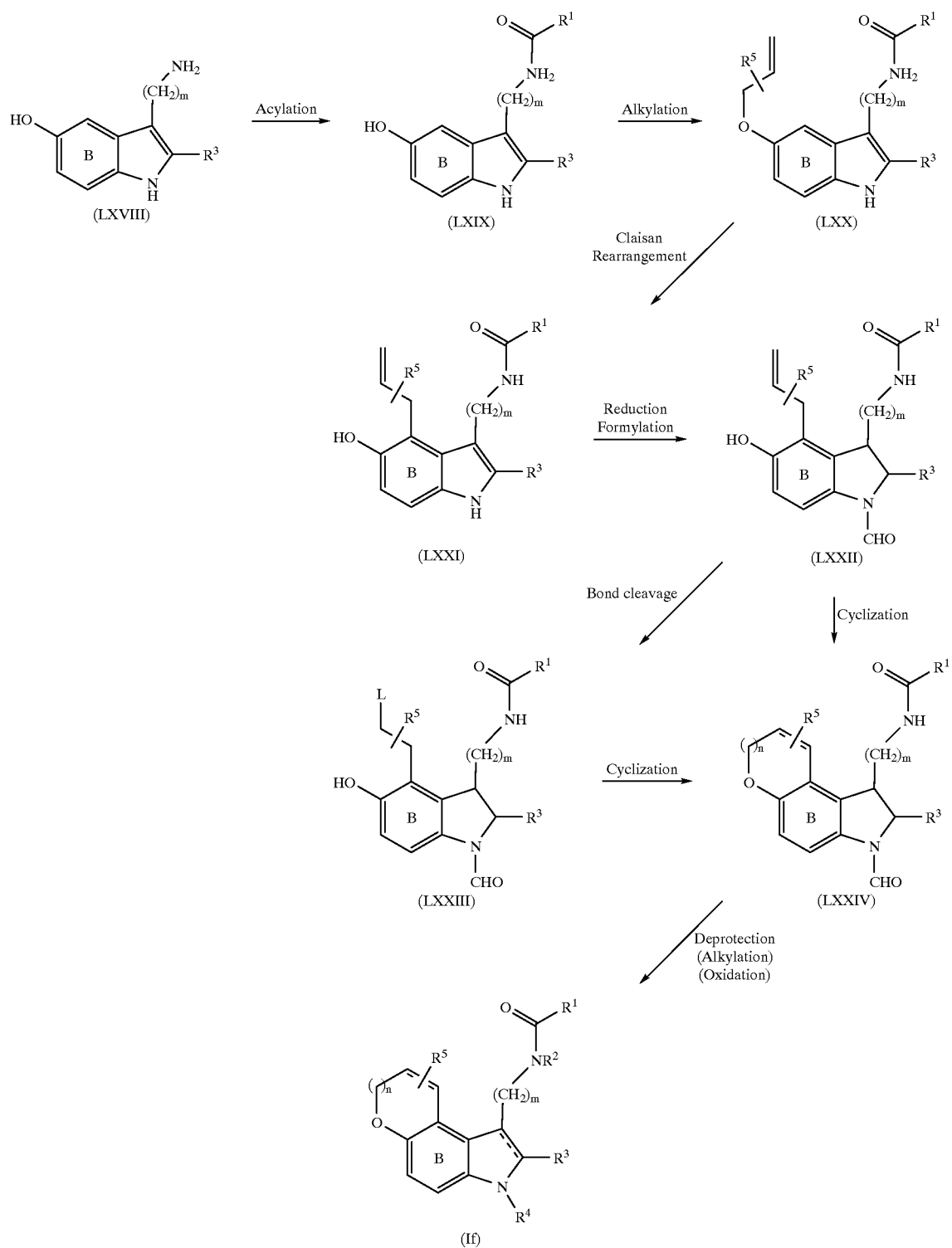

Compound (LXVIII) can be produced using per se known methods or obtained commercially such as serotonin or its salt.

Compound (LXX) can be produced from compound (LXIX) in substantially the same manner in the production of compound (L) from compound (XVIII).

Compound (LXXI) can be produced from compound (LXX) in substantially the same manner in the production of compound (LI) from compound (L).

Compound (LXXII) can be produced by subjecting compound (LXXI) to reduction, then, by subjecting the resultant to formylation. As the reducing agent, a metal hydride complex compound such as sodium cyano borohydride is commonly employed. As the solvent, use is made of, usually, an organic acid such as acetic acid and propionic acid or a mixture of the organic acid with an inert solvent (e.g. ethers such as diethyl ether, tetrahydrofuran, etc.; and hydrocarbons such as hexane, cyclohexane, etc.). The amount of the reducing agent to be employed for the reaction ranges usually from 1 to 30 equivalents, preferably from 3 to 10 equivalents. The reaction temperature ranges from −20 to 100° C., preferably from 0 to 80° C. The reaction time ranges usually from 30 minutes to 12 hours, preferably from 30 minutes to 3 hours. The subsequent formylation may be conducted in accordance with the conditions described in, for example, the chapter "Protection for the Amino Group" of "Protective Groups in Organic Synthesis" (2nd Ed., 1991), T. W.Green. The product (LXXII) can optionally be isolated from the reaction mixture by a conventional method, which can readily be purified by means of, for example recrystallization, distillation and chromatography.

The compound (LXXIII) can be produced from compound (LXXII) in substantially the same manner as inn the production of compound (LII) from compound (LI).

The compound (LXXIV) can be produced from compound (LXXIII) in substantially the same manner as in the production of compound (Ia) from compound (LII).

Compound (LXXIV) can be obtained using per se known methods, for example, cyclization reaction using acid catalyst (e.g., hydrochloric acid, sulfuric acid, $BF_3$ etherate, etc.), peracid (e.g., m-chloroperbenzoic acid, etc.) or halogen (e.g., iodine, bromine, etc.).

Compound (If) can be produced by removing the formyl group of compound (LXXIV) in the presence of an acid catalyst or a basic catalyst. As the reaction conditions for removing the formyl group, reference is made to the description in the Chapter "Protection for the Amino Group" of "Protective Groups in Organic Synthesis" (2nd Ed., 1991) T. W.Green.

And, when desired, alkylation or oxidation to indole from indoline may be conducted.

Just after their isomerization, the configurational isomers (E- and Z forms) of the above-mentioned compounds (XII), (XV), (XXXIV), (XXXV), (LVII), (LXIV) or (LXV) can be isolated and purified by per se means of separation, for example, extraction, recrystallization, distillation, chromatography or the like to obtain pure compounds. If desired, the isomerization of the double-bond moiety in these compounds may be conducted by means of the methods described in "Shin Jikken Kagaku Koza (New Lectures on Experimental Chemistry)" Vol. 14 (edited by Japan Chemical Society), pp. 251–253; "Jikken Kagaku Koza (Lectures on Experimental Chemistry 19)", 4th Ed., pp. 273–274 (edited by the Japan Chemical Society), or methods analogous thereto, for example, methods, under heating, using an acid catalyst, a transition metal catalyst, a metal catalyst, a radical catalyst or a strong base catalyst or a light irradiation to obtain the corresponding pure isomers.

Compound (I) includes stereoisomers, depending on the substituents therein. The present invention encompasses not only single isomers but also mixtures of these.

If desired, any of the above-mentioned reaction steps may be accompanied by known de-protection, acylation, alkylation, hydrogenation, oxidation, reduction, carbon-chain extension and substituent-exchange reaction, either singly or in a combination of two or more of such reactions, to obtain compound (I). For these reactions, for example, referred to are the methods described in "Shin Jikken Kagaku Koza (New lectures on Experimental Chemistry)", Vols. 14 and 15 (edited by Japan Chemical Society, published in 1977, 1978) or methods analogous thereto.

In the above-mentioned reaction steps for producing the compounds of the present invention and those for producing the starting compounds for the compounds of the invention, in the case where the starting compounds for these have, as substituents, an amino group, carboxyl group and/or hydroxy group, these groups may be protected by ordinary protective groups such as those generally employed in peptide chemistry. After the reaction, the protective groups may be removed to obtain the intended products.

The amino-protective group includes, for example, formyl group, $C_{1-6}$ alkyl-carbonyl groups (e.g., acetyl, propionyl, etc.), $C_{1-6}$ alkyloxycarbonyl groups (e.g., methoxycarbonyl, ethoxycarbonyl, etc.), $C_{6-10}$ arylcarbonyl groups (e.g., benzoyl group, etc.), $C_{7-11}$ aralkyl-carbonyl groups (e.g., benzylcarbonyl, etc.), trityl group, phthaloyl group, N,N-dimethylaminomethylene group, etc. These protective groups may optionally be substituted by one to three substituents such as halogen atoms (e.g., fluorine, chlorine, bromine, iodine, etc.) and a nitro group.

The carboxyl-protective group includes, for example, $C_{1-6}$ alkyl groups (e.g., methyl, ethyl, propyl, isopropyl, butyl, tert-butyl, etc.), $C_{6-10}$ aryl group (e.g., phenyl group, etc.) trityl group, silyl group, etc. These protective groups may optionally be substituted by one to three substituents such as halogen atoms (e.g., fluorine, chlorine, bromine, iodine, etc.), formyl group, $C_{1-6}$ alkyl-carbonyl groups (e.g., acetyl propionyl, butylcarbonyl, etc.) and nitro group.

The hydroxy-protective group includes, for example, $C_{1-6}$ alkyl groups (e.g., methyl, ethyl, propyl, isopropyl, butyl, tert-butyl, etc.), $C_{6-10}$ aryl group (e.g., phenyl group, etc.), $C_{7-11}$ aralkyl groups (e.g., benzyl group, etc.), $C_{1-6}$ alkyl-carbonyl groups (e.g., acetyl, propionyl, etc.), $C_{6-10}$ aryl carbonyl group (e.g., benzoyl group, etc.), $C_{7-11}$ aralkyl-carbonyl groups (e.g., benzylcarbonyl, etc.), tetrahydropyranyl group, tetrahydrofuranyl group, silyl group, etc. These protective groups may optionally be substituted by one to three substituents such as halogen atoms (e.g., fluorine, chlorine, bromine, iodine, etc.), $C_{1-6}$ alkyl groups (e.g., methyl, ethyl, propyl, etc.), $C_{6-10}$ aryl carbonyl group (e.g., phenyl group), $C_{7-11}$ aralkyl groups (e.g., benzyl, etc.) and nitro group.

These protective groups may be removed by per se known methods or the methods analogous thereto. For example, employable is a reduction or a method using an acid, a base, ultraviolet rays, hydrazine, phenylhydrazine, sodium N-methyldithiocarbamate, tetrabutylammonium fluoride or palladium acetate.

The compound (I) of the present invention can be isolated and purified in accordacne with known means, for example, solvent extraction, liquid conversion, solvent transfer, crystallization, recrystallization or chromatography. The starting compounds and their salts for the compound (I) of the invention can also be isolated and purified by known method such as those mentioned above but, as the case may be, they can be directly used in the next reaction step without being isolated.

In the case where the compound (I) is purified by recrystallization, for example, employable are water, alcohols (e.g., methanol, ethanol, n-propanol, iso-propanol, etc.), aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, iso-propyl ether, tetrahydrofuran, dioxane, etc.), ketones (e.g., acetone, methyl ethyl ketone, etc.), nitriles (e.g., acetonitrile, etc.), sulfoxides (e.g., dimethylsulfoxide, etc.), acid amides (e.g., N,N-dimethylformamide, etc.), esters (e.g., ethyl acetate, etc.), carboxylic acids (e.g., acetic acid, propionic acid, etc.), etc. These can be used singly or, if desired, as mixtures comprising two or more at suitable ratios, for example, at 1/1 to 1/10.

In the case where the products are obtained as free compounds in the above-mentioned reaction steps, they can be converted into their salts by per se known methods. In the case where they are obtained as salts, the salts can be converted into free compounds or other salts by ordinary methods. The compound (I) thus obtained can be isolated and purified from the reaction mixtures by known means, for example, solvent transfer, concentration, solvent extraction, fractionating distillation, crystallization, recrystallization or chromatography.

Where the compound (I) exist as configurational isomers, diastereomers or conformers, it can be isolated separately, if desired, in accordance with the above-mentioned means of separation and purification. Mixtures of optically-active compound (I) can be isolated into (+)-form and (−)-form by means of ordinary optical resolution.

The compound of the formula (i)

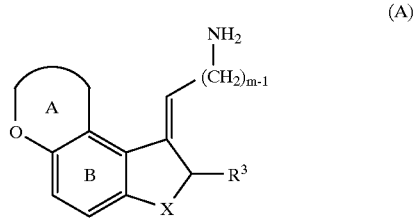

(A)

wherein the symbols are as defined above, or (ii)

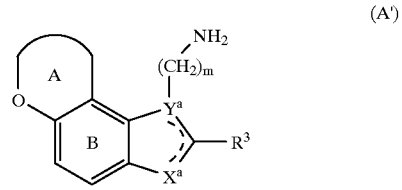

(A')

wherein the symbols are as defined above, or a salt thereof, as obtained in the reaction processes for the production of the above-mentioned compound (I) is novel compound and can be used as a starting material for the production of the compound of the present invention. Among them, the following are preferred:

2-(1,6-dihydro-2H-indeno[5,4-b]furan-8-yl)ethylamine,
2-(1,6,7,8-tetrahydro-2H-indeno[5,4-b]furan-8-yl) ethylamine, and salts of these.

The compound (I) of the present invention shows a high binding affinity for melatonin receptor and compound (I) is highly selective especially in ML-1 receptor. The compound has low toxicity, while having few side effects, and is therefore useful in medicines.

The compound (I) of the present invention acts as melatonin agonists in mammals (e.g., mouse, rat, hamster, rabbit, feline, canine, bovine, sheep, monkey, human, etc.) and is useful as a composition with a binding affinity for melatonin receptor, especially composition agonistic towards melatonin receptor, and, therefore, it can be used for preventing and curing biorhythmic control disorders and various other disorders that may be affected by melatonin, for example, sleep-awake rhythm disorders, jet-lag, shift-work syndrome, seasonal melancholia, genital and neuroendocrine disorders, senile dementia, Alzheimer's disease, various disorders accompanied by aging (e.g., for preventing aging, etc.), cerebrovascular disorders (e.g., cerebral hemorrhage, etc.), cranial injury, spinal injury, stress, epilepsy, convulsions, anxiety, depression, Parkinsonism, hypertension, glaucoma, cancer, insomnia and diabetes. It is also acts as melatonin antagonists in mammals. In addition, it is also effective for immunoregulation, nootropic, tranquilization and ovulatory regulation (e.g., contraception). The compound (I) of the present invention can be used, for example, in biorhythm regulators, preferably medicines for sleep disorder (e.g., sleep-inducing medicines, etc.), sleep-awake rhythm regulators (including those for controlling sleep-awake rhythm), medicines for physiological syndromes caused by time-zone changes, for example, so-called jet-lag, etc.

The compound (I) of the present invention has low toxicity and can be administered safely through peroral or parenteral routes (e.g., for local administration, rectal administration, intravenous administration, etc.), either directly or as pharmaceutical compositions to be mixed with pharmaceutically acceptable carriers by using per se known methods, for example, as tablets (including sugar-coated tablets, film-coated tablets), powders, granules, capsules (including soft capsules), liquids, injections, suppositories, sustained release preparations, plasters and also as chewing gum, etc. The amount of the compound (I) in the composition of the present invention is approximately 0.01 to nearly 100% by weight of the total weight of the composition. The dose of the composition varies, depending on the subject to which the composition is administered, the administration route, the disorder, etc. For example, when the composition is administered to an adult patient suffering from sleep disorders, it is preferable to administer once daily or severally divided dosages in an amount of approximately 0.0005 to 2 mg/kg body weight, preferably approximately 0.001 to 1 mg/kg body weight, more preferably approximately 0.001 to 0.5 mg/kg body weight, in terms of the amount of the active ingredient, compound (I). The composition may be used with other active ingredients (e.g., benzodiazepine-type medicines comprising benzodiazepine compounds such as triazolam, diazepam, alprazolam, estazolam, etc.; regulating agents of sleep rhythm comprising fatty acid derivatives such as butoctamide and its salt, etc.; sleep ruducing substances comprising cis-9,10-octadecenamide, etc.) Such other active ingredient and the compound (I) may be mixed by means of per se known methods to give pharmaceutical compositions (e.g., tablets, powders, granules, capsules including soft capsules, liquids, injections, suppositories, sustained release preparations, etc.); or they are separately formulated into different preparations, which may be administered to one and the same subject either simultaneously or at different times.

Pharmaceutically acceptable carriers employable in the production of the composition of the present invention include various organic and inorganic carrier substances which are known to be usable in pharmaceutical compositions. For example, they include excipients, lubricants, binders, disintegrants, etc. in solid compositions; solvents, solubilizers, suspending agents, isotonizing agents, buffers, pain-easing agents, etc. in liquid compositions. If desired, ordinary preservatives, antioxidants, colorants, sweeteners, adsorbents, moisturizers, and other additives may also be employed.

Excipients employable in the present invention include, for example, lactose, white sugar, D-mannitol, starch, corn starch, crystalline cellulose, light silicic acid anhydride, etc.

Lubricants include, for example, magnesium stearate, calcium stearate, talc, colloidal silica, etc.

Binders include, for example, crystalline cellulose, white sugar, D-mannitol, dextrin, hydroxypropyl cellulose, hydroxypropylmethyl cellulose, polyvinyl pyrrolidone, starch, sucrose, gelatin, methyl cellulose, sodium carboxymethyl cellulose, etc.

Disintegrants include, for example, starch, carboxymethyl cellulose, calcium carboxymethyl cellulose, sodium crosscarmellose, sodium carboxymethyl starch, L-hydroxypropyl cellulose, etc.

Solvents include, for example, water for injection, alcohol, propyleneglycol, macrogol, sesame oil, corn oil, olive oil, etc.

Solubilizers include, for example, polyethyleneglycol, propyleneglycol, D-mannitol, benzyl benzoate, ethanol, trisaminomethane, cholesterol, triethanolamine, sodium carbonate, sodium citrate, etc.

Suspending agents include, for example, surfactants such as stearyl triethanolamine, sodium laurylsulfate, laurylaminopropionic acid, lecithin, benzalkonium chloride, benzetonium chloride, glycerin monostearate, etc.; hydrophilic polymers such as polyvinyl alcohol, polyvinyl pyrrolidone, sodium carboxymethyl cellulose, methyl cellulose, hydroxymethyl cellulose, hydroxyethyl cellulose, hydroxypropyl cellulose, etc.

Isotonizing agents include, for example, glucose, D-sorbitol, sodium chloride, glycerin, D-mannitol, etc.

Buffers include, for example, buffer liquids such as phosphates, acetates, carbonates, citrates, etc.

Pain-easing agents include, for example, benzyl alcohol, etc.

Preservatives include, for example, parahydroxybenzoates, chlorobutanol, benzyl alcohol, phenethyl alcohol, dehydroacetic acid, sorbic acid, etc.

Antioxidants include, for example, sulfites, ascorbic acid, α-tocopherol, etc.

BEST MODE FOR CARRYING OUT THE INVENTION

Examples

The present invention is described in detail by means of the following reference examples, examples, formulation examples and experimental examples, which, however, serve merely to illustrate the embodiments of the invention but not to restrict the invention. Various modifications and changes can be made in the present invention without departing from the spirit and scope of the invention.

"Room temperature" as referred to in the following reference examples and examples generally indicates a temperature of from about 10° C. to 35° C. Unless otherwise specifically indicated, "%" is percent by weight.

The abbreviations referred to herein are defined as follows:

s: singlet
d: doublet
t: triplet
q: quartet
m: multiplet
br: broad
J: coupling constant
Hz: hertz
$CDCl_3$: deuterochloroform
$d_6$-DMSO: (dimethylsulfoxide)-$d_6$
$D_2O$: deuterium oxide
NMR: proton nuclear magnetic resonance BINAP: 2,2'-bis(diphenylphosphino)-1,1'-binaphthyl
T-BINAP: 2,2'-bis[di(4-methylphenyl)phosphino]-1,1'-binaphthyl
DM-BINAP: 2,2'-bis[di(3,5-dimethylphenyl)phosphino]-1,1'-binaphthyl

Reference Example 1

2,3-Dihydrobenzofuran-5-carbaldehyde

Titanium chloride (28 ml) was dropwise added to a dichloromethane (100 ml) solution containing 2,3-dihydrobenzofuran (10.0 g, 83.2 mmols) and dichloromethyl methyl ether (11.3 ml, 0.125 mmols), while cooling with ice. The mixture was stirred for 1 hour, while still cooling with ice, and then water was added thereto. Dichloromethane was removed under reduced pressure, and the residue was extracted with ethyl acetate. The extract was washed with a saturated saline solution, then dried with anhydrous magnesium sulfate and concentrated under reduced pressure. The residue was purified through silica-gel chromatography (hexane/ethyl acetate=1/1) to obtain 11.4 g (yield: 92%) of the target compound. This was oily.

NMR ($CDCl_3$) δ: 3.28 (2H, t, J=8.8 Hz), 4.70 (2H, t, J=8.8 Hz), 6.88 (1H, d, J=8.4 Hz), 7.67 (1H, dd, J=1.0 Hz, 8.4 Hz), 7.75 (1H, d, J=1.0 Hz), 9.83 (1H, s)

Reference Example 2

Ethyl (E)-3-(2,3-dihydrobenzofuran-5-yl)- 2-propenoate

60% sodium hydride (3.39 g, 84.6 mmols) was added to a tetrahydrofuran (150 ml) solution of triethyl phosphonoacetate (19.0 g, 84.6 mmols) while cooling with ice, and the mixture was stirred for 20 minutes. To this was dropwise added a tetrahydrofuran (15 ml) solution of 2,3-dihydrobenzofuran-5-carbaldehyde (11.4 g, 76.9 mmols) and stirred further for 1 hour. Water was added to the reaction mixture, which was then extracted with ethyl acetate. The extract was washed with a saturated saline solution, then dried with anhydrous magnesium sulfate and concentrated under reduced pressure. The residue was purified through silica-gel column chromatography (hexane/ethyl acetate=from 95/5 to 9/1) to obtain 14.7 g (yield: 88%) of the target compound. This was oily.

NMR ($CDCl_3$) δ: 1.33 (3H, t, J=7.2 Hz), 3.23 (2H, t, J=8.8 Hz), 4.25 (2H, q, J=7.2 Hz), 4.63 (2H, t, J=8.8 Hz), 6.28 (1H, d, J=16.0 Hz), 6.79 (1H, d, J=8.4 Hz), 7.31 (1H, d, J=8.4 Hz), 7.41 (1H, s), 7.64 (1H, d, J=16.0 Hz)

Reference Example 3

Ethyl 3-(2,3-Dihydrobenzofuran-5-yl)propionate

5% Palladium-carbon (1 g, containing 50% water) was added to an ethanol (150 ml) solution of ethyl (E)-3-(2,3-dihydrobenzofuran-5-yl)-2-propenoate (14.7 g, 66.7 mmols), and the mixture was stirred in a hydrogen atmosphere at room temperature for 2 hours. The reaction mixture was filtered, and the filtrate was concentrated under reduced pressure to obtain 14.6 g (yield: 99%) of the target compound. This was oily.

NMR ($CDCl_3$) δ: 1.24 (3H, t, J=7.2 Hz), 2.57 (2H, t, J=7.8 Hz), 2.88 (2H, t, J=7.8 Hz), 3.18 (2H, t, J=8.6 Hz), 4.13 (2H, q, J=7.2 Hz), 4.55 (2H, t, J=8.6 Hz), 6.70 (1H, d, J=8.2 Hz), 6.94 (1H, d, J=8.2 Hz), 7.05 (1H, s);

The compound obtained herein was used in the next reaction without being further purified.

Reference Example 4

Ethyl 3-(7-Bromo-2,3-dihydrobenzofuran-5-yl)propionate

Bromine (10.5 g, 65.8 mmols) was dropwise added to an acetic acid (150 ml) solution containing ethyl 3-(2,3-dihydrobenzofuran-5-yl)propionate (14.5 g, 65.8 mmols) and sodium acetate (5.94 g, 72.4 mmols), and the mixture was stirred at room temperature for 1 hour. The reaction mixture was filtered, and the filtrate was concentrated under reduced pressure. Water was added to the residue, which was then extracted with ethyl acetate. The extract was washed with a saturated saline solution and then dried with anhydrous magnesium sulfate. This was concentrated under reduced pressure to obtain 19.2 g (yield: 97%) of the target compound. This was oily.

NMR (CDCl$_3$) δ: 1.25 (3H, t, J=7.2 Hz), 2.57 (2H, t, J=7.6 Hz), 2.85 (2H, t, J=7.6 Hz), 3.28 (2H, t, J=8.8 Hz), 4.13 (2H, q, J=7.2 Hz), 4.65 (2H, t, J=8.8 Hz), 6.97 (1H, s), 7.11 (1H, s);

The compound obtained herein was used in the next reaction without being further purified.

Reference Example 5

3-(7-Bromo-2,3-dihydrobenzofuran-5-yl)propionic Acid

An aqueous solution (100 ml) of sodium hydroxide (15 g) was added to a tetrahydrofuran (20 ml) solution of ethyl 3-(7-bromo-2,3-dihydrobenzofuran-5-yl)propionate (19.1 g, 63.8 mmols), and the mixture was stirred at room temperature for 3 hours. The reaction mixture was made acidic with hydrochloric acid added thereto, and this was then extracted with ethyl acetate. The extract was washed with a saturated saline solution, then dried with anhydrous magnesium sulfate and concentrated under reduced pressure. The residue was recrystallized from ethyl acetate/hexane to obtain 12.8 g (yield: 73%) of the target compound.

m.p.: 117–118° C.; NMR (CDCl$_3$) δ: 2.64 (2H, t, J=7.4 Hz), 2.87 (2H, t, J=7.4 Hz), 3.82 (2H, t, J=8.8 Hz), 4.65 (2H, t, J=8.8 Hz), 6.97 (1H, s), 7.11 (1H, s), hidden (1H)

Reference Example 6

4-Bromo-1,2,6,7-tetrahydro-8H-indeno[5,4-b]furan-8-one

Thionyl chloride (10.1 ml, 0.139 mols) was added to 3-(7-bromo-2,3-dihydrobenzofuran-5-yl)propionic acid (12.7 g, 46.2 mmols), the mixture was stirred at 75° C. for 30 minutes, and the reaction mixture was then concentrated under reduced pressure to obtain an acid chloride. The thus-prepared acid chloride was dropwise added to a 1,2-dichloroethane (100 ml) suspension of anhydrous aluminium chloride (6.77 g, 50.8 mmols) while cooling with ice, and the mixture was stirred for 30 minutes. The reaction mixture was poured into water and then extracted with ethyl acetate. The extract was washed with a saturated saline solution, then dried with anhydrous magnesium sulfate and concentrated under reduced pressure. The residue was purified through silica-gel column chromatography (hexane/ethyl acetate=8.2) and then recrystallized from ethyl acetate/isopropyl ether to obtain 1.00 g (yield: 9%) of the target compound.

m.p.: 149–150° C.; NMR (CDCl$_3$) δ: 2.64–2.72 (2H, m), 3.08 (2H, t, J=5.8 Hz), 3.57 (2H, t, J=9.0 Hz), 4.76 (2H, t, J=9.0 Hz), 7.41–7.43 (1H, m)

Reference Example 7

(E)-(4-bromo-1,6,7,8-tetrahydro-2H-indeno[5,4-b]furan-8-ylidene)acetonitrile

60% Sodium hydride (0.17 g, 4.35 mmols) was added to a tetrahydrofuran (20 ml) solution of diethyl cyanomethylphosphonate (0.77 g, 4.35 mmols) while cooling with ice, and the mixture was stirred for 20 minutes. To this was added a tetrahydrofuran (10 ml) solution of 4-bromo-1,2,6,7-tetrahydro-8H-indeno[5,4-b]furan-8-one (1.00 g, 3.95 mmols), and the mixture was stirred at room temperature further for 2 hours. Water was added to the reaction mixture, which was then extracted with ethyl acetate. The extract was washed with a saturated saline solution, then dried with anhydrous magnesium sulfate and concentrated under reduced pressure. The residue was purified through silica-gel column chromatography (hexane/ethyl acetate=from 85/15 to 8/2) and then recrystallized from ethyl acetate/isopropyl ether to obtain 0.47 g (yield: 43%) of the target compound.

m.p.: 200–203° C.; NMR (CDCl$_3$) δ: 3.02–3.18 (4H, m), 3.41 (2H, t, J=8.8 Hz), 4.77 (2H, t, J=8.8 Hz), 5.42–5.46 (1H, m), 7.31 (1H, s)

Reference Example 8

3-(3-Fluoro-4-methoxyphenyl)propionic Acid

Malonic acid (7.5 g, 72.1 mmols) and piperidine (0.84 g, 9.83 mmols) were added to a pyridine (20 ml) solution of 3-fluoro-4-methoxybenzaldehyde (10.1 g, 65.5 mmols), and the mixture was stirred under heat at 120° C. for 7 hours. The reaction mixture was poured into water containing ice, and the powder that precipitated was taken out through filtration. The powder was dried and dissolved in acetic acid (300 ml) without being further purified. To this was added 5% palladium-carbon (3 g, containing 50% water), and the mixture was stirred in a hydrogen atmosphere at room temperature for 2 hours. The reaction mixture was filtered, and the filtrate was concentrated under reduced pressure to obtain 8.54 g (yield: 66%) of the target compound.

m.p.: 114–117° C.; NMR (CDCl$_3$) δ: 2.65 (2H, t, J=7.5 Hz), 2.89 (2H, t, J=7.5 Hz), 3.87 (3H, s), 6.80–7.00 (3H, m), hidden (1H)

Reference Example 9

5-Fluoro-6-methoxy-1-indanone

In the same manner as in Reference Example 6, the target compound was obtained from 3-(3-fluoro-4-methoxyphenyl)propionic acid. The yield was 91%.

m.p.: 152–153° C. (recrystallized from methanol/ethyl acetate); NMR (CDCl$_3$) δ: 2.71 (2H, t, J=5.7 Hz), 3.08 (2H, t, J=5.7 Hz), 3.92 (3H, s), 7.17 (1H, d, J=10.3 Hz), 7.29 (d, J=8.1 Hz); Elemental Analysis for C$_{10}$H$_9$FO$_2$: Calcd.: C 66.66; H 5.03; Found: C 66.82; H 5.06

Reference Example 10

(E)-(5-fluoro-6-methoxyindan-1-ylidene) acetonitrile

In the same manner as in Reference Example 7, the target compound was obtained from 5-fluoro-6-methoxy-1-indanone and diethyl cyanomethylphosphonate. The yield was 75%.

m.p.: 197–199° C. (recrystallized from hexane/ethyl acetate); NMR (CDCl$_3$) δ: 3.00–3.19 (4H, m), 3.92 (3H, s), 5.53 (1H, t, J=2.2 Hz), 7.02 (1H, d, J=7.6 Hz), 7.07 (1H, d, J=10.3 Hz); Elemental Analysis for C$_{12}$H$_{10}$FNO: Calcd.: C 70.93; H 4.96; N 6.89; Found: C 70.65; H 5.13; N 6.99

Reference Example 11

2-(5-Fluoro-6-methoxyindan-1-yl)ethylamine

In the same manner as in Example 18 to be mentioned later herein, the target compound was obtained from (E)-(5-fluoro-6-methoxyindan-1-ylidene)acetonitrile. The yield was 88%. The compound was oily.

NMR (CDCl$_3$) δ: 1.50–1.80 (2H, m), 1.90–2.08 (1H, m), 2.20–2.40 (1H, m), 2.67–2.90 (4H, m), 3.00–3.20 (1H, m), 3.87 (3H, s), 6.80 (1H, d, J=8.1 Hz), 6.92 (1H, d, J=11.0 Hz), hidden (2H)

Reference Example 12

N-[2-(5-fluoro-6-methoxyindan-1-yl)ethyl) propionamide

Propionyl chloride (2.5 g, 27.0 mmols) was gradually and dropwise added to a tetrahydrofuran (20 ml) solution containing 2-(5-fluoro-6-methoxyindan-1-yl)ethylamine (4.35 g, 20.8 mmols) and triethylamine (4.21 g, 41.6 mmols) while cooling with ice. After having been stirred at room temperature for 2 hours, the reaction mixture was poured into water, and the organic substance was extracted out with ethyl acetate. The extract was washed with a saturated saline solution and water and then dried with anhydrous magnesium sulfate, and the solvent was removed through distillation under reduced pressure. The resulting residue was purified through silica-gel column chromatography (ethyl acetate/hexane=90/10) to obtain 4.87 g (yield: 88%) of the target compound.

m.p.: 76–78° C.; NMR (CDCl$_3$) δ: 1.16 (3H, t, J=7.7 Hz), 1.47–1.81 (2H, m), 1.94–2.41 (2H, m), 2.21 (2H, q, J=7.7 Hz), 2.70–2.90 (2H, m), 3.00–3.20 (1H, m), 3.38 (2H, q, J=7.3 Hz), 3.87 (3H, s), 5.50 (1H, br s), 6.82 (1H, d, J=8.1 Hz), 6.92 (1H, d, J=11.4 Hz); Elemental Analysis for C$_{15}$H$_{20}$NFO$_2$: Calcd.: C 67.90; H 7.60; N 5.28; Found: C 67.83; H 7.27; N 5.25

Reference Example 13

N-[2-(5-fluoro-6-hydroxyindan-1-yl)ethyl]propionamide

Boron tribromide (7.9 g, 31.5 mmols) was gradually and dropwise added to a dichloromethane (100 ml) solution of N-[2-(5-fluoro-6-methoxyindan-1-yl)ethyl]propionamide (4.18 g, 15.8 mmols) while cooling with ice. After having been stirred for 2 hours while still cooling with ice, the reaction mixture was poured into water containing ice and then stirred at room temperature for 3 hours, and the organic substance was extracted with ethyl acetate. The extract was washed with a saturated saline solution and water and then dried with anhydrous magnesium sulfate, and the solvent was removed through distillation under reduced pressure. The resulting residue was purified through silica-gel column chromatography (ethyl acetate/hexane=9/1) to obtain 3.68 g (yield: 93%) of the target compound.

m.p.: 93–96° C. (recrystallized from ethyl acetate/hexane); NMR (CDCl$_3$) δ: 1.20 (3H, t, J=7.7 Hz), 1.47–1.80 (2H, m), 1.88–2.10 (1H, m), 2.22 (2H, q, J=7.7 Hz), 2.20–2.40 (1H, m), 2.65–2.90 (2H, m), 2.95–3.13 (1H, m), 3.37 (2H, q, J=7.5 Hz), 5.59 (1H, br s), 6.09 (1H, br s), 6.83 (1H, d, J=8.4 Hz), 6.89 (1H, d, J=10.6 Hz); Elemental Analysis for C$_{14}$H$_{18}$NFO$_2$: Calcd.: C 66.91; H 7.22; N 5.57; Found: C 66.84; H 7.10; N 5.54

Reference Example 14

N-(2-(5-fluoro-6-(2-propynyloxy)indan-1-yl)ethyl]propionamide

Potassium carbonate (1.37 g, 9.95 mmols) and propargyl bromide (2.4 g, 19.9 mmols) were added to a dimethylformamide (10 ml) solution of N-[2-(5-fluoro-6-hydroxyindan-1-yl)ethyl]propionamide (0.5 g, 1.99 mmols) and stirred at 120° C. for 2 hours. The reaction solution was poured into water, and the organic substance was extracted out with ethyl acetate. The extract was washed with a saturated saline solution and water and then dried with anhydrous magnesium sulfate, and the solvent was removed through distillation under reduced pressure. The resulting residue was purified through silica-gel column chromatography (ethyl acetate) to obtain 0.56 g (yield: 97%) of the target compound.

m.p.: 78–81° C. (recrystallized from ethyl acetate); NMR (CDCl$_3$) δ: 1.16 (3H, t, J=7.5 Hz), 1.50–1.83 (2H, m), 1.91–2.11 (1H, m), 2.21 (2H, q, J=7.5 Hz), 2.20–2.41 (1H, m), 2.55 (1H, t, J=2.3 Hz), 2.65–2.95 (2H, m), 3.00–3.20 (1H, m), 3.38 (2H, q, J=7.5 Hz), 4.74 (2H, d, J=2.2 Hz), 5.47 (1H, br s), 6.91 (1H, s), 6.96 (1H, s)

Reference Example 15

Ethyl 3-(6,7-dibromo-2,3-dihydrobenzofuran-5-yl)propionate

Bromine (0.80 g, 5.01 mmol) was added dropwise to a mixture of ethyl 3-(7-bromo-2,3-dihydrobenzofuran-5-yl)propionate (1.0 g, 3.34 mmol) and iron (10 mg) in acetic acid (10 ml) and the reaction mixture was stirred at 50° C. for 5 hours. The reaction mixture was filtered and the filtrate was concentrated under reduced pressure. Water was added to the residue and the organic matter was extracted with ethyl acetate. The extract was washed with a saturated aqueous sodium bicarbonate solution, a saturated aqueous sodium chloride solution and water and then dried over anhydrous magnesium sulfate and the solvent was distilled off under reduced pressure. The residue was purified by silica gel column chromatography (ethyl acetate:hexane=1:3) to give 0.67 g (yield: 53%) of the target compound.

m.p.: 42–43° C.; NMR (CDCl3) δ: 1.25 (3H, t, J=7.3 Hz), 2.60 (2H, t, J=7.7 Hz), 3.07 (2H, t, J=7.7 Hz), 3.27 (2H, t, J=8.8 Hz), 4.14 (2H, q, J=7.3 Hz), 4.68 (2H, t, J=8.8 Hz), 7.06 (1H, s)

Reference Example 16

3-(6,7-Dibromo-2,3-dihydrobenzofuran-5-yl)propionic acid

In the same manner as in Reference Example 5, the target compound was obtained from ethyl 3-(6,7-dibromo-2,3-dihydrobenzofuran-5-yl)propionate. The yield was 93%.

m.p.: 177–178° C. (recrystallized from ethyl acetate/hexane); NMR (CDCl$_3$) δ: 2.67 (2H, t, J=7.5 Hz), 3.08 (2H, t, J=7.5 Hz), 3.27 (2H, t, J=8.8 Hz), 4.68 (2H, t, J=8.8 Hz), 7.07 (1H, s)

Reference Example 17

4,5-Dibromo-1,2,6,7-tetrahydro-8H-indeno[5,4-b]furan-8-one

In the same manner as in Reference Example 6, the target compound was obtained from 3-(6,7-dibromo-2,3-dihydrobenzofuran-5-yl)propionic acid. The yield was 88%.

m.p.: 224–226° C. (recrystallized from chloroform/isopropyl ether); NMR (CDCl$_3$) δ: 2.72 (2H, t, J=5.9 Hz), 3.05 (2H, t, J=5.9 Hz), 3.55 (2H, t, J=9.0 Hz), 4.79 (2H, t, J=9.0 Hz)

Reference Example 18

1,2,6,7-Tetrahydro-8H-indeno[5,4-b]furan-8-one

5% Palladium carbon (50% hydrous, 2.9 g) and sodium acetate (17.9 g, 0.22 mol) were added to a solution of 4,5-dibromo-1,2,6,7-tetrahydro- 8H-indeno[5,4-b]furan-8-one (29.0 g, 87.4 mmol) in acetic acid (550 ml), and the mixture was catalytically reduced in a hydrogen atmosphere at ordinary temperature and ordinary pressure. After absorption of the calculated amount of hydrogen, the palladium carbon was filtered off and the solvent was distilled off under reduced pressure. Water was added to the residue and the organic matter was extracted with ethyl acetate. The extract was washed with a saturated aqueous sodium bicarbonate solution, a saturated aqueous sodium chloride solution and water and then dried over anhydrous magnesium sulfate, and the solvent was distilled off under reduced pressure. The residue obtained was purified by silica gel column chromatogarphy (ethyl acetate:hexane=15:85) to give the target compound. The yield was 13.5 g (89%).

m.p.: 133–134° C. (recrystallized from ethyl acetate/hexane); NMR (CDC13) δ: 2.68 (2H, t, J=5.9 Hz), 3.08 (2H, t, J=5.9 Hz), 3.47 (2H, t, J=8.8 Hz) 4.65 (2H, t, J=8.8 Hz), 7.01 (1H, d, J=8.1 Hz), 7.21 (1H, d, J=8.1 Hz); Elemental Analysis for $C_{11}H_{10}O_2$: Calcd.: C 75.84; H 5.79; Found: C 75.69; H 5.75

Reference Example 19

(E)-(1,6,7,8-tetrahydro-2H-indeno[5,4-b]furan-8-ylidene)acetonitrile

In the same manner as in Reference Example 7, the target compound was obtained from 1,2,6,7-tetrahydro-8H-indeno[5,4-b]furan-8-one and diethyl cyanomethyl-phosphonate. The yield was 60%.

m.p.: 149–151° C. (recrystallized from methanol); NMR (CDCl$_3$) δ: 3.00–3.20 (4H, m), 3.31 (2H, t, J=8.8 Hz), 4.67 (2H, t, J=8.8 Hz) 5.45 (1H, t, J=2.4 Hz), 6.86 (1H, d, J=8.1 Hz), 7.11 (1H, d, J) =8.1 Hz); Elemental Analysis for $C_{13}H_{11}NO$: Calcd.: C 79.17; H 5.62; N, 7.10; Found: C 79.21; H 5.82; N, 7.18

Reference Example 20

(S)-2-(1,6,7,8-tetrahydro-2H-indeno[5,4-b]furan-8-yl) ethylamine hydrochloride

A Hastelloy autoclave (200 mL) was charged with (E)-2-(1,6,7,8-tetrahydro-2H-indeno[5,4-b]furan-8-ylidene) ethylamine (1.00 g, 5.00 mmol.), Ru$_2$Cl$_4$[(R)-BINAP]$_2$NEt$_3$ (21.0 mg) and methanol (10 mL) under nitrogen atmosphere. Into the vessel, hydrogen gas was introduced up to 100 atmospheric pressure. The mixture was stirred for 20 hours at 50° C. The reaction system was depressurized to normal, followed by determination of the conversion and the optical purity of the product, (S)-2-(1,6,7,8-tetrahydro-2H-indeno [5,4-b]furan-8-yl) ethylamine), by means of high performance liquid chromatography. The conversion was 100% and the optical purity was 88.8%e.e.

Toluene (10 mL) was added to the residue (1.02 g) obtained by concentration under reduced pressure. The mixture was cooled on an ice-bath, to which was added, while stirring, 2% hydrochloric acid (10 mL). The reaction mixture was stirred for 30 minutes, which was concentrated under reduced pressure to leave the residue (1.21 g). The concentrate was dissolved in methanol (5 mL), to which was added acetone (10 mL). The mixture was cooled to 0° C., which was then subjected to filtration to collect the title compound (0.64 g). Further, the filtrate was concentrated under reduced pressure. The concentrate (0.34 g) was recrystallized from a mixture of methanol (1.5 mL) and acetone (3.0 mL) to give the title compound (0.17 g, total yield 0.81 g, yield 68%). This hydrochloride was processed with a 5% aqueous solution of sodium hydroxide to give (S)-2-(1,6,7,8-tetrahydro-2H-indeno[5,4-b]furan-8-yl) ethylamine. The optical purity of the product was determined by means of high performance liquid chromatography, which was 100%e.e.

Reference Example 21

(S)-2-(1,6,7,8-tetrahydro-2H-indeno[5,4-b]furan-8-yl] ethylamine

A Hastelloy autoclave (200 mL) was charged with (S)-2-(1,6,7,8-tetrahydro-2H-indeno[5,4-b]furan-8-yl) ethylamine (0.20 g, 1.00 mmol.), Ru$_2$Cl4[(R)-BINAP]$_2$NEt$_3$ (0.42 g), methanol (20 mL) and methylene chloride (5 mL) under nitrogen atmosphere. The mixture was heated up to 50° C., followed by introducing hydrogen gas into the vessel up to 50 atmospheric pressure. The reaction mixture was stirred for 15 minutes at 50° C., which was then cooled to room temperature and depressurized to normal pressure. To the reaction mixture was added a solution of (E)-2-(l,6,7,8-tetrahydro-2H-indeno[5,4-b]furan-8-ylidene) ethylamine (20.0 g, 99.4 mmol.) in methanol (30 mL). Into the reaction vessel was again introduced hydrogen gas up to 100 atmospheric pressure. The reaction mixture was stirred for 20 hours at 55° C. The pressure in the vessel was reverted to normal, then the conversion and the optical purity of the product, ((S)-2-(1,6,7,8-tetrahydro-2H-indeno[5,4-b]furan-8-yl) ethylamine), were determined by means of high performance liquid chromatography. The conversion was 100% and the optical purity of 90.3%e.e.

Reference Example 22

(S)-2-(1,6,7,8-tetrahydro-2H-indeno[5,4-b]furan-8-yl) ethylamine

A Hastelloy autoclave (100 mL) was charged with (E)-2-(1,6,7,8-tetrahydro-2H-indeno[5,4-b]furan-8-ylidene) ethylamine (0.50 g, 2.50 mmol.), Ru$_2$Cl$_4$[(R)-T-BINAP]$_2$NEt$_3$ (5.0 mg) and methanol (5.0 mL) under nitrogen atmosphere, followed by introducing hydrogen gas up to 100 atmospheric pressure. The reaction mixture was stirred for 20 hours at 50° C. The pressure in the vessel was reverted to normal, and the conversion and the optical purity of the product, ((S)-2-(1,6,7,8-tetrahydro-2H-indeno[5,4,b]furan-8-yl)ethylamine were determined by means of high performance liquid chromatography. The conversion was 100% and the optical purity was 74.0%e.e.

Reference Examples 23 to 25

Only the catalyst in Reference Example 22 was replaced with Ru(OCOCH$_3$)$_2$[(R)-BINAP], Ru(OCOCH$_3$)$_2$[(R)-T-BINAP] or Ru$_2$Cl$_4$[(R)-DM-BINAP]$_2$NEt$_3$, and the hydrogenation was conducted in the same manner as in Reference Example 22 to obtain the following results:

| Catalyst | Conversion | Optical purity |
| --- | --- | --- |
| R.Ex.23 Ru(OAc)$_2$((R)-BINAP) | 100% | 75.4% ee |
| R.Ex.24 Ru(OAc)$_2$((R)-T-BINAP) | 100% | 74.0% ee |
| R.Ex.25 Ru$_2$Cl$_4$((R)-DM-BINAP)$_2$NEt$_3$ | 100% | 36.4% ee |

For the determination of the conversion and the optical purity by means of high performance liquid chromatography in Reference Examples 20 to 25, the following conditions were employed.

High performance liquid chromatography: SHIMAZU SCL-10A
Column: ULTRON ES-OVM (4.6 mm×150 mm, SHINWA CHEMICAL INDUSTRIES LTD.)
Mobile phase: 40 mmol/L $KH_2PO_4$ aq. sol./ethanol=90/10 (pH=7.5 NaOH)
Wave length: UV 280 nm
Flow rate: 1.0 mL/min.

Reference Example 26

(E)-(6-methoxyindan-1-ylidene)acetonitrile

In substantially the same manner as in Reference Example 7, the title compound was produced from diethyl 6-methoxy-1-indanone and diethyl cyanomethylphosphonate (yield 73%).

m.p.: 92–95° C. (recrystallized from ethyl acetate) NMR ($CDCl_3$) δ: 2.97–3.20 (4H, m), 3.84 (3H, s), 5.61 (1H, t, J=2.6 Hz), 6.95–7.03 (2H, m), 7.26 (1H, dd, J=0.7 & 8.1 Hz); Elemental Analysis for $C_{12}H_{11}NO$: Calcd.: C 77.81; H 5.99; N 7.56; Found: C 77.79; H 6.01; N 7.58

Reference Example 27

(E)-2-(6-methoxyindan-1-ylidene)ethylamine hydrochloride

To a solution of (E)-(6-methoxyindan-1-ylidene) acetonitrile (5.0 g, 27 mmol.) in ethanol (50 mL) were added a saturated ammonia/ethanol solution (250 mL) and Raney cobalt (10 g). The mixture was stirred for 5 hours at room temperature under hydrogen atmosphere (5 kgf/cm$^2$). The Raney cobalt was filtered off, and the solvent was distilled off under reduced pressure to leave (E)-2-(6-methoxyindan-1-ylidene)ethylamine. This oily residue was dissolved in ethanol (20 mL). The solution was cooled to –40° C., to which was added a saturated hydrogen chloride/ethanol solution. The resulting crystalline precipitate was collected by filtration to obtain the title compound (yield 4.3 g, 71%).

m.p.: 177–179° C.; NMR ($d_6$-DMSO, $D_2O$) δ: 2.76–3.00 (4H, m), 3.40–3.65 (2H, m), 3.77 (3H, s), 5.98 (1H, t, J=7.5 Hz), 6.85 (1H, dd, J=2.2 & 8.4 Hz), 7.01 (1H, d, J=2.2 Hz), 7.22 (1H, d, J=8.4 Hz), 8.22 (2H, br s); Elemental Analysis for $C_{12}H_{15}NO\cdot HCl$: Calcd.: C 63.85; H 7.14; N 6.21; Cl 15.71; Found: C 63.53; H 6.85; N 6.16; Cl 15.40

Reference Example 28

(E)-N-[2-(6-methoxyindan-1-ylidene)ethyl]propionamide

In substantially the same manner as in Reference Example 12, the title compound was produced from (E)-2-(6-methoxyindan-1-ylidene)ethylamine and propionyl chloride (yield 78%).

m.p.: 129–131° C. (recrystallized from ethyl acetate); NMR ($CDCl_3$) δ: 1.18 (3H, t, J=7.5 Hz), 2.24 (2H, q, J=7.5 Hz), 2.73–2.86 (2H, m), 2.90–3.20 (2H, m), 3.81 (3H, s), 4.04 (2H, t, J=6.2 Hz), 5.55 (1H, br s), 5.88 (1H, m), 6.79 (1H, dd, J=2.4 & 8.1 Hz), 6.93 (1H, d, J=2.4 Hz), 7.14 (1H, d, J=8.1 Hz); Elemental Analysis for $C_{15}H_{19}NO_2$: Calcd.: C 73.44; H 7.81; N 5.71; Found: C 72.91; H 7.81; N 5.58

Reference Example 29

(S)-N-[2-(6-methoxyindan-1-yl)ethyl)propionamide (E)-N-[2-(6-methoxyindan-1-ylidene)ethyl] propionamide (3.5 g, 14.26 mmol.) and $Ru(OCOCH_3)_2[(S)$-BINAP] (120 mg, 142 µmol. were added to degasified absolute methanol (70 mL). The solution was stirred for 3 hours at 70° C. in an autoclave (hydrogen pressure 90 atm.). The reaction mixture was subjected to analysis by means of chiral column high performance liquid chromatography to find that the asymmetric yield of (S)-N-[2-(6-methoxyindan-1-yl) ethyl]propionamide was 95%e.e, while the chemical yield of it was 99%.

The reaction mixture was concentrated to dryness under reduced pressure. The resulting oily residue was purified by means of a short column chromatography (silica gel 7 g), followed by recrystallization from ethyl acetate/hexane to afford the title compound (yield 2.92 g, 83%), whose optical purity was not lower than 99%e.e. and chemical purity was not lower than 99%.

$[\alpha]_D^{20}$=–7.0° (c 1.000, ethanol); m.p.: 76–77° C. (recrystallized from ethyl acetate/hexane); NMR ($CDCl_3$) δ: 1.15 (3H, t, J=8 Hz), 1.56–1.64 (1H, m), 1.72 (1H, qd, J=8 & 13 Hz), 2.04 (1H, dtd, J=4, 8 & 13 Hz), 2.19 (2H, q, J=8 Hz), 2.32 (1H, dtd, J=4, 8 & 13 Hz), 2.77 (1H, td, J=8 & 16 Hz), 2.85 (1H, dtd, J=4, 8 & 16 Hz), 3.11 (1H, ddt, J=4, 8 & 14 Hz), 3.34 (3H, s), 3.37–3.41 (2H, m), 5.53 (1H, br s), 6.71 (1H, dd, J=2 & 8 Hz), 6.75 (1H, d, J=2 Hz), 7.10 (1H, d, J=8 Hz); Elemental Analysis for $C_{15}H_{21}NO_2$: Calcd.: C 72.84; H 8.56; N 5.66; Found: C 72.59; H 8.50; N 5.84

Reference Example 30

(S)-N-[2-(5-bromo-6-methoxyindan-1-yl)ethyl]propionamide

In substantially the same manner as in Reference Example 4, the title compound was produced from (S)-N-(6-methoxyindan-1-yl)ethyl]propionamide and bromine (yield 86%).

$[\alpha]D^{20}$=+5.20 (c 1.000, ethanol); m.p.: 105–107° C. (recrystallized from ethyl acetate/hexane); NMR ($CDCl_3$) δ: 1.16 (3H, t, J=7.7 Hz), 1.49–1.81 (2H, m), 1.98–2.41 (2H, m), 2.21 (2H, q, J=7.7 Hz), 2.69–2.98 (2H, m), 3.00–3.20 (1H, m), 3.39 (2H, q, J=7.3 Hz), 3.88 (3H, s), 5.48 (1H, br s), 6.78 (1H, s), 7.37 (1H, s); Elemental Analysis for $C_{15}H_{20}BrNO_2$: Calcd.: C 55.23; H 6.18; N 4.29; Found: C 55.15; H 6.18; N 4.25

Reference Example 31

(S)-N-[2-(5-bromo-6-hydroxyindan-1-yl)ethyl]propionamide

A solution of (S)-N-[2-(5-bromo-6-methoxyindan-1-yl) ethyl]propionamide (56.7 g, 174 mmol.) in dichloromethane (400 mL) was cooled to –30° C. To the solution was added dropwise slowly boron tribromide (95.8 g, 382 mmol.). The reaction mixture was stirred for 30 minutes while keeping at temperatures ranging from –20 to –15° C. The reaction mixture was poured into ice-water, which was stirred for further 10 minutes at room temperature. The organic matter was extracted with ethyl acetate. The extract solution was washed with a saturated aqueous saline solution and water, which was dried over anhydrous magnesium sulfate, followed by distilling off the solvent under reduced pressure. The residue was purified by means of silica gel column chromatography (ethyl acetate) to afford the title compound (yield 51.12 g, 94%).

$[\alpha]_D^{20}$=+2.7° (c 1.001, ethanol) m.p.: 146–148° C. (recrystallized from ethyl acetate); NMR ($CDCl_3$) δ: 1.16 (3H, t, J=7.5 Hz), 1.50–1.80 (2H, m), 1.90–2.40 (1H, m), 2.20–2.40 (1H, m), 2.24 (2H, q, J=7.5 Hz), 2.65–2.95 (2H, m), 3.00–3.18 (1H, m), 3.38 (2H, q, J=7.1 Hz), 5.82 (1H, br s), 6.86 (1H, s), 7.27 (1H, s), hidden (1H); Elemental Analysis for $C_{14}H_{18}BrNO_2$: Calcd.: C 53.86; H 5.81; N 4.49; Found: C 53.85; H 5.78; N 4.52

Reference Example 32

(S)-N-[2-(6-allyloxy-5-bromoindan-1-yl)ethyl]propionamide

A solution of (S)-N-[2-(5-bromo-6-hydroxyindan-1-yl)ethyl]propionamide (48.8 g, 156 mmol.) in N,N-dimethylformamide (110 mL) was cooled with ice, to which was gradually added sodium hydride (6.35 g, 172 mmol., content 65%). The mixture was stirred for about 15 minutes. When the bubbling of hydrogen gas ceased, allyl bromide (22.7 g, 188 mmol.) was added, and the mixture was stirred for 30 minutes under ice-cooling. The reaction mixture was poured into ice-water, which was neutralized with dilute hydrochloric acid. The organic matter was extracted with ethyl acetate. The extract solution was washed with a saturated aqueous saline solution and water, which was then dried over magnesium sulfate, followed by distilling off the solvent under reduced pressure. The residue was purified by means of silica gel gel column chromatography (ethyl acetate) to afford the title compound (yield 52.97 g, 96%).

$[\alpha]_D^{20}$=+3.7° (c 1.003, ethanol); m.p.: 86–87° C. (recrystallized from ethyl acetate/hexane); NMR (CDCl$_3$) δ: 1.16 (3H, t, J=7.5 Hz), 1.48–1.80 (2H, m), 1.90–2.40 (2H, m), 2.20 (2H, q, J=7.5 Hz), 2.70–2.91 (2H, m), 3.00–3.20 (1H, m), 3.37 (2H, q, J=7.4 Hz), 4.59 (2H, m), 5.25–5.60 (3H, m), 5.97–6.20 (1H, m), 6.76 (1H, s), 7.37 (1H, s); Elemental Analysis for C$_{17}$H$_{22}$BrNO$_2$: Calcd.: C 57.96; H 6.29; N 3.98; Found: C 57.91; H 6.28; N 4.04

Reference Example 33

(S)-N-[2-(7-allyl-5-bromo-6-hydroxyindan-1-yl)ethyl]propionamide

A suspension of (S)-N-[2-(6-allyloxy-5-bromoindan-1-yl)ethyl]propionamide (50.75 g, 144 mmol.) in N,N-diethylaniline (150 mL) was stirred for 2.5 hours at 200–205° C. under argon atmosphere. The reaction mixture was cooled, followed by distilling off N,N-diethylaniline under reduced pressure to leave an oily residue. To the residue were added water (50 mL), 2N HCl (50 mL) and ethyl acetate (100 mL). The mixture was subjected to extraction twice to extract the organic matter. The extract solution was washed with a saturated aqueous saline solution and water, which was then dried over anhydrous magnesium sulfate, followed by distilling off the solvent under reduced pressure. The residue was purified by means of silica gel column chromatography (ethyl acetate:hexane=7:3) to afford the title compound (yield 40.6 g, 80%).

$[\alpha]_D^{20}$=−51.3° (c 1.003, ethanol); m.p.: 85–87° C. (recrystallized from ethyl acetate/hexane); NMR (CDCl$_3$) δ: 1.14 (3H, t, J=7.6 Hz), 1.45–2.13 (4H, m), 2.18 (2H, q, J=7.6 Hz), 2.68–3.65 (7H, m), 4.93–5.13 (2H, m), 5.41 (1H, br s), 5.49 (1H, s), 5.89–6.10 (1H, m), 7.20 (1H, s); Elemental Analysis for C$_{17}$H$_{22}$BrNO$_2$: Calcd.: C 57.96; H 6.29; N 3.98; Br 22.68; Found: C 57.95; H 6.22; N 4.00; Br 22.52

Reference Example 34

(S)-N-[2-(5-bromo-6-hydroxy-7-(2-hydroxyethyl)indan-1-yl)ethyl]propionamide

A solution of (S)-N-[2-(7-allyl-5-bromo-6-hydroxyindan-1-yl)ethyl]propionamide (588 mg, 1.67 mmol.) in methanol (30 mL) was cooled to about −70° C., to which was introduced ozone for 5 minutes. After confirming the disappearance of the starting material, an excess amount of powdery sodium borohydride (510 mg, 13.4 mmol.) was added to reaction mixture at about −70° C. to decompose ozonide. The reaction mixture was warmed to room temperature, which was neutralized with dilute hydrochloric acid, followed by extracting the organic matter with a mixture of ethyl acetate:butanol=1:1. The extract solution was dried over anhydrous magnesium sulfate, from which the solvent was distilled off under reduced pressure. The residue was then washed with diethyl ether to afford the title compound (yield 0.59 g, 99%).

$[\alpha]D^{20}$=−43.7° (c 1.002, ethanol) m.p.: 85–87° C. (recrystallized from ethyl acetate/methanol); NMR (CDCl$_3$) δ: 1.13 (3H, t, J=7.5 Hz), 1.40–2.10 (4H, m), 2.17 (2H, q, J=7.5 Hz), 2.62–3.01 (4H, m), 3.07–3.22 (1H, m), 3.28 (2H, q, J=6.8 Hz), 3.89 (2H, br s), 5.47 (1H, t, J=3.7 Hz), 6.31 (1H, br s), 7.20 (1H, s), 9.07 (1H, s); Elemental Analysis for C$_{16}$H$_{22}$BrNO$_3$: Calcd.: C 53.94; H 6.22; N 3.93; Br 22.43; Found: C 53.97; H 6.09; N 3.97; Br 22.40

Reference Example 35

(S)-N-[2-(6-hydroxy-7-(2-hydroxyethyl)indan-1-yl)ethyl]propionamide

A methanol suspension of (S)-N-[2-(5-bromo-6-hydroxy-7-(2-hydroxyethyl)indan-1-yl)ethyl]propionamide (590 mg, 1.66 mmol.), triethylamine (184 mg, 1.82 mmol.) and 5% palladium-carbon (100 mg) was subjected to catalytic reduction under hydrogen atmosphere. At the time when the calculated volume of hydrogen was absorbed, the catalyst was filtered off. The filtrate was made weakly acidic with dilute hydrochloric acid, followed by extracting the organic matter with a mixture of ethyl acetate:butanol=1:1. The extract solution was dried over anhydrous magnesium sulfate, then the solvent was distilled off under reduced pressure, followed by washing with diethyl ether to afford the title compound (yield 0.42 g, 91%).

$[\alpha]_D^{20}$=−69.7 (c 1.002, ethanol); m.p.: 144–146° C. (recrystallized from ethyl acetate/methanol); NMR (CDCl$_3$) δ: 1.12 (3H, t, J=7.7 Hz), 1.45–2.10 (4H, m), 2.16 (2H, q, J=7.7 Hz), 2.60–3.00 (4H, m), 3.10–3.23 (1H, m), 3.29 (2H, q, J=6.8 Hz), 3.86 (2H, q, J=5.5 Hz), 5.00 (1H, t, J=4.4 Hz), 6.41 (1H, br s), 6.69 (1H, d, J=7.9 Hz), 6.91 (1H, d, J=7.9 Hz), 8.86 (1H, s); Elemental Analysis for C$_{16}$H$_{23}$NO$_3$: Calcd.: C 69.29; H 8.36; N 5.05; Found: C 69.46; H 8.28; N 5.11

Reference Example 36

6,7-Dimethoxy-1-indanone

In substantially the same manner as in Reference Example 18, the title compound was produced from 4-bromo-6,7-dimethoxy-1-indanone (yield 84%) as an oily product.

NMR (CDCl$_3$) δ: 2.69 (2H, t, J=6.0 Hz), 3.04 (2H, t, J=6.0 Hz), 3.89 (3H, s), 4.00 (3H, s), 7.10 (1H, d, J=8.4 Hz), 7.19 (1H, d, J=8.4 Hz)

Reference Example 37

(E)-(6,7-dimethoxyindan-1-ylidene)acetonitrile

In substantially the same manner as in Reference Example 7, the title compound was produced from 6,7-dimethoxy-1-indanone and diethyl cyanomethyl phosphonate (yield 81%).

m.p.: 111–113° C. (recrystallized from ethyl acetate); NMR (CDCl$_3$) δ: 2.95–3.15 (4H, m), 3.87 (3H, s), 3.91 (3H, s), 6.24 (1H, t, J=2.4 Hz), 6.95 (1H, d, J=8.6 Hz), 7.00 (1H, d, J=8.6 Hz); Elemental Analysis for C$_{13}$H$_{13}$NO$_2$: Calcd.: C 72.54; H 6.09; N 6.51; Found: C 72.38; H 6.11; N 6.53

Reference Example 38

2-(6,7-dimethoxyindan-1-yl)ethylamine hydrochloride

To a suspension of (E)-(6,7-dimethoxyindan-1-ylidene) acetonitrile (1.8 g, 8.36 mmol.) in ethanol (10 mL) were added Raney nickel (2.5 g, W2) and 4M ammonium/ethanol solution (20 mL). The mixture was stirred for 6 hours at 60° C. under hydrogen atmosphere (4 to 5 atm.). The reaction mixture was subjected to filtration, and the filtrate was concentrated under reduced pressure. The concentrate was dissolved in ethanol (50 mL), to which was added 5% Pd-C (0.2 g, 50% hydrous). The mixture was stirred for 4 hours at room temperature under hydrogen atmosphere (normal pressure). The reaction mixture was subjected to filtration, and the filtrate was concentrated to leave (E)-2-(6,7-dimethoxyindan-1-yl)ethylamine. The compound was dissolved in ethanol (2 mL), to which was added a saturated hydrogen chloride/ethanol solution. The resulting crystalline precipitate was collected by filtration to afford the title compound (yield 1.68 g, 78%).

m.p.: 141–143° C. (recrystallized from ethanol); NMR ($d_6$-DMSO) δ: 1.59–1.83 (2H, m), 1.95–2.26 (2H, m), 2.60–2.94 (4H, m), 3.21–3.41 (1H, m), 3.75 (3H, s), 3.76 (3H, s), 6.83 (1H, d, J=8.4 Hz), 6.89 (1H, d, J=8.4 Hz), 7.99 (2H, br s); Elemental Analysis for $C_{18}H_{19}NO_2 \cdot HCl$: Calcd.: C 60.58; H 7.82; N 5.43; Cl 13.75; Found: C 60.03; H 7.55; N 5.66; Cl 14.11

Reference Example 39

N-[2-(6,7-dimethoxyindan-1-yl)ethyl]acetamide

In substantially the same manner as in Reference Example 12, the tile compound was produced from 2-(6,7-dimethoxyindan-1-yl)ethylamine and acetyl chloride (yield 83%).

m.p.: 79–81° C. (recrystallized from ethyl acetate/hexane); NMR ($CDCl_3$) δ: 1.70–1.93 (3H, m), 1.95 (3H, s), 2.15–2.36 (1H, m), 2.67–3.21 (3H, m), 3.25–3.53 (2H, m), 3.85 (3H, s), 3.87 (3H, s), 5.90 (1H, br s), 6.75 (1H, d, J=8.1 Hz), 6.91 (1H, d, J=8.1 Hz); Elemental Analysis for $C_{15}H_{21}NO_3$: Calcd.: C 68.42; H 8.94; N 5.32; Found: C 68.16; H 7.78; N 5.35

Reference Example 40

N-[2-(6,7-dimethoxyindan-1-yl)ethyl]propionamide

In substantially the same manner as in Reference Example 12, the title compound was produced from 2-(6,7-dimethoxyindan-1-yl)ethylamine and propionyl chloride (yield 86%).

m.p.: 90–92° C. (recrystallized from ethyl acetate/hexane); NMR ($CDCl_3$) δ: 1.14 (3H, t, J=7.7 Hz), 1.70–1.94 (3H, m), 2.10–2.36 (1H, m), 2.18 (2H, q, J=7.7 Hz), 2.65–3.20 (3H, m), 3.25–3.55 (2H, m), 3.85 (3H, s), 3.87 (3H, s), 5.90 (1H, br s), 6.75 (1H, d, J=8.0 Hz), 6.90 (1H, d, J=8.0 Hz); Elemental Analysis for $C_{16}H_{23}NO_3$: Calcd.: C 69.29; H 8.36; N 5.05; Found: C 69.23; H 8.09; N 5.14

Reference Example 41

N-[2-(6,7-dimethoxyindan-1-yl)ethyl]butyramide

In substantially the same manner as in Reference Example 12, the title compound was produced from 2-(6,7-dimethoxyindan-1-yl)ethylamine and butyryl chloride (yield 84%).

m.p.: 66–68° C. (recrystallized from ethyl acetate/hexane); NMR ($CDCl_3$) δ: 0.94 (3H, t, J=7.3 Hz), 1.57–1.95 (5H, m), 2.10–2.35 (1H, m), 2.13 (2H, t, J=7.3 Hz), 2.66–3.20 (3H, m), 3.26–3.55 (2H, m), 3.85 (3H, s), 3.87 (3H, s), 5.87 (1H, br s), 6.75 (1H, d, J=8.1 Hz), 6.90 (1H, d, J=8.1 Hz); Elemental Analysis for $C_{17}H_{25}NO_3$: Calcd.: C 70.07; H 8.65; N 4.81; Found: C 69.84; H 8.43; N 4.80

Reference Example 42

N-[2-(6,7-dihydroxyindan-1-yl)ethyl]propionamide

In substantially the same manner as in Reference Example 31, the title compound was produced from N-[2-(6,7-dimethoxyindan-1-yl)ethyl]propionamide (yield 73%).

m.p.: 98–101° C. (recrystallized from ethyl acetate/hexane); NMR ($CDCl_3$) δ: 1.21 (3H, t, J=7.5 Hz), 1.60–1.98 (3H, m), 2.10–2.30 (1H, m), 2.31 (2H, q, J=7.5 Hz), 2.60–3.15 (3H, m), 3.22–3.40 (1H, m), 3.52–3.75 (1H, m), 5.95 (1H, s), 6.01 (1H, br s), 6.63 (1H, d, J=7.9 Hz), 6.74 (1H, d, J=7.9 Hz), 9.62 (1H, s); Elemental Analysis for $C_{14}H_{19}NO_3$: Calcd.: C 67.45; H 7.68; N 5.62; Found: C 67.35; H 7.60; N 5.66

Reference Example 43

N-[2-(6,7-dihydroxyindan-1-yl)ethyl]butyramide

In substantially the same manner as in Reference Example 31, the title compound was produced from N-[2-6,7-dimethoxyindan-1-yl)ethyl]butyramide (yield 92%) as an oily product.

NMR ($CDCl_3$) δ: 0.96 (3H, t, J=7.5 Hz), 1.60–2.00 (5H, m), 2.10–2.30 (1H, m), 2.23 (2H, t, J=7.5 Hz), 2.60–2.78 (1H, m), 2.80–3.00 (1H, m), 3.03–3.21 (1H, m), 3.22–3.40 (1H, m), 3.42–3.61 (1H, m), 6.20 (1H, br s), 6.38 (1H, br s), 6.62 (1H, d, J=7.7 Hz), 6.74 (1H, d, J=7.7 Hz), 9.13 (1H, br s)

Reference Example 44

6-methoxy-7-nitro-1-indanone

To a solution of 6-methoxy-1-indanone (30.0 g, 185 mmol.) in conc. sulfuric acid (130 mL) was added a solution of potassium nitrate (24.3 g, 0.24 mol.) in conc. sulfuric acid (100 mL), while maintaining the inner temperature below 0° C. The mixture was stirred for 20 minutes at the same temperature, which was then poured into ice-water, followed by extraction with ethyl acetate. The extract solution was washed with water and an aqueous solution of sodium hydrogencarbonate, which was then dried over anhydrous magnesium sulfate, followed by distilling off the solvent under reduced pressure. The residue was recrystallized from ethyl acetate/hexane to afford the title compound (yield 21.7 g, 58%).

m.p.: 155–158° C.; NMR ($CDCl_3$) δ: 2.78 (2H, t, J=5.6 Hz), 3.13 (2H, t, J=5.6 Hz), 3.94 (3H, s), 7.34 (1H, d, J=8.4 Hz), 7.56 (1H, d, J=8.4 Hz)

Reference Example 45

(E)-(6-methoxy-7-nitroindan-1-ylidene)acetonitrile

In substantially the same manner as in Reference Example 7, the title compound was produced from 6-methoxy-7-nitro-1-indanone and diethyl cyanomethylphosphonate (yield 84%).

m.p.: 138–141° C. (recrystallized from ethyl acetate/isopropyl ether); NMR ($CDCl_3$) δ: 3.00–3.20 (4H, m), 3.92 (3H, s), 5.42 (1H, t, J=2.6 Hz), 7.14 (lH, d, J=8.6 Hz), 7.43 (1H, d, J=8.6 Hz)

Reference Example 46

(E)-(7-amino-6-methoxyindan-1-ylidene)acetonitrile

In substantially the same manner as in Reference Example 3, the title compound was produced from (E)-(6-methoxy-7-nitroindan-1-ylidene)acetonitrile (yield 79%).

m.p.: 119–121° C. (recrystallized from hexane/ethyl acetate); NMR (CDCl$_3$) δ: 2.90–3.20 (4H, m), 3.87 (3H, s), 4.23 (2H, br s), 5.60 (1H, t, J=2.2 Hz), 6.69 (1H, d, J=8.0 Hz), 6.84 (1H, d, J=8.0 Hz)

Reference Example 47

N-[2-(7-amino-6-methoxyindan-1-yl)ethyl]acetamide

In substantially the same manner as in Reference Example 38, 2-(7-amino-6-methoxyindan-1-yl)ethylamine was produced from (E)-(7-amino-6-methoxyindan-1-ylidene) acetonitrile. The crude product thus obtained was used, without further purification, for the reaction described below. 1-Ethyl-3-(3-dimethylaminopropyl)carbodiimide hydrochloride (3.3 g, 17.2 mmol.) and 1-hydroxybenzotriazole monohydrate (2.2 g, 14.4 mmol.) were suspended in N,N-dimethylformamide (30 mL). To the suspension was added, under ice-cooling, acetic acid (0.65 mL). This reaction mixture was stirred for one hour at room temperature, which was again cooled with ice. To the mixture was added dropwise a solution of the above-mentioned crude 2-(7-amino-6-methoxyindan-1-yl) ethylamine in N,N-dimethylformamide (10 mL). The mixture was stirred for 30 minutes, which was poured into water. The mixture was subjected to extraction with ethyl acetate. From the organic layer was extracted the hydrochloride with 2N hydrochloric acid. Then, the aqueous layer thus obtained was adjusted to pH 10 with a 4N aqueous solution of sodium hydroxide. From the aqueous layer, the organic matter was extracted with ethyl acetate, which was dried over anhydrous magnesium sulfate, followed by distilling off the solvent under reduced pressure. The residue was purified by means of silica gel column chromatography (ethyl acetate:ethanol=10:1) to afford the title compound (yield 1.6 g, 66%).

m.p.: 94–97° C. (recrystallized from ethyl acetate/isopropyl ether); NMR (CDCl$_3$) δ: 1.60–2.10 (6H, m), 2.20 (1H, m), 2.74 (1H, m), 2.92 (1H, m), 3.18 (1H, m), 3.32 (2H, q, J=5.0 Hz), 3.78 (2H, br s), 3.83 (3H, s), 5.70 (1H, br s), 6.59 (1H, d, J=8.0 Hz), 6.60 (1H, d, J=8.0Hz)

Reference Example 48

N-[2-(7-amino-6-methoxyindan-1-yl)ethyl]propionamide

In substantially the same manner as in Reference Example 47, the title compound was produced from (E)-(7-amino-6-methoxyindan-1-ylidene)acetonitrile and propionic acid (yield 40%).

m.p.: 71–73° C. (recrystallized from ethyl acetate/isopropyl ether); NMR (CDCl$_3$) δ: 1.09 (3H, t, J=7.5 Hz), 1.6–2.0 (3H, m), 2.12 (2H, q, J=7.5 Hz), 2.25 (1H, m), 2.7–3.2 (3H, m), 3.34 (2H, q, J=5.0 Hz), 3.80 (2H, br s), 3.83 (3H, s), 5.67 (1H, br s), 6.59 (1H, d, J=8.0 Hz), 6.66 (1H, d, J=8.0 Hz)

Reference Example 49

N-[2-(7-amino-6-methoxyindan-1-yl)ethyl]butyramide

In substantially the same manner as in Reference Example 47, the title compound was produced from (E)-(7-amino-6-methoxyindan-1-ylidene)acetonitrile and butyric acid (yield 71%).

m.p.: 65–68° C. (recrystallized from ethyl acetate/isopropyl ether); NMR (CDCl$_3$) δ: 0.91 (3H, t, J=7.3 Hz), 1.50–2.40 (8H, m), 2.60–3.20 (3H, m), 3.34 (2H, q, J=5.1 Hz), 3.80 (2H, br s), 3.83 (3H, s), 5.67 (1H, br s), 6.59 (1H, d, J=8.2 Hz), 6.66 (1H, d, J=8.2 Hz)

Reference Example 50

N-[2-(7-amino-6-hydroxyindan-1-yl)ethyl]acetamide hydrochloride

To a solution of N-[2-(7-amino-6-methoxyindan-1-yl)ethyl]acetamide (1.1 g, 4.4 mmol.) in dichloromethane (20 mL) was added dropwise gradually boron tribromide (2.1 mL, 22.1 mmol.). The mixture was stirred for 30 minutes at the same temperature. The reaction mixture was poured into ice-water, which was subjected to extraction with 10% methanol/chloroform. The extract solution was dried over anhydrous magnesium sulfate, followed by distilling off the solvent under reduced pressure. The residue was purified by means of silica gel column chromatography (chloroform:methanol=10:1) to afford N-[2-(7-amino-6-hydroxyindan-1-yl)ethyl]acetamide (yield 630 mg, 61%). A portion of the product was dissolved in ethanol, to which was added a saturated hydrochloric acid/ethanol solution. The solvent was distilled off under reduced pressure. The resulting crystalline precipitate was recrystallized from ethanol to afford the title compound.

m.p.: 225–228° C. (recrystallized from ethanol); NMR (d$_6$-DMSO) δ: 1.30–1.80 (2H, m), 1.83 (3H, s), 1.90–2.20 (2H, m), 2.60–3.50 (5H, m), 6.79 (1H, d, J=8.2 Hz), 6.99 (1H, d, J=8.2 Hz), 7.96 (1H, br s), 10.32 (1H, br s), hidden (2H)

Reference Example 51

N-[2-(7-amino-6-hydroxyindan-1-yl)ethyl]propionamide

In substantially the same manner as in Reference Example 50, the title compound was produced from N-[2-(7-amino-6-methoxyindan-1-yl)ethyl]propionamide (yield 88%) as an oily product.

NMR (CDCl$_3$) δ: 1.11 (3H, t, J=7.5 Hz), 1.60–2.00 (3H, m), 2.14 (2H, q, J=7.5 Hz), 2.23 (1H, m), 2.70–2.90 (2H, m), 3.19 (1H, m), 3.34 (2H, q, J=5.1 Hz), 4.10 (2H, br s), 5.69 (1H, br s), 6.52 (1H, d, J=7.6 Hz), 6.60 (1H, d, J=7.6 Hz), hidden (1H)

Reference Example 52

N-[2-(7-amino-6-hydroxyindan-1-yl)ethyl]butyramide

In substantially the same manner as in Reference Example 50, the title compound was produced from N-[2-(7-amino-6-methoxyindan-1-yl)ethyl]butyramide (yield 89%) as an oily product.

NMR (CDCl$_3$) δ: 0.90 (3H, t, J=7.2 Hz), 1.50–1.90 (6H, m), 2.04 (2H, t, J=7.2 Hz), 2.23 (1H, m), 2.60–2.90 (2H, m), 3.10–3.40 (3H, m), 4.40 (2H, br s), 5.86 (1H, br s), 6.50 (1H, d, J=8.0 Hz), 6.62 (1H, d, J=8.0 Hz)

Reference Example 53

N-[2-(5-bromo-6-(2-propynyl)oxyindan-1-yl)ethyl]propionamide

In substantially the same manner as in Reference Example 32, the title compound was produced from N-[2-(5-bromo-6-hydroxyindan-1-yl)ethyl]propionamide and propargyl bromide (yield 99%).

m.p.: 104–107° C. (recrystallized from ethyl acetate/hexane); NMR (CDCl$_3$) δ: 1.16 (3H, t, J=7.6 Hz), 1.50–2.40 (6H, m), 2.55 (1H, t, J=2.3 Hz), 2.7–3.2 (3H, m), 3.38 (2H, t, J=7.6 Hz), 4.76 (2H, d, J=2.3 Hz), 5.48 (1H, br s), 6.93 (1H, s), 7.38 (1H, s)

Reference Example 54

N-[2-(6-allyloxy-5-bromoindan-1-yl)ethyl]propionamide

In substantially the same manner as in Reference Example 32, the title compound was produced from N-[2-(5-bromo-6-hydroxyindan-1-yl)ethyl]propionamide and allyl bromide (yield 93%).

NMR (CDCl$_3$) δ: 1.16 (3H, t, J=7.5 Hz), 1.60–2.20 (4H, m), 2.32 (2H, q, J=7.5 Hz), 2.6–3.2 (3H, m), 3.32 (2H, q, J=5.3 Hz), 4.60 (2H, d, J=4.6 Hz), 5.28 (1H, d, J=10.6 Hz), 5.43 (1H, s), 5.52 (1H, br s), 6.05 (1H, m), 6.78 (1H, s), 7.35 (1H, s)

Reference Example 55

N-[2-(5-bromo-6-(2-methyl-2-propenyl)oxyindan-1-yl)ethyl]propionamide

In substantially the same manner as in Reference Example 32, the title compound was produced from N-[2-(5-bromo-6-hydroxyindan-1-yl)ethyl]propionamide and methallyl chloride (yield 84%).

m.p.: 105–108° C. (recrystallized from ethyl acetate/hexane); NMR (CDCl$_3$) δ: 1.16 (3H, t,J=7.6 Hz), 1.86 (3H, s), 1.9–2.4 (6H, m), 2.80 (2H, m), 3.08 (1H, m), 3.38 (2H, q, J=7.6 Hz), 4.47 (2H, s), 5.00 (1H, s), 5.17 (1H, s), 5.40 (1H, br s), 6.76 (1H, s), 7.37 (1H, s)

Reference Example 56

N-[2-(7-allyl-5-bromo-6-hydroxyindan-1-yl)ethyl]propionamide

In substantially the same manner as in Reference Example 33, the title compound was produced from N-[2-(5-bromo-6-allyloxyindan-1-yl)ethyl]propionamide (yield 87%) as an oily product.

NMR (CDCl$_3$) δ: 1.14 (3H, t, J=7.6 Hz), 1.50–2.10 (4H, m), 2.18 (2H, q, J=7.6 Hz), 2.70–3.70 (7H, m), 4.90–5.20 (2H, m), 5.41 (1H, br s), 5.49 (1H, s), 5.90–6.20 (1H, m), 7.20 (1H, s)

Reference Example 57

N-[2-(5-bromo-6-hydroxy-7-(2-methyl-2-propenyl)indan-1-yl) ethyl]propionamide

In substantially the same manner as in Reference Example 33, the title compound was produced from N-[2-(5-bromo-6-(2-methyl-2-propenyl)oxyindan-1-yl)ethyl]propionamide (yield 91%).

m.p.: 89–91° C. (recrystallized from ethyl acetate/hexane); NMR (CDCl$_3$) δ: 1.14 (3H, t, J=7.6 Hz), 1.40–1.80 (2H, m), 1.80 (3H, s), 1.90–2.10 (2H, m), 2.17 (2H, q, J=7.6 Hz), 2.60–3.50 (7H, m), 4.49 (1H, s), 4.79 (1H, s), 5.32 (1H, br s), 5.47 (1H, s), 7.21 (1H, s)

Reference Example 58

(R)-N-[2-(6-methoxyindan-1-yl)ethyl]acetamide

A solution prepared by adding degasified absolute methanol (70 mL) to (E)-N-[2-(6-methoxyindan-1-ylidene) ethyl]acetamide (119.0 mg, 0.515 mmol.) and Ru(OCOCH$_3$)$_2$ [(R)-BINAP] (40 mg, 50 μmol.) was transferred to an autoclave, which was stirred for 6 hours at 50° C. under hydrogen pressure of 100 atm. The reaction mixture was subjected to high performance liquid chromatography using a chiral column to find that the asymmetric yield of (R)-N-[2-(6-methoxyindan-1-yl)ethyl]acetamide was 81%ee and the chemical yield was 82%.

Reference Example 59

(S)-N-[2-(6-ethoxyindan-1-yl)ethyl)propionamide

A solution prepared by adding degasified absolute methanol (70 mL) to (E)-N-[2-(6-ethoxyindan-1-ylidene) ethyl]propionamide (239.5 mg, 0.924 mmol.) and Ru(OCOCH$_3$)$_2$ [(S)-BINAP] (78 mg, 93 μmol.) was transferred to an autoclave, which was stirred for 6 hours at 50° C. under vapor pressure of 100 atm. The reaction mixture was subjected to analysis by means of high performance chromatography using a chiral column to find that the asymmetric yield of (S)-N-[2-(6-ethoxyindan-1-yl)ethyl]propionamide was 95%e.e. and the chemical yield was 88%.

Reference Example 60

(R)-N-[2-(6-methoxyindan-1-yl)ethyl]propionamide

A solution prepared by adding degasified absolute methanol (70 mL) to (Z)-N-[2-(6-methoxyindan-1-ylidene) ethyl]propionamide (258.5 mg, 1.05 mmol.) and Ru(OCOCH$_3$)$_2$ [(S)-BINAP] (84 mg, 100 μmol.) was transferred to an autoclave, which was stirred for 3 hours at 70° C. under hydrogen pressure of 100 atm. The reaction mixture was subjected to analysis by means of high performance liquid chromatography using a chiral column to find that the asymmetric yield of (R)-N-[2-(6-methoxyindan-1-yl)ethyl]propionamide was 80%e.e. and the chemical yield was 95%.

Reference Example 61

(R)-N-(2-(6-methoxyindan-1-yl)ethyl]propionamide

A solution prepared by adding 70 ml of degasified absolute methanol to (Z)-N-[2-(6-methoxyindan-1-ylidene)ethyl]propionamide (245,5 mg, 1.0 mmol.) and Ru$_2$Cl$_4$[(S)-BINAP]$_2$NEt$_3$ (169 mg, 100 μmol.) was transferred to an autoclave, which was stirred for 6 hours at 70° C. under hydrogen pressure of 100 atm. The reaction mixture was subjected to analysis by means of high performance liquid chromatography using a chiral column to find that the asymmetric yield of (R)-N-[2-(6-methoxyindan-1-yl)ethyl]propionamide was 86%e.e. and the chemical yield was 82%.

Reference Example 62

6-Hydroxy-7-nitro-indanone

In substantially the same manner as in Reference Example 45, the title compound was produced from 6-hydroxy-1-indanone (yield 61%).

m.p.: 218–220° C. (recrystallized from ethanol/hexane); NMR (CDCl$_3$) δ: 2.37 (2H, t, J=5.5 Hz), 2.74 (2H, t, J=5.5 Hz), 2.95 (1H, s), 6.95 (1H, d, J=8.4 Hz), 7.15 (1H, d, J=8.4 Hz)

Reference Example 63

Ethyl [(4-nitro-3-oxoindan-5-yl)oxy]acetate

To a solution of 6-hydroxy-7-nitro-1-indanone (8.0 g, 41 mmol.) in N,N-dimethylformamide (50 mL) was added potassium carbonate (11.7 g, 82 mmol.). The mixture was stirred under ice-cooling, to which was added dropwise ethyl bromoacetate (5.5 mL, 50 mmol.). The reaction mixture was then stirred for one hour at room temperature, which was poured into ice-water, followed by extracting the organic matter with ethyl acetate. The extract solution was washed with a saturated aqueous saline solution and water, which was then dried over anhydrous magnesium sulfate. The solvent was distilled off under reduced pressure. The resulting crystalline precipitate was collected by filtration and washed with hexane to afford the title compound (yield 10.8 g, 94%).

Reference Example 64

Ethyl [(4-amino-3-oxoindan-5-yl)oxy]acetate

In substantially the same manner as in Reference Example 3, the title compound was produced from ethyl [(4-nitro-3-oxoindan-5-yl)oxy]acetate (yield 98%).

NMR (CDCl$_3$) δ: 1.29 (3H, t, J=7.1 Hz), 2.3–3.0 (4H, m), 4.28 (2H, q, J=7.1 Hz), 4.61 (2H, s), 5.89 (2H, br s), 6.53 (1H, d, J=8.2 Hz), 6.87 (1H, d, J=8.2 Hz)

Reference Example 65

7,8-Dihydroindeno[5,4-b][1,4]oxazine-2,9(1H,3H)-dione

To a solution of ethyl [(4-amino-3-oxoindan-5-yl) oxy] acetate (8.7 g, 34.9 mmol.) in toluene (200 mL) was added potassium t-butoxide (400 mg, 3.6 mmol.). The mixture was refluxed for 12 hours under argon atmosphere. The reaction mixture was cooled, which was poured into water, followed by neutralization with dilute hydrochloric acid. The organic matter was extracted with ethyl acetate, which was washed with a saturated aqueous saline solution and water, followed by drying over anhydrous magnesium sulfate. The solvent was distilled off under reduced pressure. The residue was purified by means of silica gel column chromatography (hexane:ethyl acetate=1:1) to afford the title compound (yield 4.8 g, 66%).

m.p.: 136–139° C. (recrystallized from ethyl acetate/hexane); NMR (CDCl$_3$) δ: 2.74 (2H, t, J=5.8 Hz), 3.10 (2H, t, J=5.8 Hz), 4.68 (2H, s), 7.01 (1H, d, J=7.2 Hz), 7.17 (1H, d, J=7.2 Hz), 9.52 (1H, br s)

Reference Example 66

(E)-(1,2,3,7,8,9-hexahydro-2-oxoindeno[5,4-b][1,4]oxazin-9-ylidene)acetonitrile

In substantially the same manner as in Reference Example 7, the title compound was produced from 7,8-dihydroindeno [5,4-b][1,4]oxazine-2,9(1H,3H)-dione and diethyl cyanomethylphosphonate (yield 86%).

m.p.: 158–161° C. (recrystallized from chloroform); NMR (CDCl$_3$) δ: 3.00–3.20 (4H, m), 4.62 (2H, s), 5.62 (1H, t, J=2.3 Hz), 6.97 (1H, d, J=8.2 Hz), 7.06 (1H, d, J=8.2 Hz), 8.07 (1H, br s)

Reference Example 67

N-[2-(5-Hydroxyindol-3-yl)ethyl]propionamide

To a solution of serotonin hydrochloride (10 g, 47.5 mmol.) in water (50 mL) were added, under argon atmosphere, tetrahydrofuran (20 mL) and a solution of sodium carbonate (5.3 g) in water (20 mL). The mixture was cooled to 0° C., to which was added propionic anhydride (6.2 g, 49.9 mmol.). The mixture was stirred for 2 hours at room temperature. The reaction mixture was subjected to extraction with ethyl acetate. The extract solution was washed with 1N HCl, a saturated aqueous solution of sodium hydrogencarbonate and water, which was dried and then concentrated to afford the title compound (yield 10.0 g, 98.0%) as an oily product. This compound was used, without refining further, for the subsequent reaction.

NMR (d$_6$-DMSO) δ: 1.01 (3H, t, J=7.6 Hz), 2.09 (2H, q, J=7.6 Hz), 2.73 (2H, t, J=7.2 Hz), 3.30 (2H, q, J=7.2 Hz), 3.72 (1H, br s), 6.61 (1H, dd, J=8.8 & 2.2 Hz), 6.85 (1H, d, J=2.2 Hz), 7.04 (1H, s), 7.15 (1H, d, J=8.8 Hz), 7.91 (1H, t, J=7.2 Hz), 10.45 (1H, s)

Reference Example 68

N-[2-(5-allyloxyindol-3-yl)ethyl]propionamide

Allyl bromide (11 g, 90.8 mmol.) was added, under argon atmosphere, to a mixture of N-[2-(5-hydroxyindol-3-yl) ethyl]propionamide (20.0 g, 92.5 mmol.), cesium carbonate (31.6 g, 97 mmol.) and N,N-dimethylformamide (150 mL) at 0° C. The reaction mixture was stirred for one hour at 50° C., to which was added water. The product was extracted with ethyl acetate. The extract solution was washed with water and dried. The solvent was then distilled off to leave the title compound (yield 20.0 g, 79.4%) as an oily product. This product was used, without further purification, for the subsequent reaction.

NMR (CDCl$_3$) δ: 1.11 (3H, t, J=7.6 Hz), 2.14 (2H, q, J=7.6 Hz), 2.92 (2H, t, J=7.0 Hz), 3.58 (2H, q, J=7.0 Hz), 4.57 (2H, dt, J=5.6 & 1.6 Hz), 5.28 (1H, dq, J=10.6 & 1.4 Hz), 5.35 (1H, dq, J=17.2 & 1.4 Hz), 5.61 (1H, t, J=7.0 Hz), 6.10 (1H, m), 6.89 (1H, dd, J=8.8 & 2.2 Hz), 6.99 (1H, d, J=2.2 Hz), 7.05 (1H, d, J=2.6 Hz), 7.25 (1H, d, J=8.8 Hz), 8.33 (1H, br s)

Reference Example 69

N-[2-(4-allyl-5-hydroxyindol-3-yl)ethyl]propionamide

In N,N-diethylaniline (100 mL) was dissolved N-[2-5-allyloxyindol-3-yl)ethyl]propionamide (20.0 g, 73.4 mmol.). The solution was heated for 6 hours at 200° C. under argon atmosphere. The reaction mixture was cooled. The solvent then separated was removed, and the residue was dissolved in ethyl acetate. This solution was washed with 1N HCl and a saturated aqueous solution of sodium hydrogencarbonate, followed by drying and concentration. The concentrate was purified by means of silica gel column chromatography (hexane: ethyl acetate=8:2) to give 14.1 g (yield 71%) of the title compound.

NMR (d$_6$-DMSO) δ: 1.03 (3H, t, J=7.2 Hz), 2.11 (2H, q, J=7.2 Hz), 2.91 (2H, t, J=7.4 Hz), 3.31 (2H, q, J=7.4 Hz), 3.67 (2H, d, J=5.2 Hz), 4.86 (1H, d, J=9.2 Hz), 4.90 (1H, d, J=8.0 Hz), 6.00 (1H, m), 6.68 (1H, d, J=8.4 Hz), 7.02 (1H, d, J=8.4 Hz), 7.87 (1H, t, J=5.0 Hz), 8.35 (1H, s), 10.49 (1H, s), hidden (1H)

Reference Example 70

N-[2-(4-allyl-2,3-dihydro-5-hydroxyindol-3-yl)ethyl] propionamide

To a solution of N-[2-(4-allyl-5-hydroxyindol-3-yl)ethyl] propionamide (3.73 g, 14.3 mmol) in acetic acid (20 mL) was added sodium cyanoborohydride (2.7 g, 43.0 mmol) portionwise maintaining the reaction temperature around 15° C. The mixture was stirred for 1 hour maintaining the temperature 15 to 20° C. and then poured into water. The product was extracted with ethyl acetate. The extract was washed with saturated aqueous sodium hydrogen carbonate solution, brine and water, dried over anhydrous magnesium sulfate and evaporated to afford the title compound. This compound was used for the subsequent reaction without further purification.

Reference Example 71

N-[2-(4-allyl-1-formyl-2,3-dihydro-5-hydroxyindol-3-yl) ethyl]propionamide

Formic acid (3.3 g, 71.7 mmol) and acetic anhydride (7.32g, 71.7 mmol) was mixed under ice-cooling and the mixture was stirred for 10 minutes. To the mixture was added a solution of N-[2-(4-allyl-2,3-dihydro-5-hydroxyindol-3-yl)ethyl]propionamide in formic acid (10 mL). The mixture was stirred for 1 hour under ice-cooling and poured into water. The product was extracted with 10% methanol/ethyl acetate. The extract was washed with saturated aqueous sodium hydrogen carbonate solution, brine and water, dried over anhydrous magnesium sulfate and evaporated. The residue was purified by silica gel column chromatography (ethyl acetate:methanol=9:1) to afford the title compound (yield 2.0 g, 46% from N-[2-(4-allyl-5-hydroxyindol-3-yl)ethyl]propionamide).

m.p.: 173–175 ° C. (recrystallized from methanol/ethyl acetate); NMR ($d_6$-DMSO) δ: 1.01 (3H, dt, J=1.6 & 7.6 Hz), 1.30–1.50 (1H, m), 1.60–1.87 (1H, m), 2.08 (2H, dq, J=1.6 & 7.6 Hz), 3.00–3.50 (5H, m), 3.60–4.10 (2H, m), 4.90–5.10 (2H, m), 5.80–6.04 (1H, m), 6.65 (1H, d, J=8.4 Hz), 7.08, 7.59 (1H, d×2, J=8.4 Hz), 7.86 (1H, br s), 8.36, 8.85 (1H, s×2), 9.17, 9.23 (1H, s×2); Elemental Analysis for $C_{17}H_{22}N_2O_3$: Calcd.: C 67.53; H 7.33; N 9.26; Found: C 67.25; H 7.26; N 9.25

Reference Example 72

N-[2-[1-formyl-2,3-dihydro-5-hydroxy-4-(2-hydroxyethyl)indol-3-yl]ethyl]propionamide In substantially the same manner as in Reference Example 34, the title compound was produced from N-[2-(4-allyl-1-formyl-2,3-dihydro-5-hydroxyindol-3-yl)ethyl]propionamide as an oily product (yield 66%).

NMR ($d_6$-DMSO) δ: 1.00 (3H, dt, J=2.2 & 7.4 Hz), 1.30–1.55 (1H, m), 1.58–2.02 (1H, m), 2.06 (2H, dq, J=2.2 & 7.4 Hz), 2.50–2.80 (2H, m), 2.95–3.20 (2H, m), 3.22–4.00 (5H, m), 4.70–4.80 (1H, m), 6.62 (1H, d, J=8.4 Hz), 7.05, 7.57 (1H, d×2, J=8.4 Hz), 7.81 (1H, br s), 8.36, 8.84 (1H, s×2), 9.16, 9.21 (1H, s×2)

Reference Example 73

N-[2-(5-hydroxyindol-3-yl)ethyl]butyramide

In substantially the same manner as in Reference Example 67, the title compound was produced from serotonin hydrochloride and butyryl chloride as an oily product (yield 39%)

NMR ($d_6$-DMSO) δ: 0.86 (3H, t, J=7.4 Hz), 1.49 (2H, sextet, J=7.4 Hz), 2.05 (2H, q, J=7.4 Hz), 2.72 (2H, t, J=7.4 Hz), 3.29 (2H, q, J=6.8 Hz), 6.59 (1H, dd, J=8.4 & 1.8 Hz), 6.83 (1H, d, J=1.8 Hz), 7.03 (1H, s), 7.12 (1H, d, J=8.4 Hz), 7.87 (1H, t, J=7.4 Hz), 8.59 (1H, s), 10.47 (1H, s)

Reference Example 74

N-[2-(5-allyloxyindol-3-yl)ethyl]butyramide

In substantially the same manner as in Reference Example 68, the title compound was produced from N-[2-(5-hydroxyindol-3-yl)ethyl]butyramide and allyl bromide as an oily product (yield 91%).

NMR (CDCl$_3$) δ: 0.90 (3H, t, J=7.4 Hz), 1.62 (2H, sextet, J=7.4 Hz), 2.09 (2H, t, J=7.4 Hz), 2.92 (2H, t, J=7.0 Hz), 3.61 (2H, q, J=7.0 Hz), 4.57 (2H, d, J=5.6 Hz), 5.27 (1H, dq, J=10.2 & 1.4 Hz), 5.43 (1H, dq, J=17.2 & 1.4 Hz), 5.63 (1H, t, J=7.0 Hz), 5.80–6.20 (1H, m), 6.89 (1H, dd, J=8.8 & 2.2 Hz), 6.98 (1H, d, J=1.8 Hz), 7.05 (1H, d, J=2.2 Hz), 7.25 (1H, d, J=8.8 Hz), 8.37 (1H, br s)

Reference Example 75

N-[2-(4-allyl-5-hydroxyindol-3-yl)ethyl]butyramide

In substantially the same manner as in Reference Example 69, the title compound was produced from N-[2-(5-allyloxyindol-3-yl)ethyl]butyramide as an oily product (yield 90%).

NMR ($d_6$-DMSO) δ: 0.88 (3H, t, J=7.4 Hz), 1.54 (2H, sextet, J=7.4 Hz), 2.07 (2H, t, J=7.4 Hz), 2.90 (2H, t, J=7.4 Hz), 3.31 (2H, q, J=7.4 Hz), 3.67 (2H, d, J=5.2 Hz), 4.86 (1H, dd, J=9.2 & 1.8 Hz), 4.93 (1H, d, J=1.4 Hz), 5.80–6.20 (1H, m), 6.68 (1H, d, J=8.4 Hz), 6.99 (1H, s), 7.02 (1H, d, J=8.4 Hz), 7.90 (1H, t, J=5.0 Hz), 8.36 (1H, s), 10.49 (1H, s)

Reference Example 76

N-[2-(4-allyl-2,3-dihydro-5-hydroxyindol-3-yl)ethyl]butyramide

In substantially the same manner as in Reference Example 70, the title compound was produced from N-[2-(4-allyl-5-hydroxyindol-3-yl)ethyl]butyramide as an oily product (yield 84%).

NMR ($d_6$-DMSO) δ: 0.86 (3H, t, J=7.3 Hz), 1.40–1.80 (4H, m), 2.06 (2H, t, J=7.3 Hz), 3.00–3.70 (8H, m), 4.91–5.07 (2H, m), 5.80–6.01 (1H, m), 6.63 (1H, d, J=8.3 Hz), 6.71 (1H, d, J=8.3 Hz), 7.88 (1H, t, J=5.5 Hz), 9.13 (1H, s)

Reference Example 77

N-[2-(4-allyl-1-formyl-2,3-dihydro-5-hydroxyindol-3-yl)ethyl]butyramide

In substantially the same manner as in Reference Example 71, the title compound was produced from N-[2-(4-allyl-2,3-dihydro-5-hydroxyindol-3-yl)ethyl]butyramide as an oily product (yield 75%).

NMR ($d_6$-DMSO) δ: 0.86 (3H, t, J=7.3 Hz), 1.25–1.83 (4H, m), 2.04 (2H, t, J=7.3 Hz), 3.00–3.40 (5H, m), 3.60–4.03 (2H, m), 4.90–5.10 (2H, m), 5.80–6.01 (1H, m), 6.64 (1H, d, J=8.4 Hz), 7.08, 7.59 (1H, d×2, J=8.4 Hz), 7.88 (1H, br s), 8.36, 8.85 (1H, s×2), 9.17, 9.22 (1H, s×2); Elemental Analysis for $C_{18}H_{24}N_2O_3$: Calcd.: C 68.33; H 7.65; N 8.85; Found: C 68.17; H 7.65; N 8.99

Reference Example 78

N-[2-[1-formyl-2,3-dihydro-5-hydroxy-4-(2-hydroxyethyl)indol-3-yl]ethyl]butyramide In substantially the same manner as in Reference Example 34, the title compound was produced from N-[2-(4-allyl-1-formyl-2,3-dihydro-5-hydroxyindol-3-yl)ethyl]butyramide as an oily product (yield 69%).

NMR ($d_6$-DMSO) δ: 0.85 (3H, t, J=7.3 Hz), 1.38–1.81 (4H, m), 2.03 (2H, t, J=7.3 Hz), 2.50–2.82 (2H, m), 2.98–4.00 (7H, m), 4.74–4.83 (1H, m), 6.62 (1H, d, J=8.1 Hz), 7.06, 7.57 (1H, d×2, J=8.1 Hz), 7.83 (1H, br s), 8.35, 8.83 (1H, s×2), 9.17, 9.22 (1H, s×2)

Reference Example 79

(2,3-dihydrobenzofuran-5-yl)methanol

To a solution of 2,3-dihydrobenzofuran-5-carbaldehyde (30.0 g, 0.202 mol) in methanol (150 mL) was added sodium borohydride (3.83 g, 0.101 mol) under ice-cooling. The mixture was stirred for 15 minutes at ambient temperature and then diluted with water. The product was extracted with ethyl acetate. The extract was washed with brine, dried over anhydrous magnesium sulfate and evaporated. The residue was purified by silica gel column chromatography (hexane:ethyl acetate=1:1) to afford the title compound (yield 27.6 g, 91%) as an oily product.

NMR (CDCl$_3$) δ: 1.67 (1H, s), 3.20 (2H, t, J 8.6 Hz), 4.57 (2H, t, J=8.6 Hz), 4.58 (2H, s), 6.76 (1H, d, J=8.0 Hz), 7.10 (1H, d, J=8.0 Hz), 7.22 (1H, s)

Reference Example 80

5-bromomethyl-2,3-dihydrobenzofuran

To a solution of (2,3-dihydrobenzofuran-5-yl)methanol (29.0 g, 0.193 mol) in tetrahydrofuran (150 mL) was added phosphorous tribromide (34.8 g, 0.129 mol) under ice/salt-cooling. The mixture was stirred for 20 minutes and then poured into water. The mixture was extracted with ethyl acetate. The extract was washed with brine, dried over anhydrous magnesium sulfate and evaporated to afford the title compound (yield 27.6 g, 91%).

m.p.: 57–60° C.; NMR (CDCl$_3$) δ: 3.20 (2H, t, J=8.8 Hz), 4.51 (2H, s), 4.59 (2H, t, J=8.8 Hz), 6.73 (1H, d, J=8.2 Hz), 7.14 (1H, d, J=8.2 Hz), 7.24 (1H, s)

Reference Example 81

Ethyl 3-(2,3-dihydrobenzofuran-5-yl)-2-phenylpropionate

To a solution of lithium hexamethyldisilazide solution, prepared from 1,1,1,3,3,3-hexamethyldisilazane (37.4 g, 0.232 mol), n-butyllithium (127 mL, 1.6 M hexane solution) and tetrahydrofuran (150 mL), was added a solution of ethyl phenylacetate (33.3 g, 0.203 mol) in tetrahydrofuran (20 mL) at −78° C. The mixture was stirred for 15 minutes and then a solution of 5-bromomethyl-2,3-dihydrobenzofuran (41.0 g, 0.193 mol) in tetrahydrofuran (50 mL) was added. The mixture was stirred for further 20 minutes, diluted with water and warmed up to room temperature. The product was extracted with ethyl acetate. The extract was washed with brine, dried over anhydrous magnesium sulfate and evaporated. The residue was purified by silica gel column chromatography (hexane:ethyl acetate=9:1) to afford the title compound as an oily product (yield 54.5 g, 95%).

NMR (CDCl$_3$) δ: 1.13 (3H, t, J=6.8 Hz), 2.93 (1H, dd, J=6.2 & 13.8 Hz), 3.14 (2H, t, J=8.8 Hz), 3.32 (1H, dd, J=9.0 & 13.8 Hz), 3.78 (1H, dd, J=6.2 & 9.0 Hz), 4.00–4.15 (2H, m), 4.52 (2H, t, J=8.8 Hz), 6.64 (1H, d, J=8.2 Hz), 6.87 (1H, d, J=8.2 Hz), 6.96 (1H, s), 7.21–7.38 (5H, m)

Reference Example 82

Ethyl 3-(7-bromo-2,3-dihydrobenzofuran-5-yl)-2-phenylpropionate

In substantially the same manner as in Reference Example 4, the title compound was produced from 3-(2,3-dihydrobenzofuran-5-yl)-2-phenylpropionic acid as an oily product (yield 97%).

NMR (CDCl$_3$) δ: 1.15 (3H, t, J=7.2 Hz), 2.89 (1H, dd, J=6.2 & 13.8 Hz), 3.23 (2H, t, J=8.6 Hz), 3.29 (1H, dd, J=8.8 & 13.8 Hz), 3.75 (1H, dd, J=6.2 & 8.8 Hz), 4.12 (2H, q, J=7.2 Hz), 4.62 (2H, t, J=8.6 Hz), 6.87 (1H, s), 7.04 (1H, s), 7.30–7.32 (5H, m)

Reference Example 83

Ethyl 3-(6,7-dibromo-2,3-dihydrobenzofuran-5-yl)-2-phenylpropionate

In substantially the same manner as in Reference Example 15, the title compound was produced from ethyl 3-(7-bromo-2,3-dihydrobenzofuran-5-yl)-2-phenylpropionate as an oily product (yield 35%).

NMR (CDCl$_3$) δ: 1.14 (3H, t, J=7.0 Hz), 3.11 (1H, dd, J=5.4 & 14.0 Hz), 3.19 (2H, t, J=8.8 Hz), 3.50 (1H, dd, J=9.4 & 14.0 Hz), 3.96 (1H, dd, J=5.4 & 9.4 Hz), 4.08 (2H, q, J=7.0 Hz), 4.64 (2H, t, J=8.8 Hz), 6.92 (1H, s), 7.28–7.32 (5H, m)

Reference Example 84

3-(6,7-dibromo-2,3-dihydrobenzofuran-5-yl)-2-phenylpropionic acid

In substantially the same manner as in Reference Example 5, the title compound was produced from ethyl 3-(6,7-dibromo-2,3-dihydrobenzofuran-5-yl)-2-phenylpropionate (yield 56%).

m.p.: 188–189° C. (ethyl acetate/hexane); NMR (CDCl$_3$) δ: 3.06–3.21 (3H, m), 3.50 (1H, dd, J=8.8 & 14.0 Hz), 4.01 (1H, dd, J=5.8 Hz, 8.8 Hz), 4.63 (2H, t, J=8.8 Hz), 6.85 (1H, s), 7.32 (5H, s), hidden (1H)

Reference Example 85

4,5-dibromo-1,2,6,7-tetrahydro-7-phenyl-8H-indeno[5,4-b]furan-8-one

In substantially the same manner as in Reference Example 6, the title compound was produced from 3-(6,7-dibromo-2,3-dihydrobenzofuran-5-yl)-2-phenylpropionic acid (yield 81%).

m.p.: 208–211° C.; NMR (CDCl$_3$) δ: 3.19 (1H, dd, J=3.9 & 17.7 Hz), 3.55 (2H, t, J=9.0 Hz), 3.61 (1H, dd, J=8.3 & 17.7 Hz), 3.92 (1H, dd, J=3.9 & 8.3 Hz), 4.81 (2H, t, J=9.0 Hz), 7.15–7.45 (5H, m)

Reference Example 86

1,2,6,7-tetrahydro-7-phenyl-8H-indeno[5,4-b]furan-8-one

In substantially the same manner as in Reference Example 18, the title compound was produced from 4,5-dibromo-1,2,6,7-tetrahydro-7-phenyl-8H-indeno[5,4-b]furan-8-one (yield 70%).

m.p.: 108–110° C.; NMR (CDCl$_3$) δ: 3.12 (1H, dd, J=4.0 & 16.8 Hz), 3.38 (2H, t, J=8.8 Hz), 3.53 (1H, dd, J=8.1& 16.8 Hz), 3.79 (1H, dd, J=4.0 & 8.1 Hz), 4.57 (2H, t, J=8.8 Hz), 6.98 (1H, d, J=8.4 Hz), 7.07–7.29 (6H, m)

Reference Example 87

(E)-(1,6,7,8-tetrahydro-7-phenyl-2H-indeno[5,4-b]furan-8-ylidene)acetonitrile, and (1,6-dihydro-7-phenyl-2H-indeno[5,4-b]furan-8-yl)acetonitrile To a boiling solution of 1,2,6,7-tetrahydro-7-phenyl-8H-indeno[5,4-b]furan-8-one (4.4 g, 17.6 mmol) in tetrahydrofuran (100 mL) was added the phosphonate ylide solution, prepared from diethyl cyanomethylphosphonate (3.27 g, 18.5 mmol), sodium hydride (60% oil dispersion, 0.73 g, 18.5 mmol) and tetrahydrofuran (80 mL). The mixture was refluxed for 1.5 hours. To this solution was added the same amount of the phosphonate ylide solution additionally. The mixture was refluxed for further 30 minutes, cooled and then poured into water. The product was extracted with ethyl acetate. The extract was washed with water, dried and evaporated. The residue was purified by silica gel column chromatography (hexane:ethyl acetate=9:1), followed by crystallization from ethyl acetate/diisopropylether to afford the mixture of (A) (E)-(1,6,7,8-tetrahydro-7-phenyl-2H-indeno[5,4-b]furan-8-ylidene)acetonitrile and (B) (1,6-dihydro-7-phenyl-2H-indeno[5,4-b]furan-8-yl)acetonitrile (A:B=1:2) (yield 0.85 g, 18%).

m.p.: 123–126° C.; NMR (CDCl$_3$) δ: (A) 3.03 (1H, dd, J=17.2 & 1.8 Hz), 3.32 (2H, dt, J=11.4 & 2.2 Hz), 3.59 (1H, dd, J=17.2 & 8.4 Hz), 4.48 (1H, dt, J=8.4 & 1.8 Hz), 4.68 (2H, t, J=11.4 Hz), 5.53 (1H, d, J=1.8 Hz), 6.91 (1H, d, J=8.0 Hz), 7.10–7.60 (6H, m) (B) 3.61 (2H, t, J=8.8 Hz), 3.68 (2H, s), 3.75 (2H, s), 4.68 (2H, t, J=8.8 Hz), 6.73 (1H, d , J=8.0 Hz), 7.10–7.60 (6H, m)

Example 1

N-[2-(1,6,7,8-tetrahydro-2H-indeno[5,4-b]furan-8-yl)ethyl]acetamide

Aqueous 1 N sodium hydroxide solution (1.5 ml) and acetic anhydride (0.050 ml, 0.528 mmols) were added to a tetrahydrofuran (1.5 ml) solution of 2-(1,6,7,8-tetrahydro-2H-indeno[5,4-b]furan-8-yl)ethylamine hydrobromide (0.10 g, 0.352 mmols), and the mixture was stirred at room temperature for 30 minutes. Water was added to the reaction mixture, which was then extracted with ethyl acetate. The extract was washed with a saturated saline solution, then dried with anhydrous magnesium sulfate and concentrated under reduced pressure. The residue was recrystallized from isopropyl ether/hexane to obtain 0.057g (yield: 66%) of the target compound.

m.p.: 78–79° C.; NMR (CDCl$_3$) δ: 1.53–2.12 (3H, m), 1.96 (3H, s),2.20–2.38 (1H, m),2.70–2.96 (2H, m),3.02–3.40 (5H, m), 4.45–4.68 (2H, m), 5.46 (1H, br s), 6.62 (1H, d, J=8.0 Hz), 6.96 (1H, d, J=8.0 Hz); Elemental Analysis for $C_{15}H_{19}NO_2$: Calcd.: C 73.44; H 7.81; N 5.71; Found: C 73.55; H 7.90; N 5.60

Example 2

N-[2-(1,6,7,8-tetrahydro-2H-indeno[5,4-b]furan-8-yl)ethyl]propionamide

In the same manner as in Example 1, the target compound was obtained from 2-(1,6,7,8-tetrahydro-2H-indeno[5,4-b]furan-8-yl)ethylamine hydrobromide and propionyl chloride. The yield was 78%.

m.p.: 102–104° C. (recrystallized from isopropyl ether/hexane); NMR (CDCl$_3$) δ: 1.14 (3H, t, J=7.6 Hz), 1.55–2.38 (4H, m), 2.18 (2H, q, J=7.6 Hz), 2.69–2.99 (2H, m), 3.02–3.40 (5H, m), 4.42–4.63 (2H, m), 5.61 (1H, br s), 6.62 (1H, d, J=7.8 Hz), 6.95 (1H, d, J=7.8 Hz); Elemental Analysis for $C_{16}H_{21}NO_2$: Calcd.: C 74.10; H 8.16; N 5.40; Found: C 74.20; H 8.37; N 5.25

Example 3

N-[2-(3,7,8,9-tetrahydropyrano[3,2-e]indol-1-yl)ethyl]acetamide

In the same manner as in Example 1, the target compound was obtained from 2-(3,7,8,9-tetrahydropyrano[3,2-e]indol-1-yl)ethylamine and acetic anhydride. The yield was 54%.

m.p.: 185–186° C. (recrystallized from methanol/isopropyl ether); NMR (CDCl$_3$) δ: 1.96 (3H, s), 2.03–2.15 (2H, m), 3.09 (2H, t, J=6.8 Hz), 3.20 (2H, t, J=6.8 Hz), 3.56 (2H, q, J=6.4 Hz), 4.18 (2H, t, J=7.0 Hz), 5.60 (1H, br s), 6.73 (1H, d, J=8.8 Hz), 6.96 (1H, d, J=2.2 Hz), 7.09 (1H, d, J=8.8 Hz), 7.98 (1H, br s); Elemental Analysis for $C_{15}H_{18}N_2O_2$: Calcd.: C 69.74; H 7.02; N 10.84; Found: C 69.69; H 7.09; N 10.79

Example 4

N-[2-(3,7,8,9-tetrahydropyrano[3,2-e]indol-1-yl)ethyl]propionamide

In the same manner as in Example 1, the target compound was obtained from 2-(3,7,8,9-tetrahydropyrano[3,2-e]indol-1-yl)ethylamine and propionyl chloride. The yield was 67%.

m.p.: 147–148° C. (recrystallized from methanol/isopropyl ether); NMR (CDCl$_3$) δ: 1.14 (3H, t, J=7.6 Hz), 2.02–2.16 (2H, m), 2.17 (2H, q, J=7.6 Hz), 3.08 (2H, t, J=7.0 Hz), 3.19 (2H, t, J=7.0 Hz), 3.57 (2H, q, J=6.2 Hz), 4.18 (2H, t, J=5.0 Hz), 5.60 (1H, br s), 6.72 (1H, d, J=8.4 Hz), 6.94 (1H, d, J=2.2 Hz), 7.09 (1H, d, J=8.4 Hz), 8.11 (1H, br s); Elemental Analysis for $C_{16}H_{20}N_2O_2$: Calcd.: C 70.56; H 7.40; N 10.29; Found: C 70.69; H 7.54; N 10.27

Example 5

N-[2-(3,7,8,9-tetrahydropyrano[3,2-e]indol-1-yl)ethyl]butyramide

In the same manner as in Example 1, the target compound was obtained from 2-(3,7,8,9-tetrahydropyrano[3,2-e]indol-1-yl)ethylamine and butyryl chloride. The yield was 62%.

m.p.: 154–155° C. (recrystallized from methanol/isopropyl ether); NMR (CDCl$_3$) δ: 0.93 (3H, t, J=7.2 Hz), 1.57–1.73 (2H, m), 2.06–2.16 (4H, m), 3.08 (2H, t, J=6.8 Hz), 3.19 (2H, t, J=6.4 Hz), 3.52–3.63 (2H, m), 4.18 (2H, t, J=5.2 Hz), 5.58 (1H, br s), 6.72 (1H, d, J=8.4 Hz), 6.94 (1H, d, J=2.6 Hz), 7.09 (1H, d, J=8.4 Hz), 8.05 (1H, br s); Elemental Analysis for $C_{17}H_{22}N_2O_2$: Calcd.: C 71.30; H 7.74; N 9.78; Found: C 71.45; H 7.86; N 9.78

Example 6

N-[2-(1,2,3,7,8,9-hexahydropyrano[3,2-e]indol-1-yl)ethyl]acetamide

Platinum oxide (45 mg) and hydrochloric acid (2 ml) were added to an ethanol (40 ml) solution of N-[2-3,7,8,9-tetrahydropyrano[3,2-e]indol-1-yl)ethyl]acetamide (0.90 g, 3.48 mmols), and the mixture was stirred in a hydrogen atmosphere (at from 4 to 5 atmospheres) at 50° C. for 6 hours. The reaction mixture was filtered, and the filtrate was concentrated under reduced pressure. The residue was neutralized with a saturated, aqueous sodium hydrogencarbonate solution, then saturated with salt and extracted with ethyl acetate. The extract was washed with a saturated saline solution, then dried with anhydrous magnesium sulfate and concentrated under reduced pressure. The residue was recrystallized from ethyl acetate/isopropyl ether to obtain 0.53 g (yield: 59%) of the target compound.

m.p.: 137–138° C.; NMR (CDCl$_3$) δ: 1.78–2.05 (4H, m), 1.90 (3H, s), 2.68 (2H, t, J=6.6 Hz), 2.96–3.14 (1H, m), 3.31–3.50 (3H, m), 3.65 (1H, t, J=9.4 Hz), 3.98–4.10 (1H, m), 4.15–4.26 (1H, m ), 6.13 (1H, br s), 6.49 (1H, d, J=8.4 Hz), 6.57 (1H, d, J=8.4 Hz), hidden (1H); Elemental Analysis for $C_{15}H_{20}N_2O_2$: Calcd.: C 69.20; H 7.74; N 10.76; Found: C 69.65; H 7.74; N 10.61

Example 7

N-[2-(1,2,3,7,8,9-hexahydropyrano[3,2-e]indol-1-yl)ethyl]propionamide

In the same manner as in Example 6, the target compound was obtained from N-[2-(3,7,8,9-tetrahydropyrano[3,2-e]indol-1-yl)ethyl]propionamide. The yield was 42%.

m.p.: 106–107° C. (recrystallized from ethyl acetate/isopropyl ether); NMR (CDCl$_3$) δ: 1.11 (3H, t, J=7.6 Hz), 1.76–2.08 (4H, m), 2.13 (2H, q, J=7.6 Hz), 2.68 (2H, t, J=6.4 Hz), 2.99–3.16 (1H, m), 3.31–3.51 (3H, m), 3.65 (1H, t, J=9.4 Hz), 3.98–4.10 (1H, m), 4.15–4.24 (1H, m), 6.10 (1H, br s), 6.48 (1H, d, J=8.4 Hz), 6.56 (1H, d, J=8.4 Hz), hidden (1H); Elemental Analysis for $C_{16}H_{22}N_2O_2$: Calcd.: C 70.04; H 8.08; N 10.21; Found: C 70.18; H 8.34; N 10.13

Example 8

N-[2-(1,2,3,7,8,9-hexahydropyrano[3,2-e]indol-1-yl)ethyl]butyramide

In the same manner as in Example 6, the target compound was obtained from N-[2-(3,7,8,9-tetrahydropyrano[3,2-e]indol-1-yl)ethyl]butyramide. The yield was 55%.

m.p.: 91–93° C. (recrystallized from ethyl acetate/isopropyl ether); NMR (CDCl$_3$) δ: 0.92 (3H, t, J=7.2 Hz), 1.53–1.71 (2H, m), 1.76–1.88 (2H, m), 1.91–2.10 (2H, m), 2.05 (2H, q, J=8.2 Hz), 2.68 (2H, t, J=6.6 Hz), 2.99–3.16 (1H, m), 3.30–3.50 (3H, m), 3.64 (1H, t, J=9.2 Hz), 3.98–4.09 (1H, m), 4.15–4.23 (1H, m), 6.11 (1H, br s), 6.48 (1H, d, J=8.4 Hz), 6.56 (1H, d, J=8.4 Hz), hidden (1H); Elemental Analysis for $C_{17}H_{24}N_2O_2$: Calcd.: C 70.80; H 8.39; N 9.71; Found: C 70.55; H 8.45; N 9.68

Example 9

N-[2-(5-fluoro-3,7,8,9-tetrahydrocyclopenta[f][1]-benzopyran-9-yl)ethyl]propionamide A bromobenzene (15 ml) solution of N-[2-(5-fluoro-6-(2-propionyloxy)indan-1-yl)ethyl]propionamide (0.55 g, 1.90 mmols) was stirred at 250° C. in a sealed tube for 8 hours. The reaction mixture was cooled, and then the solvent was removed through distillation under reduced pressure. The resulting residue was purified through silica-gel column chromatography (ethyl acetate) to obtain 0.27 g (yield: 49%) of the target compound.

m.p.: 108–110° C. (recrystallized from ethyl acetate/hexane); NMR (CDCl$_3$) δ: 1.14 (3H, t, J=7.5 Hz), 1.50–1.81 (2H, m), 1.89–2.30 (2H, m), 2.18 (2H, q, J=7.5 Hz), 2.55–3.00 (2H, m), 3.16–3.40 (3H, m), 4.66–4.92 (2H, m), 5.40 (1H, br s), 5.88 (1H, dt, J=9.9 Hz, 3.7 Hz), 6.43–6.53 (1H, m), 6.80 (1H, d, J=10.6 Hz)

Example 10

N-[2-(5-fluoro-1,2,3,7,8,9-hexahydrocyclopenta[f][1]benzopyran-9-yl)ethyl]propionamide In the same manner as in Reference Example 3, the target compound was obtained from N-[2-(5-fluoro-3,7,8,9-tetrahydrocyclopenta[f][1]benzopyran-9-yl)ethyl] propionamide. The yield was 80%.

m.p.: 106–108° C. (recrystallized from ethyl acetate/hexane); NMR (CDCl$_3$) δ: 1.14 (3H, t, J=7.7 Hz), 1.47–1.84 (2H, m), 1.84–2.27 (4H, m), 2.17 (2H, q, J=7.7 Hz), 2.60–3.01 (4H, m), 3.05–3.20 (1H, m), 3.21–3.41 (2H, m), 4.05–4.20 (1H, m), 4.27–4.39 (1H, m), 5.40 (1H, br s), 6.77 (1H, d, J=10.6 Hz)

Example 11

(S)-N-[2-(1,6,7,8-tetrahydro-2H-indeno[5,4-b]-furen-8-yl)ethyl]propionamide

N-[2-(1,6,7,8-tetrahydro-2H-indeno[5,4-b]furan-8-yl)ethyl]propionamide was optically resolved by high performance column chromatography [apparatus: LC Module 1 (Nippon Millipore Ltd.); column: Ceramospher RU-1 (10 (i.d.)×250 mm, Shiseido); mobile phase: methanol; flow rate: 4.4 ml/min; column temperature:50° C.; sample concentration: 17% (w/v); amount injected: 8.5 mg) to give the target compound.

[α]$_D^{20}$=−57.8° (c 1.004, chloroform); m.p.: 11.3–115° C. (recrystallized from ethyl acetate); NMR (CDCl$_3$) δ: 1.14 (3H, t, J=7.7 Hz), 1.52–2.40 (4H, m), 2.17 (2H, q, J=7.7 Hz), 2.69–3.00 (2H, m), 3.01–3.40 (5H, m), 4.42–4.64 (2H, m), 5.40 (1H, br s), 6.62 (1H, d, J=7.7 Hz), 6.95 (1H, d, J=7.7 Hz); Elemental Analysis for C$_{16}$H$_{21}$NO$_2$: Calcd.: C 74.10; H 8.16; N 5.40; Found: C 73.86; H 7.97; N 5.47

Example 12

(R)-N-[2-(1,6,7,8-tetrahydro-2H-indeno[5,4-b]-furan-8-yl)ethyl]propionamide

N-[2-(1,6,7,8-tetrahydro-2H-indeno[5,4-b]furan-8-yl)ethyl]propionamide was optically resolved by high performance column chromatography in the same manner as in Example 11 to give the target compound.

[α]$_D^{20}$=+57.80 (c 1.005, chloroform); m.p.: 113–115° C. (recrystallized from ethyl acetate); NMR (CDCl$_3$) δ: 1.14 (3H, t, J=7.7 Hz), 1.52–2.40 (4H, m), 2.17 (2H, q, J=7.7 Hz), 2.69–3.00 (2H, m), 3.01–3.40 (5H, m), 4.42–4.64 (2H, m), 5.40 (1H, br s), 6.62 (1H, d, J=7.7 Hz), 6.95 (1H, d, J=7.7 Hz); Elemental Analysis for C$_{16}$H$_{21}$NO$_2$: Calcd.: C 74.10; H 8.16; N 5.40; Found: C 73.97; H 7.97; N 5.47

Example 13

N-[2-(1,6,7,8-tetrahydro-2H-indeno[5,4-b]furan-8-yl)ethyl]butyramide

In the same manner as in Example 1, the target compound was obtained from 2-(1,6,7,8-tetrahydro-2H-indeno[5,4-b] furan-8-yl)ethylamine hydrochloride and butyryl chloride. The yield was 67%.

m.p.: 55–57° C. (recrystallized from ethyl acetate); NMR (CDCl$_3$) δ: 0.94 (3H, t, J=7.3 Hz), 1.51–1.90 (4H, m), 1.92–2.08 (1H, m), 2.12 (2H, t, J=7.3 Hz), 2.17–2.38 (1H, m), 2.68–2.98 (2H, m), 3.00–3.40 (5H, m), 4.41–4.68 (2H, m), 5.43 (1H, br s), 6.62 (1H, d, J=8.0 Hz), 6.96 (1H, d, J=8.0 Hz); Elemental Analysis for C$_{17}$H$_{23}$NO$_2$: Calcd.: C 74.69; H 8.48; N 5.12; Found: C 74.59; H 8.33; N 5.36

Example 14

N-[2-(1,6-dihydro-2H-indeno[5,4-b]furan-8-yl)ethyl]acetamide

Acetyl chloride (0.24 g, 3.03 mmol) was slowly added dropwise to an ice-cooled solution of 2-(1,6-dihydro-2H-indeno[5,4-b]furan-8-yl)ethylamine hydro-chloride (0.6 g, 2.52 mmol) and triethylamine (0.64 g, 6.31 mmol) in N,N-dimethylformamide (60 mL). After overnight stirring at room temperature, the reaction mixture was concentrated and poured into water, and the organic matter was extracted with ethyl acetate. The extract was washed with a satruated aqueous sodium chloride solution and water and then dried over anhydrous magnesium sulfate, and the solvent was distilled off under reduced pressure. The residue obtained was purified by silica gel column chromatography (ethyl acetate:methanol=98:2) and further recrystallized from ethyl acetate to give 425 mg (yield: 70%) of the target compound.

m.p.: 153–155° C. (recrystallized from ethyl acetate); NMR (CDCl$_3$) δ: 1.98 (3H, s), 2.80 (2H, m), 3.31 (2H, br s), 3.43 (2H, t, J=8.6 Hz), 3.57 (2H, q, J=7.0 Hz), 4.60 (2H, d, J=8.6 Hz), 5.62 (1H, br s), 6.30 (1H, s), 6.67 (1H, d, J=7.9 Hz), 7.18 (1H, d, J=7.9 Hz); Elemental Analysis for C$_{15}$H$_{17}$NO$_2$: Calcd.: C 74.05; H 7.04; N 5.76; Found: C 73.98; H 7.06; N 5.92

Example 15

N-[2-(1,6-dihydro-2H-indeno[5,4-b]furan-8-yl)-ethyl]propionamide

In the same manner as in Example 14, the target compound was obtained from 2-(1,6-dihydro-2H-indeno-[5,4-b]furan-8-yl)ethylamine hydrochloride and propionyl chloride. The yield was 90%.

m.p.: 131–133° C. (recrystallized from ethyl acetate/hexane); NMR (CDCl$_3$) δ: 1.15 (3H, t, J=7.7 Hz), 2.20 (2H, q, J=7.7 Hz), 2.80 (2H, m), 3.31 (2H, br s), 3.44 (2H, t, J=8.6 Hz), 3.58 (2H, q, J=7.0 Hz), 4.60 (2H, d, J=8.6 Hz), 5.60 (1H, br s), 6.29 (1H, s), 6.68 (1H, d, J=7.9 Hz), 7.19 (1H, d, J=7.9 Hz); Elemental Analysis for C$_{16}$H$_{19}$NO$_2$: Calcd.: C 74.68; H 7.44; N 5.44; Found: C 74.59; H 7.34; N 5.71

Example 16

N-[2-(1,6-dihydro-2H-indeno[5,4-b]furan-8-yl)-ethyl]butyramide

In the same manner as in Example 14, the target compound was obtained from 2-(1,6-dihydro-2H-indeno-[5,4-b] furan-8-yl)ethylamine hydrochloride and butyryl chloride. The yield was 95%.

m.p.: 131–133° C. (recrystallized from ethyl acetate/hexane); NMR (CDCl$_3$) δ: 0.94 (3H, t, J=7.3 Hz), 1.58–1.76 (2H, m), 2.14 (2H, q, J=7.5 Hz), 2.80 (2H, m), 3.31 (2H, br s), 3.44 (2H, t, J=8.6 Hz), 3.58 (2H, q, J=6.8 Hz), 4.60 (2H, d, J=8.6 Hz), 5.60 (1H, br s), 6.29 (1H, s), 6.67 (1H, d, J=7.9 Hz), 7.18 (1H, d, J=7.9 Hz); Elemental Analysis for C$_{17}$H$_{21}$NO$_2$: Calcd.: C 75.25; H 7.80; N 5.16; Found: C 75.25; H 7.73; N 5.23

The chemical structures of the compounds obtained in Examples 1 to 16 are shown in Table 1 below.

TABLE 1

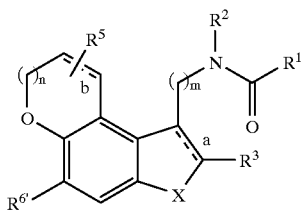

| Example No. | $R^1$ | $R^2$ | $R^3$ | $R^5$ | $R^{6'}$ | X | m | n | a | b | Optical rotation |
|---|---|---|---|---|---|---|---|---|---|---|---|
| 1 | Me | H | H | H | H | $CH_2$ | 2 | 0 | – | – | |
| 2 | Et | H | H | H | H | $CH_2$ | 2 | 0 | – | – | |
| 3 | Me | H | H | H | H | NH | 2 | 1 | = | – | |
| 4 | Et | H | H | H | H | NH | 2 | 1 | = | – | |
| 5 | Pr | H | H | H | H | NH | 2 | 1 | = | – | |
| 6 | Me | H | H | H | H | NH | 2 | 1 | – | – | |
| 7 | Et | H | H | H | H | NH | 2 | 1 | – | – | |
| 8 | Pr | H | H | H | H | NH | 2 | 1 | – | – | |
| 9 | Et | H | H | H | F | $CH_2$ | 2 | 1 | – | = | |
| 10 | Et | H | H | H | F | $CH_2$ | 2 | 1 | – | – | |
| 11 | Et | H | H | H | H | $CH_2$ | 2 | 0 | – | – | – |
| 12 | Et | H | H | H | H | $CH_2$ | 2 | 0 | – | – | + |
| 13 | Pr | H | H | H | H | $CH_2$ | 2 | 0 | – | – | |
| 14 | Me | H | H | H | H | $CH_2$ | 2 | 0 | = | – | |
| 15 | Et | H | H | H | H | $CH_2$ | 2 | 0 | = | – | |
| 16 | Pr | H | H | H | H | $CH_2$ | 2 | 0 | = | – | |

Example 17

2-(1,6-Dihydro-2H-indeno[5,4-b]furan-8-yl)ethylamine hydrochloride

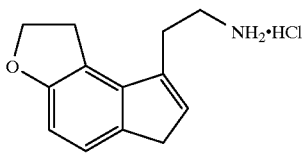

A saturated ammonia/ethanol solution (150 ml) and Raney cobalt (8.4 g) were added to an ethanol (150 ml) solution of (E)-(1,6,7,8-tetrahydro-2H-indeno[5,4-b]-furan-8-ylidene)acetonitrile (2.6 g, 13.2 mmol), and the reaction mixture was stirred at room temperature in a hydrogen atmosphere (5 kgf/cm²) for 3 hours. The Raney cobalt was filtered off and the solvent was distilled off under reduced pressure to give 2-(1,6,7,8-tetrahydro-2H-indeno(5,4-b]furan-8-ylidene)-ethylamine. To this residue was added a saturated hydrogen chloride/ethanol solution (100 ml), followed by 1 hour of heating under reflux. The reaction solution was concentrated and the residue obtained was recrystallized from ethanol to give 2.75 g (yield: 88%) of the target compound.

m.p.: 243–245° C. (recrystallized from ethanol); NMR ($d_6$-DMSO, $D_2O$) δ: 2.90 (2H, t, J=7.7 Hz), 3.13 (2H, t, J=7.7 Hz), 3.28 (2H, s) 3.40 (2H, t, J=8.7 Hz), 4.56 (2H, t, J=8.7 Hz), 6.41 (1H, s), 6.62 (1H, d, J=7.9 Hz), 7.19 (1H, d, J=7.9 Hz); Elemental Analysis for $C_{13}H_{15}NO.HCl$: Calcd.: C 65.68; H 6.78; N 5.89; Cl, 14.91; Found: C 65.81; H 6.83; N 5.90; Cl, 14.89

Example 18

2-(1,6,7,8-Tetrahydro-2H-indeno[5,4-b]furan-8-yl)ethylamine hydrobromide.

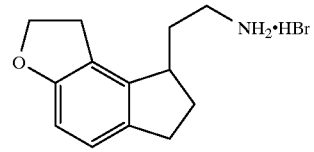

Raney nickel (0.4 g, W2) and 4 M ammonia/ethanol solution (10 ml) were added to an ethanol (30 ml) suspension of (E)-(4-bromo-1,6,7,8-tetrahydro-2H-indeno[5,4-b]furan-8-ylidene)acetonitrile (0.44 g, 1.59 mmols) and stirred in a hydrogen atmosphere (at from 4 to 5 atmospheres) at room temperature for 5 hours. The reaction mixture was filtered, and the filtrate was concentrated under reduced pressure. The residue was dissolved in ethanol (50 ml), and 5% palladium-carbon (1 g, containing 50% water) was added thereto and stirred in a hydrogen atmosphere (at ordinary pressure) at room temperature for 4 hours. The reaction mixture was filtered, and the filtrate was concentrated under reduced pressure to obtain 0.42 g (yield: 93%) of the target compound. This was amorphous.

NMR ($CDCl_3$) δ: 1.58–1.83 (2H, m), 1.97–2.36 (2H, m), 2.70–2.96 (6H, m), 3.03–3.36 (3H, m), 4.42–4.64 (2H, m), 6.61 (1H, d, J=8.2 Hz), 6.95 (1H, d, J=8.2 Hz)

Example 19

(S)-N-[2-(1,6,7,8-tetrahydro-2H-indeno[5,4-b]furan-8-yl)ethyl]propionamide

Propionyl chloride (2.57 g, 27.8 mmol.) was gradually added dropwise, under ice-cooling, to a solution of (S)-2-(1,6,7,8-tetrahydro-2H-indeno[5,4-b]furan-8-yl) ethylamine hydrochloride (5.55 g, 23.1 mmol.) and triethylamine (4.7 g, 46.3 mmol.) in N,N-dimethylformamide (100 ml). The mixture was stirred for one hour at room temperature, which was then poured into water, followed by extracting the organic matter with ethyl acetate. The extract solution was washed with a saturated aqueous saline solution and water, which was then dried over anhydrous magnesium sulfate, followed by distilling off the solvent under reduced pressure. The residue was purified by means of silica gel column chromatography (ethyl acetate:methanol=98:2) to afford the title compound (yield 5.25 g, 88%).

m.p.: 113–115° C. (recrystallized from ethyl acetate); NMR ($CDCl_3$) δ: 1.14 (3H, t, J=7.7 Hz), 1.52–2.40 (4H, m), 2.17 (2H, q, J=7.7 Hz), 2.69–3.00 (2H, m), 3.01–3.40 (5H, m), 4.42–4.64 (2H, m), 5.40 (1H, br s), 6.62 (1H, d, J=7.7 Hz), 6.95 (1H, d, J=7.7 Hz); Elemental Analysis for $C_{16}H_{21}NO_2$: Calcd.: C 74.10; H 8.16; N 5.40; Found: C 73.83; H 8.12; N 5.23

Example 20

(S)-N-[2-(1,6,7,8-tetrahydro-2H-indeno[5,4-b]furan-8-yl)ethyl]propionamide

To a solution of (S)-N-[2-(6-hydroxy-7-(2-hydroxyethyl)indan-1-yl)ethyl]propionamide (5 g, 18 mmol.) in pyridine (14.6 mL), was added dropwise, while maintaining the temperature at about –10° C. under cooling with ice, methanesulfonyl chloride (1.4 mL, 18 mmol.). The reaction mixture was stirred for 25 minutes at temperatures ranging from –10 to –5° C. To the reaction mixture was further added dropwise methanesulfonyl chloride (0.7 mL, 9 mmol.). The mixture was stirred for further 25 minutes at temperatures ranging from –10 to –5° C. To the reaction mixture were added gradually ethyl acetate (10 mL) and a saturated aqueous solution of sodium hydrogencarbonate (10 mL). The mixture was warmed to room temperature, followed by stirring for 30 minutes. The organic matter was extracted with ethyl acetate, which was washed with 2N HCl and water, followed by drying over anhydrous magnesium sulfate. The solvent was then distilled off under reduced pressure. The residue was dissolved in ethyl acetate (20 mL). To the solution was added triethylamine (4.6 g, 45.1 mmol.), and the mixture was heated under reflux for 40 minutes. To the reaction mixture was added 2N HCl, which was subjected to extraction with ethyl acetate. The extract solution was washed with a saturated aqueous solution of sodium hydrogencarbonate and water, which was dried over anhydrous magnesium sulfate, followed by distilling off the solvent. The residue was purified by means of silica gel column chromatography (ethyl acetate) to afford the title compound (yield 4.04 g, 86%).

$[\alpha]_D^{20}$=−57.8° (c 1.004, chloroform); m.p.: 113–115° C. (recrystallized from ethyl acetate); NMR (CDCl$_3$) δ: 1.14 (3H, t, J 7.7 Hz), 1.52–2.40 (4H, m), 2.17 (2H, q, J=7.7 Hz), 2.69–3.00 (2H, m), 3.01–3.40 (5H, m), 4.42–4.64 (2H, m), 5.40 (1H, br s), 6.62 (1H, d, J=7.7 Hz), 6.95 (1H, d, J=7.7 Hz); Elemental Analysis for C$_{16}$H$_{21}$NO$_2$: Calcd.: C 74.10; H 8.16; N 5.40; Found: C 73.86; H 7.97; N 5.47

Example 21

N-[2-(7,8-dihydro-6H-indeno[4,5-d]-1,3-dioxol-8-yl)ethyl]propionamide

Hexamethyl phosphoramide (5 mL) was cooled with ice, to which was gradually added sodium hydride (0.28 g, 7.5 mmol.), content 65%). To this mixture was added dropwise a solution of N-[2-(6,7-dihydroxyindan-1-yl)ethyl]propionamide (0.85 g, 3.41 mmol.) in hexamethyl phosphoramide (5 mL) at room temperature over 6 minutes. At the time when the bubbling of hydrogen gas ceased, diiodomethane (1.1 g, 4.1 mmol.) was added dropwise to the reaction mixture, followed by stirring for two hours at room temperature. The reaction mixture was poured into water, which was neutralized with dilute hydrochloric acid, followed by extracting the organic matter with ethyl acetate. The extract solution was washed with a saturated aqueous saline solution and water, which was then dried over anhydrous magnesium sulfate, followed by distilling off the solvent under reduced pressure. The residue was purified by means of silica gel column chromatography (ethyl acetate) to afford the title compound (yield 280 mg, 31%).

m.p.: 102–104° C. (recrystallized from ethyl acetate/hexane); NMR (CDCl$_3$) δ: 1.16 (3H, t, J=7.7 Hz), 1.70–1.89 (2H, m), 1.90–2.10 (1H, m), 2.15–2.40 (1H, m), 2.20 (2H, q, J=7.7 Hz), 2.68–3.00 (2H, m), 3.13–3.36 (2H, m), 3.40–3.59 (1H, m), 3.68(1H, br s), 5.92 (2H, dd, J=1.5 & 9.9 Hz), 6.67 (2H, s); Elemental Analysis for C$_{15}$H$_{19}$NO$_3$: Calcd.: C 68.94; H 7.33; N 5.36; Found: C 68.89; H 7.28; N 5.42

Example 22

N-[2-(7,8-dihydro-6H-indeno[4,5-d]-1,3-dioxol-8-yl)ethyl]butyramide

A solution of N-[2-(6,7-dihydroxyindan-1-yl)ethyl]butyramide (1.13 g, 4.29 mmol.), dibromomethane (2.98 g, 17.2 mmol.), potassium carbonate (1.78 g, 12.9 mmol.) and copper-(II) oxide (34 mg, 0.43 mmol.) in N,N-dimethylformamide (15 mL) was stirred for 3 hours at 110° C. The reaction mixture was cooled, which was poured into water, followed by neutralizing with dilute hydrochloric acid. The organic matter was extracted with ethyl acetate. The extract solution was washed with a saturated aqueous saline solution and water, which was then dried over anhydrous magnesium sulfate, followed by distilling off the solvent under reduced pressure. The residue was purified by means of silica gel column chromatography (ethyl acetate) to afford the title compound (yield 785 mg, 67%).

m.p.: 71–73° C. (recrystallized from ethyl acetate/hexane); NMR (CDCl$_3$) δ: 0.95 (3H, t, J=7.3 Hz), 1.57–2.40 (6H, m), 2.15 (2H, t, J=7.5 Hz), 2.67–3.00 (2H, m), 3.15–3.34 (2H, m), 3.39–3.58 (1H, m), 5.67 (1H, s), 5.91 (2H, dd, J=1.5 & 9.5 Hz), 6.67 (2H, s); Elemental Analysis for C$_{16}$H$_{21}$NO$_3$: Calcd.: C 69.79; H 7.69; N 5.09; Found: C 69.75; H 7.40; N 5.28

Example 23

N-[2-(2,3,8,9-tetrahydro-7H-indeno[4,5-b]-1,4-dioxyn-9-yl)ethyl]propionamide

In substantially the same manner as in Example 22, the title compound was produced from N-[2-(6,7-dihydroxyindan-1-yl)ethyl]propionamide and 1,2-dibromoethane (yield 80%).

m.p.: 120–122° C. (recrystallized from ethyl acetate/hexane); NMR (CDCl$_3$) δ: 1.15 (3H, t, J=7.5 Hz), 1.60–2.00 (3H, m), 2.10–2.32 (1H, m), 2.19 (2H, q, J=7.5 Hz), 2.61–3.01 (2H, m), 3.08–3.53 (3H, m), 4.25 (4H, br s), 5.67 (1H, br s), 6.69 (2H, s); Elemental Analysis for C$_{16}$H$_{21}$NO$_3$: Calcd.: C 69.79; H 7.69; N 5.09; Found: C 69.90; H 7.61; N 5.20

Example 24

N-[2-(2,3,8,9-tetrahydro-7H-indeno[4,5-b]-1,4-dioxyn-9-yl)ethyl]butyramide

In substantially the same manner as in Example 22, the title compound was produced from N-[2-(6,7-dihydroxyindan-1-yl)ethyl]butyramide and 1,2-dibromoethane (yield 90%).

m.p.: 84–87° C. (recrystallized from ethyl acetate/diethyl ether/petroleum ether); NMR (CDCl$_3$) δ: 0.95 (3H, t, J=7.7 Hz), 1.57–2.00 (5H, m), 2.14 (2H, t, J=7.3 Hz), 2.18–2.34 (1H, m), 2.61–3.01 (2H, m), 3.10–3.55 (3H, m), 4.25 (4H, s), 5.65 (1H, br s), 6.60 (2H, s); Elemental Analysis for C$_{17}$H$_{23}$NO$_3$: Calcd.: C 70.56; H 8.01; N 4.84; Found: C 70.45; H 7.85; N 4.98

Example 25

N-[2-(7,8-dihydro-6H-indeno[4,5-d]oxazol-8-yl)ethyl]acetamide

To a solution of N-[2-(7-amino-6-hydroxyindan-1-yl)ethyl]acetamide (630 mg, 2.7 mmol.) in methanol (5 mL) were added dropwise, under ice-cooling, methyl orthoformate (7.4 mL, 67.3 mmol.) and a saturated HCl/methanol (1.4 mL) solution. The reaction mixture was stirred for 30 minutes at room temperature and for further one hour at 60° C. The reaction mixture was cooled, which was poured into ice-water, followed by extracting the organic matter with chloroform. The extract solution was washed with a saturated aqueous saline solution and water, which was then dried over anhydrous magnesium sulfate, followed by distilling off the solvent. The residue was purified by means of silica gel column chromatography (chloroform:methanol= 20:1) to afford the title compound (yield 520 mg, 79%).

m.p.: 89–92° C. (recrystallized from ethyl acetate/isopropyl ether); NMR (CDCl$_3$) δ: 1.88–2.02 (3H, m), 2.04 (3H, s), 2.34–2.53 (1H, m), 2.86–3.19 (3H, m), 3.59–3.72 (2H, m), 6.94 (1H, br s), 7.25 (1H, d, J=8.4 Hz), 7.40 (1H, d, J=8.4 Hz), 8.09 (1H, s); Elemental Analysis for C$_{14}$H$_{16}$N$_2$O$_2$: Calcd.: C 68.83; H 6.60; N 11.47; Found: C 68.64; H 6.43; N 11.50

Example 26

N-[2-(7,8-dihydro-6H-indeno[4,5-d]oxazol-8-yl)ethyl]propionamide

In substantially the same manner as in Example 25, the title compound was obtained from N-[2-(7-amino-6-hydroxyindan-1-yl)ethyl]propionamide and methyl orthoformate (yield 79%).

m.p.: 81–84° C. (recrystallized from ethyl acetate/ isopropyl ether); NMR (CDCl$_3$) δ: 1.20 (3H, t, J=7.5 Hz), 1.80–2.10 (3H, m), 2.27 (2H, q, J=7.5 Hz), 2.37–2.53 (1H, m), 2.80–3.20 (3H, m), 3.55–3.80 (2H, m), 6.93 (1H, br s), 7.25 (1H, d, J=8.8 Hz), 7.40 (1H, d, J=8.8 Hz), 8.09 (1H, s); Elemental Analysis for C$_{15}$H$_{18}$N$_2$O$_2$: Calcd.: C 69.75; H 7.02; N 10.84; Found: C 69.76; H 6.90; N 10.76

Example 27

N-[2-(7,8-dihydro-6H-indeno[4,5-d]oxazol-8-yl)ethyl] butyramide

In substantially the same manner as in Example 25, the title compound was produced from N-[2-(7-amino-6-hydroxyindan-1-yl)ethyl)butyramide and methyl orthoformate (yield 90%).

m.p.: 65–68° C. (recrystallized from ethyl acetate/ isopropyl ether); NMR (CDCl$_3$) δ: 0.97 (3H, t, J=7.4 Hz), 1.67–1.80 (2H, m), 1.80–2.12 (3H, m), 2.22 (2H, q, J=7.5 Hz), 2.33–2.53 (1H, m), 2.80–3.20 (3H, m), 3.50–3.73 (2H, m), 6.90 (1H, br s), 7.25 (1H, d, J=8.0 Hz), 7.40 (1H, d, J=8.0 Hz), 8.08 (1H, s); Elemental Analysis for C$_{16}$H$_{20}$N$_2$O$_2$: Calcd.: C 70.56; H 7.40; N 10.29; Found: C 70.48; H 7.30; N 10.45

Example 28

N-[2-(5-bromo-3,7,8,9-tetrahydrocyclopenta[f][1]benzopyran-9-yl)ethyl]propionamide A solution of N-[2-(5-bromo-6-(2-propynyl)oxyindan-1-yl)ethyl]propionamide (2.9 g, 8.4 mmol.) in bromobenzene (30 mL) was stirred for 18 hours in a sealed tube at 200° C. The reaction mixture was cooled and, then, the solvent was distilled off under reduced pressure. The residue was purified by means of silica gel column chromatography (ethyl acetate) to afford the title compound (yield 2.5 g, 85%).

m.p.: 110–111° C. (recrystallized from ethyl acetate/ hexane); NMR (CDCl$_3$) δ: 1.14 (3H, t, J=7.5 Hz), 1.50–2.50 (5H, m), 2.60–3.10 (3H, m), 3.15–3.25 (1H, m), 3.32 (2H, q, J=7.5 Hz), 4.80–4.90 (2H, m), 5.40 (1H, br s), 5.88 (1H, dt, J=10.0 & 3.8 Hz), 6.45 (1H, dd, J=1.6 & 9.8 Hz), 7.18 (1H, s); Elemental Analysis for C$_{17}$H$_{20}$BrNO$_2$: Calcd.: C 58.30; H 5.76; N 4.00; Br 22.81; Found: C 58.17; H 5.54; N 3.98; Br 22.65

Example 29

N-[2-(5-bromo-1,2,3,7,8,9-hexahydrocyclopenta[f][1]benzopyran-9-yl)ethyl)propionamide To a solution of N-[2-(5-bromo-3,7,8,9-tetrahydrocyclopenta[f][1]benzopyran-9-yl)ethyl] propionamide (1.2 g, 3.4 mmol.) in ethanol (10 mL) was added 5% Pd-C (120 mg, 50% hydrous). The mixture was stirred for one hour at room temperature under hydrogen atmosphere. The reaction mixture was subjected to filtration. The filtrate was concentrated under reduced pressure. The concentrate was purified by means of silica gel column chromatography (ethyl acetate) to afford the title compound (yield 327 mg, 27%).

m.p.: 114–116° C. (recrystallized from ethyl acetate/ hexane); NMR (CDCl$_3$) δ: 1.14 (3H, t, J=7.6 Hz), 1.50–2.30 (7H, m), 2.60–3.20 (6H, m), 3.30 (2H, q, J=7.6 Hz), 4.10–4.22 (1H, m), 4.30–4.42 (1H, m), 5.40 (1H, br s), 7.22 (1H, s); Elemental Analysis for C$_{17}$H$_{22}$BrNO$_2$: Calcd.: C 57.96; H 6.29; N 3.98; Br 22.68; Found: C 57.84; H 6.20; N 4.01; Br 22.42

Example 30

N-[2-(2,3,4,5,6,7-hexahydrocyclopenta[f][1]benzopyran-9-yl)ethyl]propionamide

To a solution of N-[2-(5-bromo-2,3,4,5,6,7-hexahydrocyclopenta[f][1]benzopyran-9-yl)ethyl] propionamide (200 mg, 0.6 mmol.) in ethanol (5 mL) was added 5% Pd-C (200 mg, 50% hydrous). The mixture was stirred for 3 hours at room temperature under hydrogen atmosphere. The reaction mixture was subjected to filtration. The filtrate was then concentrated under reduced pressure. The concentrate was purified by means of silica gel column chromatography to afford the title compound (yield 130 mg, 85%).

m.p.: 85–88° C. (recrystallized from ethyl acetate/ isopropyl ether); NMR (CDCl$_3$) δ: 1.16 (3H, t, J=7.6 Hz), 1.80–2.10 (6H, m), 2.15 (2H, q, J=7.6 Hz), 2.60–3.50 (7H, m), 4.00–4.30 (2H, m), 5.35 (1H, br s), 6.63 (1H, d, J=8.2 Hz), 6.94 (1H, d, J=8.2 Hz); Elemental Analysis for C$_{17}$H$_{23}$NO$_2$: Calcd.: C 74.69; H 8.48; N 5.12; Found: C 74.56; H 8.25; N 5.16

Example 31

N-[2-(4-bromo-2,2-dimethyl-1,6,7,8-tetrahydro-2H-indeno[5,4-b]furan-8-yl)ethyl]propionamide A solution of N-[2-(5-bromo-6-hydroxy-7-(2-methyl-2-propenyl)indan-1-yl)ethyl]propionamide (2.4 g, 6.5 mmol.) in methylene chloride (40 mL) was cooled with ice. To the solution was added dropwise gradually a diethyl ether boron trifluoride complex (4.0 mL, 32.5 mmol.). The reaction mixture was stirred for 3 hours under ice-cooling, which was poured into ice-water, followed by extracting the organic matter with ethyl acetate. The extract solution was washed with water and a saturated aqueous solution of sodium hydrogencarbonate, which was dried over anhydrous magnesium sulfate, followed by distilling off the solvent under reduced pressure. The residue was recrystallized from ethyl acetate/isopropyl ether to afford the title compound (yield 2.1 g, 89%).

m.p.: 98–101° C. (recrystallized from ethyl acetate/ isopropyl ether); NMR (CDCl$_3$) δ: 1.15 (3H, t, J=7.5 Hz), 1.48 (3H, s), 1.54 (3H, s), 1.76–2.02 (2H, m), 2.19 (2H, q, J=7.5 Hz), 2.25–2.38 (1H, m), 2.62–3.16 (6H, m), 3.32 (2H, q, J=5.3 Hz), 5.41 (1H, br s), 7.11 (1H, s); Elemental Analysis for C$_{18}$H$_{24}$BrNO$_2$: Calcd.: C 59.02; H 6.60; N 3.82; Br 21.81; Found: C 58.94; H 6.48; N 3.98; Br 21.97

Example 32

N-[2-(2,2-dimethyl-1,6,7,8-tetrahydro-2H-indeno[5,4-b]furan-8-yl)ethyl]propionamide In substantially the same manner as in Reference Example 35, the title compound was produced from N-[2-(4-bromo-2,2-dimethyl-1,6,7,8-tetrahydro-2H-indeno [5,4-b]furan-8-yl)ethyl]propionamide (yield 76%).

m.p.: 69–72° C. (recrystallized from ethyl acetate/ isopropyl ether); NMR (CDCl$_3$) δ: 1.14 (3H, s), 1.43 (3H, s), 1.50 (3H, s), 1.60–2.10 (2H, m), 2.13 (2H, q, J=7.5 Hz), 2.24–2.40 (1H, m), 2.60–3.20 (6H, s), 3.35 (2H, q, J=5.3 Hz), 5.39 (1H, br s), 6.55 (1H, d, J=7.6 Hz), 6.95 (1H, d, J=7.6 Hz); Elemental Analysis for C$_{18}$H$_{25}$NO$_2$: Calcd.: C 75.22; H 8.77; N 4.87; Found: C 74.98; H 8.74; N 4.96

Example 33

N-[2-(4-bromo-2-methyl-1,6,7,8-tetrahydro-2H-indeno [5,4-b]furan-8-yl)ethyl]propionamide In substantially the same manner as in Example 31, the title compound was produced from N-[2-(5-bromo-6-hydroxy-7-allylindan-1-yl)ethyl]propionamide (yield 65%).

m.p.: 131–133° C. (recrystallized from ethyl acetate/ isopropyl ether); NMR (CDCl$_3$) δ: 1.15 (3H, t, J=7.6 Hz), 1.46–2.40 (9H, m), 2.60–3.40 (7H, m), 4.90–5.03 (1H, m), 5.42 (1H, br s), 7.11 (1H, s); Elemental Analysis for C$_{17}$H$_{22}$BrNO$_2$: Calcd.: C 57.96; H 6.29; N 3.98; Br 22.68; Found: C 58.08; H 6.28; N 4.07; Br 22.80

Example 34

N-[2-(4-bromo-2-hydroxymethyl-2-methyl-1,6,7,8-tetrahydro-2H-indeno[5,4-b]furan-8-yl)ethyl]propionamide A solution of N-[2-(5-bromo-6-hydroxy-7-(2-methyl-2-propenyl)indan-1-yl)ethyl]propionamide (550 mg, 1.5 mmol.) in dichloromethane (5 mL) was cooled with ice. To the solution were added triethylamine (0.2 mL, 1.5 mmol.) and methachloroperbenzoic acid (1.0 g, 4.1 mmol.). The mixture was stirred for two hours at room temperature. The reaction mixture was poured into an aqueous solution of sodium thiosulfate. The organic matter was extracted with ethyl acetate. The extract solution was washed with 1N HCl and a saturated aqueous solution of sodium hydrogencarbonate, which was then dried over anhydrous magnesium sulfate, followed by distilling off the solvent. The residue was dissolved in dichloromethane, to which was added triethylamine (1 mL). The mixture was stirred for 2 hours at room temperature. The solvent was distilled off under reduced pressure, and the residue was purified by means of silica gel column chromatography (chloroform:methanol=10:1) to afford the title compound (yield 420 mg, 73%) as an oily product.

NMR (CDCl$_3$) δ: 1.00–1.20 (3H, m), 1.50–2.40 (10H, m), 2.60–3.81 (9H, m), 5.50 (1H, br s), 7.11 (1H, s); Elemental Analysis for C$_{18}$H$_{24}$BrNO$_3$.0.5H$_2$O: Calcd.: C 55.25; H 6.44; N 3.58; Br 20.42; Found: C 55.58; H 6.46; N 3.58; Br 20.28

Example 35

N-[2-(2-methyl-1,6,7,8-tetrahydro-2H-indeno[5,4-b]furan-8-yl)ethyl]propionamide

In substantially the same manner as in Reference Example 35, the title compound was produced from N-[2-(4-bromo-2-methyl-1,6,7,8-tetrahydro-2H-indeno[5,4-b]furan-8-yl) ethyl]propionamide (yield 76%).

m.p.: 68–72° C. (recrystallized from ethyl acetate/ isopropyl ether); NMR (CDCl$_3$) δ: 1.14 (3H, t, J=7.2 Hz), 1.43 (1.2H, d, J=6.2 Hz), 1.50 (1.8H, d, J=6.2 Hz), 1.60–2.40 (6H, m), 2.60–3.40 (7H, m), 4.80–5.00 (1H, m), 5.30–5.45 (1H, m), 6.58 (1H, d, J=8.0 Hz), 6.95 (1H, d, J=8.0 Hz); Elemental Analysis for C$_{17}$H$_{23}$NO$_2$: Calcd.: C 74.69; H 8.48; N 5.12; Found: C 74.62; H 8.55; N 5.24

Example 36

N-[2-(1,2,3,7,8,9-hexahydro-2-oxoindeno[5,4-b][1,4]oxazin-9-yl)ethyl]propionamide 1-Ethyl-3-(3-dimethylaminopropyl)carbodiimide hydrochloride (372.0 mg, 1.9 mmol.) and 1-hydroxybenzotriazole monohydrate (257 mg, 1.9 mmol.) were suspended in N,N-dimethylformamide (2.5 mL). To the suspension was added, under ice-cooling, propionic acid (0.11 mL, 1.4 mmol.). This reaction mixture was stirred for one hour at room temperature, and, then, cooled again with ice, to which was added dropwise a solution of 9-(2-aminoethyl)-1,7,8,9-tetrahydroindeno[5,4-b][1,4] oxazin-2(3H)-one (300 mg, 1.3 mmol.) in N,N-dimethylformamide (1.5 mL). The mixture was stirred for one hour under ice-cooling. The reaction mixture was poured into water, and the organic matter was extracted with ethyl acetate. The extract solution was dried over anhydrous magnesium sulfate. The solvent was distilled off, and the residue was purified by means of silica gel column chromatography (chloroform:methanol=10:1) to afford the title compound (yield 253.0 mg, 88%).

m.p.: 216–219° C. (recrystallized from ethyl acetate/ methanol); NMR (CDCl$_3$) δ: 1.18 (3H, d, J=7.5 Hz), 1.50–2.00 (3H, m), 2.10–2.30 (3H, m), 2.70–3.10 (2H, m), 3.30–3.50 (3H, m), 4.59 (2H, s), 5.97 (1H, br s), 6.81 (2H, s), 9.77 (1H, br s);

Example 37

N-[2-(1,2,3,7,8,9-hexahydro-2-oxoindeno[5,4-b](1,4]oxazin-9-yl)ethyl]butyramide

In substantially the same manner as in Example 36, the title compound was produced from 9-(2-aminoethyl)-1,7,8,9-tetrahydroindeno[5,4-b](1,4]oxazin-2(3)-one and butyric acid (yield 64%).

m.p.: 209–212° C. (recrystallized from ethyl acetate/ hexane); NMR (CDCl$_3$) δ: 0.95 (3H, t, J=7.3 Hz), 1.50–2.00 (5H, m), 2.10–2.30 (3H, m), 2.70–3.10 (2H, m), 3.20–3.50 (3H, m), 4.58 (2H, s), 5.93 (1H, br s), 6.80 (2H, s), 9.72 (1H, br s);

Example 38

N-[2-(1,2,3,7,8,9-hexahydroindeno[5,4-b][1,4]oxazin-9-yl) ethyl]propionamide

A solution of 9-(2-aminoethyl)-1,7,8,9-tetrahydro-indeno[5,4-b][1,4]oxazin-2(3H)-one (1.2 g, 5.3 mmol.) in tetrahydrofuran (30 mL) was was cooled with ice, to which was added lithium aluminum hydride (0.8 g, 21.4 mmol.). The mixture was heated for 18 hours under reflux under argon atmosphere. The reaction mixture was cooled, to which were added water (0.8 mL), a 15% aqueous solution of sodium hydroxide (0.8 mL) and water (2.4 mL), successively. The mixture was then stirred for 30 minutes at room temperature. Insolubles were filtered off, and the filtrate was concentrated under reduced pressure. Then, in substantially the same manner as in Example 36, from 2-(1,2,3,7,8,9-hexahydroindeno[5,4-b][1,4]oxazin-9-yl) ethylamine thus obtained and propionic acid, the title compound was produced (yield 250 mg, 51%).

m.p.: 80–83° C. (recrystallized from ethyl acetate/ hexane); NMR (CDCl$_3$) δ: 1.11 (3H, t, J=7.5 Hz), 1.50–2.30 (6H, m), 2.60–3.20 (3H, m), 3.32 (2H, q, J=6.7Hz), 3.43 (2H, t, J=4.4 Hz), 3.85 (1H, br s), 4.20 (2H, t, J=4.4 Hz), 5.84 (1H, br s), 6.50 (1H, d, J=8.0 Hz), 6.62 (1H, d, J=8.0 Hz);

Example 39

N-[2-(1,2,3,7,8,9-hexahydroindeno[5,4-b][1,4]oxazin-9-yl)ethyl]butyramide

In substantially the same manner as in Example 38, the title compound was produced from 9-(2-aminoethyl)-1,7,8, 9-tetrahydroindeno[5,4-b][1,4]oxazin-2(3H)-one and butyric acid (yield 61%)

m.p.: 115–118° C. (recrystallized from ethyl acetate/ hexane); NMR (CDCl$_3$) δ: 0.93 (3H, t, J=7.3 Hz), 1.50–2.30 (8H, m), 2.60–3.20 (3H, m), 3.32 (2H, q, J=6.7 Hz), 3.45 (2H, t, J=4.4Hz), 3.80 (1H, br s), 4.22 (2H, t, J=4.4 Hz), 5.54 (1H, br s), 6.52 (1H, d, J=8.0 Hz), 6.63 (1H, d, J=8.0 Hz);

Example 40

N-[2-(6-formyl-1,6,7,8-tetrahydro-2H-furo[3,2-e]indol-8-yl)ethyl]propionamide

To a solution of N-[2-[1-formyl-2,3-dihydro-5-hydroxy-4-(2-hydroxyethyl)indol-3-yl]ethyl]propionamide (0.8 g, 2.61 mmol) in pyridine (10 mL) was added methansulfonyl chloride (0.2 mL, 2.61 mmol.) around –10° C. The mixture was stirred for 20 minutes while keeping the temperature –10 to 5° C. To this was added additional methansulfonyl chloride (0.1 mL, 1.3 mmol.) and the mixture was stirred for further 15 minutes at the same temperature. The mixture was diluted with ethyl acetate(10 mL). Saturated aqueous sodium hydrogen carbonate solution (10 mL) was added slowly and the mixture was stirred for 30 minutes at room temperature. The organic layer was separated and the aqueous layer was extracted with ethyl acetate. The combined organic layer was washed with 2N-hydrochloric acid and water, dried over anhydrous magnesium sulfate and evaporated. The residue was purified by silica gel column chromatography (chloroform:methanol=9:1) to afford the title compound (yield 0.25 g, 33%).

m.p.: 139–141° C. (recrystallized from ethyl acetate); NMR (CDCl$_3$) δ: 1.15 (3H, t, J=7.6 Hz), 1.62–2.11 (2H, m), 2.19 (2H, q, J=7.6 Hz), 3.01–3.50 (5H, m), 3.70–3.95 (1H, m), 4.07–4.30 (1H, m), 4.48–4.71 (2H, m), 5.70 (1H, br s), 6.63, 6.65 (1H,d×2, J=8.4 Hz), 6.92, 7.87 (1H, d×2, J=8.4 Hz), 8.43, 8.80 (1H, s×2); Elemental analysis for C$_{16}$H$_{20}$N$_2$O$_3$: Calcd.: C 66.65; H 6.99; N 9.72; Found: C 66.43; H 7.01; N 9.73

Example 41

N-[2-(1,6,7,8-tetrahydro-2H-furo[3,2-e]indol-8-yl)ethyl] propionamide

1) To a solution of N-[2-(6-formyl-1,6,7,8-tetrahydro-2H-furo[3,2-e]indol-8-yl)ethyl]propionamide (0.18 g, 0.62 mmol.) in ethanol (5 mL) was added saturated hydrogen chloride/ethanol (15 mL). The mixture was stirred for 1.5 hours at 80° C. and then cooled. The solvent was removed in vacuo to afford the title compound as an amorphous product.

NMR (d$_6$-DMSO) δ: 1.01 (3H, t, J=7.5 Hz), 1.54–1.76 (1H, m), 1.88–2.10 (1H, m), 2.08 (2H, q, J=7.5 Hz), 3.00–3.95 (7H, m), 4.61 (2H, q, J=8.1 Hz), 6.76 (1H, d, J=8.4 Hz), 7.16 (1H, d, J=8.4 Hz), 7.98 (1H,br s), 11.23 (1H, br s), hidden (1H)

2) The hydrochloride was added to saturated aqueous sodium hydrogen carbonate solution and the resulting free base was extracted with 10% methanol/chloroform. The extract was washed with brine and water, dried over anhydrous magnesium sulfate and evaporated. The residue was purified by silica gel column chromatography (chloroform:methanol=9:1), followed by recrystallization to afford the title compound (yield 97 mg, 60%).

m.p.: 96–98° C. (recrystallized from ethyl acetate/hexane); NMR (CDCl$_3$) δ: 1.12 (3H, t, J=7.6 Hz), 1.70–2.06 (2H, m), 2.15 (2H, q, J=7.6 Hz), 2.99–3.50 (6H, m), 3.68 (1H, t, J=8.3 Hz), 4.40–4.63 (2H, m), 5.86 (1H, br s), 6.44 (1H, d, J=8.2 Hz), 6.52 (1H, d, J=8.2 Hz); Elemental analysis for C$_{15}$H$_{20}$N$_2$O$_2$: Calcd.: C 69.20; H 7.74; N 10.76; Found: C 68.80; H 7.48; N 10.73

Example 42

N-[2-(6-formyl-1,6,7,8-tetrahydro-2H-furo[3,2-e]indol-8-yl)ethyl]butyramide

In substantially the same manner as in Example 40, the title compound was produced from N-[2-[1-formyl-2,3-dihydro-5-hydroxy-4-(2-hydroxyethyl)indol-3-yl-]ethyl]butyramide as an amorphous product (yield 55%)

NMR (CDCl$_3$) δ: 0.94 (3H, t, J=7.3 Hz), 1.30–1.80 (4H, m), 2.17 (2H, t, J=7.3 Hz), 2.82–3.60 (5H, m), 3.80–4.26 (2H, m), 4.40–4.60 (2H, m), 5.77 (1H, br s), 6.61, 6.63 (1H, d×2, J=8.3 Hz), 6.92, 7.96 (1H, d×2, J=8.3 Hz), 8.40, 8.78 (1H, s×2)

Example 43

N-[2-(1,6,7,8-tetrahydro-2H-furo[3,2-e]indol-8-yl)ethyl]butyramide

In substantially the same manner as in Example 41, the title compound was produced from N-[2-(6-formyl-1,6,7,8-tetrahydro-2H-furo[3,2-e]indol-8-yl)ethyl]butyramide as an amorphous amorphous product (yield 64%).

NMR (CDCl$_3$) δ: 0.93 (3H, t, J=7.3 Hz), 1.50–1.90 (4H, m), 2.13 (2H, t, J=7.3 Hz), 3.00–3.50 (6H, m), 3.67 (1H, m), 4.40–4.60 (2H, m), 6.00 (1H, br s), 6.47 (1H, d, J=8.2 Hz), 6.55 (1H, d, J=8.2 Hz), hidden (1H)

Example 44

N-[2-(7-phenyl-1,6-dihydro-2H-indeno[5,4-b]furan-8-yl)ethyl]acetamide

In substantially the same manner as in Example 14, the title compound was produced from 2-(1,6-dihydro-7-phenyl-2H-indeno[5,4-b]furan-8-yl)ethylamine hydrochloride and acetyl chloride (yield 69%).

m.p.: 150–153° C. (recrystallized from ethyl acetate/hexane); NMR (CDCl$_3$) δ: 1.78 (3H, s), 2.96 (2H, t, J=7.2 Hz), 3.42 (2H, q, J=7.2 Hz), 3.53 (2H, t, J=8.6 Hz), 3.70 (2H, s), 4.63 (2H, t, J=8.6 Hz), 5.41 (1H, br s), 6.70 (1H, d, J=7.9 Hz), 7.21 (1H, d, J=7.9 Hz), 7.26–7.50 (5H, m)

Example 45

N-[2-(7-phenyl-1,6-dihydro-2H-indeno[5,4-b]furan-8-yl)ethyl]propionamide

In substantially the same manner as in Example 1, the title compound was produced from 2-(1,6-dihydro-7-phenyl-2H-indeno[5,4-b]furan-8-yl)ethylamine hydrochloride and propionic anhydride (yield 67%).

m.p.: 166–168° C. (recrystallized from ethyl acetate/hexane); NMR (CDCl$_3$) δ: 1.02 (3H, t, J=7.7 Hz), 2.01 (2H, q, J=7.7 Hz), 2.96 (2H, t, J=7.3 Hz), 3.44 (2H, q, J=7.3 Hz), 3.54 (2H, t, J=8.6 Hz), 3.70 (2H, s), 4.63 (2H, t, J=8.6 Hz), 5.40 (1H, br s), 6.70 (1H, d, J=8.1 Hz), 7.21 (1H, d, J=8.1 Hz), 7.26–7.50 (5H, m)

Example 46

N-[2-(7-phenyl-1,6-dihydro-2H-indeno[5,4-b]furan-8-yl)ethyl]butyramide

In substantially the same manner as in Example 14, the title compound was produced from 2-(1,6-dihydro-7-phenyl-2H-indeno[5,4-b]furan-8-yl)ethylamine hydrochloride and butyryl chloride (yield 71%).

m.p.: 172–175° C. (recrystallized from ethyl acetate/hexane); NMR (CDCl$_3$) δ: 0.86 (3H, t, J=7.3 Hz), 1.40–1.62 (2H, m), 1.95 (2H, t, J=7.3 Hz), 2.96 (2H, t, J=7.1 Hz), 3.44 (2H, q, J=7.1 Hz), 3.54 (2H, t, J=8.8 Hz), 3.70 (2H, s), 4.63 (2H, t, J=8.8 Hz), 5.41 (1H, br s), 6.70 (1H, d, J=7.7 Hz), 7.21 (1H, d, J=7.7 Hz), 7.26–7.50 (5H, m)

The chemical structures of the compounds obtained in Examples 19 to 46 are shown in Table 2 below.

TABLE 2

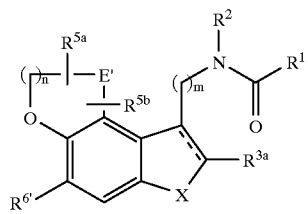

| Example No. | R$^1$ | R$^2$ | R$^{3a}$ | R$^{5a}$ | R$^{5b}$ | R$^{6'}$ | X | E' | m | n | = | Optical rotation |
|---|---|---|---|---|---|---|---|---|---|---|---|---|
| 19 | Et | H | H | H | H | H | CH$_2$ | CH$_2$CH$_2$ | 2 | 0 | – | – |
| 20 | Et | H | H | H | H | H | CH$_2$ | CH$_2$CH$_2$ | 2 | 0 | – | – |
| 21 | Et | H | H | H | H | H | CH$_2$ | CH$_2$O | 2 | 0 | – | |
| 22 | Pr | H | H | H | H | H | CH$_2$ | CH$_2$O | 2 | 0 | – | |
| 23 | Et | H | H | H | H | H | CH$_2$ | CH$_2$O | 2 | 1 | – | |
| 24 | Pr | H | H | H | H | H | CH$_2$ | CH$_2$O | 2 | 1 | – | |
| 25 | Me | H | H | H | H | H | CH$_2$ | CH=N | 2 | 0 | – | |
| 26 | Et | H | H | H | H | H | CH$_2$ | CH=N | 2 | 0 | – | |
| 27 | Pr | H | H | H | H | H | CH$_2$ | CH=N | 2 | 0 | – | |
| 28 | Et | H | H | H | H | Br | CH$_2$ | CH=CH | 2 | 1 | – | |
| 29 | Et | H | H | H | H | Br | CH$_2$ | CH$_2$CH$_2$ | 2 | 1 | – | |
| 30 | Et | H | H | H | H | H | CH$_2$ | CH$_2$CH$_2$ | 2 | 1 | – | |
| 31 | Et | H | H | Me | Me | Br | CH$_2$ | CH$_2$CH$_2$ | 2 | 0 | – | |
| 32 | Et | H | H | Me | Me | H | CH$_2$ | CH$_2$CH$_2$ | 2 | 0 | – | |

TABLE 2-continued

| Example No. | R¹ | R² | R³ᵃ | R⁵ᵃ | R⁵ᵇ | R⁶' | X | E' | m | n | = | Optical rotation |
|---|---|---|---|---|---|---|---|---|---|---|---|---|
| 33 | Et | H | H | Me | H | Br | $CH_2$ | $CH_2CH_2$ | 2 | 0 | – | |
| 34 | Et | H | H | Me | $CH_2OH$ | Br | $CH_2$ | $CH_2CH_2$ | 2 | 0 | – | |
| 35 | Et | H | H | Me | H | H | $CH_2$ | $CH_2CH_2$ | 2 | 0 | – | |
| 36 | Et | H | H | H | H | H | $CH_2$ | CONH | 2 | 1 | – | |
| 37 | Pr | H | H | H | H | H | $CH_2$ | CONH | 2 | 1 | – | |
| 38 | Et | H | H | H | H | H | $CH_2$ | $CH_2NH$ | 2 | 1 | – | |
| 39 | Pr | H | H | H | H | H | $CH_2$ | $CH_2NH$ | 2 | 1 | – | |
| 40 | Et | H | H | H | H | H | NCHO | $CH_2CH_2$ | 2 | 0 | – | |
| 41 | Et | H | H | H | H | H | NH | $CH_2CH_2$ | 2 | 0 | – | |
| 42 | Pr | H | H | H | H | H | NCHO | $CH_2CH_2$ | 2 | 0 | – | |
| 43 | Pr | H | H | H | H | H | NH | $CH_2CH_2$ | 2 | 0 | – | |
| 44 | Me | H | Ph | H | H | H | $CH_2$ | $CH_2CH_2$ | 2 | 0 | = | |
| 45 | Et | H | Ph | H | H | H | $CH_2$ | $CH_2CH_2$ | 2 | 0 | = | |
| 46 | Pr | H | Ph | H | H | H | $CH_2$ | $CH_2CH_2$ | 2 | 0 | = | |

Me: methyl
Et: ethyl
Pr: propyl
Ph: phenyl

Example 47

(E)-2-(1,6,7,8-tetrahydro-2H-indeno[5,4-b]furan-8-ylidene) ethylamine

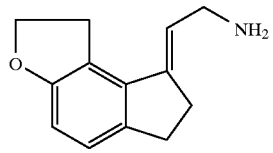

In substantially the same manner as in Example 27, the title compound was produced from (E)-(1,6,7,8-tetrahydro-2H-indeno[5,4-b]furan-8-ylidene)acetonitrile (yield 65%) as an oily product.

NMR (CDCl₃) δ: 2.61–2.78 (2H, m), 2.80–2.94 (2H, m), 3.20–3.38 (4H, m), 4.56 (2H, t, J=8.8 Hz), 5.83 (1H, m), 6.60 (1H, d, J=8.1 Hz), 6.99 (1H, d, J=8.1 Hz), hidden (2H)

Example 48

9-(2-aminoethyl)-1,7,8,9-tetrahydroindeno[5,4-b][1,4]oxazin-2(3H)-one

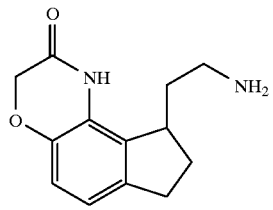

(E)-(1,2,3,7,8,9-Hexahydro-2-oxoindeno[5,4-bj[1,4]oxazin-9-ylidene)acetonitrile (3.0 g, 13.3 mmol.) and Raney nickel (14.0 g) were suspended in a saturated ammonia/ethanol solution (300 mL). The suspension was stirred for 6 hours at 40° C. under hydrogen atmosphere (5 kgf/cm²). The reaction mixture was cooled, and, then, the Raney nickel catalyst was filtered off. From the filtrate, the solvent was distilled off under reduced pressure to leave an oily residue. The residue was poured into 2N HCl, which was washed with ethyl acetate. The pH of the aqueous layer was adjusted to 10 with a 4N aqueous solution of sodium hydroxide. The organic matter was extracted from the aqueous layer with a mixture solvent of chloroform/methanol (10:1). The extract solution was dried over anhydrous magnesium sulfate, then the solvent was distilled off under reduced pressure. The residue was recrystallized from ethyl acetate/isopropyl ether to afford the title compound (yield 1.9 g, 62%).

m.p.: 128–134° C. (recrystallized from ethyl acetate/isopropyl ether); NMR (CDCl₃) δ: 1.40–1.90 (6H, m), 2.20–2.50 (2H, m), 2.70 (1H, dd, J=8.0 & 15.4 Hz), 2.90–3.00 (2H, m), 3.40 (1H, q, J=7.9 Hz), 4.44 (1H, d, J=15.0 Hz), 4.58 (1H, d, J=15.0 Hz), 6.75 (1H, d, J=8.0 Hz), 6.79 (1H, d, J=8.0 Hz)

Example 49

2-(1,2,3,7,8,9-hexahydroindeno[5,4-b][1,4]oxazin-9-yl)ethylamine

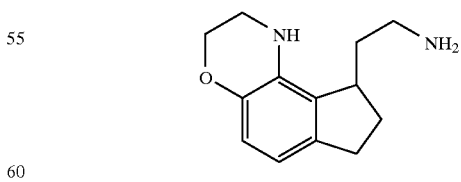

In substantially the same manner as in Example 38, the title compound was produced from 9-(2-aminoethyl)-1,7,8, 9- tetrahydroindeno[5,4-b][1,4]oxazin-2-(3H)-one (yield 80%) as an oily product.

NMR (CDCl₃) δ: 1.10–3.20 (12H, m), 3.41 (2H, m), 4.20 (2H, m), 6.49 (1H, d, J=8.0 Hz), 6.61 (1H, d, J=8.0 Hz)

Example 50

2-(1,6-dihydro-7-phenyl-2H-indeno[5,4-b]furan-8-yl)ethylamine hydrochloride

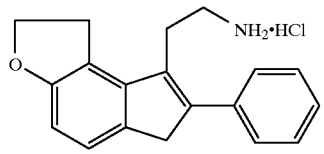

A mixture of (E)-(1,6,7,8-tetrahydro-7-phenyl-2H-indeno[5,4-b]furan-8-ylidene)acetonitrile and (1,6-dihydro-7-phenyl-2H-indeno[5,4-b]furan-8-yl)acetonitrile (0.815 mg, 2.98 mmol) was hydrogenated (5 kgf/cm$^2$) on Raney cobalt (2.8 g) in saturated ammonia/ethanol (250 ml) at room temperature for 6 hours. The catalyst was filtered off and the filtrate was concentrated. The residue was diluted with water and extracted with 10% methanol/chloroform. The extract was washed with brine and water, dried over anhydrous magnesium sulfate and evaporated. The residue was dissolved in saturated hydrogen chloride/ethanol (20 ml) and stirred for 1 hour at 80° C. After cooling the solvent was evaporated. The residue was recrystallized from ethanol to afford the title compound (yield 390 mg, 42%).

m.p.: 165–168° C. (recrystallized from ethanol); NMR (CDCl$_3$) δ: 2.87–3.14 (4H, m), 3.51 (2H, t, J=8.4 Hz), 3.72 (2H, s), 4.58 (2H, t, J=8.4 Hz), 6.63 (1H, d, J=7.9 Hz), 7.19 (1H, d, J=7.9 Hz), 7.30–7.58 (5H, m), 8.33 (2H, br s)

Formulation Example 1

| (1) Compound obtained in Example 1 | 10.0 g |
|---|---|
| (2) Lactose | 60.0 g |
| (3) Corn starch | 35.0 g |
| (4) Gelatin | 3.0 g |
| (5) Magnesium stearate | 2.0 g |

A mixture comprised of 10.0 g of the compound obtained in Example 1, 60.0 g of lactose and 35.0 g of corn starch was granulated with 30 ml of aqueous 10 wt.% gelatin solution (3.0 g as gelatin) by sieving through a 1 mm-mesh sieve, then dried and again sieved. The resulting granules were mixed with 2.0 g of magnesium stearate and then formed into tablets. The resulting core tablets were coated with a sugar coating of an aqueous suspension comprising sucrose, titanium dioxide, talc and arabic gum. The thus-coated tablets were glazed with bees wax. Thus, obtained were 1000 sugar-coated tablets.

Formulation Example 2

| (1) Compound obtained in Example 1 | 10.0 g |
|---|---|
| (2) Lactose | 70.0 g |
| (3) Corn starch | 50.0 g |
| (4) Soluble starch | 7.0 g |
| (5) Magnesium stearate | 3.0 g |

10.0 g of the compound obtained in Example 1 and 3.0 g of magnesium stearate were granulated with 70 ml of an aqueous solution of soluble starch (7.0 g as soluble starch), then dried and mixed with 70.0 g of lactose and 50.0 g of corn starch. The mixture formed into 1000 tablets.

Formulation Example 3

| (1) Compound obtained in Example 19 | 1.0 g |
|---|---|
| (2) Lactose | 60.0 g |
| (3) Corn starch | 35.0 g |
| (4) Gelatin | 3.0 g |
| (5) Magnesium stearate | 2.0 g |

A mixture comprised of 1.0 g of the compound obtained in Example 19, 60.0 g of lactose and 35.0 g of corn starch was granulated with 30 ml of aqueous 10 wt. % gelatin solution (3.0 g as gelatin) by sieving through a 1 mm-mesh sieve, then dried and again sieved. The resulting granules were mixed with 2.0 g of magnesium stearate and then formed into tablets. The resulting core tablets were coated with a sugar coating of an aqueous suspension comprising sucrose, titanium dioxide, talc and arabic gum. The thus-coated tablets were glazed with bees wax. Thus, obtained were 1000 sugar-coated tablets.

Experimental Example 1

Inhibition of 2-[$^{125}$I]iodomelatonin binding activity.

The forebrains of 7-day-old chicken (white leghorn) were homogenized with ice-cold assay buffer (50 mM Tris-HCl, pH 7.7 at 25° C.) and centrifuged at 44,000×g for 10 minutes at 4° C. The pellet was washed once with the same buffer and storred at −30° C. until use. For the assay, the frozen tissue pellet was thawed and homogenized with the assay buffer to make a protein concentration of 0.3–0.4 mg/ml. An 0.4 ml aliquot of this homogenate was incubated with a test compound and 80 pM 2-[$^{125}$I]iodomelatonin in a total volume of 0.5 ml for 90 minutes at 25° C. The reaction was terminated by adding 3 ml of ice-cold assay buffer immediately followed by vaccum filtration on Whatman GF/B which was further washed twice with 3 ml of ice-cold assay buffer. The radioactivity on the filter was determined by means of γ-counter. Specific binding was calculated by subtracting non-specific binding which was determined in the presence of 10$^{-5}$M melatonin. The 50% inhibiting concentration (IC$_{50}$) was determined by the log-probit analysis. The results are shown in Table 3.

TABLE 3

Action of inhibiting 2-[$^{125}$I]iodomelatonin binding

| Compounds of Example | IC$_{50}$ (nM) |
|---|---|
| 1 | 0.28 |
| 2 | 0.13 |
| 3 | 0.46 |
| 4 | 0.13 |
| 5 | 0.082 |
| 7 | 0.46 |
| 8 | 0.22 |
| 11 | 0.048 |
| 13 | 0.12 |
| 14 | 0.24 |
| 15 | 0.1 |
| 16 | 0.095 |
| Melatonin | 0.68 |

From the results in Table 3 above, it is understood that the compound (I) of the present invention has excellent melatonin receptor-agonistic activity.

As has been described in detail and demonstrated concretely, the compound (I) of the present invention or a salt thereof has excellent binding affinity for melatonin receptor. Therefore, the present invention provides medicines which are clinically useful for preventing and curing various disorders associated with melatonin activity in vivo. In addition, the compound (I) of the present invention or a salt thereof has excellent in vivo behavior and have excellent solubility in water.

We claim:

1. A compound of the formula:

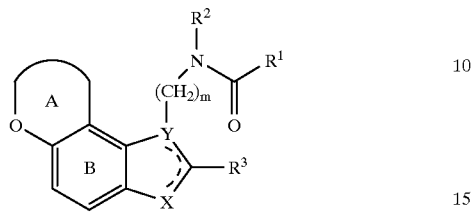

wherein $R^1$ represents an optionally substituted hydrocarbon group, an optionally substituted amino group or an optionally substituted heterocyclic group;

$R^2$ represents a hydrogen atom or an optionally substituted hydrocarbon group;

$R^3$ represents a hydrogen atom, an optionally substituted hydrocarbon group, or an optionally substituted heterocyclic group;

X represents $CHR^4$, $NR^4$, O or S in which $R^4$ represents a hydrogen atom or an optionally substituted hydrocarbon group;

Y represents C, CH or N, provided that when X is $CH_2$, Y is C or CH;

......... represents a single bond or a double bond;

ring A represents an optionally substituted, 5- to 7-membered oxygen-containing heterocyclic ring;

ring B represents an optionally substituted benzene ring; and m represents an integer of 1 to 4, or a salt thereof.

2. A compound as claimed in claim 1, wherein $R^1$ is (i) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxy, an optionally halogenated $C_{1-6}$ alkyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkylcarbamoyl, di-$C_{1-6}$ alkylcarbamoyl, $C_{6-10}$ aryl-carbamoyl, $C_{6-10}$ aryl, $C_{6-10}$ aryloxy and an optionally halogenated $C_{1-6}$ alkyl-carbonylamino, (ii) an amino group which may be substituted by 1 or 2 substituents selected from the group consisting of a $C_{1-6}$ alkyl, $C_{2-6}$ alkenyl, $C_{2-6}$ alkynyl, $C_{3-6}$ cycloalkyl and $C_{6-14}$ aryl group, each of which may be substituted by 1 to 5 substituents consisting of a halogen, nitro, cyano, hydroxy, an optionally halogenated $C_{1-6}$ alkyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy and an optionally halogenated $C_{1-6}$ alkyl-carbonylamino, or (iii) a 5- to 14-membered heterocyclic group containing, besides carbon atoms, 1 to 3 hetero atoms selected from nitrogen atom, oxygen atom and sulfur atom, which group may be substituted by 1 to 5 substituents selected from the group consisting of a halogen, $C_{1-6}$ alkyl, $C_{3-6}$ cycloalkyl, $C_{2-6}$ alkynyl, $C_{2-6}$ alkenyl, $C_{7-11}$ aralkyl, $C_{6-10}$ aryl, $C_{1-6}$ alkoxy, $C_{6-10}$ aryloxy, formyl, $C_{1-6}$ alkyl-carbonyl, $C_{6-10}$ aryl-carbonyl, formyloxy, $C_{1-6}$ alkyl-carbonyloxy, $C_{6-10}$ aryl-carbonyloxy, carboxyl, $C_{1-6}$ alkoxy-carbonyl, $C_{7-11}$ aralkyloxy-carbonyl, carbamoyl, an optionally halogenated $C_{1-4}$ alkyl, oxo, amidino, imino, amino, mono-$C_{1-4}$ alkylamino, di-$C_{1-4}$ alkylamino, 3- to 6-membered cyclic amino, $C_{1-3}$ alkylenedioxy, hydroxy, nitro, cyano, mercapto, sulfo, sulfino, phosphono, sulfamoyl, mono-$C_{1-6}$ alkylsulfamoyl, di-$C_{1-6}$ alkylsulfamoyl, $C_{1-6}$ alkylthio, $C_{6-10}$ arylthio, $C_{1-6}$ alkylsulfinyl, $C_{6-10}$ arylsulfinyl, $C_{1-6}$ alkylsulfonyl and $C_{6-10}$ arylsulfonyl;

$R^2$ is (i) a hydrogen atom or (ii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxy, an optionally halogenated $C_{1-6}$ alkyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy and an optionally halogenated $C_{1-6}$ alkyl-carbonylamino;

$R^3$ is (i) a hydrogen atom, (ii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxy, an optionally halogenated $C_{1-6}$ alkyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy and an optionally halogenated $C_{1-6}$ alkyl-carbonylamino or (iii) a 5- to 14-membered heterocyclic group containing, besides carbon atoms, 1 to 3 hetero atoms selected from nitrogen atom, oxygen atom and sulfur atom, which group may be substituted by 1 to 5 substituents selected from the group consisting of a halogen, $C_{1-6}$ alkyl, $C_{3-6}$ cycloalkyl, $C_{2-6}$ alkynyl, $C_{2-6}$ alkenyl, $C_{7-11}$ aralkyl, $C_{6-10}$ aryl, $C_{1-6}$ alkoxy, $C_{6-10}$ aryloxy, formyl, $C_{1-6}$ alkyl-carbonyl, $C_{6-10}$ aryl-carbonyl, formyloxy, $C_{1-6}$ alkyl-carbonyloxy, $C_{6-10}$ aryl-carbonyloxy, carboxyl, $C_{1-6}$ alkoxy-carbonyl, $C_{7-11}$ aralkyloxy-carbonyl, carbamoyl, an optionally halogenated $C_{1-4}$ alkyl, oxo, amidino, imino, amino, mono-$C_{1-4}$ alkylamino, di-$C_{1-4}$ alkylamino, 3- to 6-membered cyclic amino, $C_{1-3}$ alkylenedioxy, hydroxy, nitro, cyano, mercapto, sulfo, sulfino, phosphono, sulfamoyl, mono-$C_{1-6}$ alkylsulfamoyl, di-$C_{1-6}$ alkylsulfamoyl, $C_{1-6}$ alkylthio, $C_{6-10}$ arylthio, $C_{1-6}$ alkylsulfinyl, $C_{6-10}$ arylsulfinyl, $C_{1-6}$ alkylsulfonyl and $C_{6-10}$ arylsulfonyl;

$R^4$ is (i) a hydrogen atom or (ii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxy, an optionally halogenated $C_{1-6}$ alkyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-16}$ alkyl-carbamoyl, di-$C_{1-6}$ alkyl-carbamoyl, $C_{6-10}$ aryl-carbamoyl, $C_{6-10}$ aryl, $C_{6-10}$ aryloxy and an optionally halogenated $C_{1-6}$ alkyl-carbonylamino;

ring A is a 5- to 7-membered heterocyclic group optionally containing, besides carbon atoms and an oxygen atom, 1 to 3 hetero atoms selected from nitrogen atom, oxygen atom and sulfur atom, which group may be substituted by 1 to 4 substituents selected from the group consisting of (i) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxy, an optionally halogenated $C_{1-6}$ alkyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy and an optionally halogenated $C_{1-6}$ alkyl-carbonylamino, (ii) a halogen, (iii) $C_{1-6}$ alkoxy, (iv) $C_{6-10}$ aryloxy, (v) formyl, (vi) $C_{1-6}$ alkyl-carbonyl, (vii) $C_{6-10}$ aryl-carbonyl, (viii) formyloxy, (ix) $C_{1-6}$ alkyl-carbonyloxy, (x) $C_{6-10}$ aryl-carbonyloxy, (xi) carboxyl, (xii) $C_{1-6}$ alkoxy-carbonyl, (xiii) $C_{7-11}$ aralkyloxy-carbonyl, (xiv) carbamoyl, (xv) an optionally halogenated $C_{1-4}$ alkyl, (xvi) oxo, (xvii) amidino, (xviii) imino, (xix) amino, (xx) mono-$C_{1-4}$ alkylamino, (xxi) di-$C_{1-4}$ alkylamino, (xxii) 3- to 6-membered cyclic amino, (xxiii) $C_{1-3}$ alkylenedioxy, (xxiv) hydroxy, (xxv) nitro, (xxvi) cyano, (xxvii) mercapto, (xxviii) sulfo, (xxix) sulfino, (xxx) phosphono, (xxxi) sulfamoyl, (xxxii) mono-$C_{1-6}$ alkylsulfamoyl, (xxxiii) di-$C_{1-6}$ alkylsulfamoyl, (xxxiv) $C_{1-6}$ alkylthio, (xxxv) $C_{6-10}$ arylthio, (xxxvi) $C_{1-6}$ alkylsulfinyl, (xxxvii) $C_{6-10}$ arylsulfinyl, (xxxviii) $C_{1-6}$ alkylsulfonyl and (xxxix) $C_{6-10}$ arylsulfonyl; and ring B is a benzene ring which may be substituted by 1 or 2 substituents selected from the group consisting of
(i) a halogen,
(ii) a $C_{1-6}$ alkyl, $C_{2-6}$ alkenyl, $C_{2-6}$ alkynyl, $C_{3-6}$ cycloalkyl or $C_{6-14}$ aryl group which may be substituted by 1 to 5 substituents selected from the group consisting of a halogen, nitro, cyano, hydroxy, an optionally halogenated $C_{1-6}$ alkyl, $C_{16}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy and an optionally halogenated $C_{1-6}$ alkyl-carbonylamino,
(iii) an amino group which may be substituted by 1 or 2 substituents selected from the group consisting of a $C_{1-6}$ alkyl, $C_{2-6}$ alkenyl, $C_{2-6}$ alkynyl, $C_{3-6}$ cycloalkyl and $C_{6-14}$ aryl group, each of which may be substituted by 1 to 5 substituents selected from the group consisting of a halogen, nitro, cyano, hydroxy, an optionally halogenated $C_{1-6}$ alkyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy and an optionally halogenated $C_{1-6}$ alkyl-carbonylamino, (iv) a $C_{1-6}$ alkanoylamino group, (v) a $C_{1-6}$ alkoxy group which may be substituted by 1 to 3 substituents selected from the group consisting of a halogen, nitro, cyano, hydroxy, an optionally halogenated $C_{1-6}$ alkyl, $C_{1-6}$ alkoxy, amino, mono-$C_{1-6}$ alkylamino, di-$C_{1-6}$ alkylamino, carboxyl, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy and an optionally halogenated $C_{1-6}$ alkyl-carbonylamino or (vi) a $C_{1-3}$ alkylenedioxy group.

3. A compound as claimed in claim 1, wherein

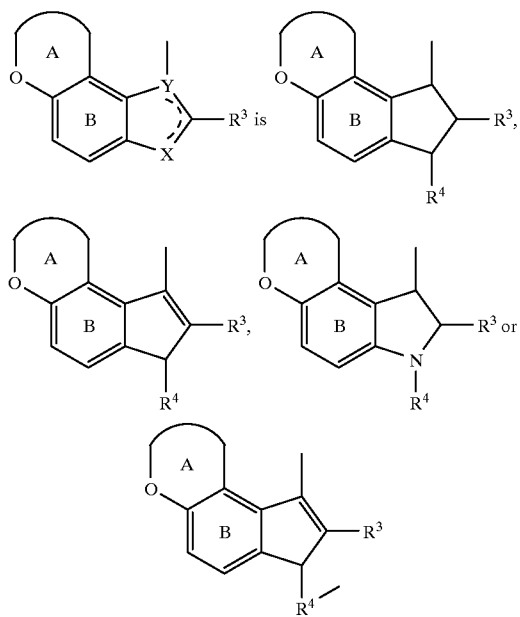

wherein $R^{4'}$ is an optionally substituted hydrocarbon group.

4. A compound as claimed in claim 1 which is a compound of the formula:

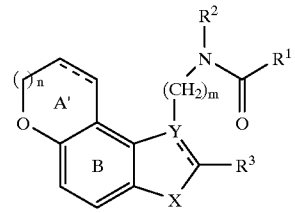

wherein ring A' is an optionally substituted, oxygen-containing heterocyclic ring;
n is an integer of 0 to 2;
---- and .... are independently a single bond or a double bond.

5. A compound as claimed in claim 1, wherein $R^1$ is
(i) an optionally substituted $C_{1-6}$ alkyl group,
(ii) an optionally substituted $C_{3-6}$ cycloalkyl group,
(iii) an optionally substituted $C_{2-6}$ alkenyl group,
(iv) an optionally substituted $C_{6-14}$ aryl group,
(v) an optionally substituted mono- or di-$C_{1-6}$ alkylamino group,
(vi) an optionally substituted $C_{6-14}$ arylamino group or
(vii) an optionally substituted 5- or 6-membered nitrogen-containing heterocyclic group.

6. A compound as claimed in claim 1, wherein $R^1$ is an optionally halogenated $C_{1-6}$ alkyl group.

7. A compound as claimed in claim 1, wherein $R^2$ is a hydrogen atom or an optionally substituted $C_{1-6}$ alkyl group.

8. A compound as claimed in claim 1, wherein $R^2$ is a hydrogen atom.

9. A compound as claimed in claim 1, wherein $R^3$ is a hydrogen atom or an optionally substituted hydrocarbon group.

10. A compound as claimed in claim 1, wherein $R^3$ is a hydrogen atom.

11. A compound as claimed in claim 1, wherein $R^4$ is a hydrogen atom or an optionally substituted $C_{1-6}$ alkyl group.

12. A compound as claimed in claim 1, wherein X is $CHR^4$.

13. A compound as claimed in claim 1, wherein X is $CHR^4$ and ......... is a single bond.

14. A compound as claimed in claim 13, wherein X is $CH_2$.

15. A compound as claimed in claim 1, wherein X is $NR^4$.

16. A compound as claimed in claim 1, wherein Y is C or CH.

17. A compound as claimed in claim 1, wherein Y is CH.

18. A compound as claimed in claim 1, wherein m is 2.

19. A compound as claimed in claim 1, wherein ring A is a tetrahydrofuran ring.

20. A compound as claimed in claim 1, wherein ring A is unsubstituted.

21. A compound as claimed in claim 1, wherein ring B is unsubstituted.

22. A compound as claimed in claim 4, wherein n is 0 or 1.

23. A compound as claimed in claim 1 which is a compound of the formula:

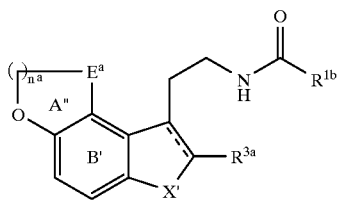

wherein $R^{1b}$ is $C_{1-6}$ alkyl,

X' is $CH_2$, NH or NCHO,

......... is a single bond or double bond, $R^{3a}$ is a hydrogen atom or phenyl, $E^a$ is $CH_2CH_2$, CH=CH, $CH_2O$, CH=N, CONH or $CH_2NH$, $n^a$ is 0 or 1, ring A" is a 5- or 6-membered oxgen-containing heterocyclic ring which may be substituted by 1 or 2 $C_{1-6}$ alkyl optionally substituted by a hydroxy, and ring B' is a benzene ring which may be substituted by a halogen.

24. A compound claimed in claim 23, wherein ......... is single bond and X' is NH.

25. A compound claimed in claim 1, which is (S)-N-[2-(1,6,7,8-tetrahydro-2H-indeno[5,4-b]furan-8-yl)ethyl]propionamide.

26. A compound claimed in claim 1, which is N-[2-(1,6,7,8-tetrahydro-2H-furo[3,2-e]indol-8-yl)ethyl]propionamide.

27. A compound claimed in claim 1, which is N-[2-(1,6,7,8-tetrahydro-2H-furo[3,2-e]indol-8-yl)ethyl]butyramide.

28. A compound claimed in claim 1, which is N-[2-(7-phenyl-1,6-dihydro-2H-indeno[5,4-b]furan-8-yl)ethyl]propionamide.

29. A compound claimed in claim 1, which is N-[2-(7-phenyl-1,6-dihydro-2H-indeno[5,4-b]furan-8-yl)ethyl]butyramide.

30. A process for producing a compound as claimed in claim 1, which comprises:

reacting a compound of the formula (i):

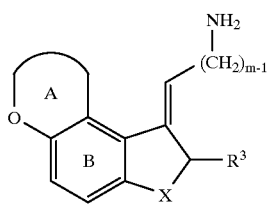

or a salt thereof, or (ii):

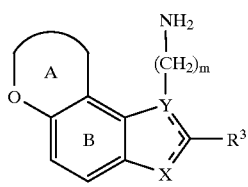

or a salt thereof, with a compound of the formula:

$R^1COOH$ or a salt or a reactive derivative thereof; and if necessary, subjecting the resultant compound to reduction and/or alkylation.

31. A process for producing a compound as claimed in claim 4, which comprises:

subjecting to cyclization a compound of the formula:

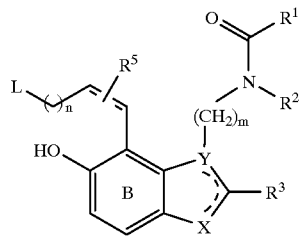

wherein $R^5$ represents a hydrogen atom, a halogen atom, an optionally substituted hydrocarbon group, an optionally substituted alkoxy group, a hydroxy group, a nitro group, a cyano group or an optionally substituted amino group; L represents a leaving group, or a salt thereof; and if necessary, subjecting the resultant compound to reduction.

32. A compound of the formula:

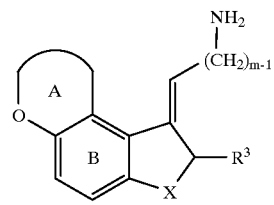

wherein $R^3$ represents a hydrogen atom, an optionally substituted hydrocarbon group, or an optionally substituted heterocyclic group;

x represents $CHR^4$, $NR^4$, O or S in which $R^4$ represents a hydrogen atom or an optionally substituted hydrocarbon group;

ring A represents an optionally substituted, 5- to 7-membered oxygen-containing heterocyclic ring;
ring B represents an optionally substituted benzene ring; and
m represents an integer of 1 to 4, or a salt thereof.

33. A compound of the formula:

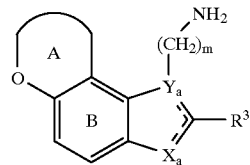

wherein $X^a$ represents $CHR^{4a}$, $NR^{4a}$, O or S in which $R^{4a}$ represents a hydrogen atom or an optionally substituted hydrocarbon group;
$Y^a$ represents C, CH or N, provided that when $X^a$ is NH or $NCH_3$, $Y^a$ is CH or N;
.... represents a single bond or a double bond;
$R^3$ represents a hydrogen atom, an optionally substituted hydrocarbon group, or an optionally substituted heterocyclic group;
ring A represents an optionally substituted, 5- to 7-membered oxygen-containing heterocyclic ring;
ring B represents an optionally substituted benzene ring; and
m represents an integer of 1 to 4, or a salt thereof.

34. A pharmaceutical composition which comprises a compound as claimed in claim 1 or a pharmaceutically acceptable salt thereof and a pharmaceutically acceptable carrier.

35. A composition as claimed in claim 34 wherein said compound or said pharmaceutically acceptable salt has a binding affinity for melatonin receptor.

36. Method for treating or preventing diseases related to the action of melatonin in mammals which comprises administrating to a subject in need thereof a therapeutically effective amount of a composition as claimed in claim 35.

37. A method as claimed in claim 36 which regulates circadian rhythm.

38. A method as claimed in claim 36 which regulates sleep-awake rhythm.

39. A method as claimed in claim 36 which regulates time zone change syndrome.

40. A method as claimed in claim 36 which treats or prevents sleep disorders.

41. A process of manufacturing a pharmaceutical composition comprising the steps of selecting a compound or pharmaceutically acceptable salt of claim 1 and admixing said compound or salt with a pharmaceutically acceptable carrier.

* * * * *

UNITED STATES PATENT AND TRADEMARK OFFICE
CERTIFICATE OF CORRECTION

PATENT NO. : 6,034,239
DATED : March 7, 2000
INVENTOR(S) : SHIGENORI OHKAWA ET AL.

It is certified that error appears in the above-identified patent and that said Letters Patent is hereby corrected as shown below:

COLUMN 1

Line 30, "melatonin" (first occurrence) should be deleted;
Line 48, "■Y" should read ---Y--;
Line 57, "U.S. Pat. No. 5,634,238" should read --(U.S. Pat. No. 5,634,238)--.

COLUMN 6

Line 52, "is" should read --are--.

COLUMN 18

Line 39, "ohters," should read --others,--.

COLUMN 28

Line 6, 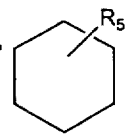 should read -- 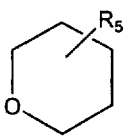 --

COLUMN 30

Line 17, "doulbe" should read --double--.

UNITED STATES PATENT AND TRADEMARK OFFICE
CERTIFICATE OF CORRECTION

PATENT NO.   : 6,034,239
DATED        : March 7, 2000
INVENTOR(S)  : SHIGENORI OHKAWA ET AL.

It is certified that error appears in the above-identified patent and that said Letters Patent is hereby corrected as shown below:

COLUMN 32

Line 48, "analogous" should read --ones analogous--;
  Line 54, "those mentioned" should be deleted.

COLUMN 33

Line 45, "(crbon-chain)" should read --(carbon-chain)--.

COLUMN 40

Line 38, "suchas" should read --such as--.

COLUMN 50

Line 42, "acetyleue" should read --acetylene--.

COLUMN 53

Line 37, "so" should read --So--.

COLUMN 64

Line 28, "exemplified" should read --exemplified by--.

COLUMN 96

Line 1, "purified" should read --be purified--.

UNITED STATES PATENT AND TRADEMARK OFFICE
CERTIFICATE OF CORRECTION

PATENT NO. : 6,034,239
DATED : March 7, 2000
INVENTOR(S) : SHIGENORI OHKAWA ET AL.

It is certified that error appears in the above-identified patent and that said Letters Patent is hereby corrected as shown below:

COLUMN 97

Line 20, "condust" should read --conduct--;
Line 36, "nicket" should read --nickel--.

COLUMN 100

Line 6, "$NH_2$" (both occurrences) should read --NH--.

COLUMN 101

Line 17, "example" should read --example,--.

COLUMN 104

Line 13, "physilogical" should read --physiological--.

COLUMN 106

Line 65, "(1H, s);" should read --(1H, s)--.

COLUMN 107

Line 65, "6:" should read δ:--.

COLUMN 110

Line 42, "(CDC13)" should read --($CDCl_3$)--.

UNITED STATES PATENT AND TRADEMARK OFFICE
CERTIFICATE OF CORRECTION

PATENT NO. : 6,034,239
DATED : March 7, 2000
INVENTOR(S) : SHIGENORI OHKAWA ET AL.

It is certified that error appears in the above-identified patent and that said Letters Patent is hereby corrected as shown below:

COLUMN 111

Line 21, "(CDC13)" should read --(CDCl$_3$)--.

COLUMN 112

Line 13, "Ru$_2$Cl4" should read --Ru$_2$Cl$_4$--.

COLUMN 113

Line 63, "ethyl)propionamide" should read
      --ethyl]propionamide--.

COLUMN 114

Line 32, "[α]D$^{20}$" should read --[α]$_D^{20}$--.

COLUMN 116

Line 8, "[α]D$^{20}$" should read --[α]$_D^{20}$--.

COLUMN 121

Line 66, "81%ee" should read --81%e.e.--.

COLUMN 122

Line 32, "245,5 mg," should read --(245.5 mg,--;
   Line 60, "which was" should be deleted.

UNITED STATES PATENT AND TRADEMARK OFFICE
CERTIFICATE OF CORRECTION

PATENT NO. : 6,034,239
DATED : March 7, 2000
INVENTOR(S) : SHIGENORI OHKAWA ET AL.

It is certified that error appears in the above-identified patent and that said Letters Patent is hereby corrected as shown below:

COLUMN 124

Line 67, "was" should read --were-.

COLUMN 128

Line 62, "(A:B = 1:2)" should read --(A:B ≒ 1:2)--.

COLUMN 131

Line 42, "11•3" should read --113--.

COLUMN 132

Line 21, "satruated" should read --saturated--.

COLUMN 134

Line 37, "which" should be deleted;
Line 38, "was" should be deleted.

COLUMN 136

Line 46, "which was" should be deleted.

COLUMN 137

Line 6, "$Cl_5Hl_8N_2O_2$:" should read --$Cl_{15}H_{18}N_2O_2$:--.

UNITED STATES PATENT AND TRADEMARK OFFICE
CERTIFICATE OF CORRECTION

PATENT NO. : 6,034,239

DATED : March 7, 2000

INVENTOR(S) : SHIGENORI OHKAWA ET AL.

It is certified that error appears in the above-identified patent and that said Letters Patent is hereby corrected as shown below:

COLUMN 141

Line 36, "amorphous" (second occurrence) should be deleted.

COLUMN 149

Line 35, "$C_{16}$" should read --$C_{1-6}$--.

COLUMN 150

Line 29, "claim 1" should read --claim 1,--.

COLUMN 151

Line 23, "claim 1" should read --claim 1,--.

UNITED STATES PATENT AND TRADEMARK OFFICE
CERTIFICATE OF CORRECTION

PATENT NO. : 6,034,239
DATED : March 7, 2000
INVENTOR(S) : SHIGENORI OHKAWA ET AL.

It is certified that error appears in the above-identified patent and that said Letters Patent is hereby corrected as shown below:

<u>COLUMN 154</u>

```
Line 3,  "claim 1"  should read --claim 1,--;
Line 6,  "claim 34" should read --claim 34,--;
Line 13, "claim 36" should read --claim 36,--;
Line 15, "claim 36" should read --claim 36,--;
Line 18, "claim 36" should read --claim 36,--;
Line 20, "claim 36" should read --claim 36,--;
Line 24, "claim 1"  should read --claim 1,--.
```

Signed and Sealed this

Eighth Day of May, 2001

Attest:

NICHOLAS P. GODICI

Attesting Officer

Acting Director of the United States Patent and Trademark Office

(12) EX PARTE REEXAMINATION CERTIFICATE (6231st)
United States Patent
Ohkawa et al.

(10) Number: US 6,034,239 C1
(45) Certificate Issued: May 20, 2008

(54) TRICYCLIC COMPOUNDS, THEIR PRODUCTION AND USE

(75) Inventors: Shigenori Ohkawa, Osaka (JP); Osamu Uchikawa, Hyogo (JP); Kohji Fukatsu, Hyogo (JP); Masaomi Miyamoto, Hyogo (JP)

(73) Assignee: Takeda Pharmaceutical Company, Limited, Chuo-Ku, Osaka (JP)

Reexamination Request:
No. 90/008,353, Nov. 30, 2006

Reexamination Certificate for:
Patent No.: 6,034,239
Issued: Mar. 7, 2000
Appl. No.: 08/812,168
Filed: Mar. 6, 1997

Certificate of Correction issued May 8, 2001.

Related U.S. Application Data
(60) Provisional application No. 60/013,733, filed on Mar. 20, 1996, and provisional application No. 60/023,090, filed on Jul. 25, 1996.

(30) Foreign Application Priority Data

Mar. 8, 1996 (JP) .............................................. 8-051491
Jul. 12, 1996 (JP) .............................................. 8-183667
Feb. 13, 1997 (JP) .............................................. 9-029185

(51) Int. Cl.
C07C 233/00 (2006.01)
C07D 307/00 (2006.01)
C07D 413/00 (2006.01)
C07D 307/92 (2006.01)
C07D 493/00 (2006.01)

(52) U.S. Cl. ........................ 544/147; 544/153; 549/387; 549/458; 564/189

(58) Field of Classification Search ........................ None
See application file for complete search history.

(56) References Cited

U.S. PATENT DOCUMENTS

| | | |
|---|---|---|
| 5,194,614 A | 3/1993 | Andrieux et al. |
| 5,225,442 A | 7/1993 | Andrieux et al. |
| 5,318,994 A | 6/1994 | Andrieux et al. |
| 5,464,872 A | 11/1995 | Langlois et al. |
| 5,661,186 A * | 8/1997 | Takaki et al. ............... 514/630 |
| 5,843,986 A | 12/1998 | Lesieur et al. |

FOREIGN PATENT DOCUMENTS

| | | |
|---|---|---|
| EP | 0591057 A1 | 4/1994 |
| JP | 07-48331 A | 2/1995 |
| WO | WO 95/29173 | 11/1995 |

OTHER PUBLICATIONS

Uchikawa et al., "Synthesis of a Novel Series of Tricyclic Indan Derivatives as Melatonin Receptor Agonists", J. Med. Chem. (2002); (45) 4222–4239.

Reppert, S.M., et al., *Melatonin Receptors Are for the Birds: Molecular Analysis of Two Receptor Subtypes Differentially Expressed in Chick Brain*, Neuron, vol. 15, 1003–1015, Nov. 1995.

* cited by examiner

*Primary Examiner*—Evelyn Huang

(57) ABSTRACT

A compound of the formula:

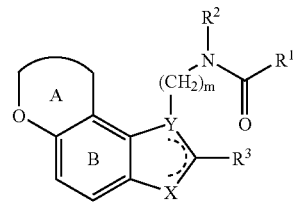

wherein $R^1$ is an optionally substituted hydrocarbon, amino or heterocyclic group; $R^2$ is H or an optionally substituted hydrocarbon group; $R^3$ is H or an optionally substituted hydrocarbon or heterocyclic group; X is $CHR^4$, $NR^4$, O or S in which $R^4$ is H or an optionally substituted hydrocarbon group; Y is C, CH or N; ring A is optionally substituted 5- to 7-membered ring; ring B is an optionally substituted benzene ring; and m is 1 to 4, or a salt thereof, a process for producing it, an intermediate for the production and a pharmaceutical composition comprising it are provided.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–23 and 28–30 are cancelled.

Claims 25, and 34–40 are determined to be patentable as amended.

Claims 24, 26–27, 31–33 and 41 were not reexamined.

25. [A] *The* compound [claimed in claim 1, which is] (S)-N-[2-(1,6,7,8-tetrahydro-2H-indeno[5,4-b]furan-8-yl) ethyl]proprionamide, *or a salt thereof.*

34. A pharmaceutical composition which comprises a compound as claimed in claim [1] *25*, or a pharmaceutically acceptable salt thereof and a pharmaceutically acceptable carrier.

35. [A] *The* composition as claimed in claim 34, wherein said compound or said pharmaceutically acceptable salt has a binding affinity for melatonin receptor.

36. [Method] *A method* for treating or preventing diseases related to the action of melatonin in mammals which comprises administrating to a subject in need thereof a therapeutically effective amount of a composition as claimed in claim 35.

37. [A] *The* method as claimed in claim 36, which regulates circadian rhythm.

38. [A] *The* method as claimed in claim 36, which regulates sleep-awake rhythm.

39. [A] *The* method as claimed in claim 36, which regulates time zone change syndrome.

40. [A] *The* method as claimed in claim 36, which treats or prevents sleep disorders.

\* \* \* \* \*